United States Patent
Sugiura et al.

(10) Patent No.: US 12,129,253 B2
(45) Date of Patent: Oct. 29, 2024

(54) METHOD FOR PRODUCING CYCLIC IMIDE COMPOUND, COMPOSITION, AND COMPOUND

(71) Applicants: FUJIFILM Corporation, Tokyo (JP); The University of Tokyo, Tokyo (JP)

(72) Inventors: Hiroki Sugiura, Kanagawa (JP); Yukio Tani, Kanagawa (JP); Tetsuya Matsushita, Kanagawa (JP); Tetsuya Watanabe, Kanagawa (JP); Toshihiro Okamoto, Tokyo (JP)

(73) Assignees: FUJIFILM Corporation, Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 17/655,293

(22) Filed: Mar. 17, 2022

(65) Prior Publication Data
US 2022/0213104 A1 Jul. 7, 2022

Related U.S. Application Data

(63) Continuation of application No. PCT/JP2020/033541, filed on Sep. 4, 2020.

(30) Foreign Application Priority Data

Sep. 20, 2019 (JP) ................. 2019-171333

(51) Int. Cl.
| C07D 471/22 | (2006.01) |
| C07D 495/22 | (2006.01) |
| C07D 513/22 | (2006.01) |

(52) U.S. Cl.
CPC ......... *C07D 471/22* (2013.01); *C07D 495/22* (2013.01); *C07D 513/22* (2013.01)

(58) Field of Classification Search
CPC ................ C07D 471/22; C07D 495/22; C07D 513/22
See application file for complete search history.

(56) References Cited

U.S. PATENT DOCUMENTS

| 2017/0018724 A1 | 1/2017 | Tsuyama et al. |
| 2018/0159043 A1 | 6/2018 | Fukuzaki et al. |

(Continued)

FOREIGN PATENT DOCUMENTS

| JP | 2015-195362 A | 11/2015 |
| JP | 2018-006745 A | 1/2018 |
| WO | 2017/022735 A1 | 2/2017 |

(Continued)

OTHER PUBLICATIONS

International Search Report issued in PCT/JP2020/033541; mailed Oct. 20, 2020.

Written Opinion of the International Searching Authority issued in PCT/JP2020/033541; mailed Oct. 20, 2020.

Yu, C.P. et al., Air-Stable Benzo[c]thiophene Diimide n-Type pi-Electron Core, Organic Letters, Jun. 5, 2019, vol. 21, No. 12, pp. 4448-4453, DOI 10.1021/acs.orglett.9b01239, scheme 1.

(Continued)

*Primary Examiner* — Susanna Moore
(74) *Attorney, Agent, or Firm* — Studebaker & Brackett PC

(57) ABSTRACT

A first object of the present invention is to provide a method for producing a cyclic imide compound with high yield and high purity. A second object of the present invention is to provide a composition that can be used in the method for producing a cyclic imide compound with high yield and high purity. A third object of the present invention is to provide an intermediate compound that can be used in the method for producing a cyclic imide compound with high yield and high purity. The method for producing a cyclic imide compound according to the present invention includes reacting a compound represented by formula (1) below with at least one amine compound to obtain a compound represented by formula (2) below.

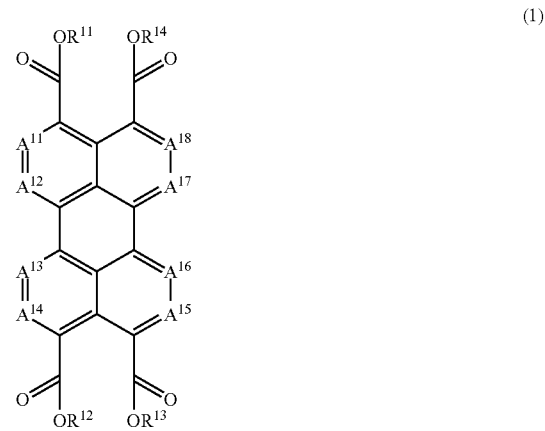

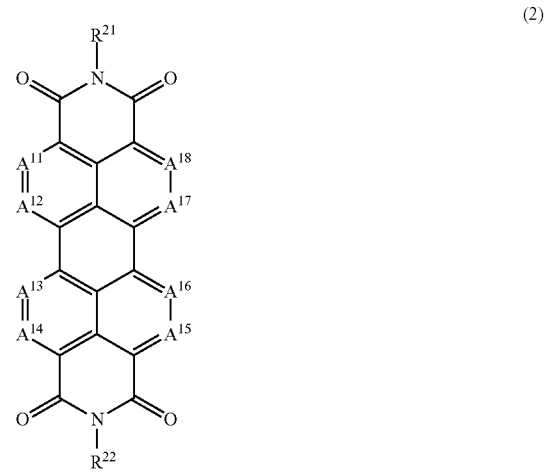

9 Claims, 4 Drawing Sheets

(56) References Cited

U.S. PATENT DOCUMENTS

2019/0131546 A1    5/2019  Fukuzaki et al.
2020/0343451 A1    10/2020 Tani et al.

FOREIGN PATENT DOCUMENTS

WO    2018/003701 A1    1/2018
WO    2019/146368 A1    8/2019

OTHER PUBLICATIONS

The extended European search report issued by the European Patent Office on Oct. 12, 2022, which corresponds to European Patent Application No. 2086528.6-1110 and is related to U.S. Appl. No. 17/655,293.

An Office Action; "Notice of Reasons for Refusal," mailed by the Japanese Patent Office on May 9, 2023, which corresponds to Japanese Patent Application No. 2021-546599 and is related to U.S. Appl. No. 17/655,293; with English language translation.

An Office Action mailed by China National Intellectual Property Administration on Jan. 5, 2024, which corresponds to Chinese Patent No. 202080064863.9 and is related to U.S. Appl. No. 17/655,293; with English language translation.

Xiong, Kai et al., "Synthesis of tetraalkyl naphthalene bisanhydride and its model condensations with amines", Tetrahedron Letters, vol. 54, No. 24, Apr. 15, 2013, pp. 3171-3175, Elsevier.

An Office Action mailed by China National Intellectual Property Administration on Jul. 5, 2024, which corresponds to Chinese Patent Application No. 20280064863.9 and is related to U.S. Appl. No. 17/655,293; with English language translation.

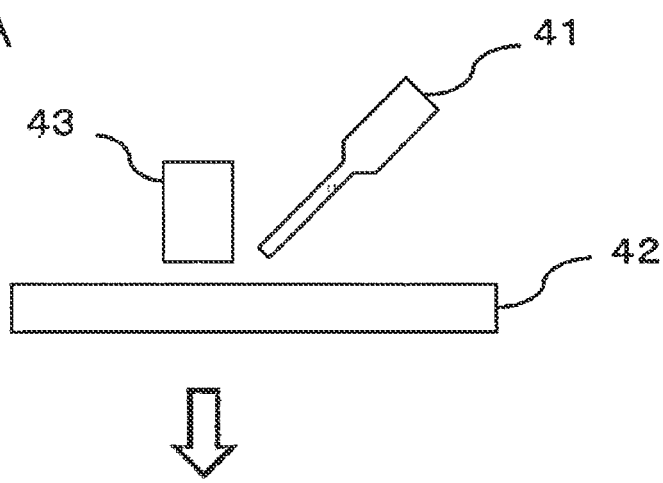
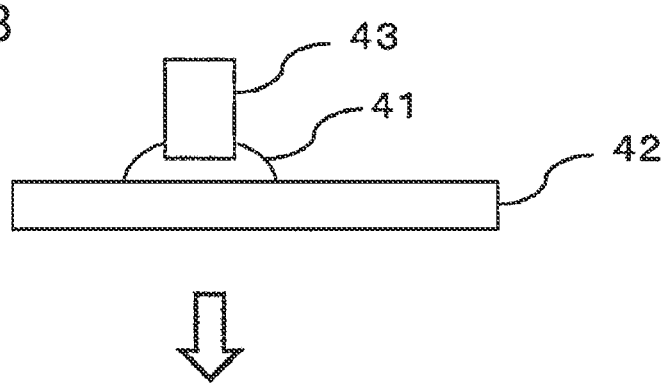
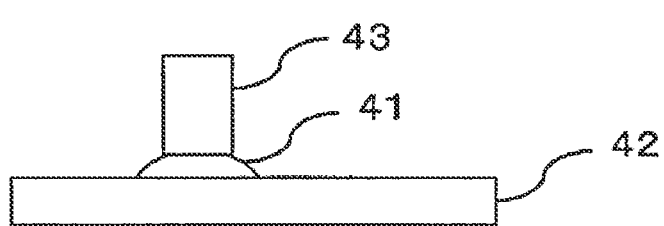

FIG. 4A
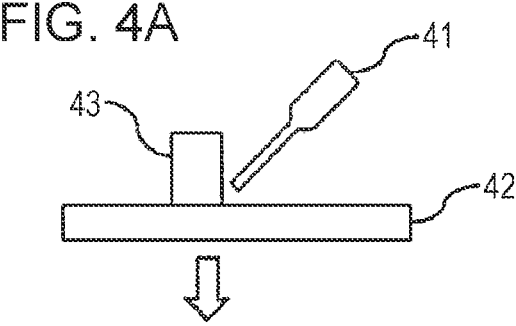
FIG. 4B1
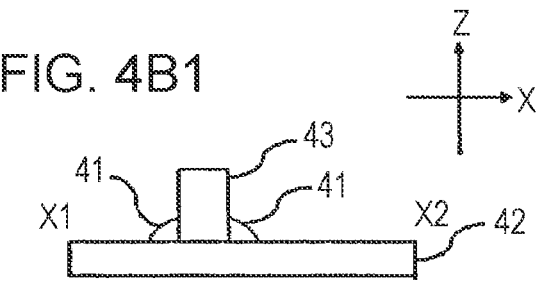
FIG. 4B2
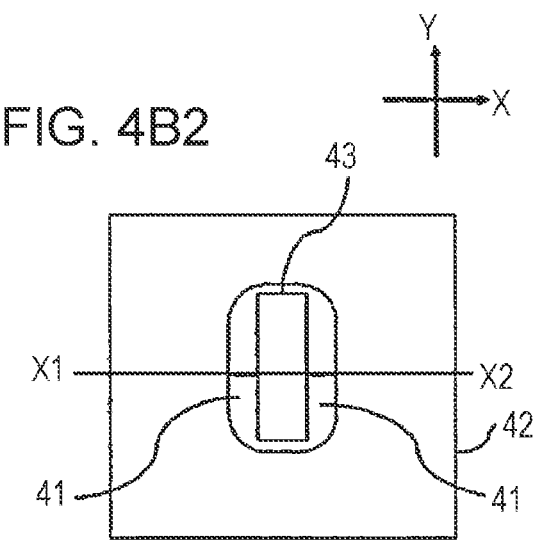
FIG. 4C
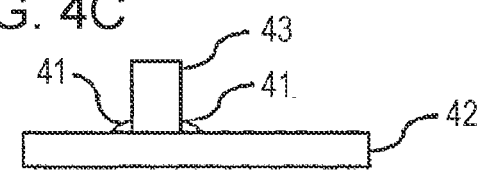
FIG. 4D
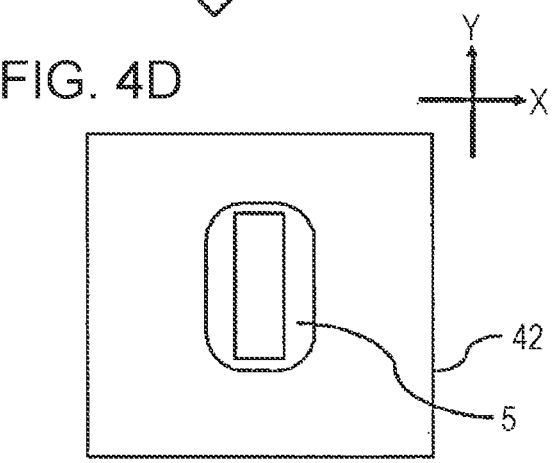

METHOD FOR PRODUCING CYCLIC IMIDE COMPOUND, COMPOSITION, AND COMPOUND

CROSS-REFERENCE TO RELATED APPLICATIONS

This application is a Continuation of PCT International Application No. PCT/JP2020/033541 filed on Sep. 4, 2020, which claims priority under 35 U.S.C. § 119(a) to Japanese Patent Application No. 2019-171333 filed on Sep. 20, 2019. The above application is hereby expressly incorporated by reference, in its entirety, into the present application.

BACKGROUND OF THE INVENTION

1. Field of the Invention

The present invention relates to a method for producing a cyclic imide compound, a composition, and a compound.

2. Description of the Related Art

It has been studied that organic thin film transistors (organic TFTs) having organic semiconductor films (organic semiconductor layers) are used in, for example, field effect transistors (FETs) for liquid crystal displays and organic electric luminescence (EL) displays and apparatuses with a logic circuit including a radio frequency identifier (RFID, RF tag) and a memory because weight reduction, cost reduction, and high flexibility can be achieved.

JP2018-6745A discloses a cyclic imide compound including an azaperylene skeleton as an organic semiconductor compound for forming such an organic semiconductor film.

SUMMARY OF THE INVENTION

As a result of studies conducted on the method for producing a cyclic imide compound including an azaperylene skeleton disclosed in JP2018-6745A, the present inventors have found that there is room for further improvement in yield and purity.

Accordingly, it is an object of the present invention to provide a method for producing a cyclic imide compound with high yield and high purity.

It is another object of the present invention to provide a composition that can be used in a method for producing a cyclic imide compound with high yield and high purity.

It is also another object of the present invention to provide an intermediate compound that can be used in a method for producing a cyclic imide compound with high yield and high purity.

As a result of thorough studies to achieve the above objects, the present inventors have found that the above objects can be achieved by a certain production method, and have completed the present invention.

That is, the present inventors have found that the above objects can be achieved by the following configurations.

[1] A method for producing a cyclic imide compound includes reacting a compound represented by formula (1) described later with at least one amine compound to obtain a compound represented by formula (2) described later.

[2] The method for producing a cyclic imide compound according to [1] includes:
a step Y1 of reacting the compound represented by the formula (1) with a first amine compound represented by formula (3) described later to obtain a compound represented by formula (4) described later;
a step Y2 of reacting the compound represented by the formula (4) with a second amine compound represented by formula (5) described later to obtain a compound represented by formula (6) described later;
a step Y3 of removing $P^{31}$ serving as a protecting group from the compound represented by the formula (6) to obtain a compound represented by formula (7) described later; and
a step Y4 of obtaining the compound represented by the formula (2) from the compound represented by the formula (7).

[3] In the method for producing a cyclic imide compound according to [1] or [2], the compound represented by the formula (1) is a compound represented by formula (8) described later, and the compound represented by the formula (2) is a compound represented by formula (9) described later.

[4] In the method for producing a cyclic imide compound according to [3], the compound represented by the formula (8) is a compound represented by formula (10) described later.

[5] In the method for producing a cyclic imide compound according to [4], the compound represented by the formula (10) is a compound represented by formula (10') described later.

[6] In the method for producing a cyclic imide compound according to [5], $X^{111}$ to $X^{116}$ represent a chlorine atom.

[7] The method for producing a cyclic imide compound according to [3] includes:
a step Y1' of reacting a compound represented by formula (X1) described later with a compound represented by formula (X2) described later to obtain a composition including a compound represented by formula (11A) described later and a compound represented by formula (11B) described later, and then reacting the composition with a first amine compound represented by formula (12) described later without subjecting the composition to column purification to obtain a compound represented by formula (13) described later;
a step Y2' of reacting the compound represented by the formula (13) with a second amine compound represented by formula (14) described later to obtain a compound represented by formula (15) described later;
a step Y3' of removing $P^{31}$ serving as a protecting group from the compound represented by the formula (15) to obtain a compound represented by formula (16) described later; and
a step Y4' of obtaining the compound represented by the formula (9) from the compound represented by the formula (16).

[8] The method for producing a cyclic imide compound according to [1] includes a step of reacting a compound represented by formula (X1) described later with a compound represented by formula (X2) described later to obtain a composition including a compound represented by formula (11A) described later and a compound represented by formula (11B) described later, and then reacting the composition with an amine compound represented by formula (14) described later without subjecting the composition to column purification to obtain a compound represented by formula (9') described later.

[9] The method for producing a cyclic imide compound according to [7] or [8] further includes a step Y0' of purifying the compound represented by the formula (X2)

before reacting the compound represented by the formula (X1) with the compound represented by the formula (X2).

[10] A composition used for synthesizing a compound represented by formula (9) described later includes at least a compound represented by formula (8) described later.

In the composition, a total content of a compound represented by formula (17) described later and a compound represented by formula (18) described later is 3.0 mass % or less relative to a total solid content of the composition.

[11] A compound is represented by formula (4) described later.

[12] A compound is represented by formula (6) described later.

[13] A compound is represented by formula (7) described later.

[14] A compound is represented by formula (11A') described later.

[15] A compound is represented by formula (11A") described later.

According to the present invention, a method for producing a cyclic imide compound with high yield and high purity can be provided.

According to the present invention, a composition that can be used in the method for producing a cyclic imide compound with high yield and high purity can be provided.

According to the present invention, an intermediate compound that can be used in the method for producing a cyclic imide compound with high yield and high purity can be provided.

BRIEF DESCRIPTION OF THE DRAWINGS

FIGS. 3A to 3C are schematic views illustrating an example of a method for forming an organic semiconductor film of an organic thin film transistor;

FIGS. 4A to 4D are schematic views for illustrating another example of a method for forming an organic semiconductor film of an organic thin film transistor;

DESCRIPTION OF THE PREFERRED EMBODIMENTS

Figure 1:
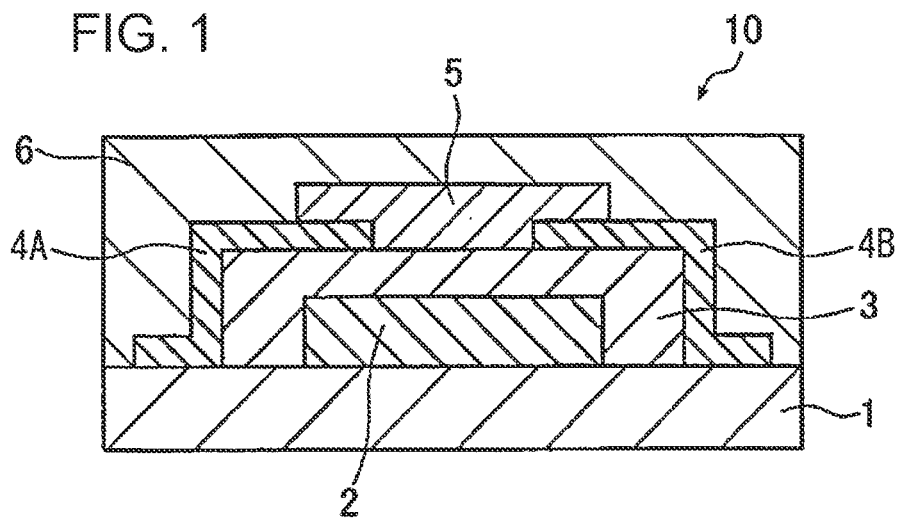
FIG. 1 is a sectional view schematically illustrating a structure of a bottom gate-bottom contact organic thin film transistor, which is an example of organic thin film transistors.

Hereafter, the method for producing a cyclic imide compound, the composition, and the compound according to embodiments of the present invention will be described in detail. The following descriptions of constituent elements may be made based on representative embodiments of the present invention. However, the present invention is not limited to such embodiments.

In this specification, every numerical range expressed using "to" means a range including numerical values before and after "to" as the lower and upper limits.

In this specification, (meth)acryloyl means acryloyl or methacryloyl.

In this specification, the expression of a compound includes not only the compound itself, but also a salt thereof and an ion thereof. Compounds whose structure is partly modified are also included as long as the intended effects are not impaired.

Compounds whose substitution or unsubstitution is not explicitly stated may have a substituent as long as the intended effects are not impaired. The same applies to a substituent, a linking group, and the like (hereafter referred to as a substituent and the like).

In this specification, when a plurality of substituents and the like are represented by a particular symbol or when a plurality of substituents and the like are simultaneously defined, the substituents and the like may be the same as or different from each other unless otherwise specified. The same also applies to the definition of the number of substituents and the like. When a plurality of substituents and the like are close (particularly adjacent) to each other, they may be linked to each other to form a ring unless otherwise specified.

In this specification, examples of the halogen atom include a fluorine atom, a chlorine atom, a bromine atom, and an iodine atom.

In the present invention, when a group can form an acyclic skeleton and a cyclic skeleton, the group includes a group having an acyclic skeleton and a group having a cyclic skeleton unless otherwise specified.

For example, aliphatic hydrocarbon groups, alkyl groups, alkenyl groups, and alkynyl groups include groups having any of linear, branched, and cyclic structures unless otherwise specified.

More specific examples of the alkyl group include a linear alkyl group, a branched alkyl group, and a cyclic (cyclo) alkyl group.

When the group can form a cyclic skeleton, the lower limit of the number of atoms of the group forming a cyclic skeleton is 3 or more and preferably 5 or more regardless of the lower limit of the number of atoms specifically described for this group. Examples of the cycloalkyl group include a bicycloalkyl group and a tricycloalkyl group.

Method for Producing Cyclic Imide Compound

A method for producing a cyclic imide compound according to an embodiment of the present invention (hereafter also referred to as "a production method according to an embodiment of the present invention") is a production method in which a compound represented by formula (1) described later is reacted with at least one amine compound to obtain a compound represented by formula (2) described later.

The present inventors have studied a method for producing a cyclic imide compound including an azaperylene skeleton, such as a compound represented by formula (2). As a result, they have found that the factor that does not satisfy a desired level of yield and purity in the production method of the related art is formation of a target cyclic imide compound via an acid anhydride intermediate. Specifically, an acid anhydride including an azaperylene skeleton has considerably low solubility in a solvent and thus is poor in terms of ease of handling and quality control, which is considered to decrease the yield and purity when an acid anhydride intermediate including an azaperylene skeleton is modified into a cyclic imide structure to synthesize a target cyclic imide compound.

On the other hand, the present inventors have lately found a novel method for producing a cyclic imide compound without using an acid anhydride intermediate. In the production method according to an embodiment of the present invention, a cyclic imide compound including an azaperylene skeleton, such as a compound represented by formula (2), can be produced in high yield and high purity. Hereafter, the production method according to an embodiment of the present invention will be described in detail.

The production method according to an embodiment of the present invention includes a step of reacting a compound represented by formula (1) below with at least one amine compound to obtain a compound represented by formula (2) below.

First, the compound represented by the formula (1) and serving as a raw material, the compound represented by the formula (2) and serving as an intended product, and the amine compound will be described.

Compound Represented by Formula (1)

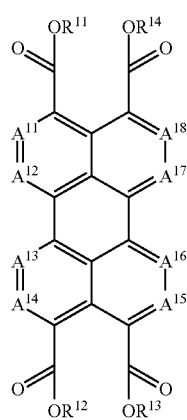
(1)

In the formula (1), $A^{11}$ to $A^{18}$ each independently represent —N= or —C($R^{15}$)=.

At least one of $A^{11}$ to $A^{18}$ represents —N=. In particular, preferably one to four of $A^{11}$ to $A^{18}$ represent —N=, more preferably one to three of $A^{11}$ to $A^{18}$ represent —N=, further preferably one or two of $A^{11}$ to $A^{18}$ represent —N=, and particularly preferably two of $A^{11}$ to $A^{18}$ represent —N=.

The nitrogen atom of —N= that may be represented by $A^{11}$ to $A^{18}$ may have a substituent. Examples thereof include an N-oxide group (N→O group) and a salt having a counter anion.

$R^{15}$ represents a hydrogen atom or a substituent.

The substituent represented by $R^{15}$ is not particularly limited, and is, for example, a group selected from the substituent group Z.

Substituent Group Z

The substituent group Z includes a halogen atom, an alkyl group, an alkenyl group, an alkynyl group, an aryl group, a heterocyclic group, a silyl group, an alkoxy group, an amino group, an aryloxy group, an acyl group, an alkoxycarbonyl group, an aryloxycarbonyl group, an acyloxy group, an acylamino group, an aminocarbonylamino group, an alkoxycarbonylamino group, an aryloxycarbonylamino group, an alkylsulfonylamino group, an arylsulfonylamino group, an alkylthio group, an arylthio group, an alkylsulfinyl group, an arylsulfinyl group, an alkylsulfonyl group, an arylsulfonyl group, a silyloxy group, a heterocyclic oxy group, a carbamoyl group, a carbamoyloxy group, a heterocyclic thio group, a sulfamoyl group, an arylazo group, a heterocyclic azo group, an imide group, a phosphino group, a phosphinyl group, a phosphinyloxy group, a phosphinylamino group, a hydrazino group, an imino group, a cyano group, a hydroxy group, a nitro group, a mercapto group, a sulfo group, a carboxy group, a hydroxamic acid group, a sulfino group, a boronic acid group (—B(OH)$_2$), a phosphato group (—OPO(OH)$_2$), a phosphono group (—PO(OH)$_2$), and a sulfato group (—OSO$_3$H).

The group selected from the substituent group Z may further have a substituent.

Examples of the halogen atom included in the substituent group Z include a fluorine atom, a chlorine atom, a bromine atom, and an iodine atom, and a fluorine atom or a chlorine atom is preferable.

The alkyl group included in the substituent group Z is not particularly limited, but is preferably an alkyl group having 1 (3) to 30 carbon atoms and more preferably an alkyl group having 1 (3) to 20 carbon atoms. The numbers in parentheses represent the number of carbon atoms in the case of cycloalkyl groups.

Examples of the alkyl group that may have a substituent and is included in the substituent group Z include a methyl group, an ethyl group, a propyl group, a 2-methylpropyl group, a butyl group, an amyl group, a pentyl group, a 1-methylpentyl group, a 2,2-dimethylpropyl group, a hexyl group, a heptyl group, an octyl group, a 2-ethylhexyl group, a nonyl group, a decyl group, a 3,7-dimethyloctyl group, an undecyl group, a dodecyl group, a tridecyl group, a tetradecyl group, a pentadecyl group, a 2,6-dimethyloctyl group, an icosyl group, a 2-decyltetradecyl group, a 2-hexyldodecyl group, a 2-ethyloctyl group, a 2-butyldecyl group, a 1-octylnonyl group, a 2-octyldecyl group, a 2-octyldecyl group, a 7-hexylpentadecyl group, a 2-octyltetradecyl group, a cyclopropyl group, a cyclobutyl group, a cyclopentyl group, a cyclohexyl group, an adamantyl group, a benzyl group, a 2-cyclohexylethyl group, a p-chlorobenzyl group, a 2-phenylethyl group, a trifluoromethyl group, a perfluoroethyl group, a 2,2,3,3,4,4,4-heptafluorobutyl group, $C_5F_{11}C_2H_4$—, $C_6F_{13}C_2H_4$—, a 3-aminopropyl group, a 4-aminobutyl group, a 5-ethoxypentyl group, a (meth)acryloyloxypropyl group, a (meth)acryloyloxypentyl group, a 4-hydroxybutyl group, a 4-sulfobutyl group, a 10-phosphonodecyl group, a 2-hydroxyethoxymethyl group, a 2-imidazolylethoxymethyl group, a 4-(N,N-dimethylamino)butyl group, and a 5-norbornenemethyl group.

The alkenyl group included in the substituent group Z is not particularly limited, but is preferably an alkenyl group having 2 to 20 carbon atoms, more preferably an alkenyl group having 2 to 12 carbon atoms, and further preferably an alkenyl group having 2 to 8 carbon atoms.

Examples of the alkenyl group that may have a substituent and is included in the substituent group Z include a vinyl group, an allyl group, a 2-butenyl group, a 1-pentenyl group, a 4-pentenyl group, a 2-(2-thiazolyl)vinyl group, a 2-(5-thiazolyl)vinyl group, a styryl group, and a 2-(2-thienyl) vinyl group.

The alkynyl group included in the substituent group Z is not particularly limited, but is preferably an alkynyl group having 2 to 20 carbon atoms, more preferably an alkynyl group having 2 to 12 carbon atoms, and further preferably an alkynyl group having 2 to 8 carbon atoms.

Examples of the alkynyl group that may have a substituent and is included in the substituent group Z include an ethynyl group, a propargyl group, a 1-pentynyl group, a trimethylsilylethynyl group, a triethylsilylethynyl group, a tri-i-propylsilylethynyl group, a p-propylphenylethynyl group, a 2-thienylethynyl group, a 2-thiazolylethynyl group, a 5-thiazolylethynyl group, and a phenylethynyl group.

The aryl group included in the substituent group Z is not particularly limited, but is preferably an aryl group having 6 to 20 carbon atoms and more preferably an aryl group having 6 to 12 carbon atoms.

Examples of the aryl group that may have a substituent and is included in the substituent group Z include a phenyl group, a naphthyl group, a 2,4,6-trimethylphenyl group, a p-(t-butyl) phenyl group, a 4-methyl-2,6-dipropylphenyl group, a 4-fluorophenyl group, a 4-trifluoromethylphenyl group, a p-pentylphenyl group, a 3,4-dipentylphenyl group, a p-heptoxyphenyl group, and a 3,4-diheptoxyphenyl group.

The heterocyclic group included in the substituent group Z is, for example, a heterocyclic group in which the number of atoms constituting a ring is three or more, and the atoms constituting the ring are constituted by at least one heteroatom and 1 to 30 carbon atoms. The heterocyclic group includes an aromatic heterocyclic group (heteroaryl group) and an aliphatic heterocyclic group.

Examples of the heteroatom constituting the ring include a nitrogen atom, an oxygen atom, and a sulfur atom. The number of the heteroatoms is not particularly limited, but is, for example, 1 or 2. The number of carbon atoms constituting the ring is preferably 3 to 20 and more preferably 5 to 12.

The heterocyclic group is preferably a five-membered ring or a six-membered ring, or a fused ring of the foregoing.

Examples of the heterocyclic group included in the substituent group Z include a thienyl group, a thiazolyl group, an imidazolyl group, a pyridyl group, a pyrimidinyl group, a quinolyl group, a furanyl group, a selenophenyl group, a piperidyl group, a morpholino group, a benzoxazolyl group, a benzimidazolyl group, a benzothiazolyl group, a 2-hexylfuranyl group, and a pyranyl group.

The silyl group that may have a substituent and is included in the substituent group Z is not particularly limited, but is preferably a silyl group having a group selected from the group consisting of an alkyl group and an aryl group as a substituent and having 3 to 40 (more preferably 3 to 30, and further preferably 3 to 24) carbon atoms.

Examples of the silyl group that may have a substituent and is included in the substituent group Z include a trimethylsilyl group, a triethylsilyl group, a triphenylsilyl group, a triisopropylsilyl group, and a dimethylphenylsilyl group.

The alkoxy group included in the substituent group Z is not particularly limited, but is preferably an alkoxy group having 1 to 20 carbon atoms, more preferably an alkoxy group having 1 to 12 carbon atoms, and further preferably an alkoxy group having 1 to 8 carbon atoms.

Examples of the alkoxy group included in the substituent group Z include a methoxy group, an ethoxy group, and a butoxy group.

The amino group that may have a substituent and is included in the substituent group Z is not particularly limited, but is preferably an amino group or an amino group having a group selected from the group consisting of an alkyl group and an aryl group as a substituent and having 1 to 20 (more preferably 1 to 10, and further preferably 1 to 6) carbon atoms.

Examples of the amino group that may have a substituent and is included in the substituent group Z include an amino group, a methylamino group, a dimethylamino group, a diethylamino group, a dibenzylamino group, and an anilino group.

The aryloxy group included in the substituent group Z is not particularly limited, but is preferably an aryloxy group having 6 to 20 carbon atoms, more preferably an aryloxy group having 6 to 16 carbon atoms, and further preferably an aryloxy group having 6 to 12 carbon atoms.

Examples of the aryloxy group included in the substituent group Z include a phenyloxy group and 2-naphthyloxy.

The acyl group included in the substituent group Z is not particularly limited, but is preferably an acyl group having 1 to 20 carbon atoms, more preferably an acyl group having 1 to 16 carbon atoms, and further preferably an acyl group having 1 to 12 carbon atoms.

Examples of the acyl group that may have a substituent and is included in the substituent group Z include an acetyl group, a hexanoyl group, a benzoyl group, a formyl group, and a pivaloyl group.

The alkoxycarbonyl group included in the substituent group Z is not particularly limited, but is preferably an alkoxycarbonyl group having 2 to 20 carbon atoms, more preferably an alkoxycarbonyl group having 2 to 16 carbon atoms, further preferably an alkoxycarbonyl group having 2 to 12 carbon atoms, and particularly preferably a methoxycarbonyl group or an ethoxycarbonyl group.

The aryloxycarbonyl group included in the substituent group Z is not particularly limited, but is preferably an aryloxycarbonyl group having 7 to 20 carbon atoms, more preferably an aryloxycarbonyl group having 7 to 16 carbon atoms, further preferably an aryloxycarbonyl group having 7 to 10 carbon atoms, and particularly preferably a phenyloxycarbonyl group.

The acyloxy group included in the substituent group Z is not particularly limited, but is preferably an acyloxy group having 2 to 20 carbon atoms, more preferably an acyloxy group having 2 to 16 carbon atoms, and further preferably an acyloxy group having 2 to 10 carbon atoms.

Examples of the acyloxy group that may have a substituent and is included in the substituent group Z include an acetoxy group, a benzoyloxy group, and a (meth)acryloyloxy group.

The acylamino group included in the substituent group Z is not particularly limited, but is preferably an acylamino group having 2 to 20 carbon atoms, more preferably an acylamino group having 2 to 16 carbon atoms, and further preferably an acylamino group having 2 to 10 carbon atoms.

Examples of the acylamino group included in the substituent group Z include an acetylamino group and a benzoylamino group.

The aminocarbonylamino group included in the substituent group Z is not particularly limited, but is preferably an aminocarbonylamino group having 2 to 20 carbon atoms, more preferably an aminocarbonylamino group having 2 to 16 carbon atoms, further preferably an aminocarbonylamino group having 2 to 12 carbon atoms, and particularly preferably a ureido group.

The alkoxycarbonylamino group included in the substituent group Z is not particularly limited, but is preferably an alkoxycarbonylamino group having 2 to 20 carbon atoms, more preferably an alkoxycarbonylamino group having 2 to 16 carbon atoms, further preferably an alkoxycarbonylamino group having 2 to 12 carbon atoms, and particularly preferably a methoxycarbonylamino group, a tert-butoxycarbonylamino group, an allyloxycarbonylamino group, a 2,2,2-trichloroethoxycarbonylamino group, a 9-fluorenylmethyloxycarbonylamino group, a 2-trimethylsilylethyloxycarbonylamino group, or a benzyloxycarbonylamino group.

The aryloxycarbonylamino group included in the substituent group Z is not particularly limited, but is preferably an aryloxycarbonylamino group having 7 to 20 carbon atoms, more preferably an aryloxycarbonylamino group having 7 to 16 carbon atoms, further preferably an aryloxycarbonylamino group having 7 to 12 carbon atoms, and particularly preferably a phenyloxycarbonylamino group.

The alkylthio group included in the substituent group Z is not particularly limited, but is preferably an alkylthio group having 1 to 20 carbon atoms, more preferably an alkylthio group having 1 to 16 carbon atoms, and further preferably an alkylthio group having 1 to 12 carbon atoms. Examples of the alkylthio group included in the substituent group Z include a methylthio group, an ethylthio group, and an octylthio group.

The arylthio group included in the substituent group Z is not particularly limited, but is preferably an arylthio group having 6 to 20 carbon atoms, more preferably an arylthio group having 6 to 16 carbon atoms, further preferably an arylthio group having 6 to 12 carbon atoms, and particularly preferably a phenylthio group.

The above-mentioned group selected from the substituent group Z may further have a substituent. Such a substituent is a group selected from the substituent group Z.

In the group further having a substituent (also referred to as a group formed in combination), the number of substituents that may be further included is not particularly limited, but is preferably 1 to 6 and more preferably 1 to 3, for example.

The group formed in combination is not particularly limited, and is, for example, a group obtained by substituting a group preferable as the group selected from the above-described substituent group Z with another group selected from the substituent group Z. Specific examples thereof include an alkyl group, an alkenyl group, or an alkynyl group having, as a substituent, a group selected from the group consisting of a halogen atom, an alkyl group, an aryl group, a heterocyclic group (heteroaryl group), an alkoxy group (including a hydroxyalkoxy group, a halogenated alkoxy group, and a heteroarylalkoxy group), an amino group, an acyloxy group, a hydroxy group, a sulfato group, a silyl group, and a phosphono group, and an alkynyl group having a halogenated aryl group or a (fluorinated) alkylaryl group as a substituent. A group obtained by removing one hydrogen atom from the compound represented by the formula (1) can also be employed.

Preferred examples of the group formed in combination include an alkyl group having a halogen atom as a substituent (halogenated alkyl group), an alkyl group having an aryl group as a substituent, an alkyl group having a heterocyclic group as a substituent, an alkenyl group having an aryl group as a substituent, an alkenyl group having a heterocyclic group as a substituent, an alkynyl group having an aryl group as a substituent, an alkynyl group having a heterocyclic group as a substituent, an alkyl group having an alkoxy group as a substituent, and an alkynyl group having a silyl group as a substituent.

The substituent represented by $R^{15}$ may form a ring. The form in which this substituent forms a ring include a form in which substituents are bonded to each other to form a ring and a form in which a plurality of substituents share one atom to form a ring.

The form in which substituents are bonded to each other to form a ring is, for example, a form in which two vinyl groups are bonded to each other to form a benzene ring together with a carbon atom to which $R^{15}$ bonds. The form in which a plurality of substituents share one atom to form a ring is, for example, a form in which two substituents are combined to give a sulfur atom (—S— group).

In particular, $R^{15}$ is preferably a hydrogen atom, a halogen atom, a cyano group, an alkyl group, an alkenyl group (e.g., an unsubstituted alkenyl group or an alkenyl group having a silyl group, an aryl group, or a heterocyclic group as a substituent), an alkynyl group (e.g., an unsubstituted alkynyl group or an alkynyl group having a silyl group, an aryl group, or a heterocyclic group as a substituent), an aryl group, a heterocyclic group, a nitro group, an alkoxy group, an alkoxycarbonyl group, or a carboxy group, and more preferably a hydrogen atom, a halogen atom, a cyano group, an alkenyl group (e.g., an unsubstituted alkenyl group or an alkenyl group having a silyl group, an aryl group, or a heterocyclic group as a substituent), an alkynyl group (e.g., an unsubstituted alkynyl group or an alkynyl group having a silyl group, an aryl group, or a heterocyclic group as a substituent), an aryl group, or a heterocyclic group.

$R^{11}$ to $R^{14}$ each independently represent an aliphatic hydrocarbon group, an aryl group, or a heteroaryl group. Herein, one of $R^{11}$ and $R^{14}$ represents an aliphatic hydrocarbon group, and the other represents an aryl group or a heteroaryl group. One of $R^{12}$ and $R^{13}$ represents an aliphatic hydrocarbon group, and the other represents an aryl group or a heteroaryl group. Preferably, $R^{12}$ and $R^{14}$ represent an aliphatic hydrocarbon group and $R^{11}$ and $R^{13}$ represent an aryl group or a heteroaryl group.

The aliphatic hydrocarbon group represented by $R^{11}$ to $R^{14}$ is not particularly limited, and may be any of linear, branched, and cyclic. The aliphatic hydrocarbon group may also be saturated or unsaturated. The aliphatic hydrocarbon group may include a heteroatom such as an oxygen atom, a sulfur atom, or a nitrogen atom, or may be halogenated.

In particular, the aliphatic hydrocarbon group represented by $R^{11}$ to $R^{14}$ is preferably a linear, branched, or cyclic alkyl group having 1 to 20 carbon atoms (preferably 1 to 10 carbon atoms), a linear, branched, or cyclic alkenyl group having 2 to 20 carbon atoms (preferably 2 to 10 carbon atoms), or a linear, branched, or cyclic alkynyl group having 2 to 20 carbon atoms (preferably 2 to 10 carbon atoms).

When the aliphatic hydrocarbon group represented by $R^{11}$ to $R^{14}$ has 2 or more carbon atoms, the solubility of the compound represented by the formula (1) is further improved, which provides synthetic advantages such as reducing the amount of reaction solvents and causing the reaction at low temperature. In some cases, the yield is improved. In particular, the aliphatic hydrocarbon group represented by $R^{11}$ to $R^{14}$ is more preferably a linear, branched, or cyclic alkyl group having 2 to 20 carbon atoms (preferably 2 to 10 carbon atoms).

The number of carbon atoms in the aryl group represented by $R^{11}$ to $R^{14}$ is not particularly limited, but is preferably 6 to 20 and more preferably 6 to 12. The aryl group may have a monocyclic structure or a fused ring structure (condensed ring structure) in which two or more rings are fused.

The aryl group is, for example, preferably a phenyl group, a naphthyl group, or an anthryl group, more preferably a phenyl group or a naphthyl group, and further preferably a phenyl group.

The number of carbon atoms in the heteroaryl group represented by $R^{11}$ to $R^{14}$ is not particularly limited, but is preferably 3 to 30 and more preferably 3 to 18.

The heteroaryl group has a heteroatom in addition to carbon atoms and hydrogen atoms. Examples of the heteroatom include a sulfur atom, an oxygen atom, a nitrogen atom, a selenium atom, a tellurium atom, a phosphorus atom, a silicon atom, and a boron atom. A sulfur atom, an oxygen atom, or a nitrogen atom is preferable.

The number of heteroatoms included in the heteroaryl group is not particularly limited, but is preferably 1 to 10, more preferably 1 to 4, and further preferably 1 or 2.

The number of ring members of the heteroaryl group is not particularly limited, but is preferably 3 to 8, more preferably 5 to 7, and further preferably 5 or 6. The heteroaryl group may have a monocyclic structure or a fused ring structure in which two or more rings are fused. In the case of a fused ring structure, an aromatic hydrocarbon ring having no heteroatom (e.g., benzene ring) may be included.

Preferred examples of the heteroaryl group include a furyl group, a thienyl group, a thiazolyl group, a pyridyl group, a quinolyl group, an isoquinolyl group, and a carbazolyl group.

The aliphatic hydrocarbon group, aryl group, and heteroaryl group represented by $R^{11}$ to $R^{14}$ may further have a substituent. The substituent is, for example, a group selected from the above-described substituent group Z. Specifically, preferred examples of the substituent include an alkyl group, an alkenyl group, an alkynyl group, an aryl group, a heteroaryl group, an alkoxy group, a thioalkyl group, an acyl group, —C(=O)NR$^{1X}$R$^{2X}$, —NR$^{3X}$C(=O)R$^{4X}$, —S(=O)$_2$NR$^{5X}$R$^{6X}$, —NR$^{7X}$S(=O)$_2$R$^{8X}$, a silyl group, a nitro group, a cyano group, or a halogen atom.

$R^{1X}$ to $R^{8X}$ represent a hydrogen atom, an aliphatic hydrocarbon group, an aryl group, or a heteroaryl group.

The aliphatic hydrocarbon group, aryl group, and heteroaryl group represented by $R^{1X}$ to $R^{8X}$ are the same as the aliphatic hydrocarbon group, aryl group, and heteroaryl group represented by $R^{11}$ to $R^{14}$, and preferred forms thereof are also the same.

In particular, the compound represented by the formula (1) is preferably a compound represented by formula (8) below, more preferably a compound represented by formula (10) below, and further preferably a compound represented by formula (10') below.

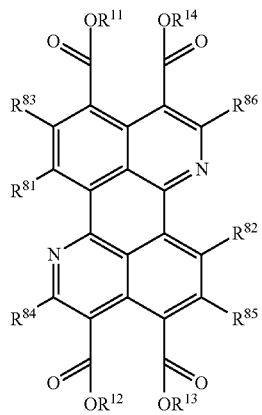

(8)

In the formula (8), $R^{11}$ to $R^{14}$ respectively have the same meaning as $R^{11}$ to $R^{14}$ in the formula (1), and preferred forms thereof are also the same. In the formula (8), preferably, $R^{12}$ and $R^{14}$ represent an aliphatic hydrocarbon group and $R^{11}$ and $R^{13}$ represent an aryl group or a heteroaryl group. $R^{81}$ to $R^{86}$ each independently represent a hydrogen atom or a substituent. The substituent represented by $R^{81}$ to $R^{86}$ is the same as the substituent represented by $R^{15}$, and preferred forms thereof are also the same.

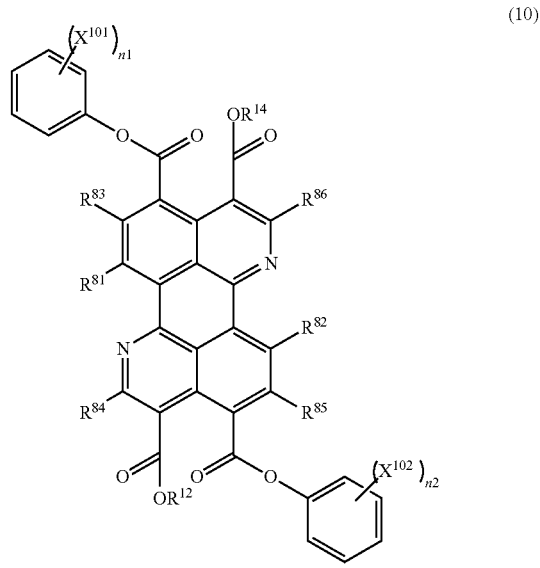

(10)

In the formula (10), $X^{101}$ and $X^{102}$ each independently represent an electron-withdrawing group.

The term "electron-withdrawing group" refers to a group having a positive Hammett substituent constant. For the electron-withdrawing group, specifically, refer to Chem. Rev. 1BBl. 97, 165-195.

Examples of the electron-withdrawing group represented by $X^{101}$ and $X^{102}$ include a halogen atom, an acyl group, an arylcarbonyl group, an alkoxycarbonyl group, an aryloxycarbonyl group, an acyloxy group, a halogenated alkyl group, a halogenated alkyloxy group, an aminocarbonyl group, an alkanesulfonyl group, an arylsulfonyl group, a cyano group, a nitro group, and a formyl group. In particular, the electron-withdrawing group is preferably a halogen atom, more preferably a fluorine atom or a chlorine atom, and further preferably a chlorine atom.

n1 and n2 each independently represent an integer of 1 to 5. From the viewpoint of further improving yield, n1 and n2 preferably represent 3 or less.

$R^{12}$ and $R^{14}$ each independently represent an aliphatic hydrocarbon group. The aliphatic hydrocarbon group represented by $R^{12}$ and $R^{14}$ is the same as the aliphatic hydrocarbon group represented by $R^{12}$ and $R^{14}$ in the formula (1), and preferred forms thereof are also the same. $R^{81}$ to $R^{86}$ respectively have the same meaning as $R^{81}$ to $R^{86}$ in the formula (8).

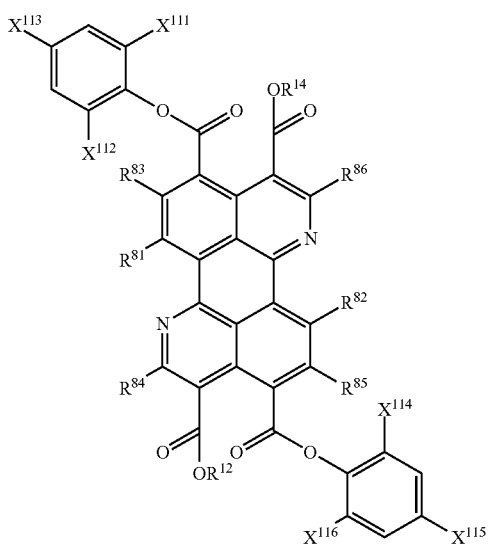

(10')

In the formula (10'), $X^{111}$ to $X^{116}$ each independently represent a halogen atom. The halogen atom represented by $X^{111}$ to $X^{116}$ is preferably a fluorine atom, a chlorine atom, a bromine atom, or an iodine atom and more preferably a chlorine atom. $R^{81}$ to $R^{86}$ respectively have the same meaning as $R^{81}$ to $R^{86}$ in the formula (8), and preferred forms thereof are also the same.

$R^{12}$ and $R^{14}$ each independently represent an aliphatic hydrocarbon group. The aliphatic hydrocarbon group represented by $R^{12}$ and $R^{14}$ has the same meaning as the aliphatic hydrocarbon group represented by $R^{12}$ and $R^{14}$ in the formula (1), and preferred forms thereof are also the same.

Hereafter, the compound represented by the formula (1) will be exemplified, but is not limited thereto.

(1)-1 to (1)-52 in Table below show combinations of $R^{11}$, $R^{12}$, $R^{13}$, and $R^{14}$ shown in each basic skeleton below. That is, when the following basic skeleton is described as an example, it is intended that the combination of $R^{11}$, $R^{12}$, $R^{13}$, and $R^{14}$ in the following basic skeleton may be any of (1)-1 to (1)-52 in Table below.

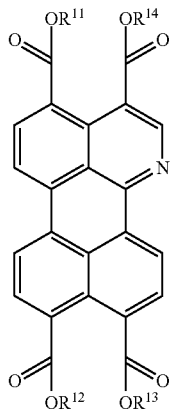

$R^{81}$ and $R^{82}$ in each basic skeleton shown below each independently represent a substituent selected from the group consisting of a hydrogen atom, a cyano group, a fluorine atom, a chlorine atom, a bromine atom, an iodine atom, a trifluoromethyl group, a trifluoromethoxy group, a trichloromethyl group, a trichloromethoxy group, a phenyl group, a 2-thiazolyl group, a 5-thiazolyl group, a 2-thienyl group, a 3-thienyl group, a styryl group, a 2-thiazolylvinyl group, a 5-thiazolylvinyl group, a 2-thienylvinyl group, a 3-thienylvinyl group, a phenylethynyl group, a 2-thiazolylethynyl group, a 5-thiazolylethynyl group, a 2-thienylethynyl group, a 3-thienylethynyl group, a trimethylsilylethynyl group, a triethylsilylethynyl group, a triisopropylethynyl group, and a 1-octynyl group. Herein, at least one of $R^{81}$ or $R^{82}$ represents a group other than hydrogen.

In Table below, "Me" represents a methyl group, and "Et" represents an ethyl group.

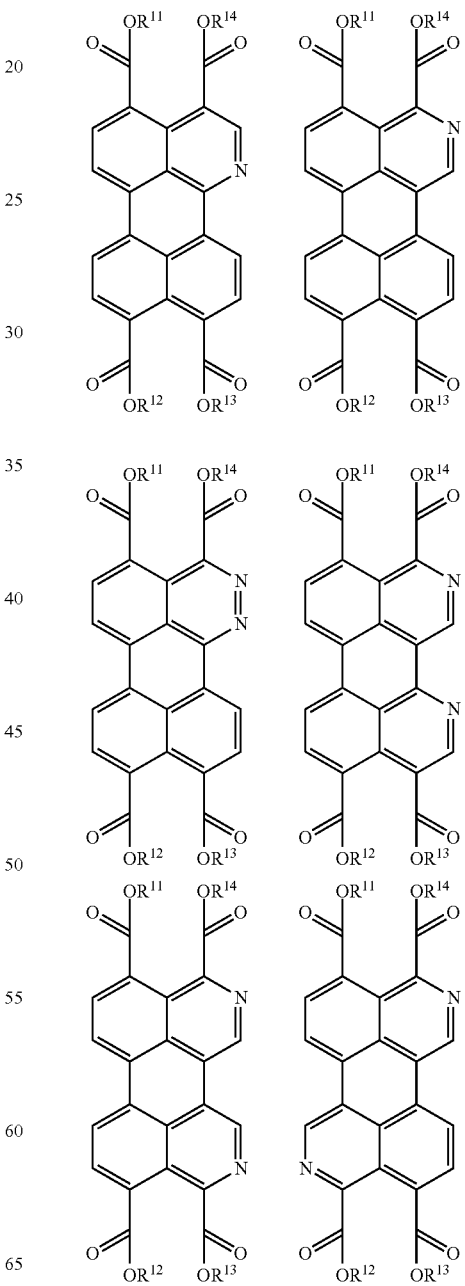

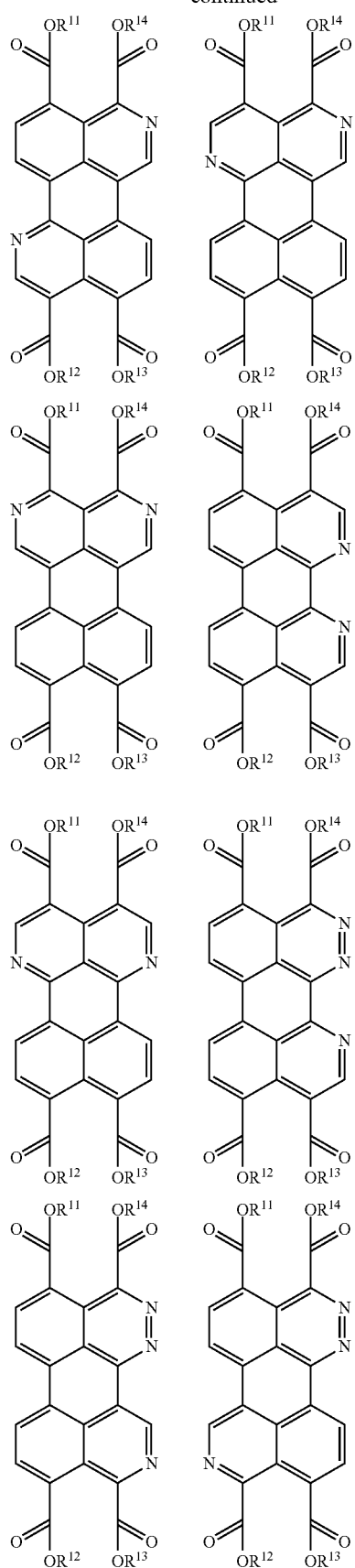
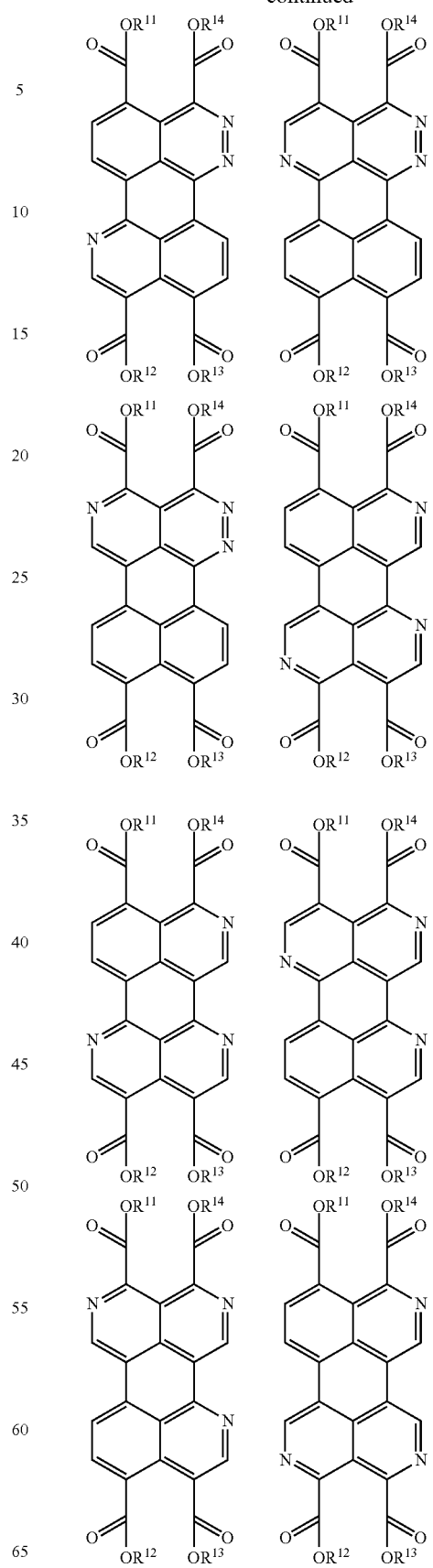

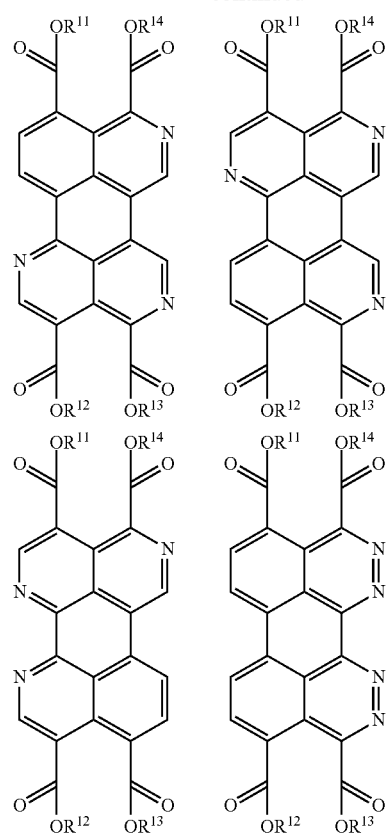
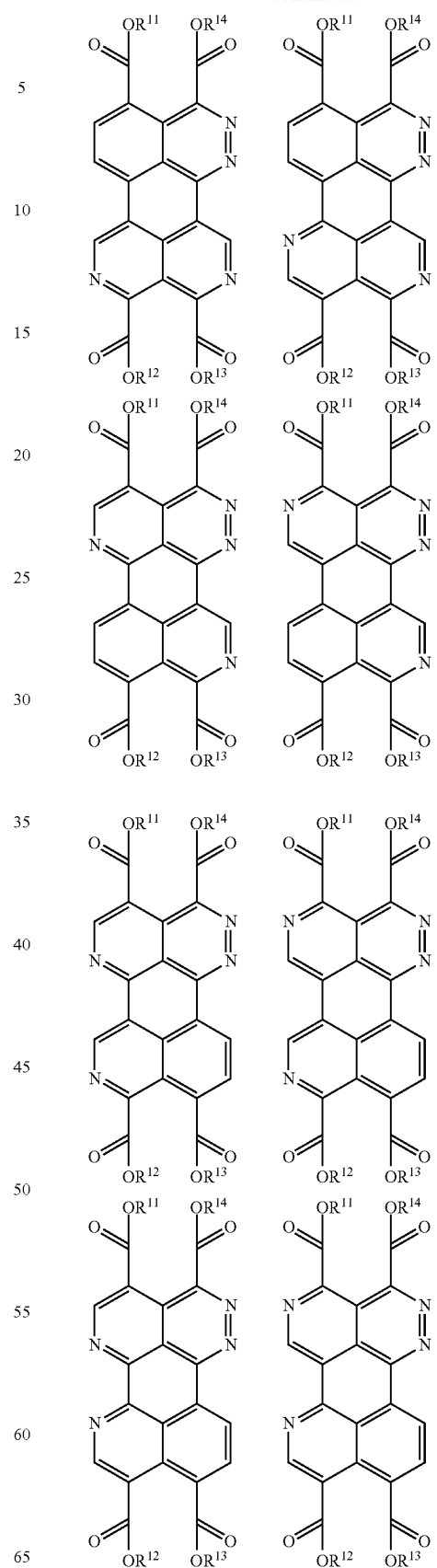

-continued
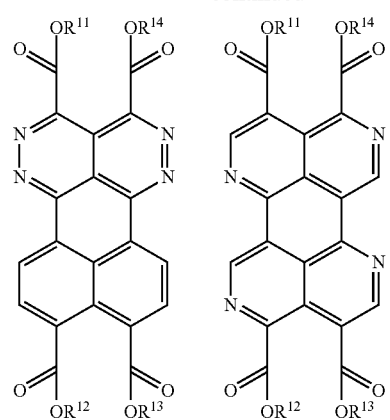
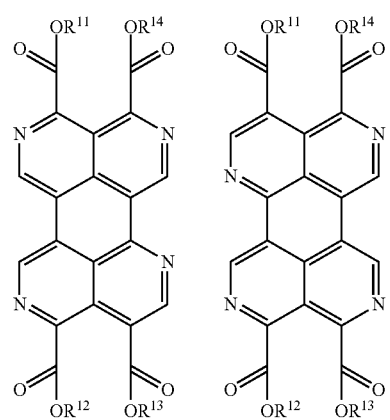
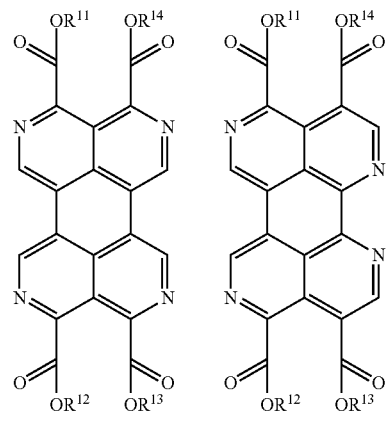
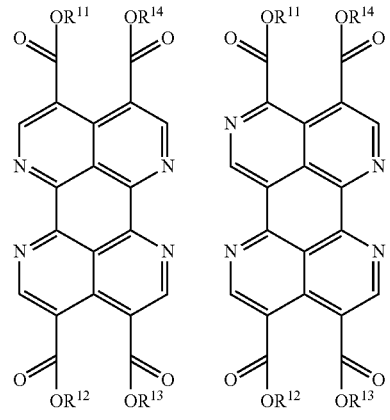
-continued
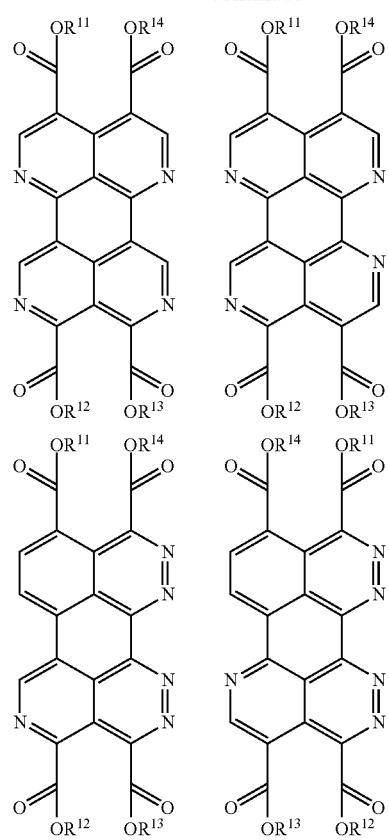
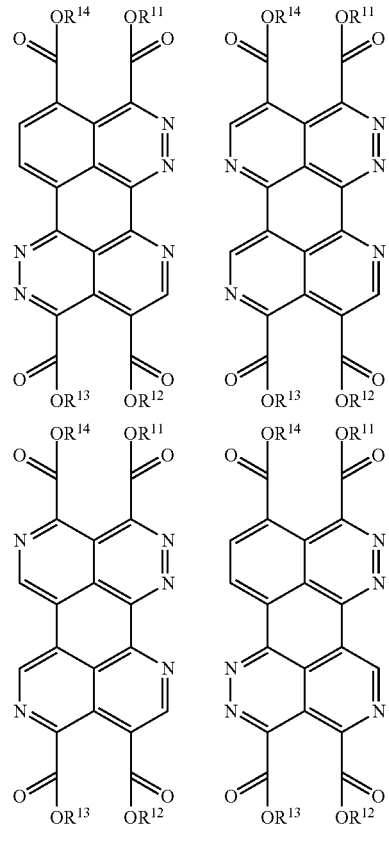

-continued

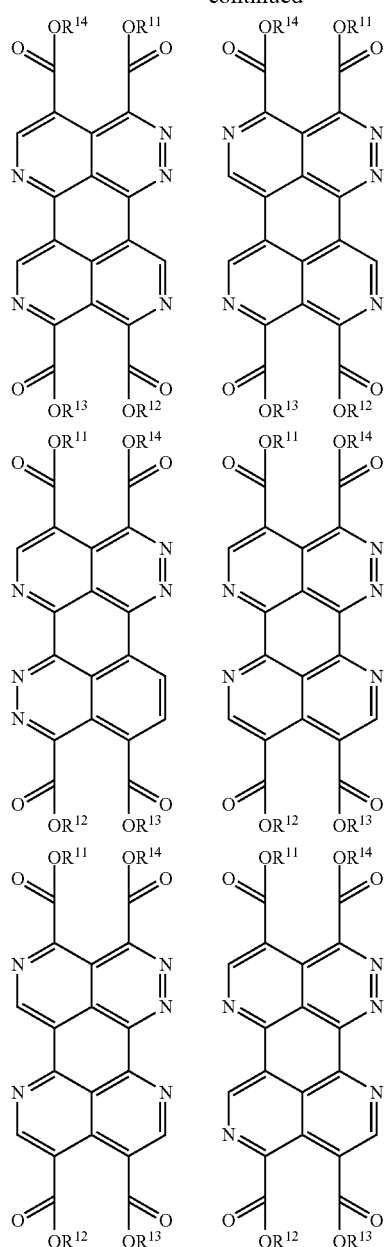

-continued

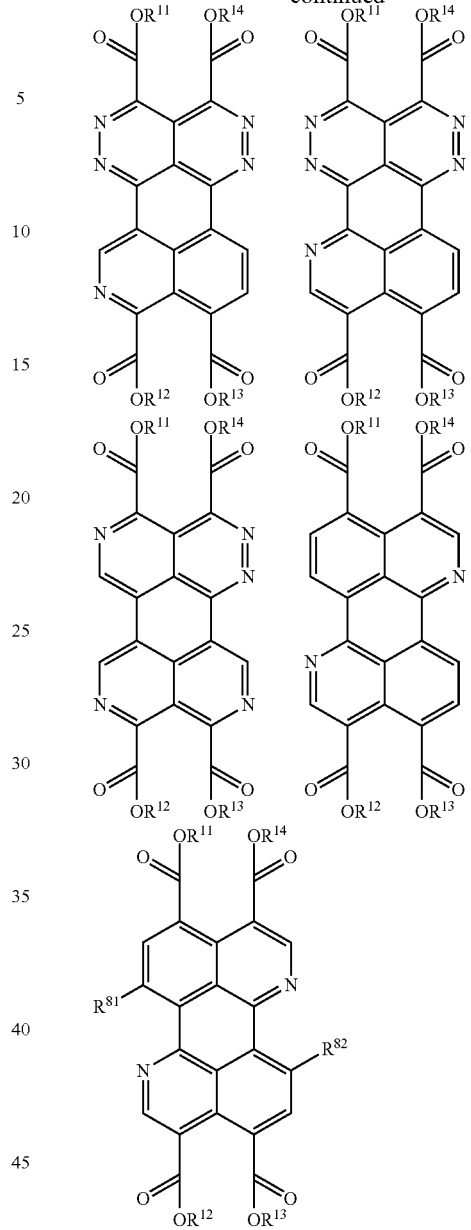

TABLE 1

| No. | $R^{11}$ | $R^{12}$ | $R^{13}$ | $R^{14}$ |
|---|---|---|---|---|
| (1)-1 | 2,4,6-trichlorophenyl | Me | 2,4,6-trichlorophenyl | Me |
| (1)-2 | phenyl | Me | phenyl | Me |
| (1)-3 | 4-nitrophenyl | Me | 4-nitrophenyl | Me |
| (1)-4 | 4-methoxyphenyl | Me | 4-methoxyphenyl | Me |
| (1)-5 | 4-methylphenyl | Me | 4-methylphenyl | Me |
| (1)-6 | 4-chlorophenyl | Me | 4-chlorophenyl | Me |
| (1)-7 | 3,4-dimethoxyphenyl | Me | 3,4-dimethoxyphenyl | Me |
| (1)-8 | 2-methoxyphenyl | Me | 2-methoxyphenyl | Me |
| (1)-9 | 4-tert-butylphenyl | Me | 4-tert-butylphenyl | Me |
| (1)-10 | 2,4,5-trichlorophenyl | Me | 2,4,5-trichlorophenyl | Me |
| (1)-11 | perfluorophenyl | Me | perfluorophenyl | Me |
| (1)-12 | 2-chlorophenyl | Me | 2-chlorophenyl | Me |
| (1)-13 | 3-nitrophenyl | Me | 3-nitrophenyl | Me |
| (1)-14 | 3-chlorophenyl | Me | 3-chlorophenyl | Me |
| (1)-15 | 2,5-dimethylphenyl | Me | 2,5-dimethylphenyl | Me |
| (1)-16 | 2-acetylphenyl | Me | 2-acetylphenyl | Me |

TABLE 1-continued

| No. | $R^{11}$ | $R^{12}$ | $R^{13}$ | $R^{14}$ |
|---|---|---|---|---|
| (1)-17 | 3,4-dimethylphenyl | Me | 3,4-dimethylphenyl | Me |
| (1)-18 | 2,4,6-trichlorophenyl | Et | 2,4,6-trichlorophenyl | Et |
| (1)-19 | 2,4,6-trichlorophenyl | propyl | 2,4,6-trichlorophenyl | propyl |
| (1)-20 | 2,4,6-trichlorophenyl | isopropyl | 2,4,6-trichlorophenyl | Isopropyl |
| (1)-21 | 2,4,6-trichlorophenyl | butyl | 2,4,6-trichlorophenyl | butyl |
| (1)-22 | 2,4,6-trichlorophenyl | tert-butyl | 2,4,6-trichlorophenyl | tert-butyl |
| (1)-23 | 2,4,6-trichlorophenyl | benzyl | 2,4,6-trichlorophenyl | benzyl |
| (1)-24 | 2,4,6-trichlorophenyl | octyl | 2,4,6-trichlorophenyl | octyl |
| (1)-25 | 2,4,6-trichlorophenyl | allyl | 2,4,6-trichlorophenyl | allyl |
| (1)-26 | 2,4,6-trichlorophenyl | methoxyethyl | 2,4,6-trichlorophenyl | methoxyethyl |
| (1)-27 | 2,4,6-trichlorophenyl | ethoxyethyl | 2,4,6-trichlorophenyl | Ethoxyethyl |
| (1)-28 | 2,4,6-trichlorophenyl | 2-ethylhexyl | 2,4,6-trichlorophenyl | 2-ethylhexyl |
| (1)-29 | 2,4,6-trichlorophenyl | isobutyl | 2,4,6-trichlorophenyl | isobutyl |
| (1)-30 | 2,4,6-trichlorophenyl | hexyl | 2,4,6-trichlorophenyl | hexyl |
| (1)-31 | 2,4,6-trichlorophenyl | cyclohexyl | 2,4,6-trichlorophenyl | Cyclohexyl |
| (1)-32 | 2,4,6-trichlorophenyl | 2-phenylethyl | 2,4,6-trichlorophenyl | 2-phenylethyl |
| (1)-33 | 2,4,6-trichlorophenyl | dodecyl | 2,4,6-trichlorophenyl | dodecyl |
| (1)-34 | 2,4,6-trichlorophenyl | 2,2,2-trifluoromethyl | 2,4,6-trichlorophenyl | 2,2,2-trifluoromethyl |
| (1)-35 | 2,4,6-trichlorophenyl | 2-(trimethylsilyl)ethyl | 2,4,6-trichlorophenyl | 2-(trimethylsilyl)ethyl |
| (1)-36 | 2,4,6-trichlorophenyl | pentyl | 2,4,6-trichlorophenyl | pentyl |
| (1)-37 | 2,4,6-trichlorophenyl | 2-bromoethyl | 2,4,6-trichlorophenyl | 2-bromoethyl |
| (1)-38 | 2,4,6-trichlorophenyl | isopentyl | 2,4,6-trichlorophenyl | Isopentyl |
| (1)-39 | 2,4,6-trichlorophenyl | 2-chloroethyl | 2,4,6-trichlorophenyl | 2-chloroethyl |
| (1)-40 | 2,4,6-trichlorophenyl | Me | 2,4,6-trichlorophenyl | Me |
| (1)-41 | 2,4,6-trichlorophenyl | 2,4,6-trichlorophenyl | Me | Me |
| (1)-42 | Me | Me | 2,4,6-trichlorophenyl | 2,4,6-trichlorophenyl |
| (1)-43 | 2,4,6-trichlorophenyl | Me | 2,4,6-trichlorophenyl | Me |
| (1)-44 | Me | 2,4,6-trichlorophenyl | Me | 2,4,6-trichlorophenyl |
| (1)-45 | 2,4,6-trichlorophenyl | 2,4,6-trichlorophenyl | Me | Me |
| (1)-46 | 2,4-dichlorophenyl | Me | 2,4-dichlorophenyl | Me |
| (1)-47 | Me | Me | 2,4-diichlorophenyl | 2,4-diichlorophenyl |
| (1)-48 | 2,6-dichlorophenyl | Me | 2,6-dichlorophenyl | Me |
| (1)-49 | 2,4,6-trichlorophenyl | cyclohexylethy | 2,4,6-trichlorophenyl | cyclohexylethy |
| (1)-50 | 2,4-dichlorophenyl | 2,4-dichlorophenyl | Me | Me |
| (1)-51 | 2,4-dichlorophenyl | Et | 2,4-dichlorophenyl | Et |
| (1)-52 | 2,4-dichlorophenyl | propyl | 2,4-dichlorophenyl | propyl |

Compound Represented by Formula (2)

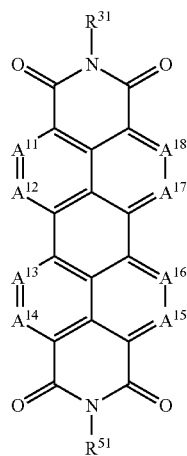

(2)

In the formula (2), $A^{11}$ to $A^{18}$ respectively have the same meaning as $A^{11}$ to $A^{18}$ in the formula (1), and preferred forms thereof are also the same.

$R^{31}$ and $R^{51}$ each independently represent a substituent.

The substituent represented by $R^{31}$ and $R^{51}$ is not particularly limited, but is preferably a group selected from the above-described substituent group Z. Specifically, the substituent is preferably an alkyl group (preferably having 1 to 30 carbon atoms and more preferably having 4 to 20 carbon atoms, and may be linear, chain-like, or cyclic), an alkenyl group, an alkynyl group, an aryl group (preferably having 6 to 20 carbon atoms), or a heterocyclic group (including at least one of the above-mentioned heteroatoms as a ring-constituting atom, preferably having a 5-membered ring, a 6-membered ring, or a fused ring thereof, the number of ring-constituting carbon atoms is preferably 3 to 20), more preferably an alkyl group, an alkenyl group, an alkynyl group, an aryl group, or a heteroaryl group, further preferably an alkyl group, an aryl group, or a heteroaryl group, and particularly preferably an alkyl group.

The above-mentioned alkyl group, alkenyl group, alkynyl group, aryl group, heterocyclic group, and heteroaryl group may further have a substituent. In the case of further having a substituent, the substituent is a group selected from the substituent group Z.

In particular, the substituent represented by $R^{31}$ and $R^{51}$ is preferably an unsubstituted alkyl group, a halogenated alkyl group, an alkyl group having an aryl group as a substituent, an alkyl group having a heterocyclic ring (preferably a heteroaryl group) as a substituent, an unsubstituted aryl group, an aryl group into which an alkyl group is introduced, an unsubstituted heterocyclic group, a heterocyclic group into which an alkyl group is introduced, an alkyl group into which a silyl group is introduced, or an alkyl group into which one or more alkoxy groups are introduced. For the alkyl group having an aryl group as a substituent and the alkyl group having a heterocyclic ring as a substituent, the aryl group and the heterocyclic ring may further have a substituent. In the case of further having a substituent, the substituent is a group selected from the substituent group Z, and preferably a halogen atom.

The compound represented by the formula (2) is particularly preferably a compound represented by formula (9) below.

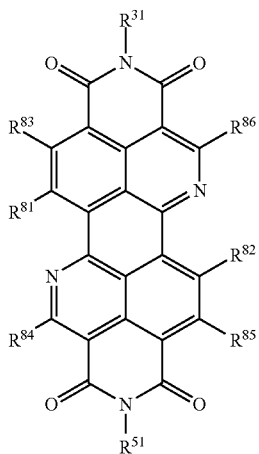

(9)

In the formula (9), $R^{31}$ and $R^{51}$ respectively have the same meaning as $R^{31}$ and $R^{51}$ in the formula (2), and preferred forms thereof are also the same. $R^{81}$ to $R^{86}$ respectively have the same meaning as $R^{81}$ to $R^{86}$ in the formula (8), and preferred forms thereof are also the same.

Hereafter, examples of the compound represented by the formula (2) are shown, but the compound represented by the formula (2) is not limited thereto.

| No. | R15A | R15B | R15C | R15D | R15E | R15G | R15H | R31 | R51 |
|---|---|---|---|---|---|---|---|---|---|
| 1 | H | H | H | H | H | H | H | $CH_3$ | $CH_3$ |
| 2 | H | H | H | H | H | H | H | $nC_6H_{13}$ | $nC_6H_{13}$ |
| 3 | H | H | H | H | H | H | H | cyclohexyl | cyclohexyl |
| 4 | H | H | H | H | H | H | H | $CH_2C_3F_7$ | $CH_2C_3F_7$ |
| 5 | H | H | H | H | H | H | H | -isoPropyl | -isoPropyl |
| 6 | H | H | H | H | H | H | H | -tert-Butyl | -tert-Butyl |
| 7 | H | H | H | H | H | H | H | $C_8H_{17}$/$C_{10}H_{21}$ branched | $C_8H_{17}$/$C_{10}H_{21}$ branched |
| 8 | H | H | H | H | Cl | Cl | Cl | $C_2H_4C_5F_{11}$ | $C_2H_4C_5F_{11}$ |
| 9 | Cl | Cl | Cl | Cl | Cl | Cl | Cl | cyclohexyl | cyclohexyl |
| 10 | F | H | H | H | F | F | H | phenyl | phenyl |

-continued
| | | | | | | | |
|---|---|---|---|---|---|---|---|
| 11 | F | F | F | F | F | F | F | 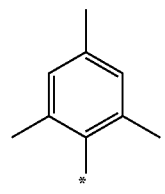 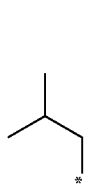 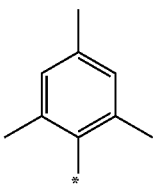  |
| 12 | CN | H | H | H | H | H | F |
| 13 | Br | H | H | H | H | H | H |
| 14 | NO₂ | H | H | H | H | H | H |
| 15 | CH₃ | nC₆H₁₃ | H | H | H | H | H |
| 16 | CH₃ | nC₆H₁₃ | H | H | H | H | H |
| 17 | CO₂CH₃ | H | H | H | H | H | H |

| No. | R¹⁵ᴬ | R¹⁵ᴮ | R¹⁵ᶜ | R¹⁵ᴰ | R¹⁵ᶠ | R¹⁵ᴳ | R¹⁵ᴴ | R³¹ | R⁵¹ |
|---|---|---|---|---|---|---|---|---|---|
| 18 | H | -Ph | H | H | H | -Ph | H | cyclopentyl | cyclopentyl |
| 19 | —COOH | H | H | H | H | H | H | CF₃ | C₂F₅ |
| 20 | H | CF₃ | H | H | H | H | H | 2,6-diisopropyl-4-methylphenyl | 4-tert-butylphenyl |
| 21 | OCH₃ | H | H | H | H | H | H | —(CH₂)₄—O—C₂H₅ | —(CH₂)₄—NH₂ |

| No. | R¹⁵ᴬ | R¹⁵ᴮ | R¹⁵ᶜ | R¹⁵ᴰ | R¹⁵ᶠ | R¹⁵ᴳ | R¹⁵ᴴ | R³¹ | R⁵¹ |
|---|---|---|---|---|---|---|---|---|---|
| 22 | H | H | H | H | H | H | H | CH₃ | CH₃ |
| 23 | H | H | H | H | H | H | H | —(CH₂)₃—CH=CH₂ | nC₆H₁₃ |

-continued

| No. | R15A | R15B | R15D | R15E | R15F | R15H | R31 | R51 |
|---|---|---|---|---|---|---|---|---|
| 24 | H | thiophen-2-yl* | H | H | H | H | cyclohexyl* | H |
| 25 | H | H | H | H | H | H | cyclohexyl* | CH$_2$C$_3$F$_7$ |
| 26 | H | H | isothiazol-3-yl* | H | furan-3-yl* | H | —(CH$_2$)$_3$—O—C(=O)—C(CH$_3$)=CH$_2$ | -isoPropyl |
| 27 | H | H | H | H | H | H | —(CH$_2$)$_4$—OH | —(CH$_2$)$_4$—SO$_3$H |

Formula (with structure):

Structure depicting a perylene-type polycyclic bisimide with substituents R$^{15A}$, R$^{15B}$, R$^{15D}$, R$^{15E}$, R$^{15F}$, R$^{15H}$ on the aromatic core, and imide nitrogens bearing R$^{31}$ and R$^{51}$.

| No. | R15A | R15B | R15D | R15E | R15F | R15H | R31 | R51 |
|---|---|---|---|---|---|---|---|---|
| 28 | H | H | H | H | H | H | CH$_3$ | CH$_3$ |
| 29 | H | H | H | H | H | H | nC$_6$H$_{13}$ | nC$_6$H$_{13}$ |
| 30 | H | H | H | H | H | H | cyclohexyl-CH$_2$* | cyclohexyl-CH$_2$* |
| 31 | H | H | H | H | H | H | CH$_2$C$_3$F$_7$ | CH$_2$C$_3$F$_7$ |

| No. | R1 | R2 | R3 | R4 | R5 | R6 | Structure A | Structure B |
|---|---|---|---|---|---|---|---|---|
| 32 | H | H | H | H | H | H | -isoPropyl | -isoPropyl |
| 33 | H | H | H | H | H | H | -tert-Butyl | -tert-Butyl |
| 34 | H | H | H | H | H | H | $C_8H_{17}$–CH($C_8H_{17}$)–CH$_2$–* | $C_8H_{17}$–CH($C_{10}H_{21}$)–CH$_2$–* |
| 35 | H | H | H | H | H | H | $C_2H_4C_5F_{11}$–* | $C_2H_4C_5F_{11}$–* |
| 36 | Cl | Cl | Cl | Cl | Cl | Cl | cyclohexyl–* | cyclohexyl–* |
| 37 | F | H | H | F | H | H | phenyl–* | phenyl–* |
| 38 | F | F | F | F | F | F | mesityl–* | mesityl–* |
| 39 | H | CN | H | CN | CN | H | neopentyl–CH$_2$–* | isobutyl–* |
| 40 | H | H | H | H | H | Br | n-C$_6$H$_{13}$–CH(n-C$_8$H$_{17}$)–(CH$_2$)$_7$–* | mesityl–* |
| 41 | H | H | H | H | H | NO$_2$ | cyclobutyl–* | cyclopropyl–* |
| 42 | H | H | H | nC$_6$H$_{13}$ | nC$_6$H$_{13}$ | CH$_3$ | benzyl–* | 4-Cl-benzyl–* |

-continued

| | | | | | | | |
|---|---|---|---|---|---|---|---|
| 43 | H | H | H | H | CO$_2$CH$_3$ | *-adamantyl | *-adamantyl |
| 44 | Ph | H | H | Ph | H | *-cyclopentyl | *-cyclopentyl |
| 45 | H | H | H | CF$_3$ | COOH | CF$_3$ | C$_2$F$_5$ |
| 46 | H | H | H | H | H | *-(2,6-diisopropyl-4-methylphenyl) | *-(4-tert-butylphenyl) |
| 47 | H | H | H | H | OCH$_3$ | *-(CH$_2$)$_n$-O-ethyl | *-(CH$_2$)$_n$-NH$_2$ |

-continued

| No. | R15B | R15C | R15D | R15F | R15G | R15H | R31 | R51 |
|---|---|---|---|---|---|---|---|---|
| 48 | H | H | H | H | H | H | CH$_3$ | CH$_3$ |
| 49 | H | H | H | H | H | H | nC$_6$H$_{13}$ | nC$_6$H$_{13}$ |
| 50 | H | H | H | H | H | H | cyclohexyl-* | cyclohexyl-* |
| 51 | H | H | H | H | H | H | CH$_2$C$_3$F$_7$ | CH$_2$C$_3$F$_7$ |
| 52 | H | H | H | H | H | H | -isoPropyl | -isoPropyl |
| 53 | H | H | H | H | H | H | -tert-Butyl | -tert-Butyl |
| 54 | H | H | H | H | H | H | C$_8$H$_{17}$/C$_8$H$_{17}$-* | C$_8$H$_{17}$/C$_{10}$H$_{21}$-* |
| 55 | H | H | H | H | H | H | C$_2$H$_4$C$_5$F$_{11}$ | C$_2$H$_4$C$_5$F$_{11}$ |
| 56 | Cl | Cl | Cl | Cl | Cl | Cl | cyclohexyl-* | cyclohexyl-* |
| 57 | F |  |  | H | F | H | phenyl-* | phenyl-* |

-continued

| | | | | | | |
|---|---|---|---|---|---|---|
| 58 | F | F | F | F | F | (trimethylphenyl) / (mesityl) |
| 59 | CN | H | H | CN | H | (isobutyl) / (neopentyl) |
| 60 | Br | H | H | H | H | (mesityl) / (long alkyl chain with nC₆H₁₃ and nC₈H₁₇ branches) |
| 61 | NO₂ | H | H | H | H | (cyclopropyl) / (cyclobutyl) |
| 62 | CH₃ | nC₆H₁₃ | H | H | H | (4-chlorobenzyl) / (benzyl) |
| 63 | CO₂CH₃ | H | H | H | H | (adamantyl) / (adamantyl) |
| 64 | H | Ph | H | Ph | Ph | (cyclopentyl) / (cyclopentyl) |
| 65 | COOH | H | H | H | H | C₂F₅ / CF₃ |

-continued
| | $R^{15A}$ | $R^{15C}$ | $R^{15D}$ | $R^{15F}$ | $R^{15G}$ | $R^{15H}$ | |
|---|---|---|---|---|---|---|---|
| 66 | H | CF$_3$ | H | H | H |  |  |
| 67 | OCH$_3$ | H | H | H | H |  |  |
| No. | $R^{15A}$ | $R^{15C}$ | $R^{15D}$ | $R^{15F}$ | $R^{15G}$ | $R^{15H}$ | $R^{31}$ | $R^{51}$ |
|---|---|---|---|---|---|---|---|---|
| 68 | H | H | H | H | H | H | CH$_3$ | CH$_3$ |
| 69 | H | H | H | H | H | H | nC$_6$H$_{13}$ | |
| 70 | H | H | H | H | H | H |  | |

-continued
| | | | | | | | |
|---|---|---|---|---|---|---|---|
| 71 | thiophen-2-yl* | H | H | H | H | thiophen-2-yl* | CH₂C₃F₇ |
| 72 | H | isothiazol-3-yl* | H | H | furan-3-yl* | methacrylate-O-butyl* | -isoPropyl |
| 73 | H | H | H | H | H | 5-hydroxypentyl* | -isoPropyl, 5-sulfopentyl* |
| No. | R¹⁵ᴬ | R¹⁵ᴮ | R¹⁵ᴰ | R¹⁵ᶠ | R¹⁵ᴳ | R¹⁵ᴴ | R³¹ | R⁵¹ |
|---|---|---|---|---|---|---|---|---|
| 74 | H | H | H | H | H | H | CH₃ | CH₃ |
| 75 | H | H | H | H | H | H | 5-cyclohexylpentyl* | nC₆H₁₃ |
| 76 | H | H | H | H | H | H | cyclohexyl* | cyclohexyl* |

-continued

| No. | | | | | | | | |
|---|---|---|---|---|---|---|---|---|
| 77 | *-（2-thienyl） | H | H | H | H | *-（2-thienyl） | *-CH₂CH₂CH₂CH₂-OC(=O)C(CH₃)=CH₂ | CH₂C₃F₇ |
| 78 | H | *-(isothiazol-3-yl) | H | H | H | *-(furan-3-yl) | -isoPropyl | -isoPropyl |
| 79 | H | H | H | H | H | H | *-(CH₂)ₙ-OH | *-(CH₂)ₙ-SO₃H |

| No. | R¹⁵ᴬ | R¹⁵ᴮ | R¹⁵ᴱ | R¹⁵ᶠ | R¹⁵ᴳ | R¹⁵ᴴ | R³¹ | R⁵¹ |
|---|---|---|---|---|---|---|---|---|
| 80 | H | H | H | H | H | H | CH₃ | CH₃ |
| 81 | Cl | H | H | H | H | H | nC₆H₁₃ | nC₆H₁₃ |
| 82 | F | H | H | H | H | H | *-cyclohexyl | *-cyclohexyl |
| 83 | H | H | H | H | H | H | CH₂C₃F₇ / *-(2-thienyl) | CH₂C₃F₇ |

-continued

| # | | | | | | | | |
|---|---|---|---|---|---|---|---|---|
| 84 | H | isothiazol-3-yl (*) | H | H | H | furan-3-yl (*) | -isoPropyl | -isoPropyl |
| 85 | H | H | H | H | H | H | -tert-Butyl | -tert-Butyl |
| 86 | H | H | H | H | H | H | CH(C$_8$H$_{17}$)(C$_{10}$H$_{21}$)* | CH(C$_8$H$_{17}$)(C$_8$H$_{17}$)* |
| 87 | H | H | H | H | H | H | C$_2$H$_4$C$_5$F$_{11}$ | C$_2$H$_4$C$_5$F$_{11}$ |
| 88 | Cl | H | H | Cl | H | H | cyclohexyl* | cyclohexyl* |
| 89 | F | H | H | F | H | H | phenyl* | phenyl* |
| 90 | F | F | F | F | F | F | 3,5-dimethylphenyl* | 3,5-dimethylphenyl* |
| 91 | F | H | F | H | F | F | isobutyl* | -(CH$_2$)$_{10}$-P(=O)(OH)$_2$ |
| 92 | Br | H | H | H | H | Br | 2,4,6-trimethylphenyl* | 2,4,6-trimethylphenyl* |
| 93 | NO$_2$ | H | H | H | H | H | cyclopropyl* | cyclobutyl* |

-continued

| # | | | | | | | |
|---|---|---|---|---|---|---|---|
| 94 | CH$_3$ | H | H | H | H | *-CH$_2$-C$_6$H$_5$ | *-CH$_2$-C$_6$H$_4$-Cl |
| 95 | CO$_2$CH$_3$ | H | H | H | H | *-adamantyl | *-adamantyl |
| 96 | H | H | H | H | H | *-cyclopentyl | *-cyclopentyl |
| 97 | -COOH | H | H | H | H | CF$_3$ | C$_2$F$_5$ |
| 98 | H | H | H | H | H | *-Si(CH$_3$)$_2$-C$_6$H$_5$ | *-C≡C-TIPS |
| 99 | OCH$_3$ | H | H | H | H | *-(CH$_2$)$_2$-O-C$_2$H$_5$ | *-(CH$_2$)$_4$-NH$_2$ |

-continued

| No. | $R^{15A}$ | $R^{15D}$ | $R^{15E}$ | $R^{15F}$ | $R^{15G}$ | $R^{15H}$ | $R^{31}$ | $R^{51}$ |
|---|---|---|---|---|---|---|---|---|
| 100 | CN | H | H | H | H | H | CH$_3$ | CH$_3$ |
| 101 | Br | H | H | H | H | Br | nC$_6$H$_{13}$ | nC$_6$H$_{13}$ |
| 102 | NO$_2$ | H | H | H | H | H | *—cyclohexyl | *—cyclohexyl |
| 103 | COOH | H | H | H | H | H | *—CH$_2$CH$_2$—O—CH$_2$CH$_2$OH | *—CH$_2$CH$_2$—O—CH$_2$CH$_2$—(imidazolyl) |
| 104 | H | H | H | H | H | H | *—(CH$_2$)$_4$—NH$_2$ | *—(CH$_2$)$_3$—N(CH$_3$)$_2$ |
| 105 | OCH$_3$ | H | H | H | H | H | *—(CH$_2$)$_4$—OH | *—(CH$_2$)$_4$—SO$_3$H |

-continued

[Structure: perylene diimide core with R³¹–N, R⁵¹–N at imide positions, and R^{15B}, R^{15F} substituents on the aromatic core]

| No. | R^{15B} | R^{15F} | R^{31} | R^{51} |
|---|---|---|---|---|
| 106 | H | H | cyclohexyl | cyclohexyl |
| 107 | H | H | CF₃ | CF₃ |
| 108 | H | H | nC₈H₁₇ | nC₈H₁₇ |
| 109 | H | H | nC₁₀H₂₁ | nC₁₀H₂₁ |
| 110 | H | H | 4-(C₈H₁₇)-phenyl | 4-(C₈H₁₇)-phenyl |
| 111 | H | H | 4-(C₄H₉)-cyclohexyl | 4-(C₄H₉)-cyclohexyl |
| 112 | H | H | benzyl | benzyl |

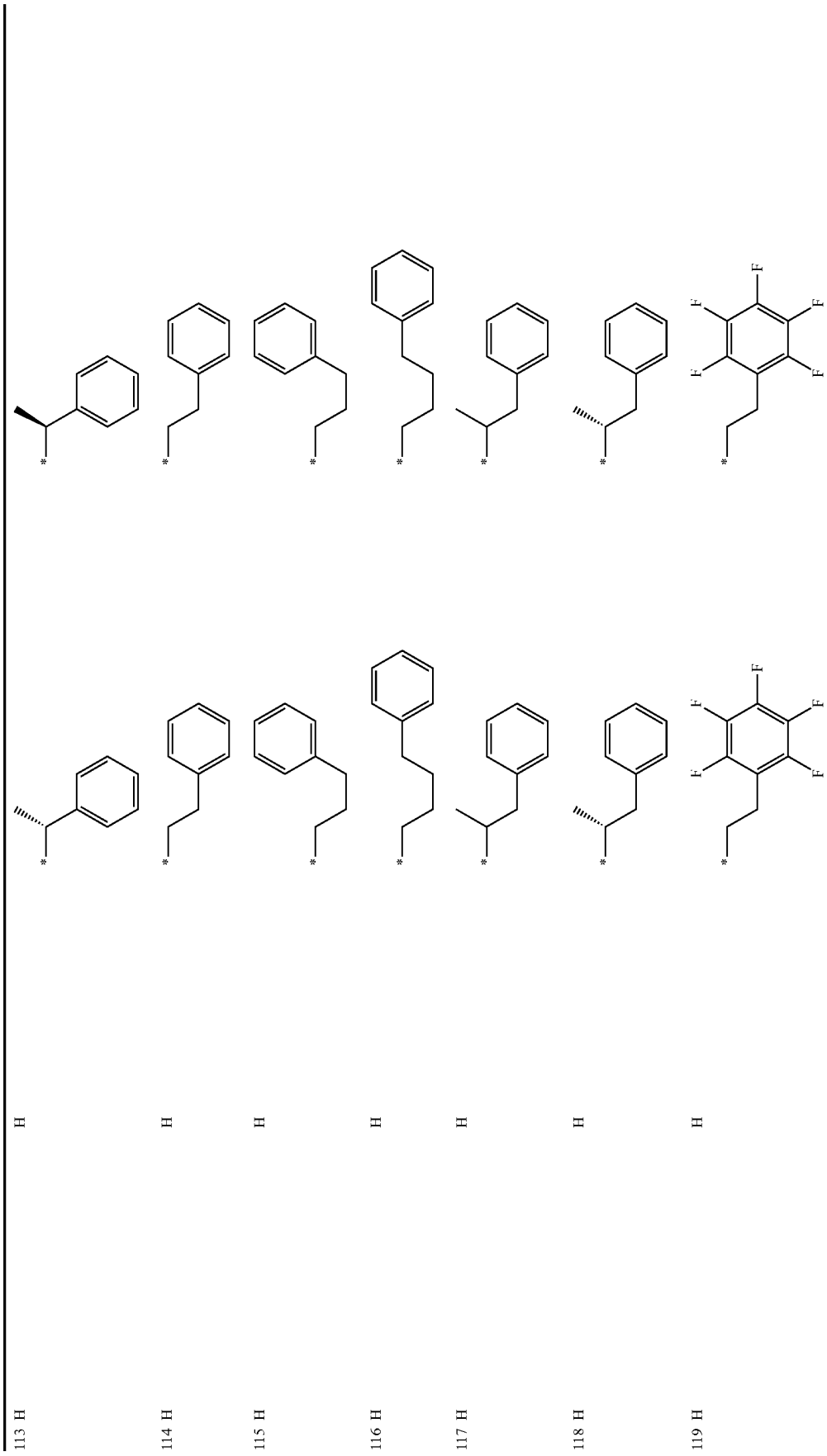

-continued

| | | |
|---|---|---|
| 120 | H | H (4-C8H17-2,3,5,6-tetrafluorophenyl)ethyl* |
| 121 | H | H (pyridin-4-yl)ethyl* |
| 122 | H | H (pyridin-3-yl)ethyl* |
| 123 | H | H (pyrimidin-2-yl)ethyl* |
| 124 | H | H (1-C10H21-pyridinium-4-yl)ethyl* I⁻ |
| 125 | H | H (4-C2H5-phenyl)ethyl* |
| 126 | H | H (4-C6H13-phenyl)ethyl* |
| 127 | H | H (4-C10H21-phenyl)ethyl* |
| 128 | H | H (4-C10H4F17-phenyl)ethyl* / phenylethyl* |

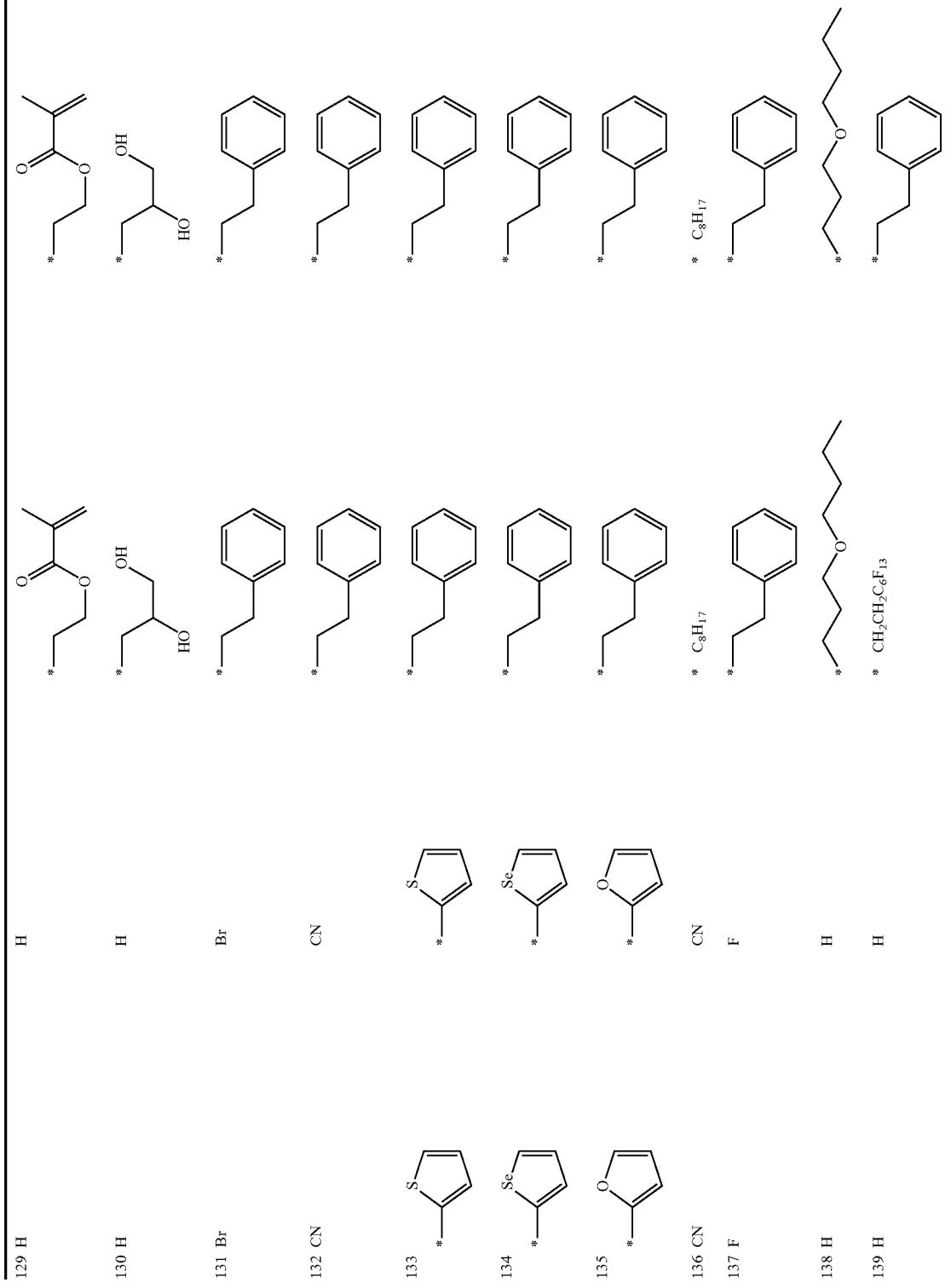

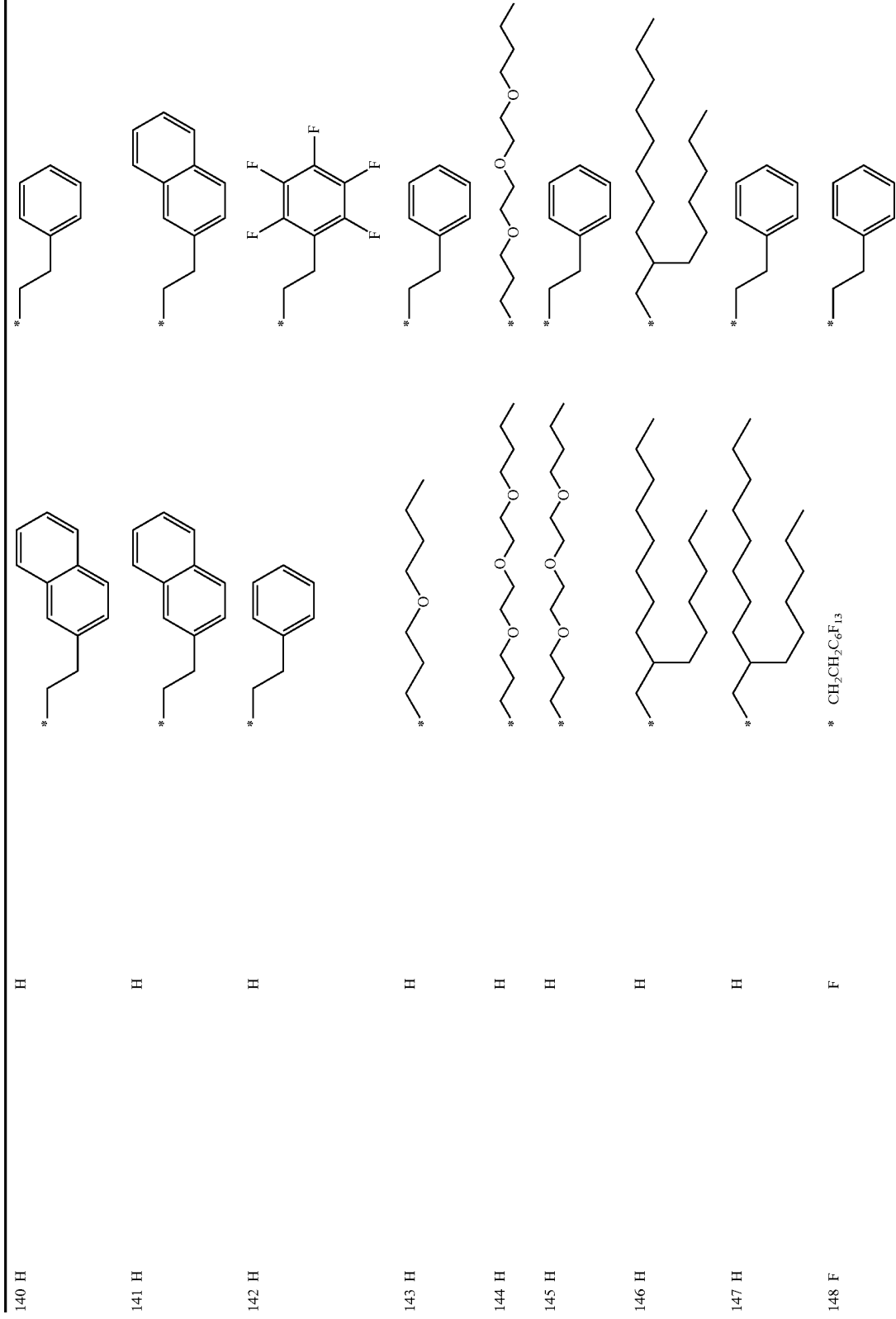

-continued

| # | Col1 | Col2 | Col3 |
|---|------|------|------|
| 149 | CN | CH₂CH₂C₆F₁₃ | CH₂CH₂-phenyl |
| 150 | Cl | * C₈H₁₇ | * C₈H₁₇ |
| 151 | CN | * C₈H₁₇ (branched) | * C₈H₁₇ (branched) |
| 152 | F | * C₈H₁₇ (branched) | * C₈H₁₇ (branched) |
| 153 | Cl | * C₈H₁₇ (branched) | * C₈H₁₇ (branched) |
| 154 | H | * C₂H₅ | * C₂H₅ |
| 155 | H | * C₃H₇ | * C₃H₇ |
| 156 | H | * C₄H₉ | * C₄H₉ |
| 157 | H | * C₅H₁₁ | * C₅H₁₁ |
| 158 | H | * C₆H₁₃ | * C₆H₁₃ |
| 159 | H | * C₇H₁₅ | * C₇H₁₅ |
|     |   | * C₈H₁₇ | * C₈H₁₇ |
| 160 | * (thiazol-2-yl) | * C₈H₁₇ | * C₈H₁₇ |
| 161 | * (thiazol-2-yl) | * C₈H₁₇ | * C₈H₁₇ |
| 162 | * | * Me | * Me |
| 163 | * | C≡CSiMe₃ | C≡CSiMe₃ |
| 164 | F | C≡CC₆H₁₃ | C≡CC₆H₁₃ |
| 165 | Br | * C₈H₁₇ | * C₈H₁₇ |
| 166 | H | * C₅H₁₁ | CH₂CH₂-phenyl |
| 167 | H | * CH=CH-phenyl | * CH=CH-phenyl |

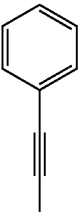

-continued

| | | |
|---|---|---|
| 181 | CN | |
| 182 | CN | |
| 183 | CN | |
| 184 | CN | |
| 185 | CN | |
| 186 | H | |
| 187 | H | |
| 188 | | |
| 189 | | |

-continued

| # | R1 | R2 | R3 |
|---|---|---|---|
| 190 | thiophene-vinyl-* | C$_8$H$_{17}$-* | C$_8$H$_{17}$-* |
| 191 | phenyl-vinyl-* | C$_8$H$_{17}$-* | C$_8$H$_{17}$-* |
| 192 | thiazole-ethynyl-* | C$_8$H$_{17}$-* | C$_8$H$_{17}$-* |
| 193 | thiazole-ethynyl-* | C$_8$H$_{17}$-* | C$_8$H$_{17}$-* |
| 194 | thiophene-ethynyl-* | C$_8$H$_{17}$-* | C$_8$H$_{17}$-* |
| 195 | phenyl-vinyl-* | C$_8$H$_{17}$-* | C$_8$H$_{17}$-* |
| 196 | H | H | cyclohexyl-ethyl-* |
| 197 | F | F | phenyl-ethyl-* |
| 198 | CN | CN | phenyl-ethyl-* |
| 199 | CN | CN | C$_8$H$_{17}$-* | (chiral 2-hexyl-*) |

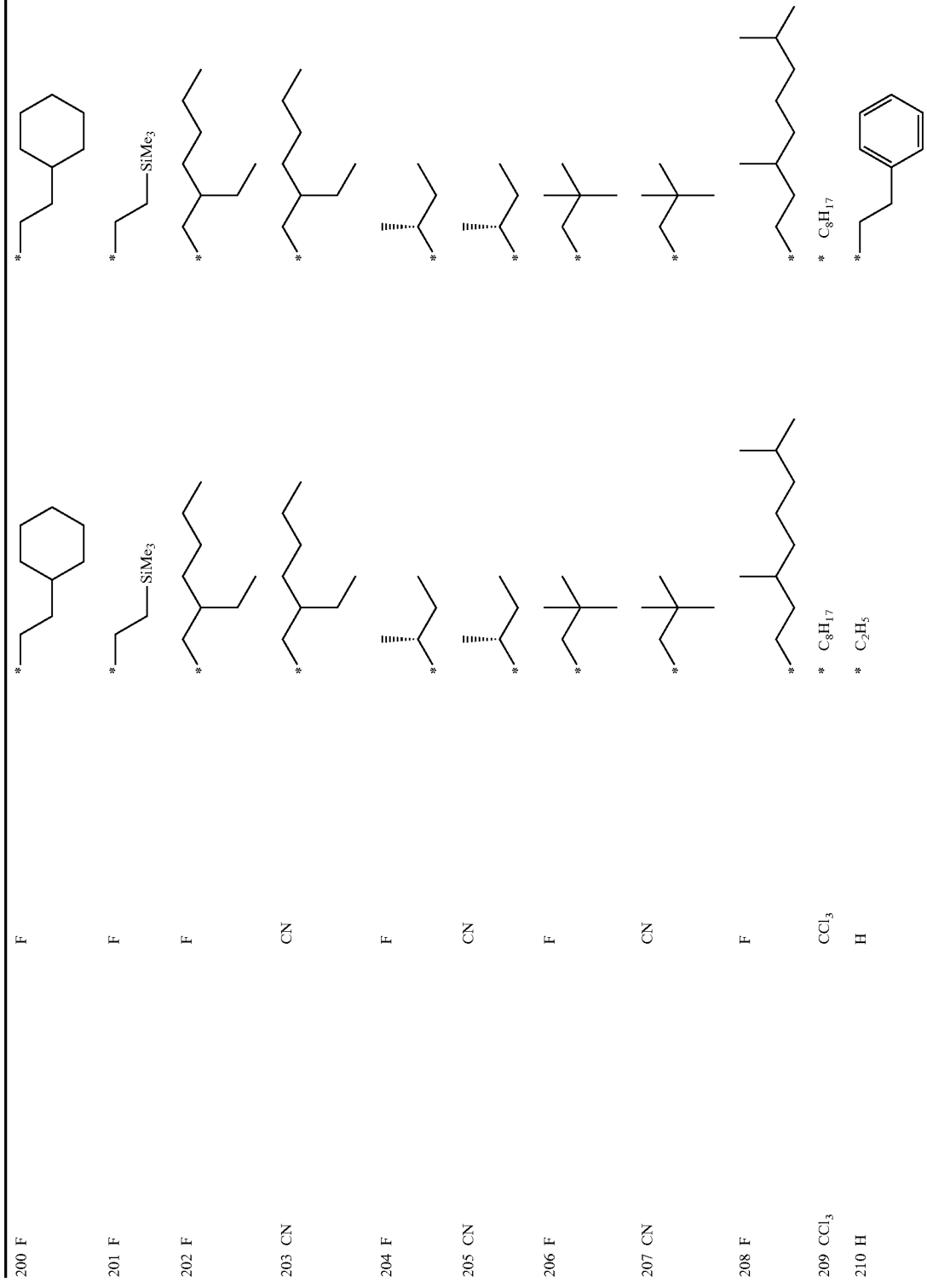

-continued

| | | |
|---|---|---|
| 211 H | H | * C₃H₇ |
| 212 H | H | * C₄H₉ |
| 213 H | H | * C₆H₁₃ |
| 214 H | H | * C₇H₁₅ |
| 215 H | H | * C₈H₁₇ |
| 216 H | H | * C₁₀H₂₁ |
| 217 H | H | * C₁₂H₂₅ |
| 218 H | H | (branched alkyl, wedge bond) |
| 219 H | H | (branched alkyl, dashed bond) |
| 220 H | H | (branched alkyl) |
| 221 F | F | (branched alkyl, wedge bond) |

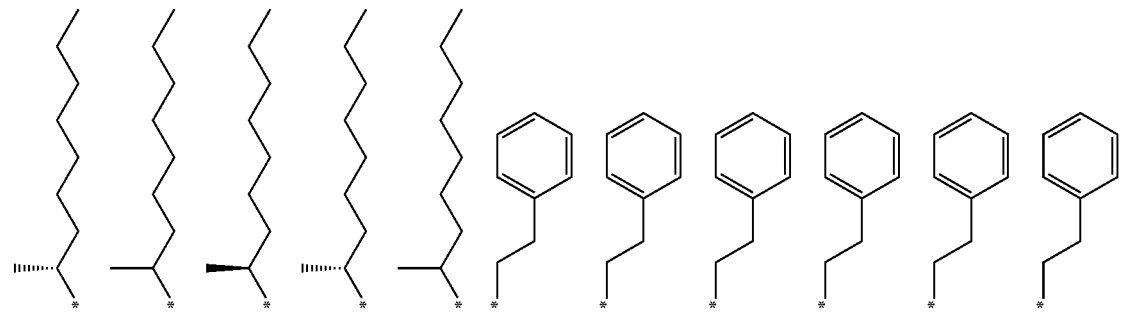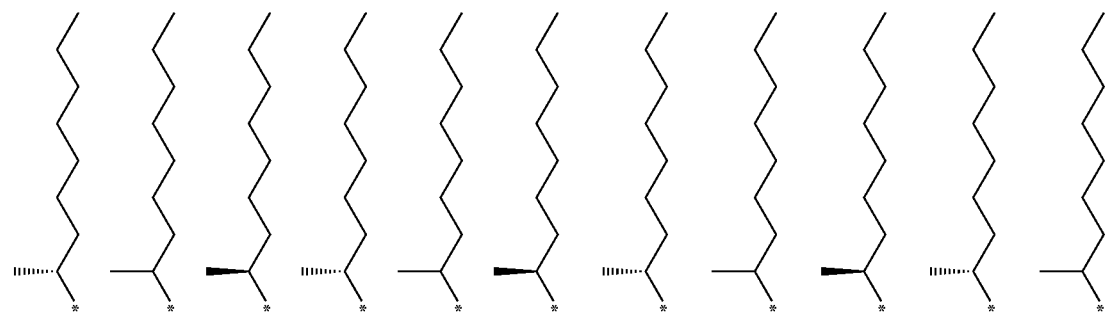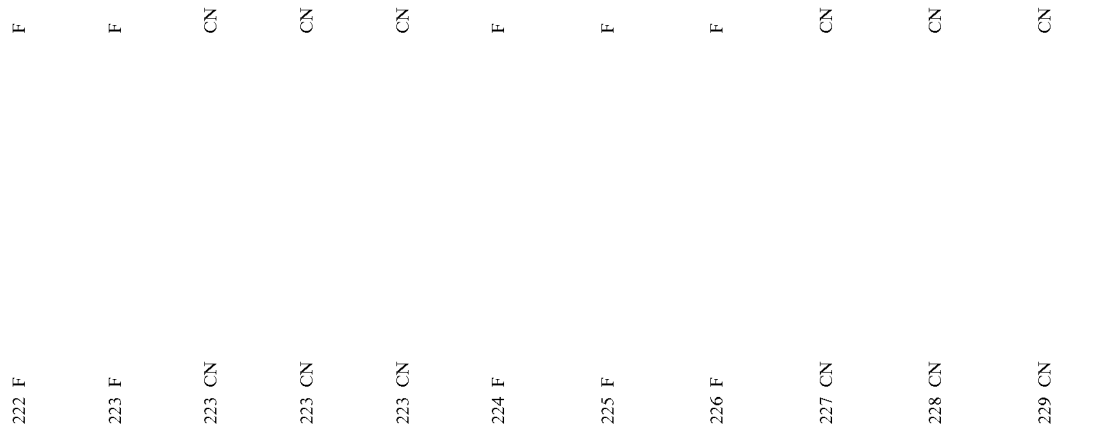

-continued
| | | | |
|---|---|---|---|
| 230 | H | 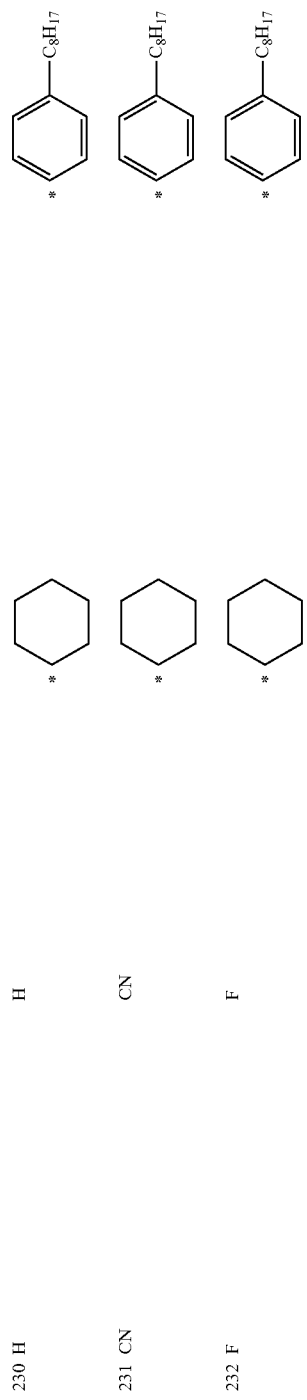 | |
| 231 | CN | | |
| 232 | F | | |
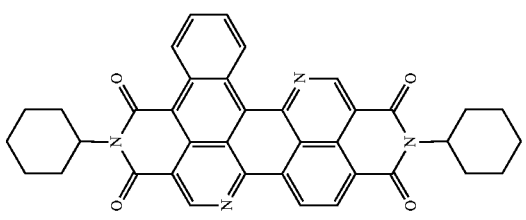

-continued
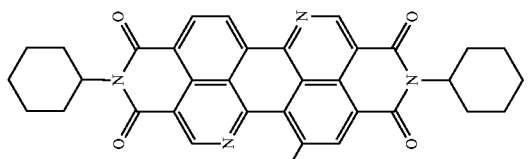
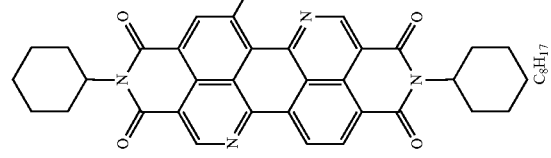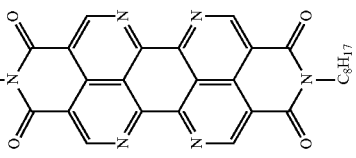

-continued
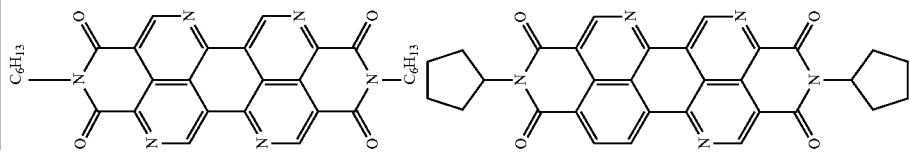

-continued
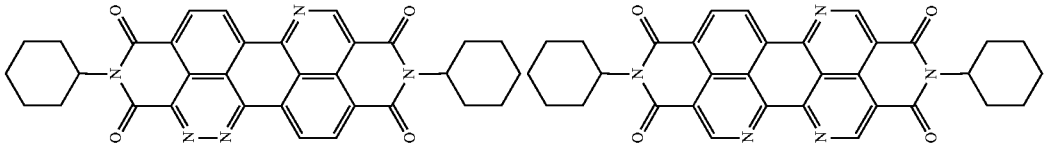

-continued
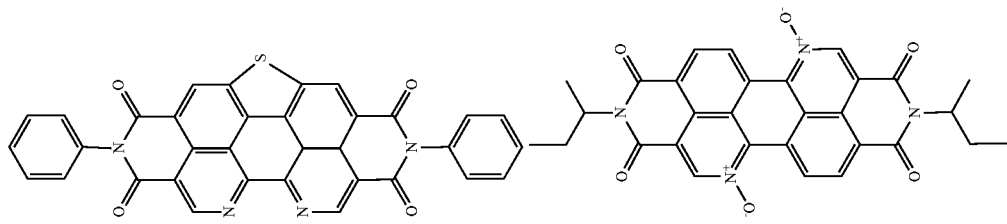

-continued
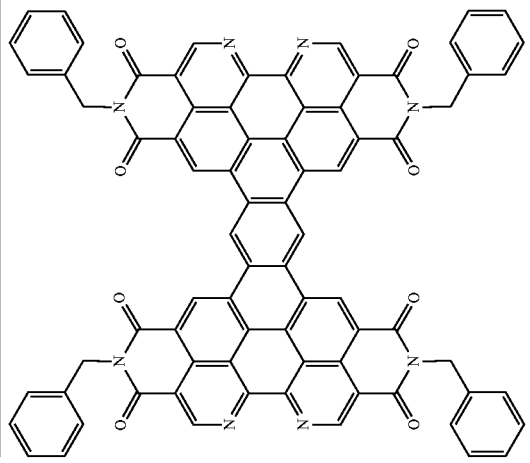
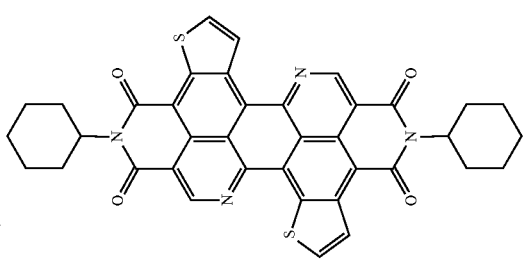

-continued
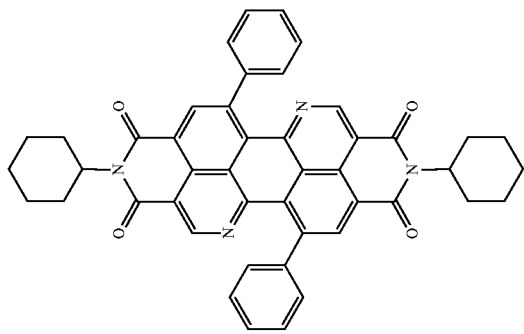

Amine Compound

In the production method according to an embodiment of the present invention, an amine compound to be reacted with the compound represented by the formula (1) is not particularly limited, but is preferably a primary amine or a protected primary amine.

The primary amine is not particularly limited, and is, for example, an amine compound represented by formula (Y1) below.

   Formula (Y1)

In the formula (Y1), $R^{Y1}$ represents a substituent.

The substituent represented by $R^{Y1}$ is not particularly limited, but is preferably a group selected from the above-described substituent group Z. Specifically, the substituent is preferably an alkyl group (the number of carbon atoms is preferably 1 to 20, from the viewpoint of carrier mobility in the case of being used as an organic semiconductor compound, the lower limit of the number of carbon atoms is more preferably 4 or more, and the upper limit of the number of carbon atoms is more preferably 15 or less and further preferably 8 or less, and may be linear, chain-like, or cyclic), an alkenyl group, an alkynyl group, an aryl group (preferably having 6 to 20 carbon atoms), or a heterocyclic group (including at least one of the above-mentioned heteroatoms as a ring-constituting atom, preferably having a 5-membered ring, a 6-membered ring, or a fused ring thereof, the number of ring-constituting carbon atoms is preferably 3 to 20), more preferably an alkyl group, an alkenyl group, an alkynyl group, an aryl group, or a heteroaryl group, further preferably an alkyl group, an aryl group, or a heteroaryl group, and particularly preferably an alkyl group.

The above-mentioned alkyl group, alkenyl group, alkynyl group, aryl group, heterocyclic group, and heteroaryl group may further have a substituent. In the case of further having a substituent, the substituent is a group selected from the substituent group Z.

In particular, the substituent represented by $R^{Y1}$ is more preferably an unsubstituted alkyl group, a halogenated alkyl group, an alkyl group having an aryl group as a substituent, an alkyl group having a heterocyclic ring (preferably a heteroaryl group) as a substituent, an unsubstituted aryl group, an aryl group into which an alkyl group is introduced, an unsubstituted heterocyclic group, a heterocyclic group into which an alkyl group is introduced, an alkyl group into which a silyl group is introduced, or an alkyl group into which one or more alkoxy groups are introduced. For the alkyl group having an aryl group as a substituent and the alkyl group having a heterocyclic ring as a substituent, the aryl group and the heterocyclic ring may further have a substituent. In the case of further having a substituent, the substituent is a group selected from the substituent group Z, and preferably a halogen atom.

Specific examples of the amine compound represented by the formula (Y1) include methylamine, ethylamine, 2-trimethylsilylethylamine, propylamine, isopropylamine, cyclopropylamine, butylamine, isobutylamine, tert-butylamine, sec-butylamine, cyclobutylamine, 3-methylbutylamine, pentylamine, neopentylamine, 2-methylbutylamine, cyclopentylamine, hexylamine, cyclohexylamine, 1-methylpentylamine, heptylamine, octylamine, 2-ethylhexylamine, 1-methyloctylamine, decylamine, dodecylamine, benzylamine, phenylethylamine, phenylpropylamine, phenylbutylamine, cyclohexylethylamine, 2-thienylethylamine, 2-thiazolylethylamine, 5-thiazolylethylamine, 2-(trimethylsilyl)ethylamine, butoxypropylamine, methoxybutylamine, methylpentylamine, aniline, p-octylaniline, p-octylphenylethylamine, p-ethylphenylethylamine, p-hexylphenylethylamine, p-decylphenylethylamine, 3,7-dimethyloctylamine, perfluorophenylethylamine, 2-thienylethylamine, 2-thiazolylethylamine, 5-thiazolylethylamine, 2-hexyldecylamine, 2-octyldodecylamine, 1H,1H-heptafluorobutylamine, 1H,1H-undecafluorobutylamine, 1H,1H,2H,2H-tridecafluorooctylamine, p-fluorophenylamine, 2-(4-pyridyl)ethylamine, 2,4-dimethoxymethylamine, 2-(3-pyridyl)ethylamine, toluidine, butoxypropylamine, and 3,6,9,12-tetraoxadecaneamine.

The protected primary amine is intended to be a compound having a structure in which one of hydrogen atoms bonded to the nitrogen atom in the formula (Y1) is protected with a protecting group. Specifically, the protected primary amine is a primary amine compound that can be used in the production method of the second embodiment described later and that is represented by formula (3).

The protected primary amine will be described later in the production method of the second embodiment.

Method for Producing Cyclic Imide Compound

The production method according to an embodiment of the present invention includes a step of reacting the compound represented by the formula (1) with at least one amine compound to obtain the compound represented by the formula (2).

Hereafter, the case where substituents represented by $R^{31}$ and $R^{51}$ in the formula (2) are the same will be described as a first embodiment, and the case where substituents represented by $R^{31}$ and $R^{51}$ in the formula (2) are not the same will be described as a second embodiment.

Production Method in First Embodiment

The production method in the first embodiment includes a step X below.

Step X: a step of heating a composition including a compound represented by formula (1) and at least one amine compound to obtain a compound represented by formula (2)

The compound represented by the formula (1), the compound represented by the formula (2), and the amine compound are as described above.

Through the step X, amidation/imidation reactions between two adjacent ester groups in the compound represented by the formula (1) and an amine compound (specifically, an amidation/imidation reaction between —COOR$^{11}$ and —COOR$^{14}$ and an amine compound, and an amidation/imidation reaction between —COOR$^{12}$ and —COOR$^{13}$ and an amine compound) are caused to form a cyclic imide compound represented by formula (2).

The amine compound may be either a primary amine or a protected primary amine, but is preferably a primary amine from the viewpoint that a deprotection step of obtaining an intended cyclic imide compound represented by the formula (2) is not necessary.

The amount of the amine compound used is preferably 2.0 to 10 molar equivalents and more preferably 2.0 to 6.0 molar equivalents relative to 1 molar equivalent of the compound represented by the formula (1).

The composition may include a solvent.

A single solvent may be used, or two or more solvents may be used in a mixed manner.

Non-limiting examples of the solvent include hydrocarbon solvents, ether solvents, amide solvents, alcohol solvents, nitrile-based solvents, and sulfoxide solvents.

Examples of the hydrocarbon solvent include pentane, hexane, heptane, octane, decane, toluene, ethylbenzene, xylene, diethylbenzene, fluorobenzene, trifluoromethylbenzene, chloroform, dichloromethane, 1,1,2,2-tetrachloroethane, 1,1,2-trichloroethane, chlorobenzene, dichlorobenzene, trichlorobenzene, mesitylene, amylbenzene, decalin, 1-methylnaphthalene, 1-ethylnaphthalene, 1-chloronaphthalene, 1-fluoronaphthalene, 1,6-dimethylnaphthalene, nitrobenzene, and tetralin.

Examples of the ether solvent include anisole, diethyl ether, dibutyl ether, diisopropyl ether, cyclopentyl methyl ether, diphenyl ether, tetrahydropyran, dioxane, dimethoxyethane, diethoxyethane, and tetrahydrofuran.

Examples of the amide solvent include N,N-dimethylformamide, N-methylpyrrolidone, N-ethylpyrrolidone, 1,3-dimethyl-2-imidazolidinone, and N,N-dimethylacetamide.

Examples of the alcohol solvent include methanol, ethanol, propanol, isopropanol, amyl alcohol, benzyl alcohol, ethylene glycol, diethylene glycol, propylene glycol, and glycerol.

Examples of the nitrile-based solvent include acetonitrile and benzonitrile.

Examples of the sulfoxide solvent include dimethyl sulfolane and sulfolane.

In particular, the solvent is preferably a solvent having a boiling point of 70° C. or higher and more preferably a solvent having a boiling point of 90° C. or higher.

Examples of the solvent having a boiling point of 90° C. or higher include heptane, octane, decane, toluene, ethylbenzene, xylene, diethylbenzene, fluorobenzene, trifluoromethylbenzene, chlorobenzene, dichlorobenzene, trichlorobenzene, mesitylene, amylbenzene, decalin, 1-methylnaphthalene, 1-ethylnaphthalene, 1-chloronaphthalene, 1-fluoronaphthalene, 1,6-dimethylnaphthalene, nitrobenzene, 1,1,2,2-tetrachloroethane, 1,1,2-trichloroethane, benzonitrile, tetralin, anisole, dibutyl ether, cyclopentyl methyl ether, diphenyl ether, dioxane, diethoxyethane, N,N-dimethylformamide, N-methylpyrrolidone, N-ethylpyrrolidone, 1,3-dimethyl-2-imidazolidinone, N,N-dimethylacetamide, 1-propanol, 1-butanol, isobutyl alcohol, 2-butanol, amyl alcohol, benzyl alcohol, ethylene glycol, diethylene glycol, propylene glycol, glycerol, dimethyl sulfoxide, and sulfolane.

When the composition includes a solvent, the content of the solvents is preferably 75.0 to 99.9 mass % and more preferably 80.0 to 98.0 mass % relative to the total mass of the composition.

The reaction temperature is not particularly limited, but is preferably 20° C. to 250° C. and more preferably 50° C. to 200° C.

The reaction time varies depending on the solvent used and the reaction conditions including a reaction temperature, but is normally 1 to 24 hours and preferably 1 to 20 hours.

After completion of the heating reaction, if necessary, the obtained compound represented by the formula (2) may be purified by separation and purification means including washing, extraction, drying, filtration, concentration, recrystallization, reprecipitation, crystallization, centrifugation, adsorption, column purification, and/or sublimation purification, and is preferably purified by separation and purification means including sublimation purification.

As described above, the compound represented by the formula (1) is preferably the compound represented by the formula (8), and the compound represented by the formula (2) is preferably the compound represented by the formula (9).

Hereafter, a preferred embodiment (hereafter, also referred to as "first embodiment-1") of the method for producing the compound represented by the formula (9) (the formula (9') shown later corresponds to a compound in which $R^{31}$ and $R^{51}$ represent the same substituent in the formula (9)) from the compound represented by the formula (8) (the formula (11A) shown later corresponds to the formula (8)).

Preferred Embodiment of Method for Producing Compound Represented by Formula (9) (First Embodiment-1)

The production method according to the first embodiment-1 includes a step X' below.

Step X': a step of reacting a compound represented by formula (X1) below with a compound represented by formula (X2) below to obtain a composition including a compound represented by formula (11A) below and a compound represented by formula (11B) below, and then reacting the composition with a first amine compound represented by formula (14) below without subjecting the composition to column purification to obtain a compound represented by formula (9') below The compound represented by the formula (9') below is a compound covered by the above-described compound represented by the formula (9). Specifically, the compound represented by the formula (9') below corresponds to a compound in which the substituents represented by $R^{31}$ and $R^{51}$ in the compound represented by the formula (9) are the same. The compound represented by the formula (11A) corresponds to the compound represented by the formula (8).

The production method according to the first embodiment-1 preferably further includes a step Y0' below.

Step Y0': a step of further purifying the compound represented by the formula (X2) before reacting the compound represented by the formula (X1) with the compound represented by the formula (X2)

The compounds represented by the formula (X1), the formula (X2), the formula (11A), and the formula (11B) in the step X' are the same as compounds represented by formula (X1), formula (X2), formula (11A), and formula (11B) in step Y1' described later, and preferred forms thereof are also the same.

The compounds represented by the formula (X1), the formula (X2), the formula (11A), and the formula (11B) will be described later in the production method according to the second embodiment.

The first amine compound represented by the formula (14) in the step X' is the same as a second amine compound represented by formula (14) in step Y1' described later, and preferred forms thereof are also the same.

The first amine compound represented by the formula (14) will be described later in the production method of the second embodiment.

In the step X', the procedure for reacting the compound represented by the formula (X1) with the compound represented by the formula (X2) to obtain the composition including the compound represented by the formula (11A) and the compound represented by the formula (11B) is the same as that in the step Y1' described later, and preferred forms thereof are also the same.

The above procedure will be described later in the production method of the second embodiment.

In the step X', the compound represented by the formula (11B) is a by-product formed in a synthesis reaction of reacting the compound represented by the formula (X1) with the compound represented by the formula (X2) to obtain the compound represented by the formula (11A). The formation of the compound represented by the formula (11B) as a by-product is probably caused by formic acid that may be included as an impurity in the compound represented by the formula (X2) (the compound represented by the formula (X2) is, for example, 2,4,6-trichlorophenyl formate). In the step X', the formation of the compound represented by the formula (11B) as a by-product can be suppressed by performing the step (step Y0') of purifying the compound represented by the formula (X2) before the reaction of the compound represented by the formula (X1) with the compound represented by the formula (X2).

The step Y0' that may be included in the production method according to the first embodiment-1 is the same as the step Y0' that may be included in the production method according to the second embodiment-1 described later, and preferred forms are also the same.

The procedure of the step Y0' will be described later in the production method according to the second embodiment.

In the step X', a step of reacting a composition obtained through a coupling reaction of the compound represented by the formula (X1) and the compound represented by the formula (X2) with the first amine compound represented by the formula (14) without column purification is performed. From the viewpoint of further improving the purity of the compound represented by the formula (9'), which is a target compound, the composition includes at least the compound represented by the formula (11A), and the content of the compound represented by the formula (11B) is preferably 3.0 mass % or less and more preferably 1.0 mass % or less relative to the total solid content of the composition. When the step Y0' is performed, the content of the compound represented by the formula (11B) in the composition of the step X' can be adjusted to 3.0 mass % or less relative to the total solid content of the composition.

The lower limit of the content of the compound represented by the formula (11B) is usually 0 mass % or more and often 0.01 mass % or more relative to the total solid content of the composition.

The term "solid content" refers to components in a composition from which solvents are removed. Even if components other than solvents in the composition are liquid, the components are regarded as solid contents.

If necessary, the composition may be purified by separation and purification means other than column purification (such as washing, extraction, drying, filtration, concentration, recrystallization, reprecipitation, crystallization, adsorption, and centrifugation) after completion of the coupling reaction.

Specifically, the step of reacting the composition with the first amine compound represented by the formula (14) is preferably a step of adding the first amine compound represented by the formula (14) to the composition and heating the mixture to obtain the compound represented by the formula (9').

The specific procedure is the same as that of the step X of the production method in the first embodiment described above, and the preferred form is also the same.

Second Embodiment

The production method according to the second embodiment includes steps Y1 to Y4 below.

Step Y1: a step of reacting the compound represented by the formula (1) with a first amine compound represented by formula (3) below to obtain a compound represented by formula (4) below Step Y2: a step of reacting the compound represented by the formula (4) with a second amine compound represented by formula (5) below to obtain a compound represented by formula (6) below Step Y3: a step of removing $P^{31}$ serving as a protecting group from the compound represented by the formula (6) to obtain a compound represented by formula (7) below Step Y4: a step of obtaining a compound represented by the formula (2) from the compound represented by the formula (7)

By the production method according to the second embodiment, a compound (2) having different substituents represented by $R^{31}$ and $R^{51}$ can be produced with high purity.

Hereafter, first, the compounds represented by the formulae (3) to (7) will be described, and then the steps Y1 to Y4 will be described.

Compounds Represented by Formulae (3) to (7)

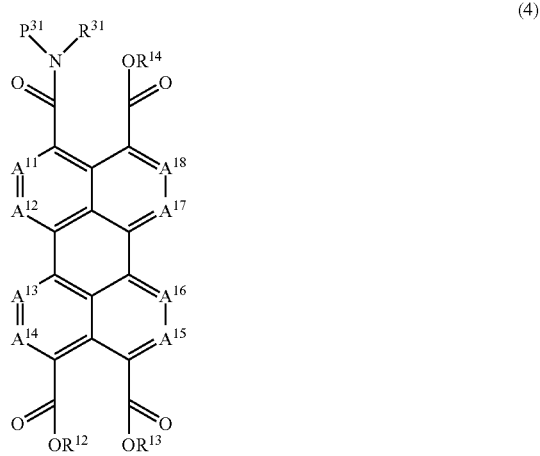

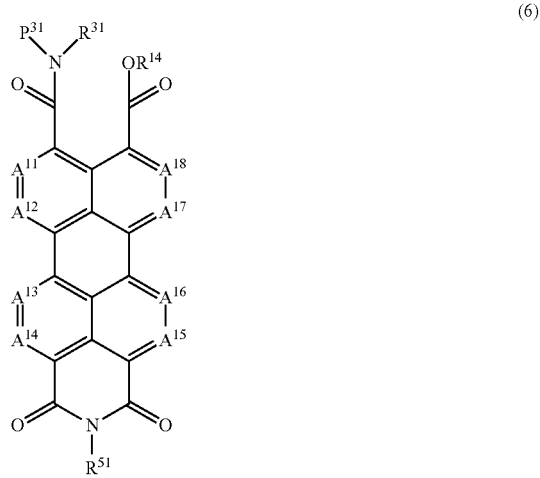

(7)

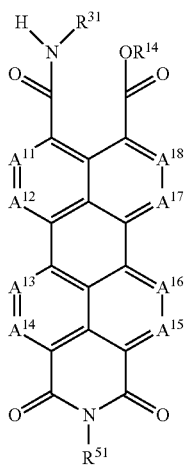

In the formula (3), $R^{31}$ represents a substituent. $P^{31}$ represents a protecting group.

In the formula (3), the substituent represented by $R^{31}$ is the same as the substituent represented by $R^{31}$ and $R^{51}$ in the formula (2).

The substituent represented by $R^{31}$ of the first amine compound represented by the formula (3) can be exemplified by the same substituents as those represented by $R^{Y1}$ of the amine compound represented by (Y1), and preferred forms thereof are also the same.

Non-limiting examples of the protecting group represented by $P^{31}$ include a (hetero)arylmethyl group (the (hetero)arylmethyl group refers to an arylmethyl group and a heteroarylmethyl group, which are specifically a benzyl group, a naphthylmethyl group, a 2-methoxybenzyl group, a p-methoxybenzyl group, a 2,4-dimethoxybenzyl group, a 3,4,5-trimethoxybenzyl group, a 3,4-dimethoxybenzyl group, a 2-thienylmethyl group, and a 2-furylmethyl group), a nitrobenzenesulfonyl group, a dinitrobenzenesulfonyl group, a tert-butoxycarbonyl group, an allyloxycarbonyl group, a benzyloxycarbonyl group, a methoxycarbonyl group, a 2,2,2-trichloroethoxycarbonyl group, a 9-fluorenylmethoxycarbonyl group, a trimethylsilylethoxycarbonyl group, and a (2-trimethylsilyl)ethanesulfonyl group. The (hetero)arylmethyl group is preferable.

The first amine compound represented by the formula (3) corresponds to the above-described protected primary amine.

In the formula (4), $A^{11}$ to $A^{18}$ and $R^{12}$ to $R^{14}$ respectively have the same meaning as $A^{11}$ to $A^{18}$ and $R^{12}$ to $R^{14}$ in the formula (1), and preferred forms thereof are also the same. $R^{31}$ and $P^{31}$ respectively have the same meaning as $R^{31}$ and $P^{31}$ in the formula (3), and preferred forms thereof are also the same.

In the formula (5), the substituent represented by $R^{51}$ is the same as that represented by $R^{51}$ in the formula (2), and preferred forms thereof are also the same.

The second amine compound represented by the formula (5) is the same as the primary amine represented by the formula (Y1), and preferred forms thereof are also the same.

In the formula (6), $A^{11}$ to $A^{18}$ and $R^{14}$ respectively have the same meaning as $A^{11}$ to $A^{18}$ and $R^{14}$ in the formula (1), and preferred forms thereof are also the same. $R^{31}$ and $P^{31}$ respectively have the same meaning as $R^{31}$ and $P^{31}$ in the formula (3), and preferred forms thereof are also the same. $R^{51}$ has the same meaning as $R^{51}$ in the formula (5), and preferred forms thereof are also the same.

In the formula (7), $A^{11}$ to $A^{18}$ and $R^{14}$ respectively have the same meaning as $A^{11}$ to $A^{18}$ and $R^{14}$ in the formula (1), and preferred forms thereof are also the same. $R^{31}$ has the same meaning as $R^{31}$ in the formula (3), and preferred forms thereof are also the same. $R^{51}$ has the same meaning as $R^{51}$ in the formula (5), and preferred forms thereof are also the same.

Hereafter, the compound represented by the formula (4), the compound represented by the formula (6), and the compound represented by the formula (7) are individually exemplified.

Formula (4)

Examples of the compound represented by the formula (4) are shown below, but the compound represented by the formula (4) is not limited thereto.

(4)-1 to (4)-71 in Table below show combinations of $R^{11}$, $R^{12}$, $R^{13}$, $R^{14}$, $R^{31}$, and $P^{31}$ shown in each basic skeleton below. In Table below, "Me" represents a methyl group, and "Et" represents an ethyl group.

$R^{81}$ and $R^{82}$ in the basic skeletons shown below each independently represent a substituent selected from the group consisting of a hydrogen atom, a cyano group, a fluorine atom, a chlorine atom, a bromine atom, an iodine atom, a trifluoromethyl group, a trifluoromethoxy group, a trichloromethyl group, a trichloromethoxy group, a 2-thiazolyl group, a 5-thiazolyl group, a 2-thienyl group, a 3-thienyl group, a styryl group, a 2-thiazolylvinyl group, a 5-thiazolylvinyl group, a 2-thienylvinyl group, a 3-thienylvinyl group, a phenylethynyl group, a 2-thiazolylethynyl group, a 5-thiazolylethynyl group, a 2-thienylethynyl group, a 3-thienylethynyl group, a trimethylsilylethynyl group, a triethylsilylethynyl group, a triisopropylethynyl group, and a 1-octynyl group. Herein, at least one of $R^{81}$ or $R^{82}$ represents a group other than hydrogen.

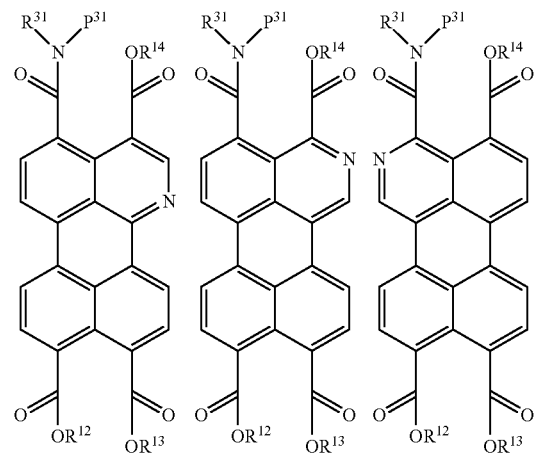

101
-continued
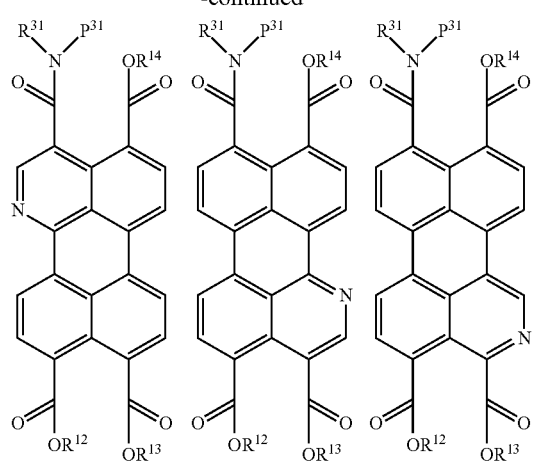
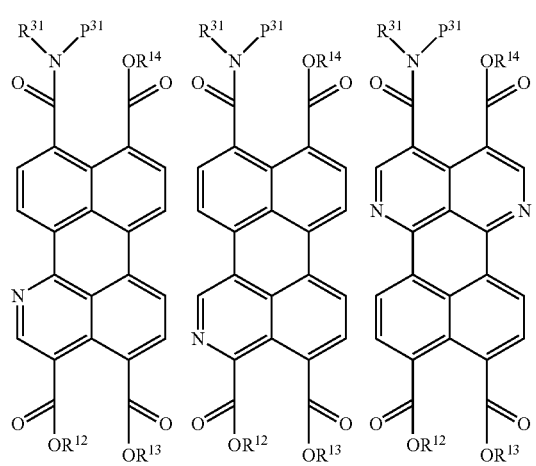
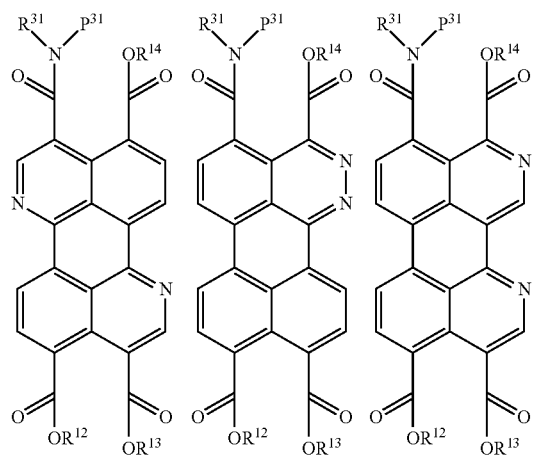
102
-continued
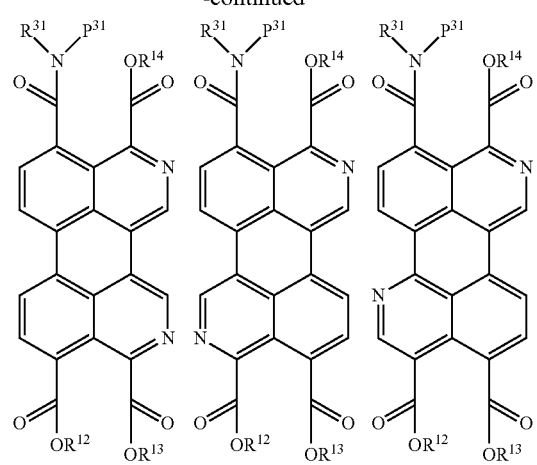
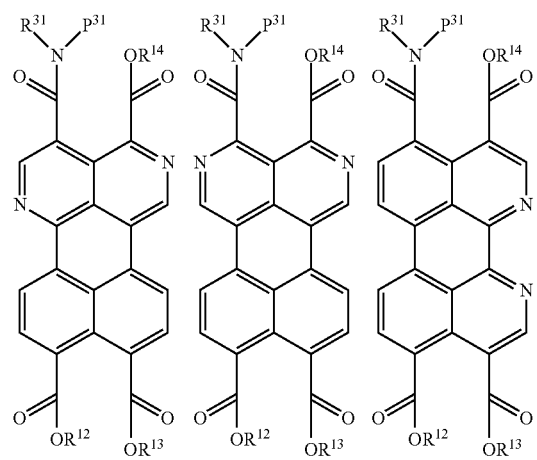
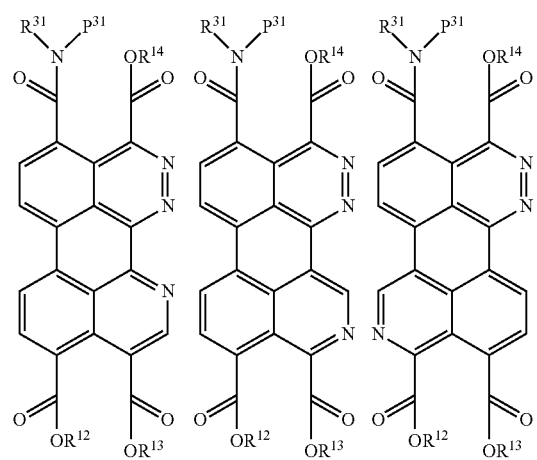

103
-continued
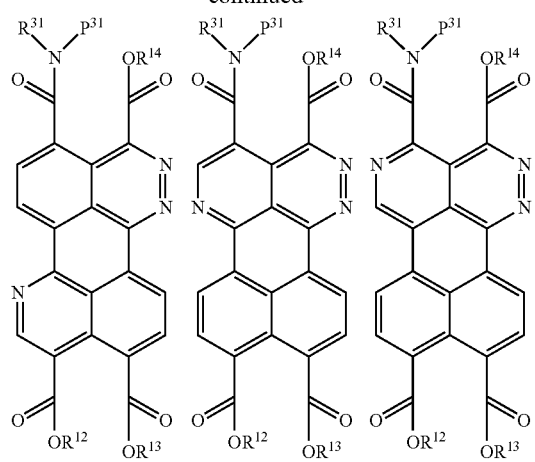
104
-continued
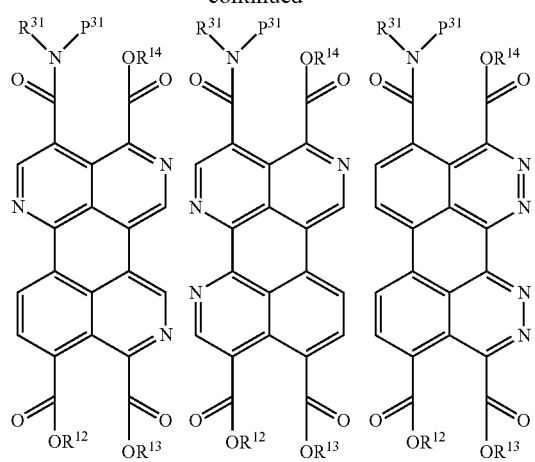
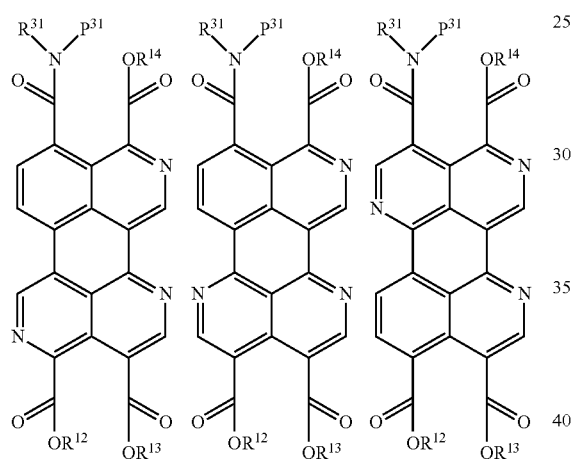
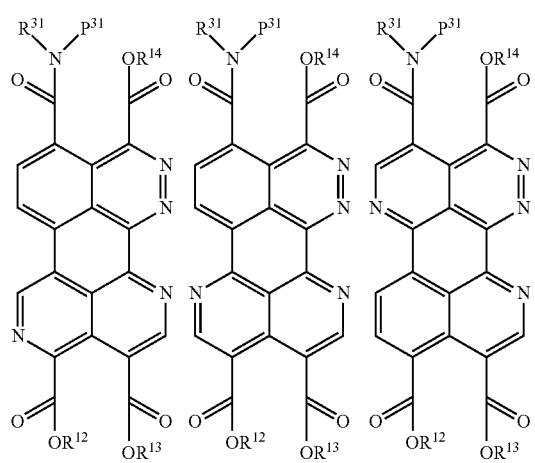
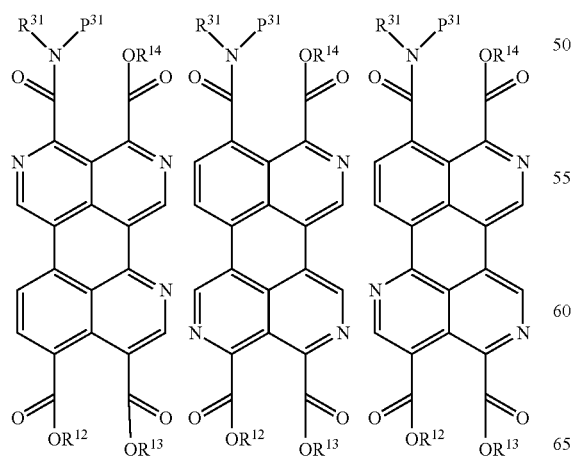
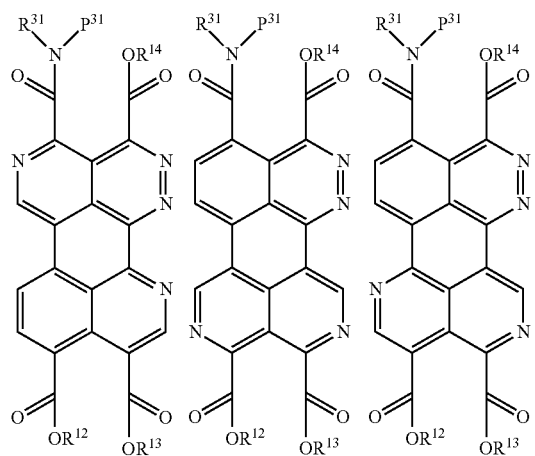

105
-continued
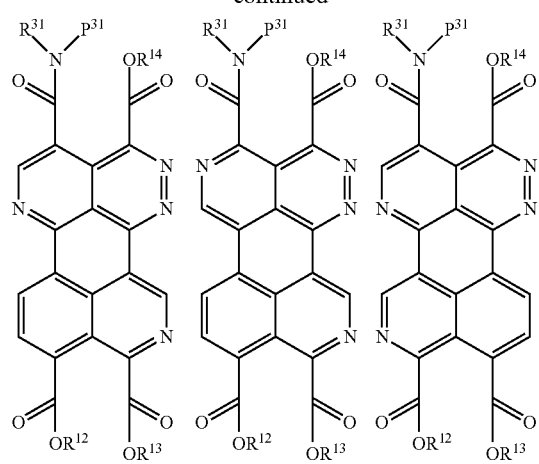
106
-continued
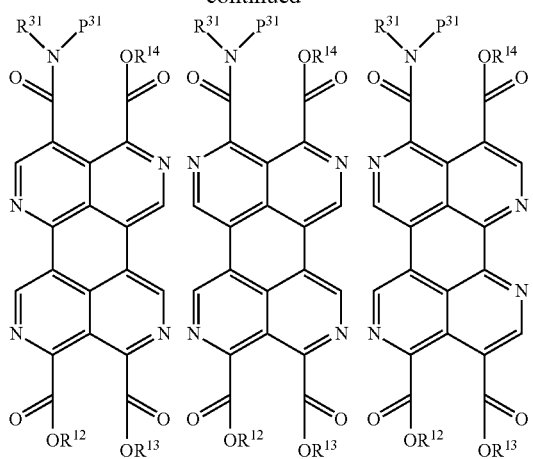
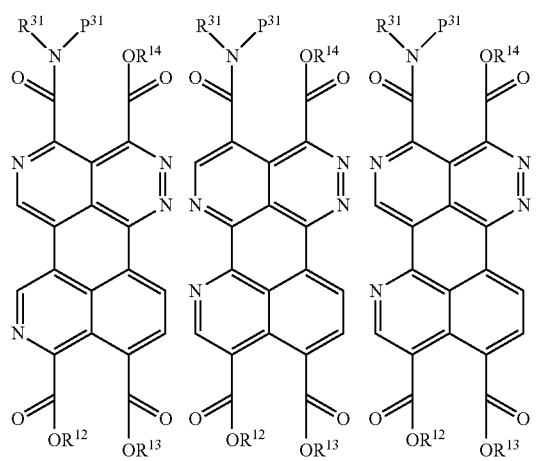
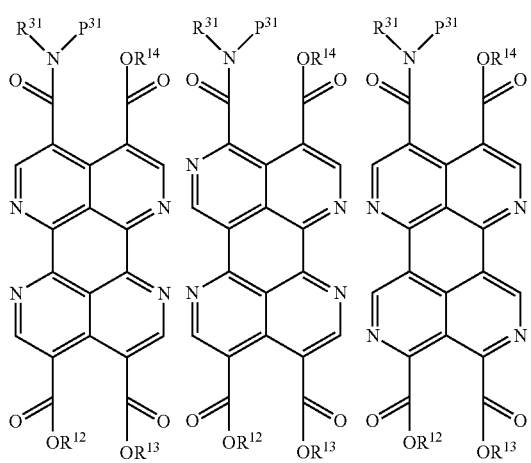
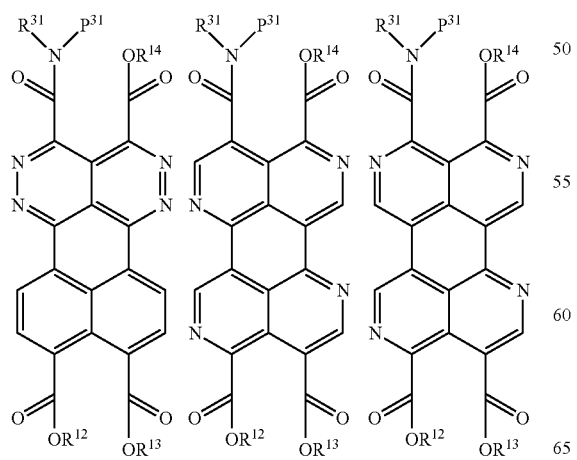
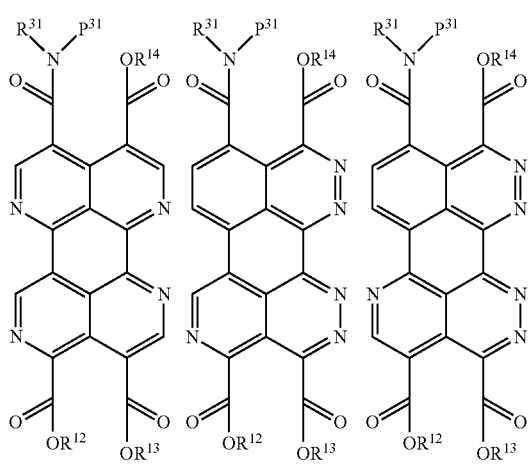

-continued
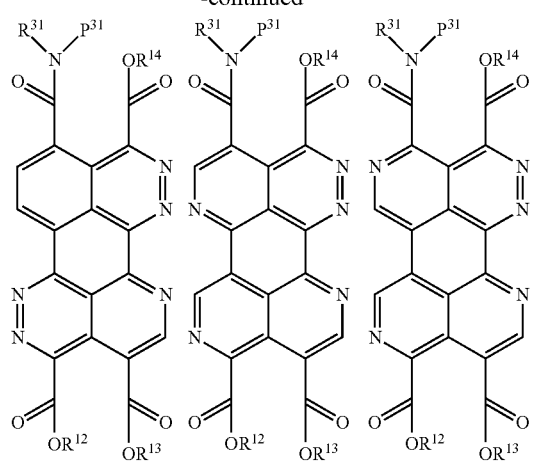
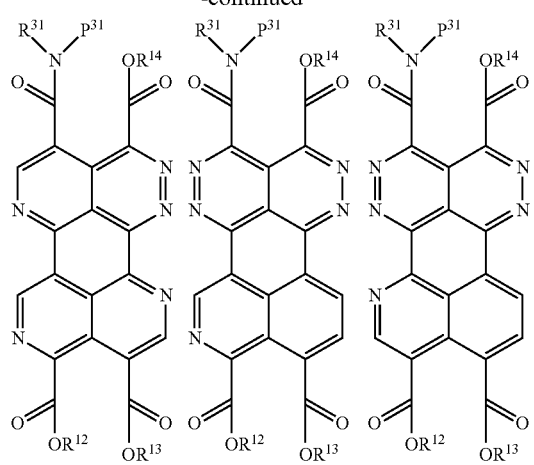
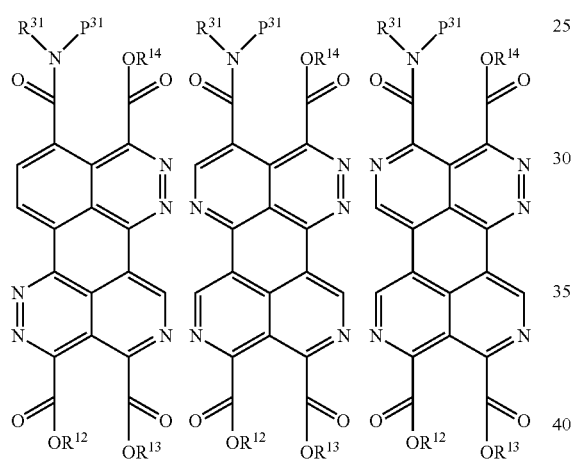
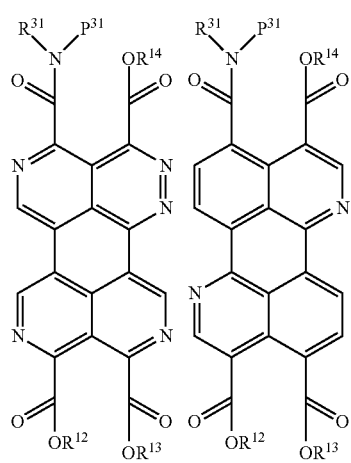
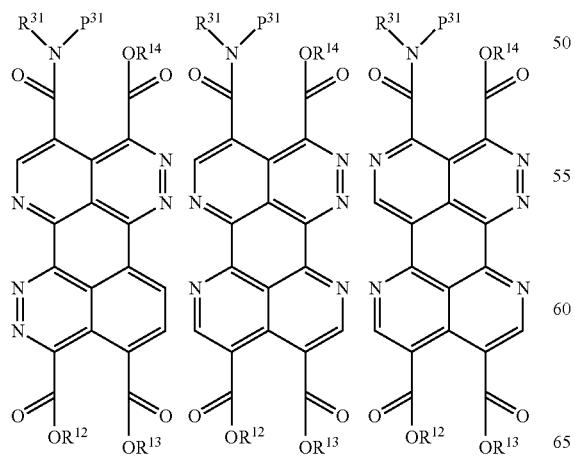
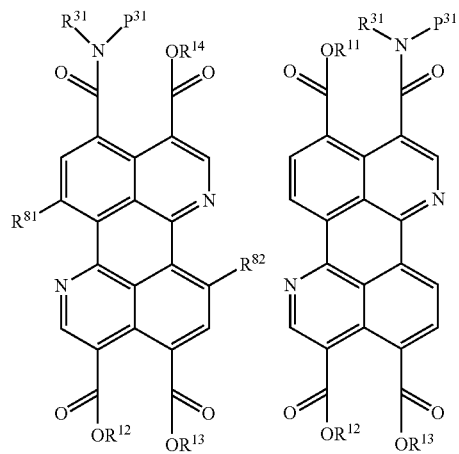

-continued

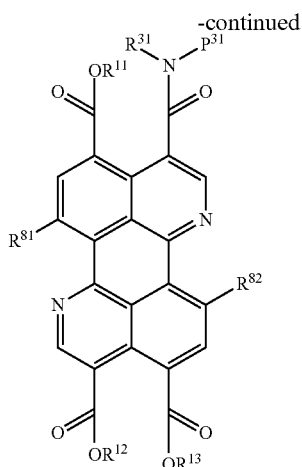

TABLE 2

| No. | R¹² | R¹³ | R¹⁴ or R¹¹ | R³¹ | P³¹ |
|---|---|---|---|---|---|
| (4)-1 | Me | 2,4,6-trichlorophenyl | Me | 2-phenylethyl | p-methoxybenzyl |
| (4)-2 | Me | 2,4,6-trichlorophenyl | Me | 2-phenylethyl | 2-nitrobenzenesulfonyl |
| (4)-3 | Me | 2,4,6-trichlorophenyl | Me | 2-phenylethyl | 2-nitrobenzenesulfonyl |
| (4)-4 | Me | 2,4,6-trichlorophenyl | Me | 2-phenylethyl | 2,4-dinitrobenzeneslufonyl |
| (4)-5 | Me | 2,4,6-trichlorophenyl | Me | 2-phenylethyl | tert-butoxycarbonyl |
| (4)-6 | Me | 2,4,6-trichlorophenyl | Me | 2-phenylethyl | allyloxycarbonyl |
| (4)-7 | Me | 2,4,6-trichlorophenyl | Me | 2-phenylethyl | Benzyloxycarbonyl |
| (4)-8 | Me | 2,4,6-trichlorophenyl | Me | 2-phenylethyl | methoxycarbonyl |
| (4)-9 | Me | 2,4,6-trichlorophenyl | Me | 2-phenylethyl | Trichloromethylcarbonyl |
| (4)-10 | Me | 2,4,6-trichlorophenyl | Me | 2-phenylethyl | 9-fluorenylmethyloxycarbonyl |
| (4)-11 | Me | 2,4,6-trichlorophenyl | Me | 2-phenylethyl | 2-(trimethylsilyl)ethoxycarbonyl |
| (4)-12 | Me | 2,4,6-trichlorophenyl | Me | pentyl | p-methoxybenzyl |
| (4)-13 | Me | 2,4,6-trichlorophenyl | Me | octyl | p-methoxybenzyl |
| (4)-14 | Me | 2,4,6-trichlorophenyl | Me | 2-cyclohexylethyl | p-methoxybenzyl |
| (4)-15 | Me | 2,4,6-trichlorophenyl | Me | 2-(2-thienyl)ethyl | p-methoxybenzyl |
| (4)-16 | Me | 2,4,6-trichlorophenyl | Me | 1-methylpentyl | p-methoxybenzyl |
| (4)-17 | Me | phenyl | Me | 2-phenylethyl | p-methoxybenzyl |
| (4)-18 | Me | 4-nitrophenyl | Me | 2-phenylethyl | p-methoxybenzyl |
| (4)-19 | Me | 4-methoxyphenyl | Me | 2-phenylethyl | p-methoxybenzyl |
| (4)-20 | Me | 4-methylphenyl | Me | 2-phenylethyl | p-methoxybenzyl |
| (4)-21 | Me | 4-chlorophenyl | Me | 2-phenylethyl | p-methoxybenzyl |
| (4)-22 | Me | 3,4-dimethoxyphenyl | Me | 2-phenylethyl | p-methoxybenzyl |
| (4)-23 | Me | 2-methoxyphenyl | Me | 2-phenylethyl | p-methoxybenzyl |
| (4)-24 | Me | 4-tert-butylphenyl | Me | 2-phenylethyl | p-methoxybenzyl |
| (4)-25 | Me | 2,4,5-trichlorophenyl | Me | 2-phenylethyl | p-methoxybenzyl |
| (4)-26 | Me | perfluorophenyl | Me | 2-phenylethyl | p-methoxybenzyl |
| (4)-27 | Me | 2-chlorophenyl | Me | 2-phenylethyl | p-methoxybenzyl |
| (4)-28 | Me | 3-nitorophenyl | Me | 2-phenylethyl | p-methoxybenzyl |
| (4)-29 | Me | 3-chlorophenyl | Me | 2-phenylethyl | p-methoxybenzyl |
| (4)-30 | Me | 2,5-dimethylphenyl | Me | 2-phenylethyl | p-methoxybenzyl |
| (4)-31 | Me | 2-acetylphenyl | Me | 2-phenylethyl | p-methoxybenzyl |
| (4)-32 | Me | 3,4-dimethylphenyl | Me | 2-phenylethyl | p-methoxybenzyl |
| (4)-33 | Et | 2,4,6-trichlorophenyl | Et | 2-phenylethyl | p-methoxybenzyl |
| (4)-34 | Propyl | 2,4,6-trichlorophenyl | Propyl | 2-phenylethyl | p-methoxybenzyl |
| (4)-35 | isopropyl | 2,4,6-trichlorophenyl | Isopropyl | 2-phenylethyl | p-methoxybenzyl |
| (4)-36 | butyl | 2,4,6-trichlorophenyl | butyl | 2-phenylethyl | p-methoxybenzyl |
| (4)-37 | tert-butyl | 2,4,6-trichlorophenyl | tert-butyl | 2-phenylethyl | p-methoxybenzyl |
| (4)-38 | benzyl | 2,4,6-trichlorophenyl | benzyl | 2-phenylethyl | p-methoxybenzyl |
| (4)-39 | octyl | 2,4,6-trichlorophenyl | octyl | 2-phenylethyl | p-methoxybenzyl |
| (4)-40 | allyl | 2,4,6-trichlorophenyl | allyl | 2-phenylethyl | p-methoxybenzyl |
| (4)-41 | methoxyethyl | 2,4,6-trichlorophenyl | methoxyethyl | 2-phenylethyl | p-methoxybenzyl |
| (4)-42 | ethoxyethyl | 2,4,6-trichlorophenyl | Ethoxyethyl | 2-phenylethyl | p-methoxybenzyl |
| (4)-43 | 2-ethylhexyl | 2,4,6-trichlorophenyl | 2-ethylhexyl | 2-phenylethyl | p-methoxybenzyl |
| (4)-44 | isobutyl | 2,4,6-trichlorophenyl | isobutyl | 2-phenylethyl | p-methoxybenzyl |
| (4)-45 | hexyl | 2,4,6-trichlorophenyl | hexyl | 2-phenylethyl | p-methoxybenzyl |
| (4)-46 | cyclohexyl | 2,4,6-trichlorophenyl | Cyclohexyl | 2-phenylethyl | p-methoxybenzyl |
| (4)-47 | 2-phenylethyl | 2,4,6-trichlorophenyl | 2-phenylethyl | 2-phenylethyl | p-methoxybenzyl |
| (4)-48 | dodecyl | 2,4,6-trichlorophenyl | dodecyl | 2-phenylethyl | p-methoxybenzyl |
| (4)-49 | 2,2,2-trifluoromethyl | 2,4,6-trichlorophenyl | 2,2,2-trifluoromethyl | 2-phenylethyl | p-methoxybenzyl |
| (4)-50 | 2-(trimethylsilyl)ethyl | 2,4,6-trichlorophenyl | 2-(trimethylsilyl)ethyl | 2-phenylethyl | p-methoxybenzyl |
| (4)-51 | pentyl | 2,4,6-trichlorophenyl | pentyl | 2-phenylethyl | p-methoxybenzyl |
| (4)-52 | 2-bromoethyl | 2,4,6-trichlorophenyl | 2-bromoethyl | 2-phenylethyl | p-methoxybenzyl |
| (4)-53 | isopentyl | 2,4,6-trichlorophenyl | Isopentyl | 2-phenylethyl | p-methoxybenzyl |

TABLE 2-continued

| No. | $R^{12}$ | $R^{13}$ | $R^{14}$ or $R^{11}$ | $R^{31}$ | $P^{31}$ |
|---|---|---|---|---|---|
| (4)-54 | 2-chloroethyl | 2,4,6-trichlorophenyl | 2-chloroethyl | 2-phenylethyl | p-methoxybenzyl |
| (4)-55 | Me | 2,4,6-trichlorophenyl | Me | 2-phenylethyl | p-methoxybenzyl |
| (4)-56 | 2,4,6-trichlorophenyl | Me | Me | 2-phenylethyl | p-methoxybenzyl |
| (4)-57 | 2,4,6-trichlorophenyl | Me | Me | 2-phenylethyl | p-methoxybenzyl |
| (4)-58 | Me | 2,4,6-trichlorophenyl | Me | 2-phenylethyl | p-methoxybenzyl |
| (4)-59 | Me | 2,4,6-trichlorophenyl | Me | 2-phenylethyl | p-methoxybenzyl |
| (4)-60 | 2,4,6-trichlorophenyl | Me | Me | 2-phenylethyl | p-methoxybenzyl |
| (4)-61 | Me | 2,4,6-trichlorophenyl | Me | 2-phenylethyl | p-methoxybenzyl |
| (4)-62 | Me | 2,4,6-trichlorophenyl | 2,4,6-trichlorophenyl | 2-phenylethyl | p-methoxybenzyl |
| (4)-63 | Me | 2,4,6-trichlorophenyl | Me | 2-phenylethyl | p-methoxybenzyl |
| (4)-64 | Me | 2,4,6-trichlorophenyl | Me | 2-phenylethyl | p-methoxybenzyl |
| (4)-65 | 2,4,6-trichlorophenyl | Me | Me | 2-phenylethyl | p-methoxybenzyl |
| (4)-66 | Me | 2,4,6-trichlorophenyl | Me | 2-phenylethyl | p-methoxybenzyl |
| (4)-67 | Me | 2,4,6-trichlorophenyl | Me | 2-phenylethyl | benzyl |
| (4)-68 | Me | 2,4,6-trichlorophenyl | Me | 2-phenylethyl | 2-methoxybenzyl |
| (4)-69 | Me | 2,4,6-trichlorophenyl | Me | 2-phenylethyl | 2,4-dimethoxybenzyl |
| (4)-70 | Me | 2,4,6-trichlorophenyl | Me | 2-phenylethyl | 3,4,5-trimethoxybenzyl |
| (4)-71 | Me | 2,4,6-trichlorophenyl | Me | 2-phenylethyl | 3,4-dimethoxybenzyl |

Formula (6)

Examples of the compound represented by the formula (6) are shown below, but the compound represented by the formula (6) is not limited thereto.

(6)-1 to (6)-59 in Table below show combinations of $R^{11}$, $R^{14}$, $R^{31}$, $R^{51}$, and $P^{31}$ shown in each basic skeleton below. In Table below, "Me" represents a methyl group, and "Et" represents an ethyl group.

$R^{81}$ and $R^{82}$ in the basic skeletons shown below each independently represent a substituent selected from the group consisting of a hydrogen atom, a cyano group, a fluorine atom, a chlorine atom, a bromine atom, an iodine atom, a trifluoromethyl group, a trifluoromethoxy group, a trichloromethyl group, a trichloromethoxy group, a 2-thiazolyl group, a 5-thiazolyl group, a 2-thienyl group, a 3-thienyl group, a styryl group, a 2-thiazolylvinyl group, a 5-thiazolylvinyl group, a 2-thienylvinyl group, a 3-thienylvinyl group, a phenylethynyl group, a 2-thiazolylethynyl group, a 5-thiazolylethynyl group, a 2-thienylethynyl group, a 3-thienylethynyl group, a trimethylsilylethynyl group, a triethylsilylethynyl group, a triisopropylethynyl group, and a 1-octynyl group. Herein, at least one of $R^{81}$ or $R^{82}$ represents a group other than hydrogen.

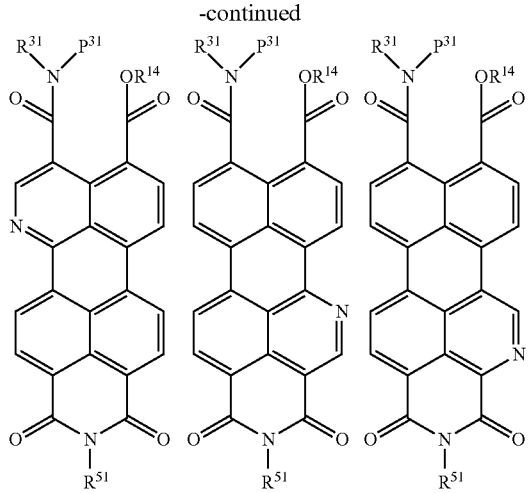

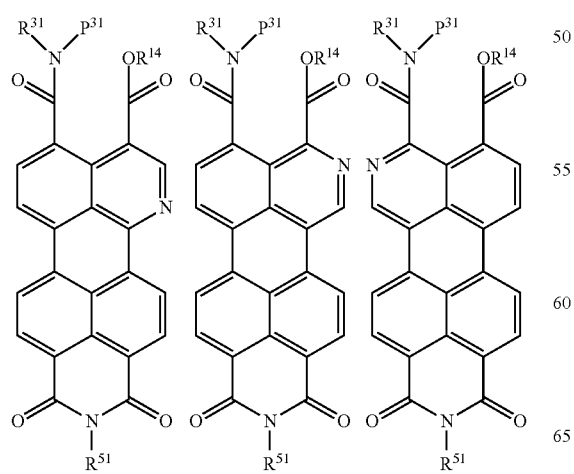

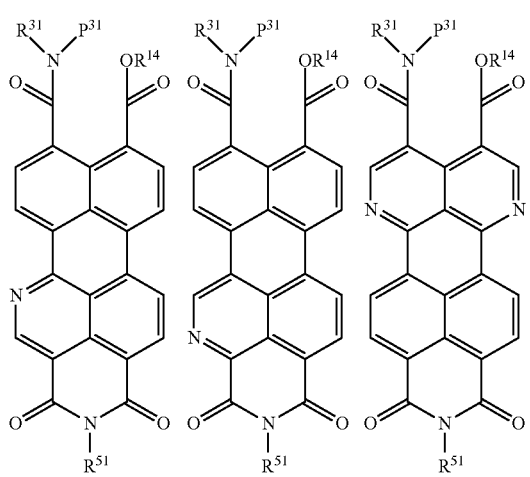

-continued
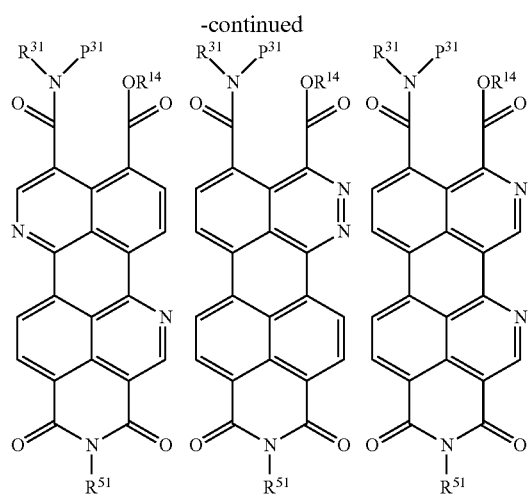
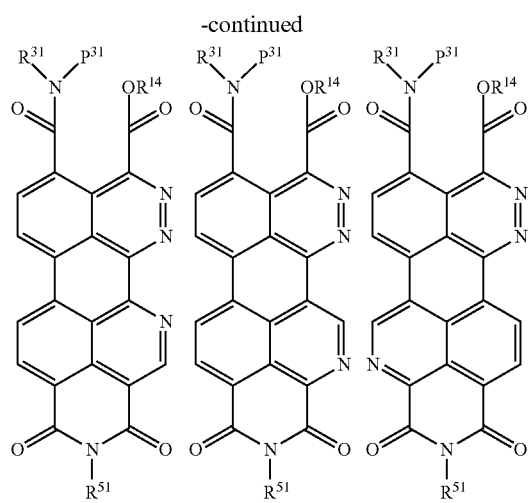
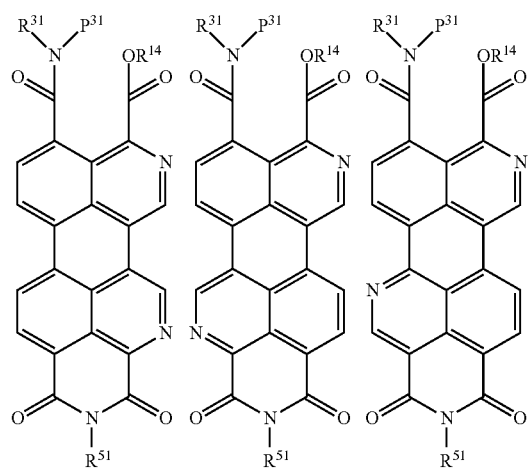
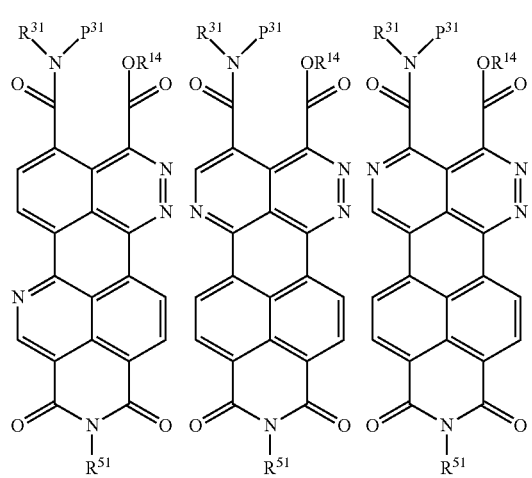
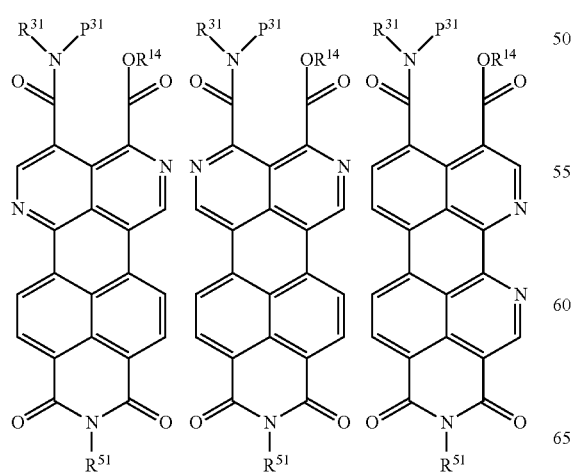
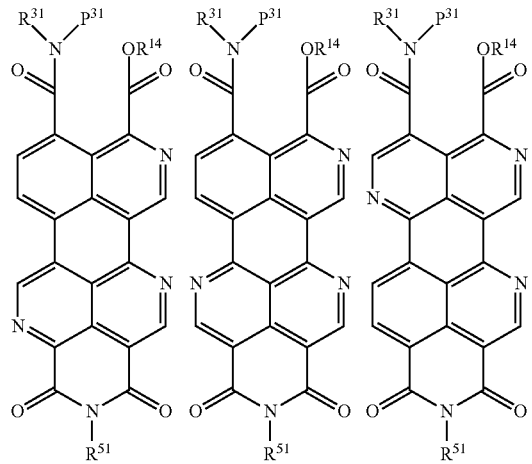

115
-continued
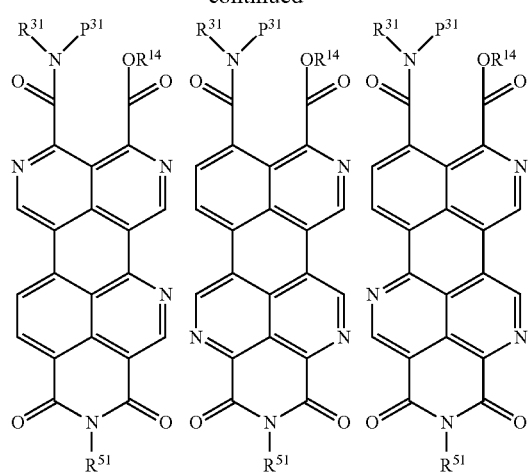
116
-continued
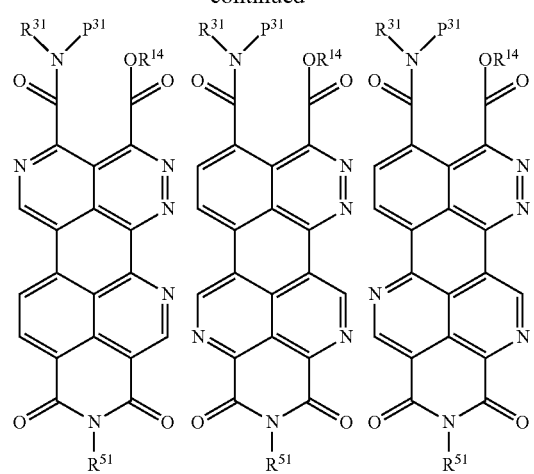
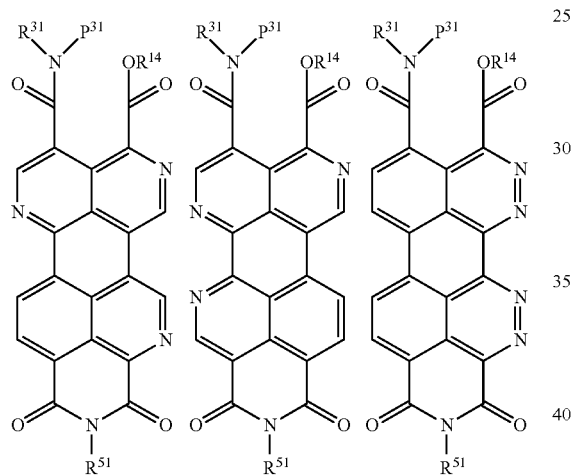
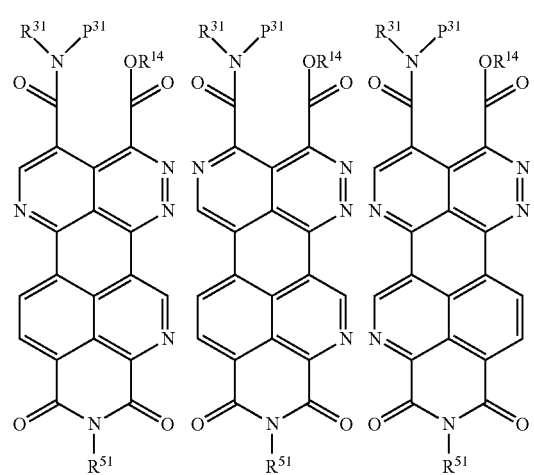
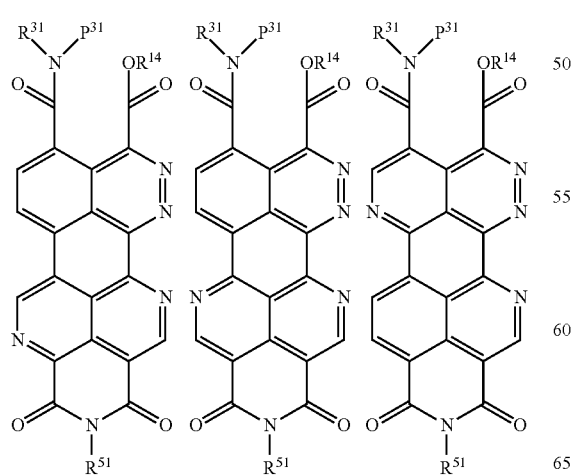
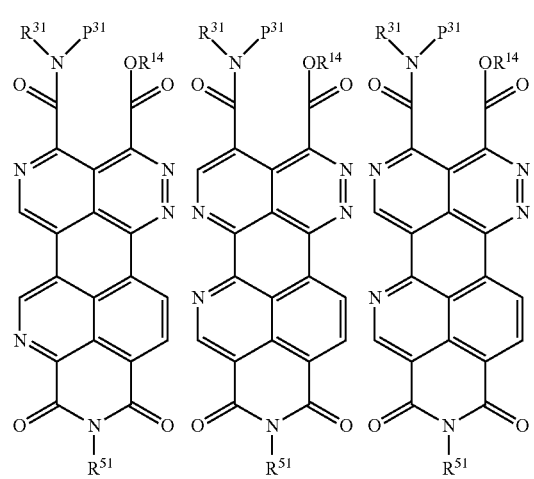

-continued
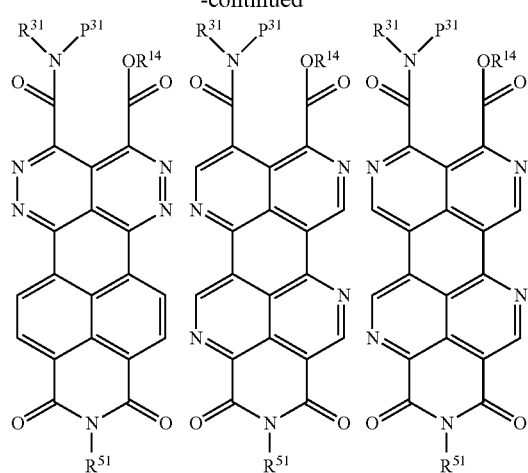
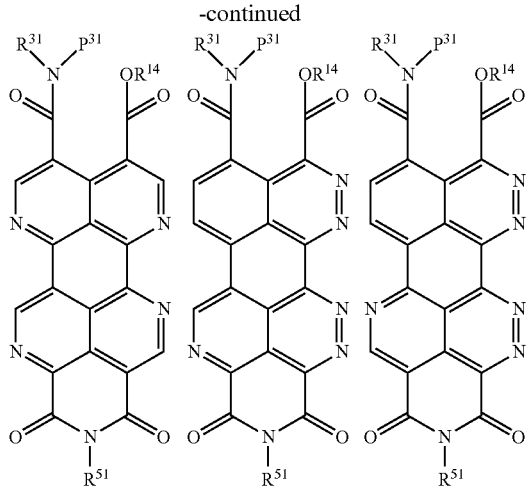
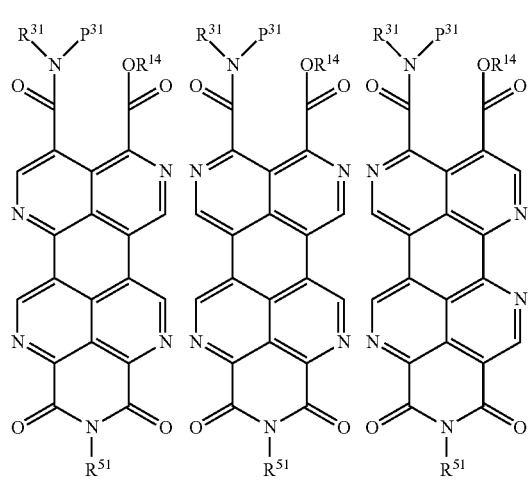
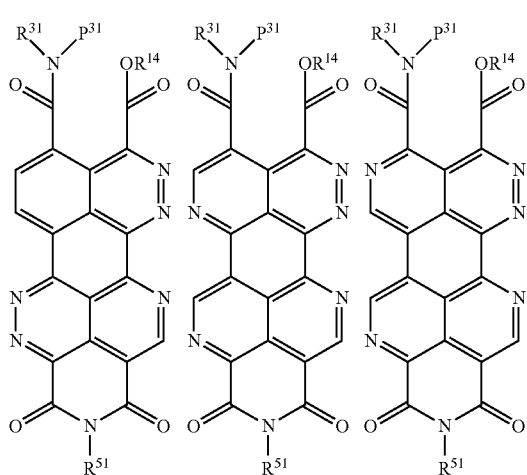
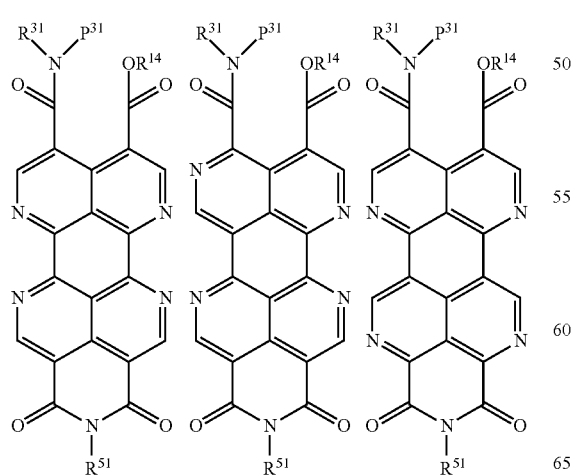
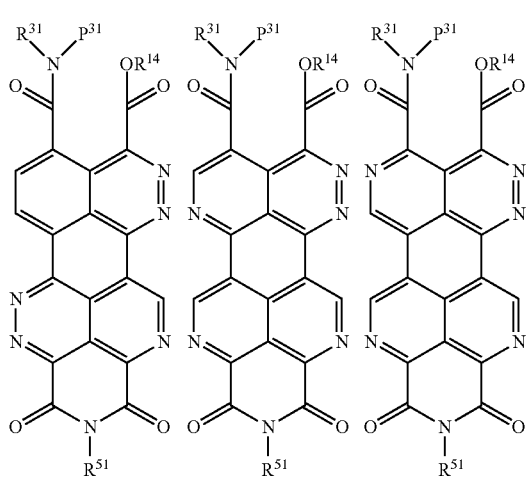

-continued

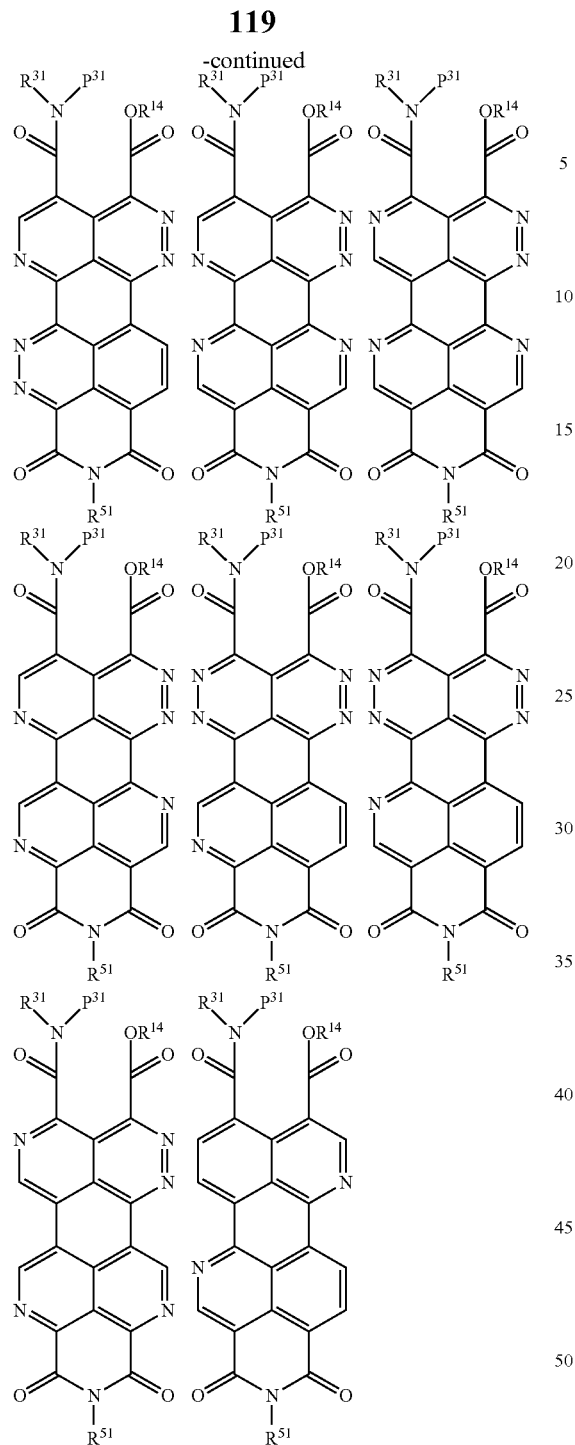

-continued

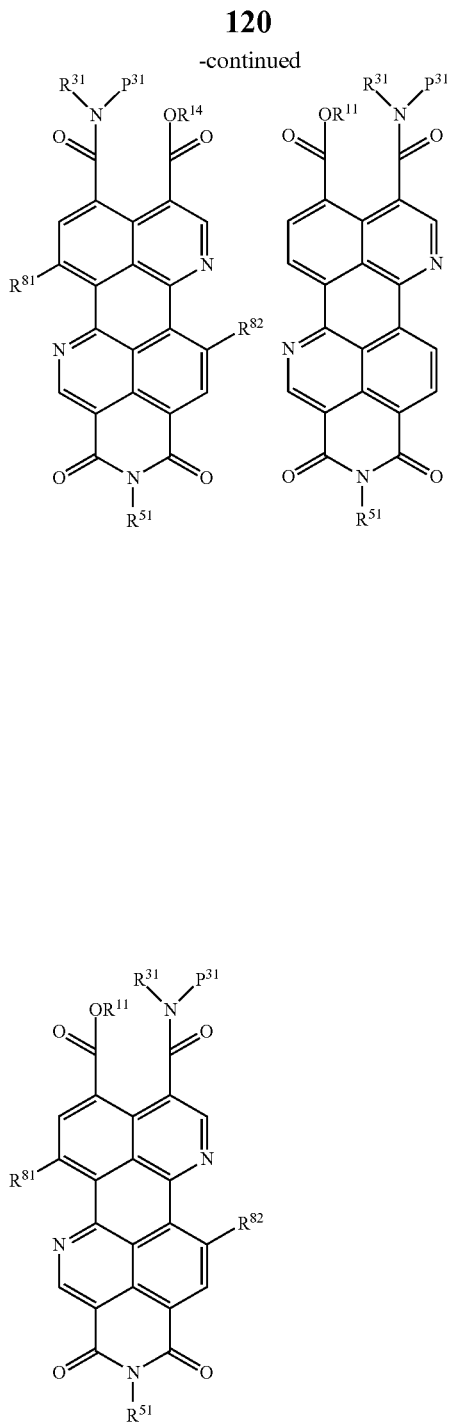

TABLE 3

| No. | $R^{14}$ or $R^{11}$ | $R^{51}$ | $R^{31}$ | $p^{31}$ |
|---|---|---|---|---|
| (6)-1 | Me | pentyl | 2-phenylethyl | p-methoxybenzyl |
| (6)-2 | Me | pentyl | 2-phenylethyl | 2-nitrobenzenesulfonyl |
| (6)-3 | Me | pentyl | 2-phenylethyl | 2-nitrobenzenesulfonyl |
| (6)-4 | Me | pentyl | 2-phenylethyl | 2,4-dinitrobenzeneslufonyl |
| (6)-5 | Me | pentyl | 2-phenylethyl | tert-butoxycarbonyl |
| (6)-6 | Me | pentyl | 2-phenylethyl | allyloxycarbonyl |
| (6)-7 | Me | pentyl | 2-phenylethyl | Benzyloxycarbonyl |
| (6)-8 | Me | pentyl | 2-phenylethyl | methoxycarbonyl |
| (6)-9 | Me | pentyl | 2-phenylethyl | Trichloromethylcarbonyl |
| (6)-10 | Me | pentyl | 2-phenylethyl | 9-fluorenylmethyloxycarbonyl |

TABLE 3-continued

| No. | $R^{14}$ or $R^{11}$ | $R^{51}$ | $R^{31}$ | $P^{31}$ |
|---|---|---|---|---|
| (6)-11 | Me | pentyl | 2-phenylethyl | 2-(trimethylsilyl)ethoxycarbonyl |
| (6)-12 | Me | 2-phenylethyl | pentyl | p-methoxybenzyl |
| (6)-13 | Me | 2-phenylethyl | octyl | p-methoxybenzyl |
| (6)-14 | Me | 2-(2-thienyl)ethyl | 2-cyclohexylethyl | p-methoxybenzyl |
| (6)-15 | Me | 2-cyclohexylethyl | 2-(2-thienyl)ethyl | p-methoxybenzyl |
| (6)-16 | Me | Phenyl | 1-methylpentyl | p-methoxybenzyl |
| (6)-17 | Me | Me | 2-phenylethyl | p-methoxybenzyl |
| (6)-18 | Me | Ethyl | 2-phenylethyl | p-methoxybenzyl |
| (6)-19 | Me | propyl | 2-phenylethyl | p-methoxybenzyl |
| (6)-20 | Me | butyl | 2-phenylethyl | p-methoxybenzyl |
| (6)-21 | Me | hexyl | 2-phenylethyl | p-methoxybenzyl |
| (6)-22 | Me | heptyl | 2-phenylethyl | p-methoxybenzyl |
| (6)-23 | Me | octyl | 2-phenylethyl | p-methoxybenzyl |
| (6)-24 | Me | 2-ethylhexyl | 2-phenylethyl | p-methoxybenzyl |
| (6)-25 | Me | nonyl | 2-phenylethyl | p-methoxybenzyl |
| (6)-26 | Me | decyl | 2-phenylethyl | p-methoxybenzyl |
| (6)-27 | Me | 3,7-dimethyloctyl | 2-phenylethyl | p-methoxybenzyl |
| (6)-28 | Me | undecyl | 2-phenylethyl | p-methoxybenzyl |
| (6)-29 | Me | 1-methylpentyl | 2-phenylethyl | p-methoxybenzyl |
| (6)-30 | Me | p-butylphenyl | 2-phenylethyl | p-methoxybenzyl |
| (6)-31 | Me | 2-ethylhexyl | 2-phenylethyl | p-methoxybenzyl |
| (6)-32 | Me | 2-perfluorophenylethyl | 2-phenylethyl | p-methoxybenzyl |
| (6)-33 | Et | 2-perfluorophenylethyl | 2-phenylethyl | p-methoxybenzyl |
| (6)-34 | Propyl | 2-(2-thienyl)ethyl | 2-phenylethyl | p-methoxybenzyl |
| (6)-35 | Isopropyl | 2-cyclohexylethyl | 2-phenylethyl | p-methoxybenzyl |
| (6)-36 | butyl | dodecyl | 2-phenylethyl | p-methoxybenzyl |
| (6)-37 | tert-butyl | Tridecyl | 2-phenylethyl | p-methoxybenzyl |
| (6)-38 | benzyl | tetradecyl | 2-phenylethyl | p-methoxybenzyl |
| (6)-39 | octyl | butoxypropyl | 2-phenylethyl | p-methoxybenzyl |
| (6)-40 | allyl | methoxylhexyl | 2-phenylethyl | p-methoxybenzyl |
| (6)-41 | methoxyethyl | pentyl | 2-phenylethyl | p-methoxybenzyl |
| (6)-42 | Ethoxyethyl | pentyl | 2-phenylethyl | p-methoxybenzyl |
| (6)-43 | 2-ethylhexyl | pentyl | 2-phenylethyl | p-methoxybenzyl |
| (6)-44 | isobutyl | pentyl | 2-phenylethyl | p-methoxybenzyl |
| (6)-45 | hexyl | pentyl | 2-phenylethyl | p-methoxybenzyl |
| (6)-46 | Cyclohexyl | pentyl | 2-phenylethyl | p-methoxybenzyl |
| (6)-47 | 2-phenylethyl | pentyl | 2-phenylethyl | p-methoxybenzyl |
| (6)-48 | dodecyl | pentyl | 2-phenylethyl | p-methoxybenzyl |
| (6)-49 | 2,2,2-trifluoromethyl | pentyl | 2-phenylethyl | p-methoxybenzyl |
| (6)-50 | 2-(trimethylsilyl)ethyl | pentyl | 2-phenylethyl | p-methoxybenzyl |
| (6)-51 | pentyl | pentyl | 2-phenylethyl | p-methoxybenzyl |
| (6)-52 | 2-bromoethyl | pentyl | 2-phenylethyl | p-methoxybenzyl |
| (6)-53 | Isopentyl | pentyl | 2-phenylethyl | p-methoxybenzyl |
| (6)-54 | 2-chloroethyl | pentyl | 2-phenylethyl | p-methoxybenzyl |
| (6)-55 | Me | pentyl | 2-phenylethyl | benzyl |
| (6)-56 | Me | pentyl | 2-phenylethyl | 2-methoxybenzyl |
| (6)-57 | Me | pentyl | 2-phenylethyl | 2,4-dimethoxybenzyl |
| (6)-58 | Me | pentyl | 2-phenylethyl | 3,4,5-trimethoxybenzyl |
| (6)-59 | Me | pentyl | 2-phenylethyl | 3,4-dimethoxybenzyl |

Formula (7)

Examples of the compound represented by the formula (7) are shown below, but the compound represented by the formula (7) is not limited thereto. (7)-1 to (7)-54 in Table below show combinations of $R^{11}$, $R^{14}$, $R^{11}$, and $R^{51}$ shown in each basic skeleton below. In Table below, "Me" represents a methyl group, and "Et" represents an ethyl group.

$R^{81}$ and $R^{82}$ in the basic skeletons shown below each independently represent a substituent selected from the group consisting of a hydrogen atom, a cyano group, a fluorine atom, a chlorine atom, a bromine atom, an iodine atom, a trifluoromethyl group, a trifluoromethoxy group, a trichloromethyl group, a trichloromethoxy group, a 2-thiazolyl group, a 5-thiazolyl group, a 2-thienyl group, a 3-thienyl group, a styryl group, a 2-thiazolylvinyl group, a 5-thiazolylvinyl group, a 2-thienylvinyl group, a 3-thienylvinyl group, a phenylethynyl group, a 2-thiazolylethynyl group, a 5-thiazolylethynyl group, a 2-thienylethynyl group, a 3-thienylethynyl group, a trimethylsilylethynyl group, a triethylsilylethynyl group, a triisopropylethynyl group, and a 1-octynyl group. Herein, at least one of $R^{81}$ or $R^{82}$ represents a group other than hydrogen.

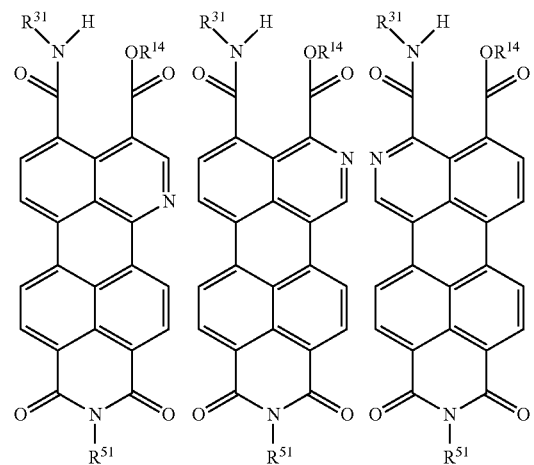

123
-continued
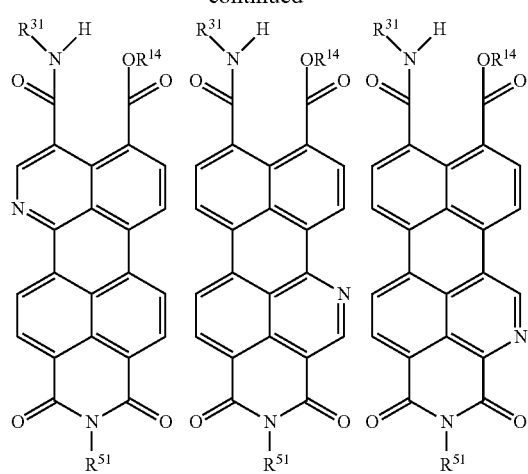
124
-continued
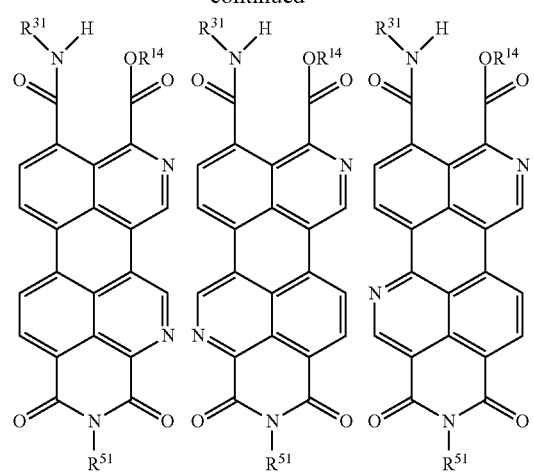
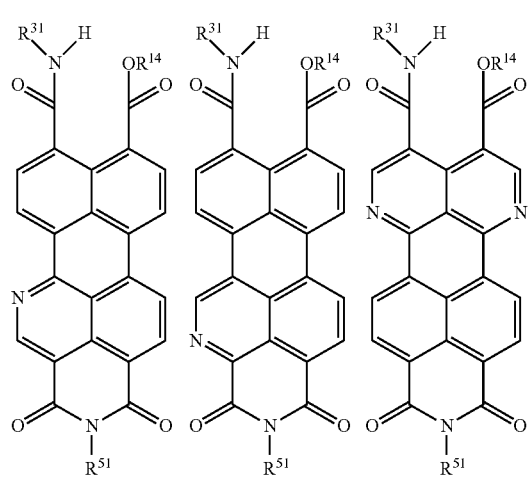
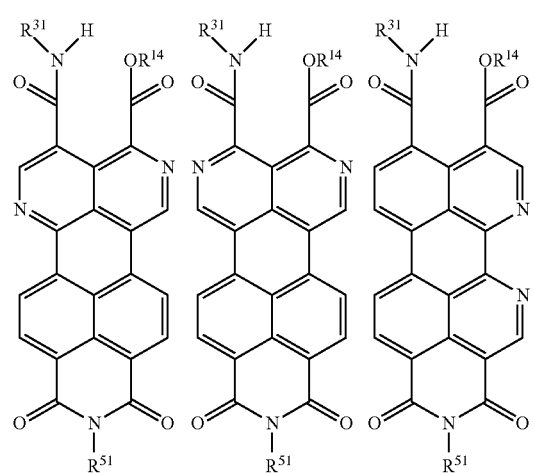
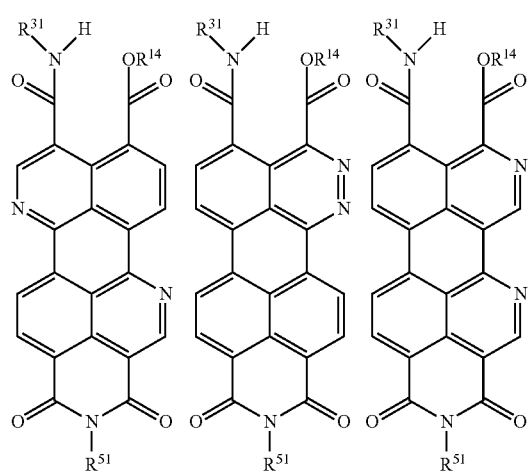
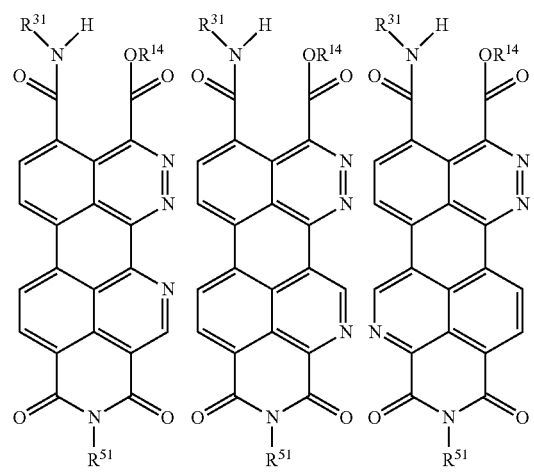

125
126
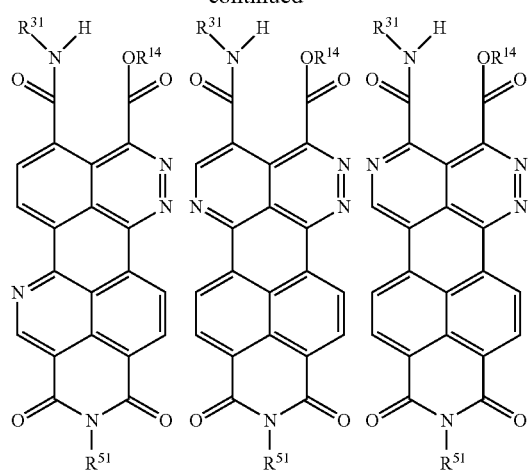
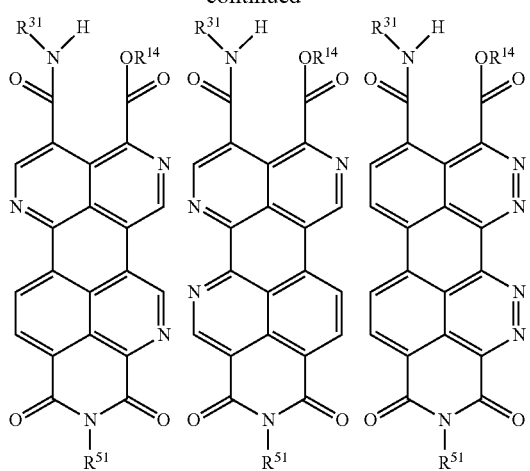
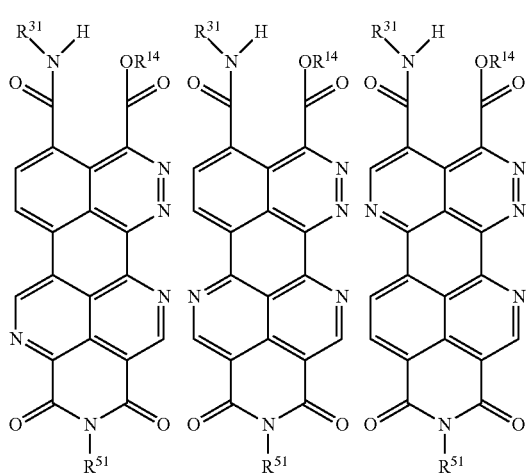
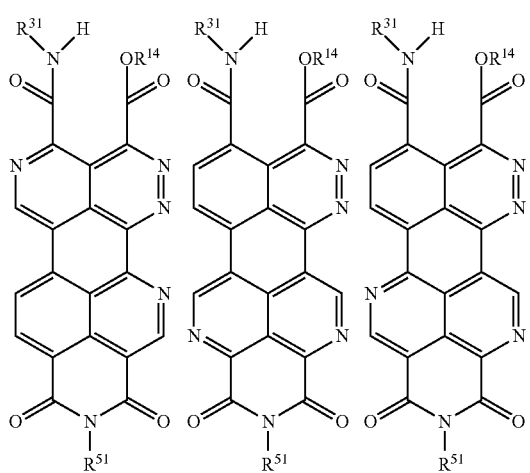

127
-continued
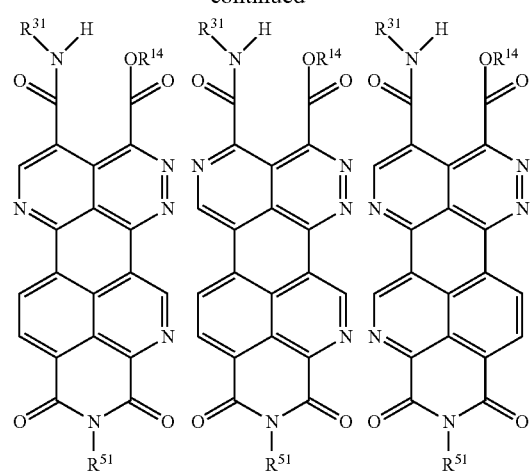
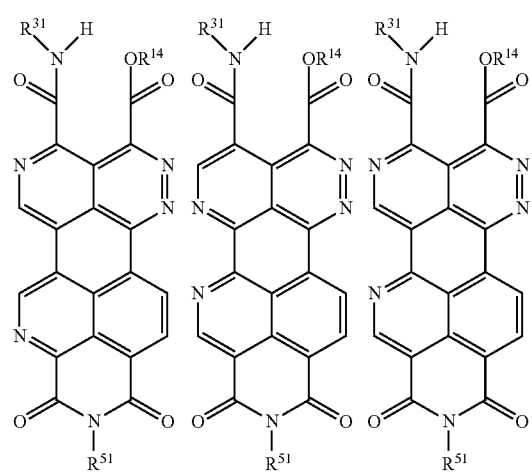
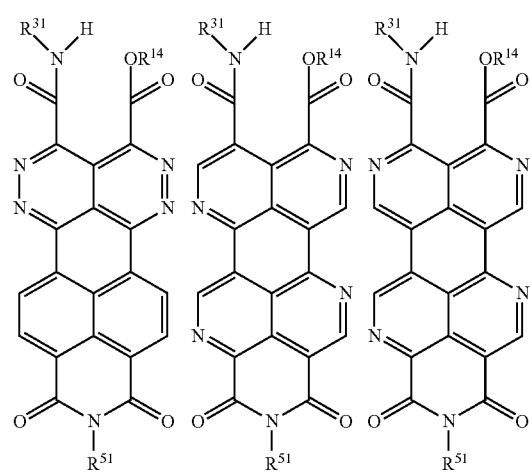
128
-continued
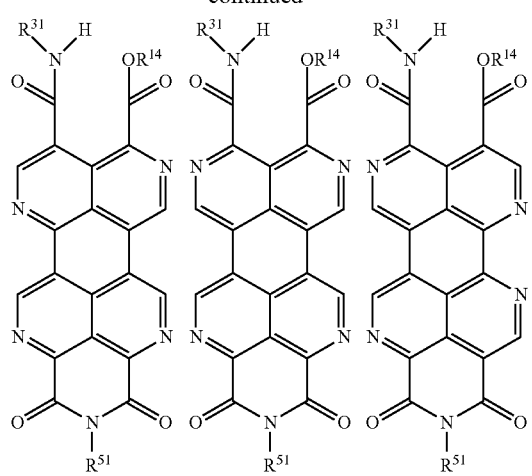
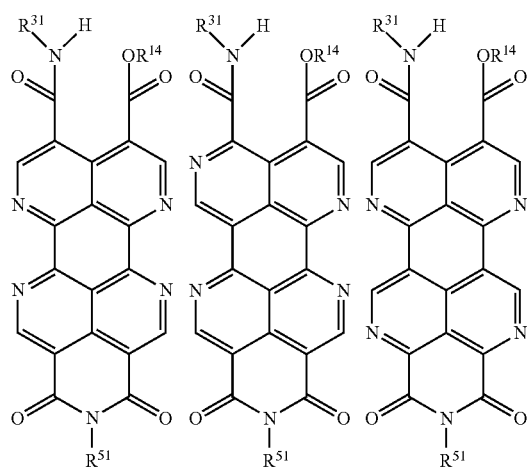
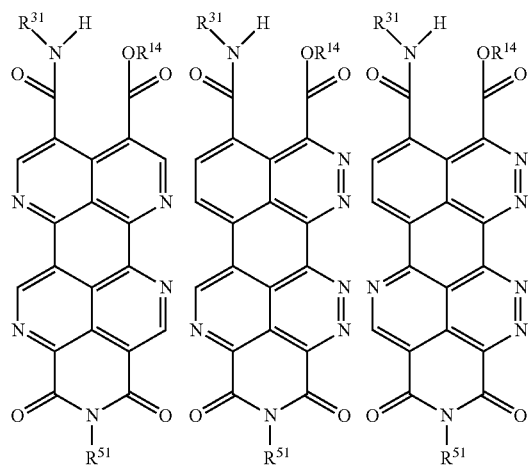

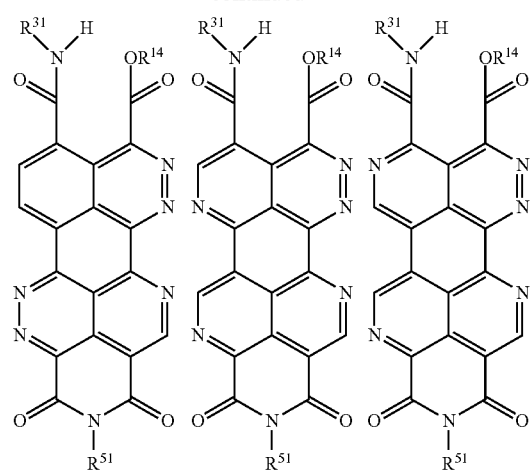
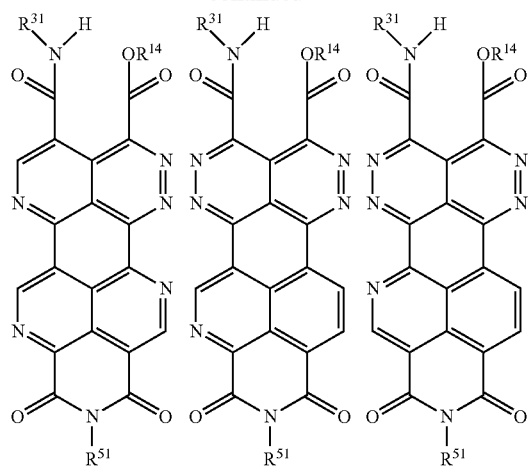
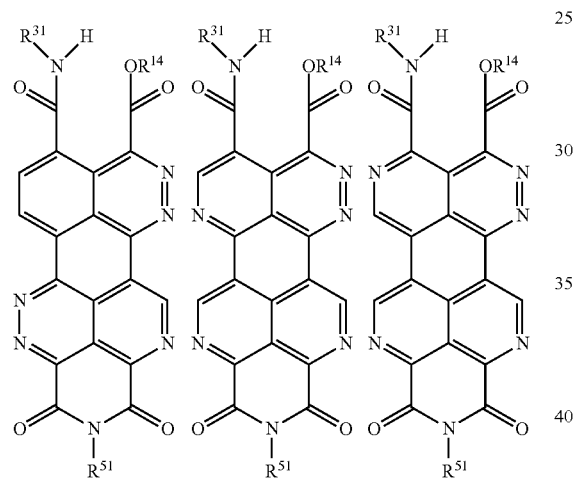
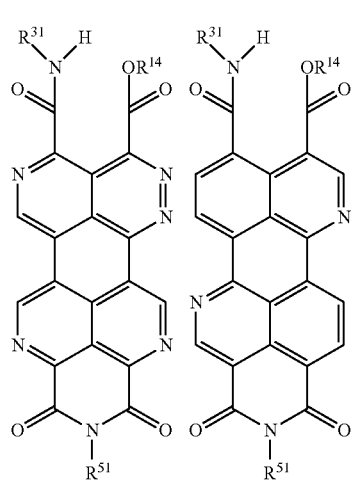
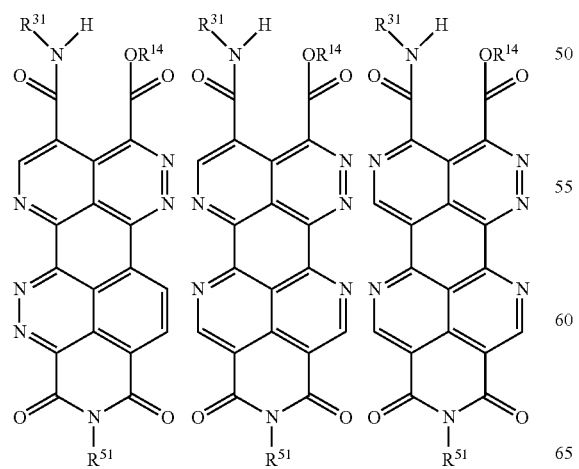
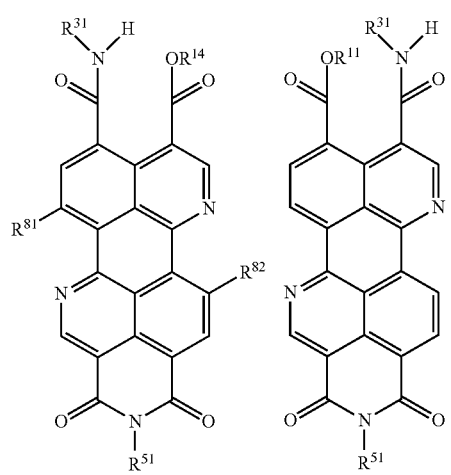

-continued

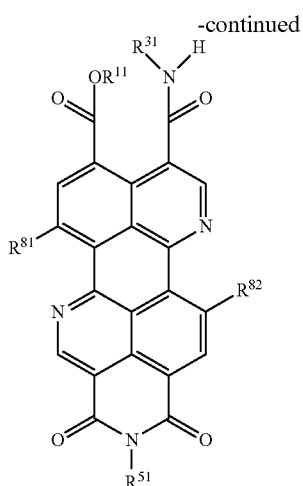

TABLE 4

| No. | $R^{14}$ or $R^{11}$ | $R^{51}$ | $R^{31}$ |
| --- | --- | --- | --- |
| (7)-1 | Me | pentyl | 2-phenylethyl |
| (7)-2 | Me | pentyl | 2-(2-thienyl)ethyl |
| (7)-3 | Me | pentyl | 2-pentafluorophenylethyl |
| (7)-4 | Me | pentyl | benzyl |
| (7)-5 | Me | pentyl | 3-propylphenyl |
| (7)-6 | Me | pentyl | octyl |
| (7)-7 | Me | pentyl | decyl |
| (7)-8 | Me | pentyl | dodecyl |
| (7)-9 | Me | 2-phenylethyl | 2-cyclohexylethyl |
| (7)-10 | Me | 2-phenylethyl | 1-methylpentyl |
| (7)-11 | Me | 2-phenylethyl | 1-methyloctyl |
| (7)-12 | Me | 2-phenylethyl | pentyl |
| (7)-13 | Me | 2-perfluorophenylethyl | octyl |
| (7)-14 | Me | 2-(2-thienyl)ethyl | 2-cyclohexylethyl |
| (7)-15 | Me | 2-cyclohexylethyl | 2-(2-thienyl)ethyl |
| (7)-16 | Me | Phenyl | 1-methylpentyl |
| (7)-17 | Me | Me | 2-phenylethyl |
| (7)-18 | Me | Ethyl | 2-phenylethyl |
| (7)-19 | Me | propyl | 2-phenylethyl |
| (7)-20 | Me | butyl | 2-phenylethyl |
| (7)-21 | Me | hexyl | 2-phenylethyl |
| (7)-22 | Me | heptyl | 2-phenylethyl |
| (7)-23 | Me | octyl | 2-phenylethyl |
| (7)-24 | Me | 2-ethylhexyl | 2-phenylethyl |
| (7)-25 | Me | nonyl | 2-phenylethyl |
| (7)-26 | Me | decyl | 2-phenylethyl |
| (7)-27 | Me | 3,7-dimethyloctyl | 2-phenylethyl |
| (7)-28 | Me | undecyl | 2-phenylethyl |
| (7)-29 | Me | 1-methylpentyl | 2-phenylethyl |
| (7)-30 | Me | p-butylphenyl | 2-phenylethyl |
| (7)-31 | Me | 2-ethylhexyl | 2-phenylethyl |
| (7)-32 | Me | 2-perfluorophenylethyl | 2-phenylethyl |
| (7)-33 | Et | 2-perfluorophenylethyl | 2-phenylethyl |
| (7)-34 | propyl | 2-(2-thienyl)ethyl | 2-phenylethyl |
| (7)-35 | Isopropyl | 2-cyclohexylethyl | 2-phenylethyl |
| (7)-36 | butyl | dodecyl | 2-phenylethyl |
| (7)-37 | tert-butyl | Tridecyl | 2-phenylethyl |
| (7)-38 | benzyl | tetradecyl | 2-phenylethyl |
| (7)-39 | octyl | butoxypropyl | 2-phenylethyl |
| (7)-40 | allyl | methoxylhexyl | 2-phenylethyl |
| (7)-41 | methoxyethyl | pentyl | 2-phenylethyl |
| (7)-42 | Ethoxyethyl | pentyl | 2-phenylethyl |
| (7)-43 | 2-ethylhexyl | pentyl | 2-phenylethyl |
| (7)-44 | isobutyl | pentyl | 2-phenylethyl |
| (7)-45 | hexyl | pentyl | 2-phenylethyl |
| (7)-46 | Cyclohexyl | pentyl | 2-phenylethyl |
| (7)-47 | 2-phenylethyl | pentyl | 2-phenylethyl |
| (7)-48 | dodecyl | pentyl | 2-phenylethyl |
| (7)-49 | 2,2,2-trifluoromethyl | pentyl | 2-phenylethyl |
| (7)-50 | 2-(trimethylsilyl)ethyl | pentyl | 2-phenylethyl |
| (7)-51 | pentyl | pentyl | 2-phenylethyl |
| (7)-52 | 2-bromoethyl | pentyl | 2-phenylethyl |

TABLE 4-continued

| No. | $R^{14}$ or $R^{11}$ | $R^{51}$ | $R^{31}$ |
|---|---|---|---|
| (7)-53 | Isopentyl | pentyl | 2-phenylethyl |
| (7)-54 | 2-chloroethyl | pentyl | 2-phenylethyl |

Step Y1

The step Y1 is a step of reacting a compound represented by formula (1) with a first amine compound represented by formula (3) to obtain a compound represented by formula (4) below. Specifically, the step Y1 is preferably a step of heating a composition including a compound represented by formula (1) and a first amine compound represented by formula (3) to obtain a compound represented by formula (4).

Through the above step Y1, an amidation reaction of —$COOR^{11}$, —$COOR^{12}$, —$COOR^{13}$, and/or —$COOR^{14}$ in the compound represented by the formula (1) with the first amine compound can be caused. If necessary, the obtained crude product is purified by separation and purification means including washing, extraction, drying, filtration, concentration, recrystallization, reprecipitation, crystallization, centrifugation, adsorption, and/or column purification to obtain the compound represented by the formula (4).

The amount of the first amine compound used and represented by the formula (3) is preferably 1.0 to 10 molar equivalents and more preferably 1.0 to 5.0 molar equivalents relative to 1 molar equivalent of the compound represented by the formula (1).

The composition may include a solvent.

A single solvent may be used, or two or more solvents may be used in a mixed manner.

Non-limiting examples of the solvent include hydrocarbon solvents, ether solvents, amide solvents, alcohol solvents, nitrile-based solvents, and sulfoxide solvents.

Examples of the hydrocarbon solvent include pentane, hexane, heptane, octane, decane, toluene, ethylbenzene, xylene, diethylbenzene, fluorobenzene, trifluoromethylbenzene, chlorobenzene, chloroform, dichloromethane, 1,1,2,2-tetrachloroethane, 1,1,2-trichloroethane, dichlorobenzene, trichlorobenzene, mesitylene, amylbenzene, decalin, 1-methylnaphthalene, 1-ethylnaphthalene, 1-chloronaphthalene, 1-fluoronaphthalene, 1,6-dimethylnaphthalene, benzonitrile, nitrobenzene, and tetralin.

Examples of the ether solvent include anisole, diethyl ether, dibutyl ether, diisopropyl ether, cyclopentyl methyl ether, diphenyl ether, tetrahydropyran, dioxane, dimethoxyethane, diethoxyethane, and tetrahydrofuran.

Examples of the amide solvent include N,N-dimethylformamide, N-methylpyrrolidone, N-ethylpyrrolidone, 1,3-dimethyl-2-imidazolidinone, and N,N-dimethylacetamide.

Examples of the alcohol solvent include methanol, ethanol, propanol, isopropanol, amyl alcohol, benzyl alcohol, ethylene glycol, diethylene glycol, propylene glycol, and glycerol.

Examples of the nitrile-based solvent include acetonitrile, propionitrile, and benzonitrile.

Examples of the sulfoxide solvent include dimethyl sulfoxide and sulfolane.

In particular, the solvent is preferably a solvent having a boiling point of 70° C. or higher and more preferably a solvent having a boiling point of 90° C. or higher.

Examples of the solvent having a boiling point of 90° C. or higher include heptane, octane, decane, toluene, ethylbenzene, xylene, diethylbenzene, fluorobenzene, trifluoromethylbenzene, chlorobenzene, dichlorobenzene, trichlorobenzene, mesitylene, amylbenzene, decalin, 1-methylnaphthalene, 1-ethylnaphthalene, 1-chloronaphthalene, 1-fluoronaphthalene, 1,6-dimethylnaphthalene, 1,1,2,2-tetrachloroethane, 1,1,2-trichloroethane, nitrobenzene, benzonitrile, tetralin, anisole, dibutyl ether, cyclopentyl methyl ether, diphenyl ether, dioxane, diethoxyethane, N,N-dimethylformamide, N-methylpyrrolidone, N-ethylpyrrolidone, 1,3-dimethyl-2-imidazolidinone, N,N-dimethylacetamide, 1-propanol, 1-butanol, isobutyl alcohol, 2-butanol, amyl alcohol, benzyl alcohol, ethylene glycol, diethylene glycol, propylene glycol, glycerol, dimethyl sulfoxide, and sulfolane.

When the composition includes a solvent, the content of the solvent is preferably 75.0 to 99.9 mass % and more preferably 80.0 to 98.0 mass % relative to the total mass of the composition.

The reaction temperature is not particularly limited, but is preferably 20° C. to 250° C. and more preferably 50° C. to 200° C.

The reaction time varies depending on the solvent used and the reaction conditions including a reaction temperature, but is normally 1 to 24 hours and preferably 1 to 20 hours.

Step Y2

The step Y2 is a step of reacting the compound represented by the formula (4) with a first amine compound represented by formula (5) to obtain a compound represented by formula (6). Specifically, the step Y2 is preferably a step of heating a composition including the compound represented by the formula (4) and a second amine compound represented by formula (5) to obtain a compound represented by formula (6).

Through the step Y2, an amidation/imidation reaction between two adjacent ester groups (—$COOR^{12}$ and —$COOR^{13}$) in the compound represented by the formula (4) and the second amine compound is caused to form an imide bond.

The amount of the second amine compound used and represented by the formula (5) is preferably 1.0 to 10.0 molar equivalents and more preferably 1.0 to 5.0 molar equivalents relative to 1 molar equivalent of the compound represented by the formula (4).

The composition may include a solvent.

A single solvent may be used, or two or more solvents may be used in a mixed manner.

The solvent is not particularly limited. For example, the solvents described in the step Y1 are exemplified, and preferred forms thereof are also the same.

When the composition includes a solvent, the content of the solvent is preferably 75.0 to 99.9 mass % and more preferably 80.0 to 98.0 mass % relative to the total mass of the composition.

The reaction temperature is not particularly limited, but is preferably 20° C. to 250° C. and more preferably 50° C. to 200° C.

The reaction time varies depending on the solvent used and the reaction conditions including a reaction temperature, but is normally 1 to 24 hours and preferably 1 to 20 hours.

After completion of the reaction, if necessary, the obtained compound represented by the formula (6) may be purified by separation and purification means including washing, extraction, drying, filtration, concentration, recrystallization, reprecipitation, crystallization, centrifugation, column purification, adsorption, and/or sublimation purification.

Step Y3

The step Y3 is a step of removing (deprotecting) $P^{31}$ serving as a protecting group from the compound represented by the formula (6) to obtain a compound represented by formula (7).

Examples of the deprotection method include a method for performing deprotection using a deprotecting reagent under acidic or basic conditions, a method for performing deprotection using an oxidizing agent, a method for performing deprotection using a Lewis acid, a method for performing deprotection using a nucleophile, a method for causing a reductive deprotection reaction (hydrogenolysis) in the presence of a metal catalyst, and a method for performing deprotection using zinc under acidic conditions.

Examples of the deprotecting reagent under acidic conditions include acids such as hydrochloric acid, hydrogen bromide/acetic acid, sulfuric acid, formic acid, methanesulfonic acid, p-toluenesulfonic acid, and trifluoroacetic acid. In particular, when the protecting group represented by $P^{31}$ is a (hetero)arylmethyl group such as a methoxybenzyl group, sulfonic acids such as sulfuric acid, methanesulfonic acid, and p-toluenesulfonic acid are preferred.

The deprotecting reagent under basic conditions may be either an inorganic base or an organic base. Examples of the inorganic base include hydroxides of alkali metals or alkaline earth metals, carbonates, and hydrogencarbonates. Examples of the organic base include amines such as triethylamine, diisopropylethylamine, piperidine, N-methylmorpholine, dimethylaminopyridine, DBU (1,8-diazabicyclo[5.4.0]-7-undecene), and DBN (1,5-diazabicyclo[4.3.0]non-5-ene; pyridine; and imidazole.

An example of the oxidizing agent is 2,3-dichloro-5,6-dicyano-p-benzoquinone.

Examples of the Lewis acid include trimethylsilyl trifluoromethanesulfonate, iodotrimethylsilane, boron trichloride, and tin(IV) chloride.

Examples of the nucleophile include thiol compounds (e.g., benzenethiol), cesium fluoride, and fluoride ions such as tetraalkylammonium fluoride.

Examples of the metal catalyst used as a deprotecting reagent include palladium catalysts (e.g., palladium carbon, palladium carbon hydroxide, and palladium oxide), platinum catalysts (e.g., platinum carbon and platinum oxide), rhodium catalysts (e.g., rhodium carbon), and ruthenium catalysts (e.g., ruthenium carbon).

The deprotection reaction is preferably performed in the presence of a solvent.

A single solvent may be used, or two or more solvents may be used in a mixed manner.

The solvent is not particularly limited. For example, the solvents described in the step Y1 are exemplified. Alternatively, an ester solvent (e.g., methyl acetate, ethyl acetate, propyl acetate, butyl acetate, and isobutyl acetate) or a ketone solvent (e.g., acetone, 2-butanone, methyl isobutyl ketone, diisobutyl ketone, cyclohexanone, isophorone, and acetophenone) may be used. In the case of using an acid and a base, water alone or a mixture of water and a solvent may be used.

The step Y3 and a step Y4 described later may be simultaneously performed. Specifically, for example, a method in which a composition including a deprotecting reagent, a compound represented by formula (6), and a solvent is heated is employed.

Step Y4

The step Y4 is a step of obtaining a compound represented by formula (2) from the compound represented by the formula (7). Specifically, the step Y4 is preferably a step of heating a composition including the compound represented by the formula (7) to obtain a compound represented by formula (2).

Through the above step Y4, an imidation reaction between —$COOR^{14}$ and an amide group in the compound represented by the formula (7) is caused to obtain a compound represented by formula (2).

The composition may include a solvent.

A single solvent may be used, or two or more solvents may be used in a mixed manner.

The solvent is not particularly limited. For example, the solvents described in the step Y1 are exemplified, and preferred forms thereof are also the same.

When the composition includes a solvent, the content of the solvent is preferably 75.0 to 99.9 mass % and more preferably 80.0 to 98.0 mass % relative to the total mass of the composition.

The reaction temperature is not particularly limited, but is preferably 20° C. to 250° C. and more preferably 50° C. to 200° C.

The reaction time varies depending on the solvent used and the reaction conditions including a reaction temperature, but is normally 1 to 24 hours and preferably 1 to 20 hours.

After completion of the reaction, if necessary, the obtained compound represented by the formula (7) may be purified by separation and purification means including washing, extraction, drying, filtration, concentration, recrystallization, reprecipitation, crystallization, centrifugation, column purification, adsorption, and/or sublimation purification, and is preferably purified by separation and purification means including sublimation purification.

As described above, the compound represented by the formula (1) is preferably the compound represented by the formula (8), and the compound represented by the formula (2) is preferably the compound represented by the formula (9).

Hereafter, a preferred embodiment (hereafter, also referred to as "second embodiment-1") of the method for producing the compound represented by the formula (9) from the compound represented by the formula (8) (the formula (11A) shown later corresponds to the formula (8)).

Preferred Embodiment of Method for Producing Compound Represented by Formula (9) (Second Embodiment-1)

The production method in the second embodiment-1 includes steps Y1' to Y4' below.

Step Y1': a step of reacting a compound represented by formula (X1) below with a compound represented by formula (X2) below to obtain a composition including a compound represented by formula (11A) and a compound represented by formula (11B), and then reacting the composition with a first amine compound represented by formula (12) without subjecting the composition to column purification to obtain a compound represented by formula (13)

Step Y2': a step of reacting the compound represented by the formula (13) with a second amine compound represented by formula (14) below to obtain a compound represented by formula (15) below Step Y3': a step of removing $P^{31}$ serving as a protecting group from the compound represented by the formula (15) to obtain a compound represented by formula (16) below Step Y4': a step of obtaining a compound represented by the formula (9) from the compound represented by the formula (16)

The production method according to the second embodiment-1 preferably further includes a step Y0' below.

Step Y0': a step of further purifying the compound represented by the formula (X2) before reacting the compound represented by the formula (X1) with the compound represented by the formula (X2)

Hereafter, first, the compounds represented by the formulae (X1), (X2), (11A), (11B), and (12) to (16) will be described, and then the procedures of the steps Y0' to Y4' will be described.

Compounds represented by formulae (X1), (X2), (11A), (11B), and (12) to (16)

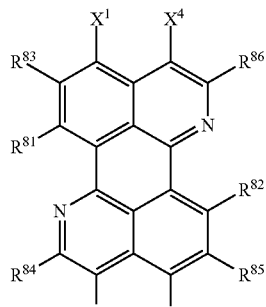

(X1)

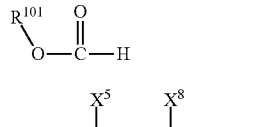

(X2)

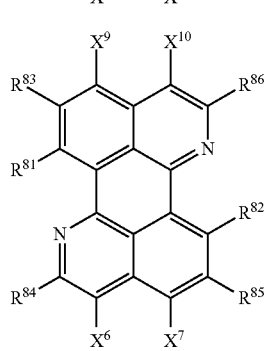

(11A)

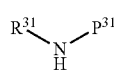

(11B)

(12)

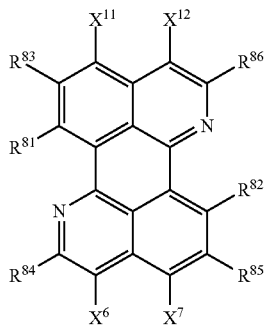

(13)

$R^{51}-NH_2$ (14)

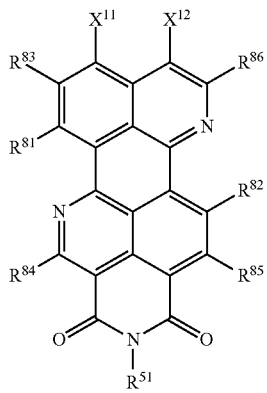

(15)

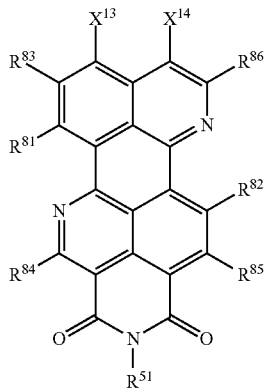

(16)

In the formula (X1), $X^1$ to $X^4$ each represent a halogen atom or $-CO-O-R^{101}$. $R^{101}$ represents an aliphatic hydrocarbon group, an aryl group, or a heteroaryl group. One of $X^1$ and $X^4$ represents a halogen atom, and the other represents $-CO-O-R^{101}$. One of $X^2$ and $X^3$ represents a halogen atom, and the other represents $-CO-O-R^{101}$.

Furthermore, from the viewpoint of ease of production of raw materials, it is preferable that $X^2$ and $X^4$ of the compound represented by the formula (X1) represent $-CO-O-R^{101}$ and $X^1$ and $X^3$ represent a halogen atom.

Two $R^{101}$ present in the formula (X1) preferably each represent an aliphatic hydrocarbon group or each represent an aryl or heteroaryl group, and more preferably each represent an aliphatic hydrocarbon group.

The aliphatic hydrocarbon group, aryl group, and heteroaryl group represented by $R^{101}$ in the formula (X1) are the same as the aliphatic hydrocarbon group, aryl group, and heteroaryl group represented by $R^{11}$ to $R^{14}$ in the formula (1), and preferred forms thereof are also the same.

$R^{81}$ to $R^{86}$ respectively have the same meaning as $R^{81}$ to $R^{86}$ in the formula (8), and preferred forms thereof are also the same.

In the formula (X2), $R^{101}$ represents an aliphatic hydrocarbon group, an aryl group, or a heteroaryl group. The aliphatic hydrocarbon group, aryl group, and heteroaryl group represented by $R^{101}$ in the formula (X2) are the same as the aliphatic hydrocarbon group, aryl group, and heteroaryl group represented by $R^{11}$ to $R^{14}$ in the formula (1), and preferred forms thereof are also the same.

In the formula (X2), $R^{101}$ more preferably represents an aryl group or a heteroaryl group.

The compound represented by the formula (X2) is preferably aryl formate or heteroaryl formate and more preferably an aryl formate substituted with an electron-withdrawing group.

In the formula (11A), $X^5$ to $X^8$ each independently represent —CO—O—$R^{101}$. Herein, $R^{101}$ in $X^5$ is different from $R^{101}$ in $X^8$. That is, one of $R^{101}$ in $X^5$ and $R^{101}$ in $X^8$ represents an aliphatic hydrocarbon group, and the other represents an aryl group or a heteroaryl group. $R^{101}$ in $X^6$ is also different from $R^{101}$ in $X^7$. That is, one of $R^{101}$ in $X^6$ and $R^{101}$ in $X^7$ represents an aliphatic hydrocarbon group, and the other represents an aryl group or a heteroaryl group.

The aliphatic hydrocarbon group, aryl group, and heteroaryl group represented by $R^{101}$ in $X^5$ to $X^8$ are the same as the aliphatic hydrocarbon group, aryl group, and heteroaryl group represented by $R^{11}$ to $R^{14}$ in the formula (1), and preferred forms thereof are also the same.

$R^{81}$ to $R^{86}$ respectively have the same meaning as $R^{81}$ to $R^{86}$ in the formula (8), and preferred forms thereof are also the same.

In the formula (11A), preferably, $R^{101}$ in $X^6$ and $X^8$ represents an aliphatic hydrocarbon group, and $R^{101}$ in $X^5$ and $X^7$ represents an aryl group or a heteroaryl group.

$R^{81}$ to $R^{86}$ respectively have the same meaning as $R^{81}$ to $R^{86}$ in the formula (8), and preferred forms thereof are also the same.

In the formula (11B), one of $X^9$ and $X^{10}$ represents a hydrogen atom, and the other represents —CO—O—$R^{101}$. $R^{101}$ has the same meaning as $R^{101}$ in the formula (X1), and preferred forms thereof are also the same. $X^6$ and $X^7$ respectively have the same meaning as $X^6$ and $X^7$ in the formula (11A), and preferred forms thereof are also the same.

$R^{81}$ to $R^{86}$ respectively have the same meaning as $R^{81}$ to $R^{86}$ in the formula (8), and preferred forms thereof are also the same.

In the formula (11B), preferably, $X^9$ represents a hydrogen atom and $X^{10}$ represents —CO—O—$R^{101}$. $R^{101}$ in $X^{10}$ and $R^{101}$ in $X^6$ preferably each represent an aliphatic hydrocarbon group or each represent an aryl or heteroaryl group, and more preferably each represent an aliphatic hydrocarbon group.

The formula (12) has the same meaning as the formula (3) described above, and preferred forms thereof are also the same. In the formula (12), $R^{31}$ represents a substituent. $P^{31}$ represents a protecting group.

In the formula (13), one of $X^{11}$ and $X^{12}$ represents —CO—O—$R^{101}$, and the other represents —CO—N($R^{31}$)($P^{31}$). $R^{101}$ has the same meaning as $R^{101}$ in the formula (X1), and preferred forms thereof are also the same. $R^{31}$ and $P^{31}$ respectively have the same meaning as $R^{31}$ and $P^{31}$ in the formula (12). $X^6$ and $X^7$ respectively have the same meaning as $X^6$ and $X^7$ in the formula (11A), and preferred forms thereof are also the same. $R^{81}$ to $R^{86}$ respectively have the same meaning as $R^{81}$ to $R^{86}$ in the formula (8), and preferred forms thereof are also the same.

In the formula (13), preferably, $X^{11}$ represents —CO—N($R^{31}$)($P^{31}$) and $X^{12}$ represents —CO—O—$R^{101}$.

The formula (14) has the same meaning as the formula (5) described above, and preferred forms thereof are also the same. In the formula (13), $R^{51}$ represents a substituent.

In the formula (15), $X^{11}$ and $X^{12}$ respectively have the same meaning as $X^{11}$ and $X^{12}$ in the formula (13). $R^{51}$ has the same meaning as $R^{51}$ in the formula (14). $R^{81}$ to $R^{86}$ respectively have the same meaning as $R^{81}$ to $R^{86}$ in the formula (8), and preferred forms thereof are also the same.

In the formula (16), one of $X^{13}$ and $X^{14}$ represents —CO—O—$R^{101}$, and the other represents —CO—N($R^{31}$)(H). $R^{51}$ has the same meaning as $R^{51}$ in the formula (14). $R^{101}$ has the same meaning as $R^{101}$ in the formula (X1), and preferred forms thereof are also the same. $R^{81}$ to $R^{86}$ respectively have the same meaning as $R^{81}$ to $R^{86}$ in the formula (8), and preferred forms thereof are also the same.

In the formula (16), preferably, $X^{13}$ represents —CO—N($R^{31}$)(H) and $X^{14}$ represents —CO—O—$R^{101}$.

Step Y1'

Step Y1' is a step of reacting a compound represented by formula (X1) with a compound represented by formula (X2) to obtain a composition including a compound represented by formula (11A) and a compound represented by formula (11B), and then reacting the composition with a first amine compound represented by formula (12) without subjecting the composition to column purification to obtain a compound represented by formula (13). The compound represented by the formula (11A) corresponds to the compound represented by the formula (8).

In the step Y1', the compound represented by the formula (11B) is a by-product formed in a synthesis reaction of reacting the compound represented by the formula (X1) with the compound represented by the formula (X2) to obtain the compound represented by the formula (11A). The formation of the compound represented by the formula (11B) as a by-product is probably caused by formic acid that may be included as an impurity in the compound represented by the formula (X2) (the compound represented by the formula (X2) is, for example, 2,4,6-trichlorophenyl formate). In the step Y1', the formation of the compound represented by the formula (11B) as a by-product can be suppressed by performing the step (step Y0') of purifying the compound represented by the formula (X2) before the reaction of the compound represented by the formula (X1) with the compound represented by the formula (X2).

The purification method in the step Y0' is not particularly limited, but is separation and purification means including washing, extraction, drying, filtration, concentration, recrystallization, reprecipitation, crystallization, centrifugation, column purification, adsorption, and/or sublimation purification. Among them, recrystallization, reprecipitation, or crystallization is preferred, and recrystallization is particularly preferred.

The reaction of the compound represented by the formula (X1) and the compound represented by the formula (X2) is not particularly limited, and a cross-coupling process in the presence of a transition metal catalyst can be applied.

The use amounts of the compound represented by the formula (X1) and the compound represented by the formula (X2) in the coupling reaction are not particularly limited. The amount of the compound represented by the formula (X2) is preferably 1.0 to 15.0 molar equivalents, more preferably 1.0 to 10.0 molar equivalents, and further preferably 1.0 to 5.0 molar equivalents relative to 1 molar equivalent of the halogen atom of the compound represented by the formula (X1).

Non-limiting examples of the transition metal catalyst include a palladium catalyst (palladium(0) catalyst or palladium(II) catalyst), a nickel catalyst (nickel(0) catalyst), an iron catalyst (iron(III) catalyst), a cobalt catalyst (cobalt(II) catalyst), and an iridium catalyst (iridium(0) catalyst). In particular, a palladium catalyst or a nickel catalyst is preferable, and a palladium catalyst is more preferable.

Non-limiting examples of the palladium catalyst include palladium acetate, tris(dibenzylideneacetone)dipalladium(0) chloroform complex, tetrakis(triphenylphosphine)palladium (0), and dichlorobis[di-tert-butyl(4-dimethylaminophenyl)phosphine]palladium(II).

The amount of the transition metal catalyst used in the coupling reaction is not particularly limited as long as it is an amount acting as a catalyst, but is preferably 0.001 to 1.0 molar equivalents and more preferably 0.01 to 0.5 molar equivalents relative to 1 molar equivalent of the halogen atom of the compound represented by the formula (X1).

The coupling reaction may be performed with addition of a ligand. The ligand is not particularly limited. For example, ligands described in ACCOUNTS OF CHEMICAL RESEARCH 2008, 41, 1461-1473; Angew. Chem. Int. Ed. 2008, 47, 6338-6361; Angew. Chem. Int. Ed. 2008, 47, 6338-6361; Journal of Synthetic Organic Chemistry Japan 2001, 59, 607-616; Aldrichimica Acta 2006, 39, 17.(b); and Schlummer, B.; Scholz, U. Adv. Synth. Catal. 2004, 346, 1599 can be used.

The coupling reaction may be performed in the presence of a base.

Examples of the base include organic bases and inorganic bases, and organic bases are preferred. Examples of the organic base include tertiary amines (e.g., trimethylamine, dimethylisopropylamine, N,N,N',N'-tetramethyldiaminomethane, N,N,N',N'-tetramethylethylenediamine, triethylamine, diisopropylethylamine, tripropylamine, tributylamine, tripentylamine, triheptylamine, trioctylamine, diazabicycloundecene, diazabicyclononene, and 1,4-diazabicyclo[2.2.2]octane) and pyridines (e.g., pyridine, 2,6-lutidine, quinoline, and isoquinoline). Examples of the inorganic base include hydroxides, carbonates, phosphates, and acetates. Specific examples of the inorganic base include sodium hydroxide, potassium hydroxide, cesium hydroxide, sodium carbonate, potassium carbonate, cesium carbonate, sodium phosphate, potassium phosphate, and sodium acetate.

The bases may be used alone or in combination of two or more.

The amount of the base used is not particularly limited, but is preferably 1.0 to 15 molar equivalents, more preferably 1.0 to 10 molar equivalents, and further preferably 1.1 to 2.0 molar equivalents relative to 1 molar equivalent of the compound represented by the formula (X2).

The coupling reaction may be performed in the presence of a solvent. A single solvent may be used, or two or more solvents may be used in a mixed manner.

The solvent is not particularly limited, and a solvent used for a transition metal catalytic reaction can be used. Examples of the solvent include a hydrocarbon solvent, an ether solvent, an amide solvent, an ester solvent, a nitrile solvent, a ketone solvent, and a sulfoxide solvent.

Examples of the hydrocarbon solvent include pentane, hexane, heptane, octane, decane, toluene, ethylbenzene, xylene, diethylbenzene, fluorobenzene, trifluoromethylbenzene, chloroform, dichloromethane, 1,1,2-trichloroethane, 1,1,2,2-tetrachloroethane, chlorobenzene, dichlorobenzene, trichlorobenzene, mesitylene, amylbenzene, decalin, 1-methylnaphthalene, 1-ethylnaphthalene, 1-chloronaphthalene, 1-fluoronaphthalene, 1,6-dimethylnaphthalene, nitrobenzene, benzonitrile, and tetralin.

Examples of the ether solvent include anisole, diethyl ether, dibutyl ether, diisopropyl ether, cyclopentyl methyl ether, diphenyl ether, tetrahydropyran, dioxane, dimethoxyethane, diethoxyethane, and tetrahydrofuran.

Examples of the amide solvent include N,N-dimethylformamide, N-methylpyrrolidone, N-ethylpyrrolidone, 1,3-dimethyl-2-imidazolidinone, and N,N-dimethylacetamide.

Examples of the ester solvent include methyl acetate, ethyl acetate, propyl acetate, butyl acetate, and isobutyl acetate.

Examples of the nitrile solvent include acetonitrile, propionitrile, and benzonitrile.

Examples of the ketone solvent include acetone, 2-butanone, methyl isobutyl ketone, diisobutyl ketone, cyclohexanone, isophorone, and acetophenone.

Examples of the sulfoxide solvent include dimethyl sulfoxide and sulfolane.

The coupling reaction may be performed in an inert gas atmosphere. Examples of the inert gas include nitrogen, helium, and argon.

The reaction temperature of the coupling reaction is not particularly limited, but is preferably 0° C. to 200° C. and more preferably 50° C. to 150° C.

The reaction time of the coupling reaction varies depending on the solvent used and the reaction conditions including a reaction temperature, but is normally 1 to 24 hours and preferably 3 to 20 hours.

In the step Y1', a step of reacting a composition obtained through a coupling reaction of the compound represented by the formula (X1) and the compound represented by the formula (X2) with the first amine compound represented by the formula (12) is performed without column purification. From the viewpoint of further improving the purity of the compound represented by the formula (9), which is a target compound, the composition includes at least the compound represented by the formula (11A), and the content of the compound represented by the formula (11B) is preferably 3.0 mass % or less and more preferably 1.0 mass % or less relative to the total solid content of the composition. When the step Y0' is performed, the content of the compound represented by the formula (11B) in the composition of the step Y1' can be adjusted to 3.0 mass % or less relative to the total solid content of the composition.

The lower limit of the content of the compound represented by the formula (11B) is usually 0 mass % or more and often 0.01 mass % or more relative to the total solid content of the composition.

The term "solid content" refers to components in a composition from which solvents are removed. Even if components other than solvents in the composition are liquid, the components are regarded as solid contents.

If necessary, the composition may be purified by separation and purification means other than column purification (such as washing, extraction, drying, filtration, concentration, recrystallization, reprecipitation, crystallization, adsorption, and centrifugation) after completion of the coupling reaction.

Specifically, the step of reacting the composition with the first amine compound represented by the formula (12) is preferably a step of adding the first amine compound represented by the formula (12) to the composition and heating the mixture to obtain the compound represented by the formula (13).

The specific procedure is the same as that of the step Y1 of the production method in the second embodiment described above, and the preferred form is also the same.

Step Y2'

The step Y2' is the same as the step Y2 of the production method in the second embodiment described above, and the preferred form is also the same.

Step Y3'

The step Y31 is the same as the step Y3 of the production method in the second embodiment described above, and the preferred form is also the same.

Step Y4'

The step Y4' is the same as the step Y4 of the production method in the second embodiment described above, and the preferred form is also the same.

Composition

The present invention also relates to a composition.

The composition according to an embodiment of the present invention is a composition used for synthesizing the above-described compound represented by the formula (9).

The composition includes at least the above-described compound represented by the formula (8).

In the composition, the total content of a compound represented by formula (17) below and a compound represented by formula (18) below is 3.0 mass % or less relative to the total solid content of the composition.

The term "solid content" refers to components in a composition from which solvents are removed. Even if components other than solvents in the composition are liquid, the components are regarded as solid contents.

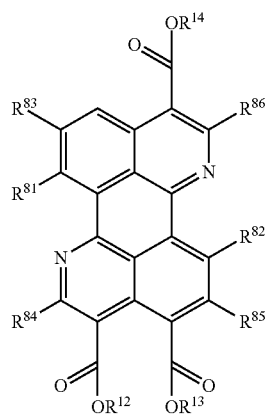

(17)

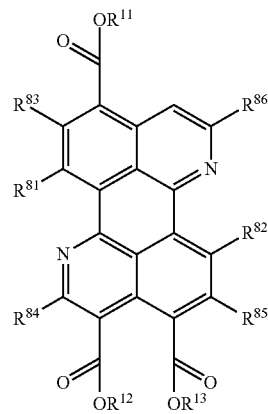

(18)

In the formulae (17) and (18), $R^{11}$ to $R^{14}$ each independently represent an aliphatic hydrocarbon group, an aryl group, or a heteroaryl group. One of $R^{12}$ and $R^{13}$ represents an aliphatic hydrocarbon group, and the other represents an aryl group or a heteroaryl group.

$R^{81}$ to $R^{86}$ respectively have the same meaning as $R^{81}$ to $R^{86}$ in the formula (8), and preferred forms thereof are also the same.

The above composition is the same as the composition obtained by reacting the compound represented by the formula (X1) with the compound represented by the formula (X2) in the step X' in the production method according to the first embodiment-1 and the composition obtained by reacting the compound represented by the formula (X1) and the compound represented by the formula (X2) in the step Y1' in the production method according to the second embodiment-1. That is, the compound represented by the formula (8) corresponds to the compound represented by the formula (11A). The compounds represented by the formula (17) and the formula (18) are covered by the compound represented by the formula (11B). The compound represented by the formula (17) corresponds to a form in which $X^9$ represents a hydrogen atom and $X^{10}$ represents —CO—O—$R^{101}$ in the compound represented by the formula (11B), and the compound represented by the formula (18) corresponds to a form in which $X^9$ represents —CO—O—$R^{101}$ and $X^{10}$ represents a hydrogen atom in the compound represented by the formula (11B).

The preferred form of the compound represented by the formula (8) is the same as that of the compound represented by the formula (11A). The preferred form of the compound represented by the formula (17) is the same as that of the compound represented by the formula (11B).

In the formula (18), $R^{11}$ and $R^{13}$ preferably each represent an aliphatic hydrocarbon group or each represent an aryl or heteroaryl group, and more preferably each represent an aliphatic hydrocarbon group.

The lower limit of the total content of the compound represented by the formula (17) and the compound represented by the formula (18) in the composition is usually 0 mass % or more and often 0.01 mass % or more relative to the total solid content of the composition.

In the composition, the content of the compound represented by the formula (8) is preferably 94.0 mass % or more, more preferably more than 97.0 mass %, and further preferably 98.0 mass % or more relative to the total mass of the composition. The upper limit of the content of the compound represented by the formula (8) in the composition is not particularly limited, but is 100 mass % or less and preferably 99.99 mass % or less.

Compound

The present invention also relates to a novel compound.

The compound according to an embodiment of the present invention is the compound represented by the formula (4), the compound represented by the formula (6), the compound represented by the formula (7), a compound represented by formula (11A') below, and a compound represented by formula (11A") below. Any of the compounds can be used as an intermediate compound for obtaining the compound represented by the formula (2). Compound represented by formula (11A')

Hereafter, the compound represented by the formula (11A') will be described. The compound represented by the formula (11A') is a compound covered by the compound represented by the formula (11A). That is, in the above-described compound represented by the formula (11A), at least one of $R^{81}$ to $R^{86}$ represents a substituent. Preferably, at least one of $R^{81}$ and $R^{82}$ represents a substituent. More preferably, both $R^{81}$ and $R^{82}$ represent substituents.

The preferred form of the compound represented by the formula (11A') is the same as that of the compound represented by the formula (11A).

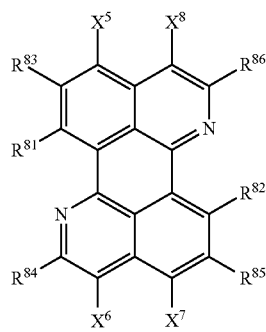

(11A')

Examples of the compound represented by the formula (11A') are shown below, but the compound represented by the formula (11A') is not limited thereto.

(8)-1 to (8)-43 in Table below show combinations of $X^5$, $X^6$, $X^7$, $X^8$, $R^{81}$, and $R^{82}$ shown in each basic skeleton below. In Table below, "Me" represents a methyl group, and "Et" represents an ethyl group.

In Table below, "ester" and "$CO_2$" are intended to indicate an oxycarbonyl group. That is, "2,4,6-trichlorophenylester" is intended to indicate "2,4,6-trichlorophenyloxycarbonyl", and "$CO_2Me$" is intended to indicate "methoxycarbonyl".

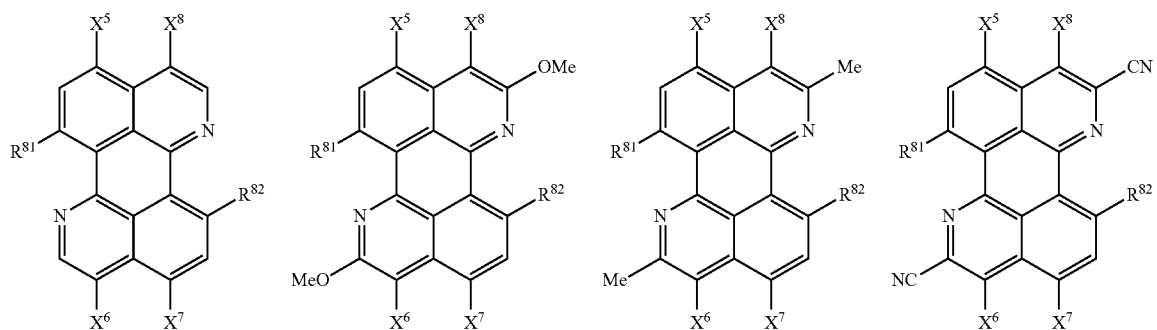

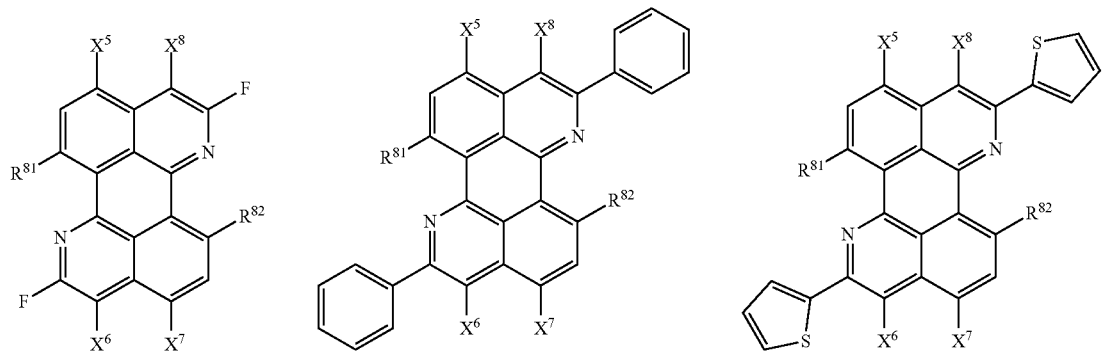

-continued

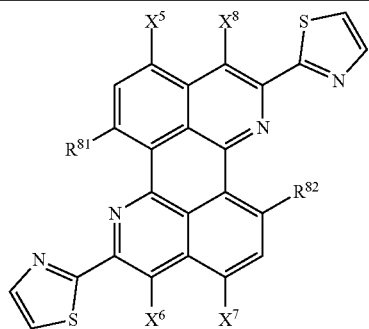
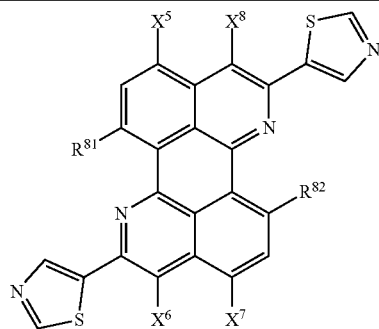
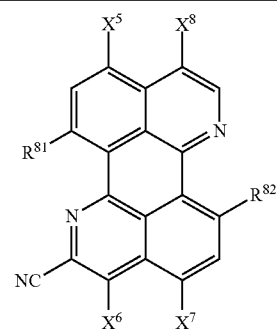

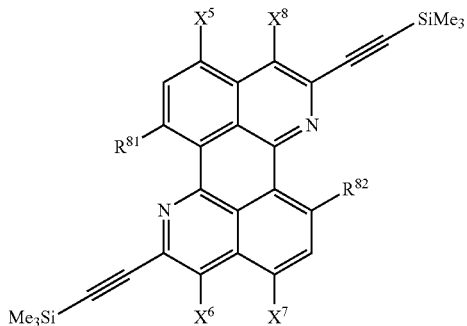

| No. | $R^5$ | $R^6$ | $R^7$ | $R^8$ | $R^{81}$ | $R^{82}$ |
|---|---|---|---|---|---|---|
| (8)-1 | 2,4,6-trichlorophenylester | CO$_2$Me | 2,4,6-trichlorophenylester | CO$_2$Me | F | F |
| (8)-2 | 2,4,6-trichlorophenylester | CO$_2$Me | 2,4,6-trichlorophenylester | CO$_2$Me | CF$_3$ | CF$_3$ |
| (8)-3 | 2,4,6-trichlorophenylester | CO$_2$Me | 2,4,6-trichlorophenylester | CO$_2$Me | CCl$_3$ | CCl$_3$ |
| (8)-4 | 2,4,6-trichlorophenylester | CO$_2$Me | 2,4,6-trichlorophenylester | CO$_2$Me | CN | CN |
| (8)-5 | 2,4,6-trichlorophenylester | CO$_2$Me | 2,4,6-trichlorophenylester | CO$_2$Me | *—≡—Si(i-propyl)$_3$ | *—≡—Si(i-propyl)$_3$ |
| (8)-6 | 2,4,6-trichlorophenylester | CO$_2$Me | 2,4,6-trichlorophenylester | CO$_2$Me | Br | Br |
| (8)-7 | 2,4,6-trichlorophenylester | CO$_2$Me | 2,4,6-trichlorophenylester | CO$_2$Me | H | Br |
| (8)-8 | 2,4,6-trichlorophenylester | CO$_2$Me | 2,4,6-trichlorophenylester | CO$_2$Me | 2-thiazolyl | 2-thiazolyl |
| (8)-9 | 2,4,6-trichlorophenylester | CO$_2$Me | 2,4,6-trichlorophenylester | CO$_2$Me | 2-(2-thiazolyl)vinyl | 2-(2-thiazolyl)vinyl |
| (8)-10 | 2,4,6-trichlorophenylester | CO$_2$Me | 2,4,6-trichlorophenylester | CO$_2$Me | 5-thiazolyl | 5-thiazolyl |
| (8)-11 | 2,4,6-trichlorophenylester | CO$_2$Me | 2,4,6-trichlorophenylester | CO$_2$Me | Br | 2-thiazolyl |
| (8)-12 | 2,4,6-trichlorophenylester | CO$_2$Me | 2,4,6-trichlorophenylester | CO$_2$Me | H | 2-thiazolyl |
| (8)-13 | 2,4,6-trichlorophenylester | CO$_2$Me | 2,4,6-trichlorophenylester | CO$_2$Me | 2-(5-thiazolyl)vinyl | 2-(5-thiazolyl)vinyl |

-continued

| | | | | | | |
|---|---|---|---|---|---|---|
| (8)-14 | 2,4,6-trichlorophenylester | CO$_2$Me | 2,4,6-trichlorophenylester | CO$_2$Me | 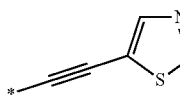 | 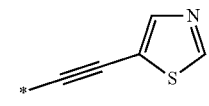 |
| (8)-15 | 2,4,6-trichlorophenylester | CO$_2$Me | 2,4,6-trichlorophenylester | CO$_2$Me | 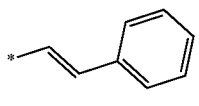 | 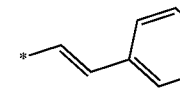 |
| (8)-16 | 2,4,6-trichlorophenylester | CO$_2$Me | 2,4,6-trichlorophenylester | CO$_2$Me | H | CN |
| (8)-17 | 2,4,6-trichlorophenylester | CO$_2$Me | 2,4,6-trichlorophenylester | CO$_2$Me | H | F |
| (8)-18 | 2,4,6-trichlorophenylester | CO$_2$Me | 2,4,6-trichlorophenylester | CO$_2$Me | H | CF$_3$ |
| (8)-19 | 2,4,6-tiichlorophenylester | CO$_2$Me | 2,4,6-trichlorophenylester | CO$_2$Me | H | CCl$_3$ |
| (8)-20 | 2,4,6-trichlorophenylester | COMe | 2,4,6-trichlorophenylester | CO$_2$Me | H | 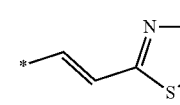 |
| (8)-21 | 2,4,6-trichlorophenylester | CO$_2$Me | 2,4,6-trichlorophenylester | CO$_2$Me | 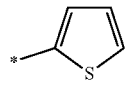 | 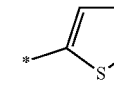 |
| (8)-22 | 2,4,6-trichlorophenylester | CO$_2$Me | 2,4,6-trichlorophenylester | CO$_2$Me | 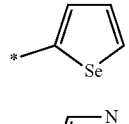 | 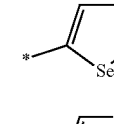 |
| (8)-23 | 2,4,6-trichlorophenylester | CO$_2$Me | 2,4,6-trichlorophenylester | CO$_2$Me | 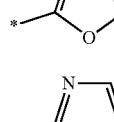 | 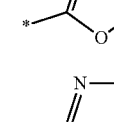 |
| (8)-24 | 2,4,6-trichlorophenylester | CO$_2$Me | 2,4,6-trichlorophenylester | CO$_2$Me | 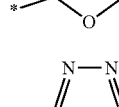 | 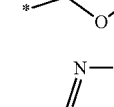 |
| (8)-25 | 2,4,6-trichlorophenylester | CO$_2$Me | 2,4,6-trichlorophenyiester | CO$_2$Me | 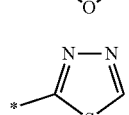 | 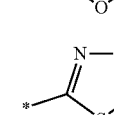 |
| (8)-26 | 2,4,6-trichlorophenylester | CO$_2$Me | 2,4,6-trichlorophenylester | CO$_2$Me | 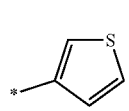 | 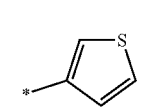 |
| (8)-27 | 2,4,6-trichlorophenylester | CO,Me | 2,4,6-trichlorophenylester | CO$_2$Me | 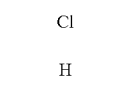 | 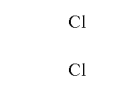 |
| (8)-28 | 2,4,6-trichlorophenylester | CO$_2$Me | 2,4,6-trichlorophenylester | CO$_2$Me | Cl | Cl |
| (8)-29 | 2,4,6-trichlorophenylester | CO$_2$Me | 2,4,8-trichlorophenylester | CO$_2$Me | H | Cl |
| (8)-30 | 2,4,6-trichlorophenylester | CO$_2$Me | 2,4,6-trichlorophenylester | CO$_2$Me | I | I |
| (8)-31 | 2,4,6-trichlorophenylester | CO$_2$Me | 2,4,6-trichlorophenylester | CO$_2$Me | H | I |
| (8)-32 | 2,4,6-trichlorophenylester | CO$_2$Me | 2,4,6-trichlorophenylester | CO$_2$Me | 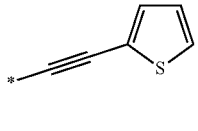 | 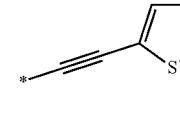 |

| | | | | | | |
|---|---|---|---|---|---|---|
| (8)-33 | 2.4.6-trichlorophenylester | CO$_2$Me | 2.4.6-trichlorophenylester | CO$_2$Me | ![thiophene with C6H13] | ![thiophene with C6H13] |
| (8)-34 | 2.4.6-trichlorophenylester | CO$_2$Me | 2.4.6-trichlorophenylester | CO$_2$Me | ![phenylacetylene] | ![phenylacetylene] |
| (8)-35 | CO$_2$Me | 2.4.6-trichlorophenylester | COaMe | 2.4.6-trichlorophenylester | F | F |
| (8)-36 | CO$_2$Me | 2A,6-trichlorophenylester | CO$_2$Me | 2,4.6-trichlorophenylester | CF$_3$ | CF$_3$ |
| (8)-37 | CONE, | 2,4,13-trichlorophenylester | CO$_2$Me | 2.4.6-trichlorophenylester | CCl$_3$ | CCl$_3$ |
| (8)-38 | CO$_2$Me | 2,4.6-trichlorophenylester | CO$_2$Me | 2.4.6-trichlorophenylester | CN | CN |
| (8)-39 | 2.4.6-trichlorophenylester | CO$_2$Et | 2.4.6-trichlorophenylester | CO$_2$Et | Br | Br |
| (8)-40 | 2.4.6-trichlorophenylester | CO$_2$C$_4$H$_9$ | 2.4.6-trichlorophenylester | CO$_2$C$_4$H$_9$ | Cl | Cl |
| (8)-41 | phenylester | CO$_2$Me | phenylester | CO$_2$Me | Br | Br |
| (8)-42 | 4-chlorophenylester | CO$_2$Me | 4-chlorophenylester | CO$_2$Me | Br | Br |
| (8)-43 | 4-nitrophenylester | CO$_2$Me | 4-nitrophenylester | CO$_2$Me | Br | Br |

Compound represented by formula (11A″)

Hereafter, the compound represented by the formula (11A″) will be described. The compound represented by the formula (11A″) is a compound covered by the compound represented by the formula (11A).

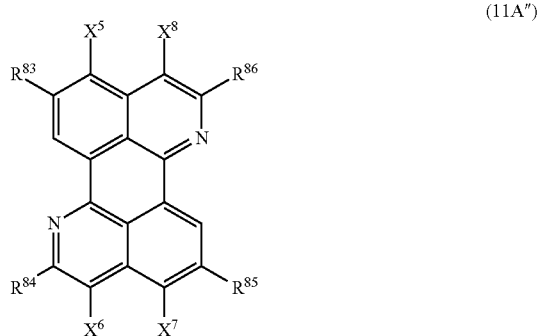

(11A″)

In the formula (11A″), $X^5$ to $X^8$ each independently represent —CO—O—$R^{101}$. Each $R^{101}$ independently represents an aliphatic hydrocarbon group, an aryl group, or a heteroaryl group.

Herein, $R^{101}$ in $X^5$ and $R^{101}$ in $X^8$ are different from each other. One of $R^{101}$ in $X^5$ and $R^{101}$ in $X^8$ represents an aliphatic hydrocarbon group, and the other represents an aryl group or a heteroaryl group. Herein, $R^{101}$ in $X^6$ and $R^{101}$ in $X^7$ are different from each other. One of $R^{101}$ in $X^6$ and $R^{101}$ in $X^7$ represents an aliphatic hydrocarbon group, and the other represents an aryl group or a heteroaryl group. In the case where the aliphatic hydrocarbon group represented by $R^{101}$ is an aliphatic hydrocarbon group having one carbon atom, the aryl group represented by $R^{101}$ is an unsubstituted aryl group or an aryl group into which two or less substituents are introduced.

$R^{83}$ to $R^{86}$ each independently represent a hydrogen atom or a substituent.

It has been confirmed that in the case where the aliphatic hydrocarbon group represented by $R^{101}$ has two or more carbon atoms, the solubility of the compound is better compared with the case where the aliphatic hydrocarbon group represented by $R^{101}$ has one carbon atom, which provides synthetic advantages such as reduction in the amount of reaction solvents and achieves higher yield in some cases.

The preferred form of the compound represented by the formula (11A″) is the same as that of the compound represented by the formula (11A).

Examples of the compound represented by the formula (11A″) are shown below, but the compound represented by the formula (11A″) is not limited thereto.

(9)-1 to (9)-38 in Table below show combinations of $X^5$, $X^6$, $X^7$, and $X^8$ shown in each basic skeleton below. In Table below, "Me" represents a methyl group, and "Et" represents an ethyl group.

In Table below, "ester" and "CO$_2$" are intended to indicate an oxycarbonyl group. That is, "2,4,6-trichlorophenylester" is intended to indicate "2,4,6-trichlorophenyloxycarbonyl", and "CO$_2$Me" is intended to indicate "methoxycarbonyl".

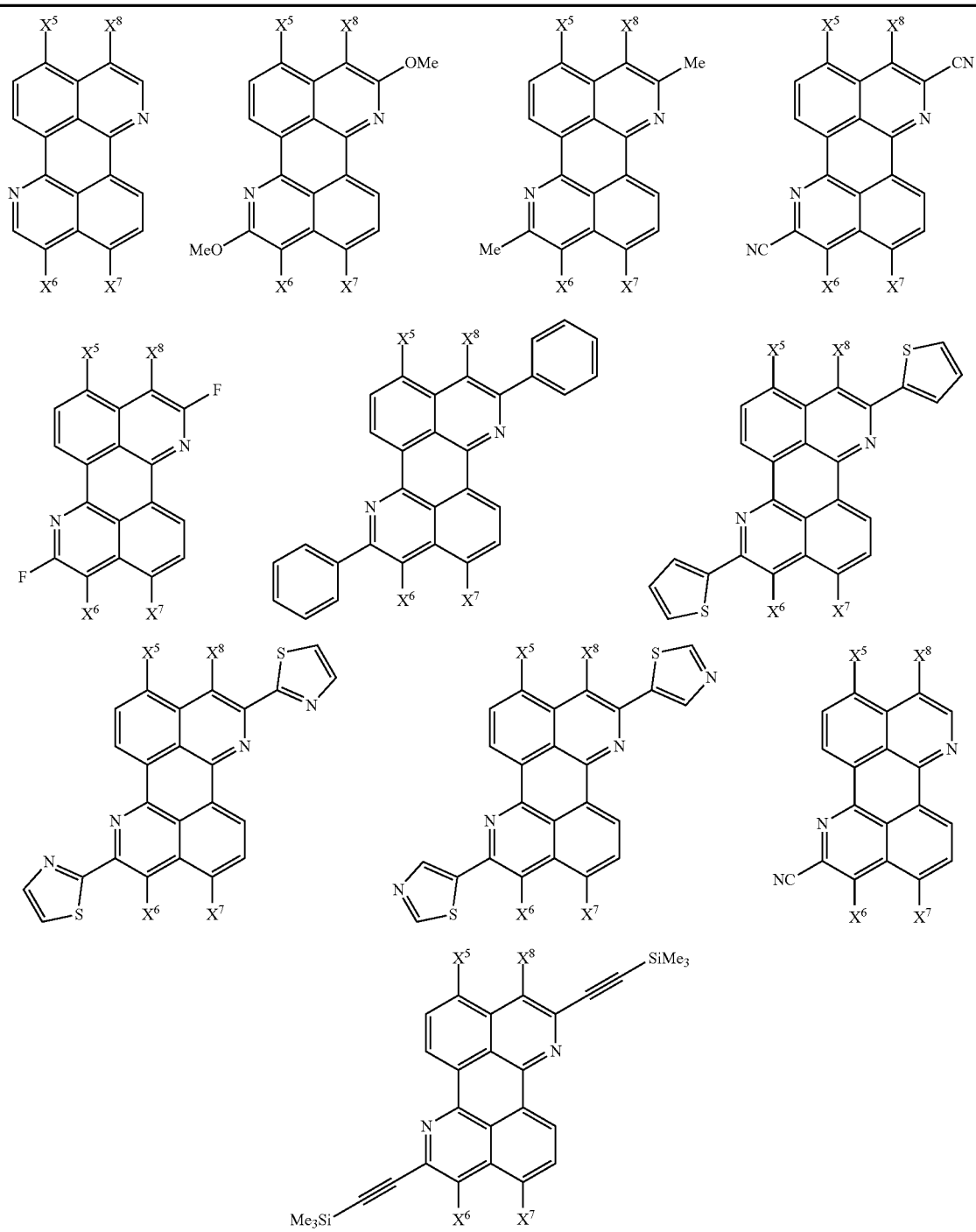
| No. | X⁵ | X⁶ | X⁷ | X⁸ |
|---|---|---|---|---|
| (9)-1 | 2,4,6-trichlorophenylester | $CO_2Et$ | 2,4,6-trichlorophenylester | $CO_2Et$ |
| (9)-2 | 2,4,6-trichlorophenylester | $CO_2{-}iPr$ | 2,4,6-trichlorophenylester | $CO_2{-}iPr$ |
| (9)-3 | 2,4,6-trichlorophenylester | $CO_2n\text{-}C_3H_7$ | 2,4,6-trichlorophenylester | $CO_2n\text{-}C_3H_7$ |
| (9)-4 | 2,4,6-trichlorophenylester | $CO_2n\text{-}C_4H_9$ | 2,4,6-trichlorophenylester | $CO_2n\text{-}C_4H_9$ |

-continued

| ID | Col A | Col B | Col C | Col D |
|---|---|---|---|---|
| (9)-5 | 2,4,6-trichlorophenylester | $CO_2n\text{-}C_5H_{11}$ | 2,4,6-trichlorophenylester | $CO_2n\text{-}C_5H_{11}$ |
| (9)-6 | 2,4,6-trichlorophenylester | $CO_2n\text{-}C_6H_{13}$ | 2,4,6-trichlorophenylester | $CO_2n\text{-}C_6H_{13}$ |
| (9)-7 | 2,4,6-trichlorophenylester | $CO_2$-cyclohexyl | 2,4,6-trichlorophenylester | $CO_2$-cyclohexyl |
| (9)-8 | 2,4,6-trichlorophenylester | $CO_2n\text{-}C_8H_{17}$ | 2,4,6-trichlorophenylester | $CO_2n\text{-}C_8H_{17}$ |
| (9)-9 | 2,4,6-trichlorophenylester | $CO_2\text{-}CH_2CH_2\text{-cyclohexyl}$ | 2,4,6-trichlorophenylester | $CO_2\text{-}CH_2CH_2\text{-cyclohexyl}$ |
| (9)-10 | 2,4,6-trichlorophenylester | $CO_2\text{-}(CH_2)_3\text{-}O\text{-}n\text{-}C_4H_9$ | 2,4,6-trichlorophenylester | $CO_2\text{-}(CH_2)_3\text{-}O\text{-}n\text{-}C_4H_9$ |
| (9)-11 | 2,4,6-trichlorophenylester | $CO_2$-2-ethylhexyl | 2,4,6-trichlorophenylester | $CO_2$-2-ethylhexyl |
| (9)-12 | 2,4,6-trichlorophenylester | $CO_2$-3,7-dimethyloctyl | 2,4,6-trichlorophenylester | $CO_2$-3,7-dimethyloctyl |
| (9)-13 | 2,4,6-trichlorophenylester | $CO_2$-allyl | 2,4,6-trichlorophenylester | $CO_2$-allyl |
| (9)-14 | 2,4,6-trichlorophenylester | $CO_2$-benzyl | 2,4,6-trichlorophenylester | $CO_2$-benzyl |
| (9)-15 | 2,4-dichlorophenylester | $CO_2Me$ | 2,4-dichlorophenylester | $CO_2Me$ |
| (9)-16 | 4-chlorophenylester | $CO_2Me$ | 4-chlorophenylester | $CO_2Me$ |
| (9)-17 | phenylester | $CO_2Me$ | phenylester | $CO_2Me$ |
| (9)-18 | 4-nitrophenylester | $CO_2Me$ | 4-nitrophenylester | $CO_2Me$ |
| (9)-19 | 2,6-dichlorophenylester | $CO_2Me$ | 2,6-dichlorophenylester | $CO_2Me$ |
| (9)-20 | 2,4-dichlorophenylester | $CO_2Et$ | 2,4-dichlorophenylester | $CO_2Et$ |
| (9)-21 | 4-chlorophenylester | $CO_2$-iPr | 4-chlorophenylester | $CO_2$-iPr |
| (9)-22 | phenylester | $CO_2n\text{-}C_3H_7$ | phenylester | $CO_2n\text{-}C_3H_7$ |
| (9)-23 | 4-nitrophenylester | $CO_2n\text{-}C_4H_9$ | 4-nitrophenylester | $CO_2n\text{-}C_4H_9$ |
| (9)-24 | 2,6-dichlorophenylester | $CO_2n\text{-}C_5H_{11}$ | 2,6-dichlorophenylester | $CO_2n\text{-}C_5H_{11}$ |
| (9)-25 | 2,4-dichlorophenylester | $CO_2n\text{-}C_6H_{13}$ | 2,4-dichlorophenylester | $CO_2n\text{-}C_6H_{13}$ |
| (9)-26 | 4-chlorophenylester | $CO_2$-cyclohexyl | 4-chlorophenylester | $CO_2$-cyclohexyl |
| (9)-27 | phenylester | $CO_2n\text{-}C_8H_{17}$ | phenylester | $CO_2n\text{-}C_8H_{17}$ |
| (9)-28 | 4-nitrophenylester | $CO_2\text{-}CH_2CH_2\text{-cyclohexyl}$ | 4-nitrophenylester | $CO_2\text{-}CH_2CH_2\text{-cyclohexyl}$ |
| (9)-29 | 2,6-dichlorophenylester | $CO_2\text{-}(CH_2)_3\text{-}O\text{-}n\text{-}C_4H_9$ | 2,6-dichlorophenylester | $CO_2\text{-}(CH_2)_3\text{-}O\text{-}n\text{-}C_4H_9$ |

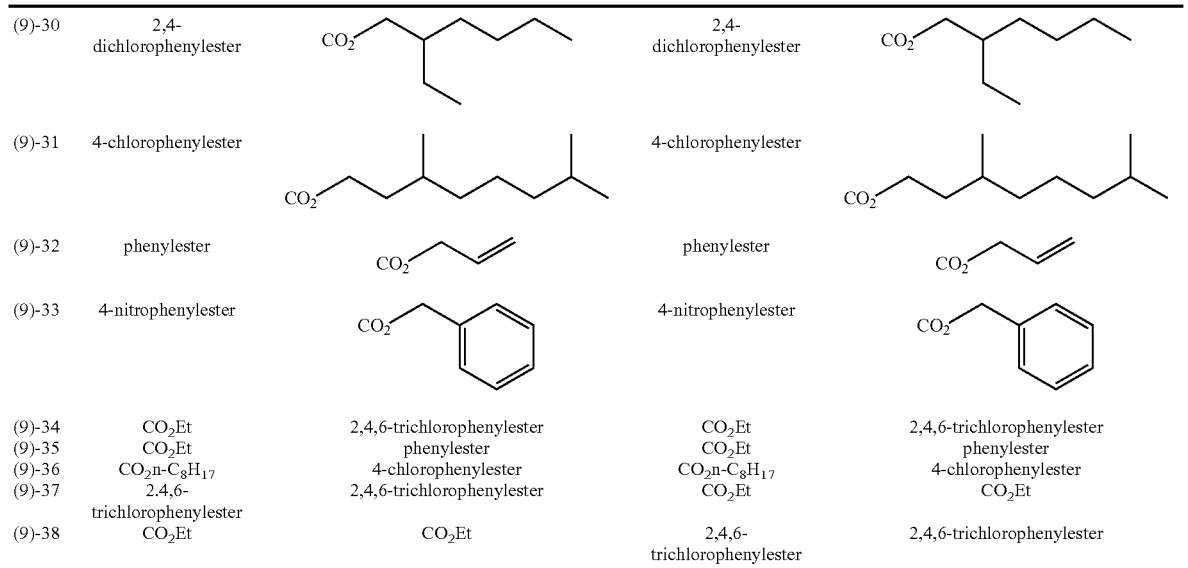

Application

The cyclic imide compound obtained by the production method according to an embodiment of the present invention is used as a material for forming an organic semiconductor film of an electronic device such as an organic thin film transistor as described later.

Examples of such a device include organic thin film transistors that control the amount of current or voltage, organic photoelectric conversion elements that convert light energy into electric power (e.g., solid image pickup elements for optical sensors, and solar cells for energy conversion), organic thermoelectric conversion elements that convert thermal energy into electric power, organic electroluminescence elements, (gas) sensors, organic rectifiers, organic inverters, and information recording elements.

Composition for Organic Thin Film Transistor

Next, a composition for organic thin film transistors will be described.

A composition for organic thin film transistors (also simply referred to as an "organic semiconductor composition" in this specification) includes a cyclic imide compound obtained by the production method according to an embodiment of the present invention (hereafter also referred to as a "particular cyclic imide compound"), and is used for forming an organic semiconductor film of an organic thin film transistor.

The particular cyclic imide compound included in the organic semiconductor composition is as described above, and a single cyclic imide compound may be used or two or more cyclic imide compounds may be used in combination.

The content of the particular cyclic imide compound in the organic semiconductor composition can be expressed as a content in the solid content excluding solvents described later. The content of the particular cyclic imide compound relative to the total mass of the solid content in the organic semiconductor composition is preferably, for example, in a preferred range of the content of the particular cyclic imide compound relative to the total mass of the organic semiconductor film described later.

Binder Polymer

The organic semiconductor composition may include a binder polymer. From the viewpoint of obtaining an organic semiconductor film having high film quality, the organic semiconductor composition preferably includes a binder polymer.

The type of binder polymer is not particularly limited, and a publicly known binder polymer can be used. Examples of the binder polymer include insulating polymers such as polystyrene, poly($\alpha$-methylstyrene), polycarbonate, polyarylate, polyester, polyamide, polyimide, polyurethane, polysiloxane, polysulfone, polymethyl methacrylate, polymethyl acrylate, cellulose, polyethylene, and polypropylene, and copolymers of the foregoing.

Other examples include rubbers such as ethylene-propylene rubbers, acrylonitrile-butadiene rubbers, hydrogenated nitrile rubbers, fluororubbers, perfluoroelastomers, tetrafluoroethylene-propylene copolymers, ethylene-propylene-diene copolymers, styrene-butadiene rubbers, polychloroprene, polyneoprene, butyl rubbers, methylphenyl silicone resins, methylphenylvinyl silicone resins, methylvinyl silicone resins, fluorosilicone resins, acrylic rubbers, ethylene acrylic rubbers, chlorosulfonated polyethylene, chloropolyethylene, epichlorohydrin copolymers, polyisoprene-natural rubber copolymers, polyisoprene rubbers, styrene-isoprene block copolymers, polyester-urethane copolymers, polyether-urethane copolymers, polyether ester thermoplastic elastomers, and rubbers including polybutadiene rubbers; and thermoplastic elastomer polymers.

Still other examples include photoconductive polymers such as polyvinylcarbazole and polysilane; conductive polymers such as polythiophene, polypyrrole, polyaniline, and polyparaphenylenevinylene; and semiconducting polymers described in Chemistry of Materials, 2014, 26, 647.

In consideration of charge mobility, the binder polymer preferably has a structure including no polar group. Herein, the polar group refers to a functional group having a heteroatom other than a carbon atom and a hydrogen atom. Polystyrene or poly($\alpha$-methylstyrene) is preferred as the binder polymer because it has a structure including no polar group. Semiconducting polymers are also preferred.

The glass transition temperature of the binder polymer is not particularly limited, and is appropriately set in accordance with the applications. For example, in order to impart strong mechanical strength to the organic semiconductor film, the glass transition temperature is preferably increased. On the other hand, in order to impart flexibility to the organic semiconductor film, the glass transition temperature is preferably decreased.

The binder polymers may be used alone or in combination of two or more.

The content of the binder polymer in the organic semiconductor composition is not particularly limited. However, from the viewpoint of further improving the carrier mobility and durability of the organic semiconductor film of the organic thin film transistor, the content of the binder polymer relative to the total mass of the solid content in the organic semiconductor composition is preferably within a preferred range of the content of the binder polymer relative to the total mass of the organic semiconductor film described later.

The weight-average molecular weight of the binder polymer is not particularly limited, but is preferably 1,000 to 10,000,000, more preferably 3,000 to 5,000,000, and further preferably 5,000 to 3,000,000. The weight-average molecular weight of the binder polymer can be determined by gel permeation chromatography (GPC).

In the organic semiconductor composition, the particular cyclic imide compound may be uniformly mixed with the binder polymer, or a part or all of the particular cyclic imide compound may be phase-separated from the binder polymer. From the viewpoint of coating easiness or coating uniformity, the particular cyclic imide compound and the binder polymer are preferably uniformly mixed with each other at least at the time of coating.

Solvent

The organic semiconductor composition may include a solvent, and preferably includes a solvent from the viewpoint of improving the coatability thereof. Such a solvent is not particularly limited as long as the above-described compound can be dissolved or dispersed. The solvent is an inorganic solvent or an organic solvent, and preferably an organic solvent. A single solvent may be used or two or more solvents may be used in combination of two or more.

Non-limiting examples of the organic solvent include hydrocarbon solvents such as hexane, octane, decane, toluene, xylene, mesitylene, ethylbenzene, diethylbenzene, amylbenzene, decalin, 1-methylnaphthalene, 1-ethylnaphthalene, 1,6-dimethylnaphthalene, and tetralin; ketone solvents such as acetone, methyl ethyl ketone, methyl isobutyl ketone, cyclohexanone, acetophenone, propiophenone, and butyrophenone; halogenated hydrocarbon solvents such as dichloromethane, chloroform, tetrachloromethane, dichloroethane, trichloroethane, tetrachloroethane, chlorobenzene, 1,2-dichlorobenzene, trifluoromethyltoluene, 1,2,4-trichlorobenzene, chlorotoluene, 1-chloronaphthalene, and 1-fluoronaphthalene; heterocyclic solvents such as pyridine, picoline, quinoline, thiophene, 3-butylthiophene, and thieno[2,3-b]thiophene; halogenated heterocyclic solvents such as 2-chlorothiophene, 3-chlorothiophene, 2,5-dichlorothiophene, 3,4-dichlorothiophene, 2-bromothiophene, 3-bromothiophene, 2,3-dibromothiophene, 2,4-dibromothiophene, 2,5-dibromothiophene, 3,4-dibromothiophene, and 3,4-dichloro-1,2,5-thiadiazole; ester solvents such as ethyl acetate, butyl acetate, amyl acetate, 2-ethylhexyl acetate, γ-butyrolactone, and phenyl acetate; alcohol solvents such as methanol, propanol, butanol, pentanol, hexanol, cyclohexanol, methyl cellosolve, ethyl cellosolve, and ethylene glycol; ether solvents such as dibutyl ether, tetrahydrofuran, dioxane, dimethoxyethane, anisole, ethoxybenzene, dimethoxybenzene, propoxybenzene, isopropoxybenzene, butoxybenzene, 2-methylanisole, 3-methylanisole, 4-methylanisole, 4-ethylanisole, dimethylanisole (any of 2,3-, 2,4-, 2,5-, 2,6-, 3,4-, 3,5-, and 3,6-), and 1,4-benzodioxane; amide or imide solvents such as N,N-dimethylformamide, N,N-dimethylacetamide, 1-methyl-2-pyrrolidone, 1-methyl-2-imidazolidinone, and 1,3-dimethyl-2-imidazolidinone; sulfoxide solvents such as dimethylsulfoxide; phosphate solvents such as trimethyl phosphate; nitrile solvents such as acetonitrile and benzonitrile; and nitro solvents such as nitromethane and nitrobenzene.

In particular, the organic solvent is preferably a hydrocarbon solvent, a ketone solvent, a halogenated hydrocarbon solvent, a heterocyclic solvent, a halogenated heterocyclic solvent, or an ether solvent, more preferably toluene, xylene, mesitylene, amylbenzene, tetralin, acetophenone, propiophenone, butyrophenone, dichlorobenzene, anisole, ethoxybenzene, propoxybenzene, isopropoxybenzene, butoxybenzene, dimethoxybenzene, chlorobenzene, dichlorobenzene, diethylbenzene, 2-methylanisole, 3-methylanisole, 4-methylanisole, 1-fluoronaphthalene, 1-chloronaphthalene, 3-chlorothiophene, or 2,5-dibromothiophene, and further preferably toluene, xylene, tetralin, acetophenone, propiophenone, butyrophenone, anisole, ethoxybenzene, propoxybenzene, butoxybenzene, 2-methylanisole, 3-methylanisole, 4-methylanisole, 1-fluoronaphthalene, 1-chloronaphthalene, 3-chlorothiophene, or 2,5-dibromothiophene.

The solvent included in the organic semiconductor composition is preferably a solvent having a boiling point of 100° C. or higher from the viewpoint of ensuring the film quality and increasing the crystal size of the above-described compound.

Examples of the solvent having a boiling point of 100° C. or higher include toluene, xylene, diethylbenzene, mesitylene, tetralin, acetophenone, propiophenone, butyrophenone, chlorobenzene, dichlorobenzene, anisole, dimethoxybenzene, ethoxybenzene, propoxybenzene, isopropoxybenzene, butoxybenzene, 2-methylanisole, 3-methylanisole, 1-methylnaphthalene, 1-fluoronaphthalene, 1-chloronaphthalene, and 4-methylanisole. In particular, the solvent is more preferably toluene, xylene, diethylbenzene, chlorobenzene, dichlorobenzene, tetralin, acetophenone, propiophenone, butyrophenone, anisole, dimethoxybenzene, ethoxybenzene, propoxybenzene, butoxybenzene, 2-methylanisole, 3-methylanisole, 1-methylnaphthalene, 1-fluoronaphthalene, 1-chloronaphthalene, or 4-methylanisole.

From the viewpoints of environmental load and toxicity to humans, the solvent having a boiling point of 100° C. or higher is preferably a non-halogen solvent (a solvent having no halogen atom in the molecule).

When the organic semiconductor composition includes a solvent, the content of the solvent is preferably 90 to 99.99 mass %, more preferably 95 to 99.98 mass %, and further preferably 96 to 99.98 mass % relative to the total mass of the organic semiconductor composition.

Other Components

The organic semiconductor composition may include components other than the particular cyclic imide compound, the binder polymer, and the solvent. Such components are various additives.

Additives commonly used for organic semiconductor compositions can be used. More specifically, the additives are surfactants, antioxidants, crystallization controlling agents, and crystal alignment controlling agents. For the surfactants and the antioxidants, reference can be made to paragraphs 0136 and 0137 in JP2015-195362A, the contents of which are incorporated herein by reference.

The content of the additives in the organic semiconductor composition is not particularly limited. From the viewpoint of achieving good film formability and further improving the carrier mobility and the heat resistance, the content of the additives relative to the total mass of the solid content in the organic semiconductor composition is preferably within a preferred range of the content of the additives relative to the total mass of the organic semiconductor film described later.

The viscosity of the organic semiconductor composition is preferably 10 mPa·s or higher from the viewpoint of printability.

Preparation Method

The preparation method of the organic semiconductor composition is not particularly limited, and an ordinary preparation method can be employed. For example, an organic semiconductor composition can be prepared by adding a predetermined amount of each component to an organic solvent and appropriately stirring the resulting mixture.

If necessary, heating may be performed during or after the stirring of each component. The heating temperature is not particularly limited and is determined within the range of, for example, 40° C. to 150° C. When the solvent is used, the temperature is determined to be a temperature that is within the above range and is lower than the boiling point of the solvent.

Organic Thin Film Transistor

Next, an organic thin film transistor (hereafter also referred to as an "organic TFT"), which is a preferred form of the above-described organic semiconductor device using the particular cyclic imide compound, will be described.

The organic TFT includes an organic semiconductor film described later. Thus, the organic TFT exhibits high carrier mobility, and a decrease in carrier mobility over time is effectively suppressed even in the atmosphere, which achieves stable driving. Ambient temperature and humidity in the atmosphere are not particularly limited as long as they are the temperature and humidity in an operation environment of organic TFTs. The temperature is, for example, room temperature (20° C.) and the humidity is, for example, 10 to 90 RH %.

The organic TFT is preferably used as an organic field effect transistor (FET), and more preferably used as an insulated gate FET in which a gate and a channel are insulated from each other.

The thickness of the organic TFT is not particularly limited. To provide a thinner transistor, the thickness of the entire organic TFT is preferably set to, for example, 0.1 to 0.5 μm.

The organic TFT has an organic semiconductor film (also referred to as an organic semiconductor layer or a semiconductor active layer) including a particular cyclic imide compound, and may further have a source electrode, a drain electrode, a gate electrode, and a gate insulating film.

The organic TFT preferably has, over a substrate, a gate electrode, an organic semiconductor film, a gate insulating film disposed between the gate electrode and the organic semiconductor film, and a source electrode and a drain electrode that are disposed in contact with the organic semiconductor film so as to be connected to each other through the organic semiconductor film. In this organic TFT, the organic semiconductor film and the gate insulating film are disposed adjacent to each other.

The structure of the organic TFT is not particularly limited as long as the organic TFT includes the above-described layers. For example, the organic TFT may have any of a bottom gate-bottom contact structure, a top gate-bottom contact structure, a bottom gate-top contact structure, and a top gate-top contact structure. The organic TFT preferably has a bottom gate structure (bottom gate-bottom contact structure or bottom gate-top contact structure) in which a gate electrode is disposed between a substrate and an organic semiconductor film.

Hereafter, an example of the organic TFT will be described with reference to the attached drawings.

Bottom Gate-Bottom Contact Organic TFT

FIG. 1 is a sectional view schematically illustrating a structure of a bottom gate-bottom contact organic TFT 10, which is an example of the organic TFT.

As illustrated in FIG. 1, the organic TFT 10 includes a substrate (base) 1, a gate electrode 2, a gate insulating film 3, a source electrode 4A and a drain electrode 4B, an organic semiconductor film 5, and a sealing layer 6 in this order.

Hereafter, a substrate (base), a gate electrode, a gate insulating film, a source electrode, a drain electrode, an organic semiconductor film, and a sealing layer, and production methods thereof will be described.

Substrate

The substrate serves to support the gate electrode, the source electrode, the drain electrode, and other layers.

The type of substrate is not particularly limited, and is, for example, a plastic substrate, a silicon substrate, a glass substrate, or a ceramic substrate. Among them, a glass substrate or a plastic substrate is preferable from the viewpoint of applicability to devices and cost.

The thickness of the substrate is not particularly limited. The upper limit of the thickness of the substrate is preferably 10 mm or less, more preferably 2 mm or less, and further preferably 1.5 mm or less. The lower limit of the thickness of the substrate is preferably 0.01 mm or more and more preferably 0.05 mm or more.

Gate Electrode

An electrode commonly used as a gate electrode of an organic TFT can be applied as the gate electrode without particular limitation.

Non-limiting examples of the material (electrode material) for forming the gate electrode include metals such as gold, silver, aluminum, copper, chromium, nickel, cobalt, titanium, platinum, magnesium, calcium, barium, and sodium; conductive oxides such as $InO_2$, $SnO_2$, and indium tin oxide (ITO); conductive polymers such as polyaniline, polypyrrole, polythiophene, polyacetylene, and polydiacetylene; semiconductors such as silicon, germanium, and gallium arsenide; and carbon materials such as fullerene, carbon nanotube, and graphite. Among these, the metal is preferable, and silver or aluminum is more preferable.

The thickness of the gate electrode is not particularly limited, but is preferably 20 to 200 nm.

The gate electrode may function as the substrate, and in this case, the substrate may be omitted.

A method for forming the gate electrode is not particularly limited. Examples of the method include a method in which the above-described electrode material is subjected to vacuum deposition (hereafter also simply referred to as "deposition") or sputtering on a substrate and a method in which an electrode-forming composition including the above-described electrode material is applied or printed. When the gate electrode is patterned, examples of the patterning method include printing methods such as inkjet printing, screen printing, offset printing, and relief printing (flexographic printing), a photolithography method, and a mask vapor deposition method.

Gate Insulating Film

The gate insulating film is not particularly limited as long as it is a layer having insulating properties, and may have a single-layer structure or a multilayer structure.

Non-limiting examples of the material for forming the gate insulating film include polymers such as polymethyl methacrylate, polystyrene, polyvinylphenol, melamine resin, polyimide, polycarbonate, polyester, polyvinyl alcohol, polyvinyl acetate, polyurethane, polysulfone, polybenzoxazole, polysilsesquioxane, epoxy resin, and phenolic resin; inorganic oxides such as silicon dioxide, aluminum oxide, and titanium oxide; and nitrides such as silicon nitride. Among them, the polymer is preferable in view of compatibility with the organic semiconductor film. The inorganic oxide is preferable and silicon dioxide is more preferable in view of uniformity of the film.

These materials may be used alone or in combination of two or more.

The thickness of the gate insulating film is not particularly limited, but is preferably 100 to 1000 nm.

A method for forming the gate insulating film is not particularly limited. Examples of the method include a method in which a gate insulating film-forming composition including the above-described material is applied onto the substrate on which the gate electrode has been formed and a method in which the above-described material is subjected to vapor deposition or sputtering.

Source Electrode and Drain Electrode

In the organic TFT, the source electrode is an electrode into which a current flows from the outside through a wiring line. The drain electrode is an electrode that sends a current to the outside through a wiring line.

The material for forming the source electrode and the drain electrode may be the same as the electrode material for forming the gate electrode. Among them, the metal is preferable, and gold or silver is more preferable.

The thickness of each of the source electrode and the drain electrode is not particularly limited, but is preferably 1 nm or more and more preferably 10 nm or more. The upper limit of the thicknesses of the source electrode and the drain electrode is preferably 500 nm or less and more preferably 300 nm or less.

The distance (gate length L) between the source electrode and the drain electrode can be appropriately determined, but is preferably 200 μm or less and more preferably 100 μm or less. The gate width W can be appropriately determined, but is preferably 5000 μm or less and more preferably 1000 μm or less. The ratio of the gate width W to the gate length L is not particularly limited. For example, the ratio W/L is preferably 10 or more and more preferably 20 or more.

A method for forming the source electrode and the drain electrode is not particularly limited. Examples of the method include a method in which the electrode material is subjected to vacuum deposition or sputtering on a substrate on which the gate electrode and the gate insulating film have been formed and a method in which an electrode-forming composition is applied or printed. The patterning method employed when the source electrode and the drain electrode are patterned is the same as the patterning method of the gate electrode.

Organic Semiconductor Film

An organic semiconductor film including a particular cyclic imide compound is used as an organic semiconductor film in an organic TFT. The number of types of particular cyclic imide compounds included in the organic semiconductor film may be one or may be two or more.

When the organic semiconductor film includes a particular cyclic imide compound, the carrier mobility of the organic semiconductor film can be improved, and the high carrier mobility can be maintained even if the organic semiconductor film is used or stored (left) in the atmosphere. The reason for this is unclear, but it is believed that the orbital energy of the lowest unoccupied molecular orbital of the particular cyclic imide compound is low.

The content of the particular cyclic imide compound in the organic semiconductor film is not particularly limited and can be appropriately set. For example, the content of the particular cyclic imide compound relative to the total mass of the organic semiconductor film is preferably 10 mass % or more, more preferably 30 mass % or more, and further preferably 50 mass % or more. The upper limit of the content is not particularly limited, and the content of the particular cyclic imide compound relative to the total mass of the organic semiconductor film may be 100 mass %. In the case where the organic semiconductor film includes a binder polymer or other components, the upper limit of the content of the particular cyclic imide compound relative to the total mass of the organic semiconductor film is preferably 90 mass % or less and more preferably 80 mass % or less.

The organic semiconductor film may include the above-described binder polymer in addition to the particular cyclic imide compound. The binder polymers may be used alone or in combination of two or more.

In the organic semiconductor film, the state of the particular cyclic imide compound and the binder polymer is not particularly limited. From the viewpoint of carrier mobility, the particular cyclic imide compound and the binder polymer are preferably phase-separated from each other in the film thickness direction.

The content of the binder polymer in the organic semiconductor film is not particularly limited and can be appropriately set. In the case where the organic semiconductor film includes a binder polymer, the content of the binder polymer relative to the total mass of the organic semiconductor film is preferably 90 mass % or less and more preferably 70 mass % or less. The lower limit of the content is not particularly limited, and the content of the binder polymer relative to the total mass of the organic semiconductor film can be set to 0 mass % or more, and is preferably 10 mass % or more and more preferably 20 mass % or more.

The organic semiconductor film may include the above-described additive in addition to the particular cyclic imide compound. The additives may be used alone or in combination of two or more.

In the case where the organic semiconductor film includes an additive, the content of the additive relative to the total mass of the organic semiconductor film is preferably 10 mass % or less, more preferably 5 mass % or less, and further preferably 1 mass % or less.

The thickness of the organic semiconductor film is appropriately determined in accordance with the organic TFT to be applied, but is preferably 10 to 500 nm and more preferably 20 to 200 nm.

This organic semiconductor film can be formed by applying the above-described organic semiconductor composition. The details of a method for forming the organic semiconductor film will be described later.

The applications of the organic semiconductor film including a particular cyclic imide compound are not limited to organic semiconductor films for organic TFTs. The organic semiconductor film can be used as an organic semiconductor film included in each of the organic semiconductor devices described above.

Sealing Layer

Since the organic TFT including the organic semiconductor film is stably driven even in the atmosphere, it is not necessary to seal the entire organic TFT and block any of the air (oxygen gas) and moisture. However, for the purpose of stable driving for a longer time, the entire organic TFT may be sealed with a metal sealing can or a sealing layer may be formed using a sealing agent.

For the sealing layer, a sealing agent (sealing layer-forming composition) commonly used for organic TFTs can be used. Examples of the sealing agent include inorganic materials such as glass and silicon nitride, polymer materials such as parylene, and low-molecular-weight materials.

The sealing layer can be formed by a typical method such as coating and drying using the sealing agent.

The thickness of the sealing layer is not particularly limited, but is preferably 0.2 to 10 µm.

Bottom Gate-Top Contact Organic TFT

Figure 2:
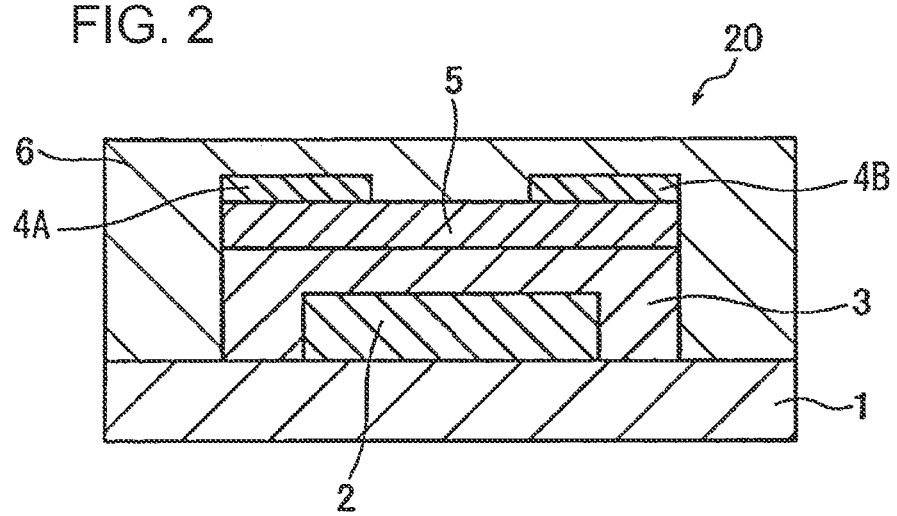
FIG. 2 is a sectional view schematically illustrating a structure of a bottom gate-bottom contact organic thin film transistor, which is another example of organic thin film transistors.

FIG. 2 is a sectional view schematically illustrating a structure of a bottom gate-top contact organic TFT 20, which is an example of the organic TFT.

As illustrated in FIG. 2, the organic TFT 20 includes a substrate 1, a gate electrode 2, a gate insulating film 3, an organic semiconductor film 5, a source electrode 4A and a drain electrode 4B, and a sealing layer 6 in this order.

The organic TFT 20 is the same as the organic TFT 10, except that the layer structure (lamination form) is different. Therefore, the substrate, the gate electrode, the gate insulating film, the source electrode, the drain electrode, the organic semiconductor film, and the sealing layer are the same as those in the bottom gate-bottom contact organic TFT described above, and thus the description thereof is omitted.

Method for Producing Organic TFT

A method for producing an organic TFT is not particularly limited as long as the method has a step of applying an organic semiconductor composition onto a substrate to form an organic semiconductor film.

The gate electrode, the gate insulating film, the source electrode, the drain electrode, and the sealing layer can each be formed or deposited by the above methods.

Hereafter, a step of forming an organic semiconductor film will be described.

In this step, the above-described organic semiconductor composition is used.

In the present invention, the phrase "applying an organic semiconductor composition onto a substrate" covers not only a form in which an organic semiconductor composition is directly applied onto a substrate, but also a form in which an organic semiconductor composition is applied above a substrate, that is, on another layer disposed on the substrate. The other layer (a layer that is in contact with the organic semiconductor film and serves as a base of the organic semiconductor film) onto which the organic semiconductor composition is applied is naturally determined in accordance with the structure of the organic TFT. For example, when the organic TFT is a bottom gate organic TFT, the organic semiconductor composition is applied onto at least a surface of the gate insulating film.

When the organic semiconductor film is formed, the substrate may be heated or cooled. By changing the temperature of the substrate, the film quality or the packing of the particular cyclic imide compound in the film can be controlled.

The temperature of the substrate is not particularly limited. For example, the temperature of the substrate is preferably set within a range of 0° C. to 200° C., more preferably within a range of 15° C. to 100° C., and further preferably within a range of 20° C. to 95° C.

The method for forming the organic semiconductor film is not particularly limited as long as the organic semiconductor film including the particular cyclic imide compound can be formed. The method is, for example, a vacuum process or a solution process, and is preferably a solution process.

Examples of the vacuum process include physical vapor deposition methods such as vacuum deposition, sputtering, ion plating, and molecular beam epitaxy (MBE); and chemical vapor deposition (CVD) methods such as plasma polymerization. In particular, the vacuum deposition is preferable.

In the solution process, the above-described organic semiconductor composition is preferably used.

The particular cyclic imide compound is stable even in the atmosphere as described above. Thus, the solution process can be performed in the atmosphere, and the organic semiconductor composition can be applied in a large area.

A common method for applying an organic semiconductor composition in the solution process can be employed. Examples of the method include coating methods such as a drop casting method, a casting method, a dip coating method, a die coater method, a roll coater method, a bar coater method, and a spin coating method; various printing methods such as an inkjet method, a screen printing method, a gravure printing method, a flexographic printing method, an offset printing method, and a microcontact printing method; and a Langmuir-Blodgett (LB) method. Among them, a drop casting method, a casting method, a spin coating method, an inkjet method, a gravure printing method, a flexographic printing method, an offset printing method, or a microcontact printing method is preferable.

The method for applying an organic semiconductor composition in a preferred embodiment of the solution process described later is preferably an inkjet method, a gravure printing method, a flexographic printing method, an offset printing method, or a microcontact printing method and more preferably a flexographic printing method, a microcontact printing method, or an inkjet method.

In the solution process, it is preferable to dry the organic semiconductor composition applied onto the substrate, and it is more preferable to gradually dry the organic semiconductor composition. By drying the organic semiconductor composition applied onto the substrate, a crystal of the particular cyclic imide compound can be precipitated to form an organic semiconductor film.

The method for drying an organic semiconductor composition is preferably natural drying, or heat drying on a heated substrate followed by drying under reduced pressure from the viewpoint of film quality. The temperature of the substrate during natural drying or heat drying is preferably 20° C. to 100° C. and more preferably 50° C. to 80° C. The time of natural drying or heat drying is preferably 0.5 to 20 hours and more preferably 1 to 10 hours.

The temperature of the substrate during drying under reduced pressure is preferably 20° C. to 100° C. and more preferably 40° C. to 80° C. The time of drying under reduced pressure is preferably 1 to 20 hours and more preferably 2 to 10 hours. The pressure during drying under reduced pressure is preferably $10^{-6}$ to $10^{-4}$ Pa and more preferably $10^{-5}$ to $10^{-3}$ Pa.

The thus-dried organic semiconductor composition may be shaped into a predetermined shape or a pattern shape as necessary.

Embodiment of Solution Process

Hereafter, the preferred embodiment of the solution process will be described with reference to the attached drawings, but the solution process is not limited to the following embodiment.

An embodiment of the solution process is a method in which an organic semiconductor composition (hereafter also referred to as a "coating liquid") is dropped (applied) onto a part of a surface of a substrate so as to be in contact with a substrate and a member disposed on the substrate (hereafter also simply referred to as a "member"), and then the dropped coating liquid is dried. The substrate and the member used in this embodiment will be described later.

In this embodiment, the member is kept in contact with the substrate, or the member is not fixed to the substrate and is kept at a constant distance from the substrate.

As long as the substrate and the member keep the above-described state, the relative positional relationship between the substrate and the member may be fixed or changed when the coating liquid is dropped or dried. In terms of production efficiency, the relative positional relationship between the substrate and the member is preferably changed by moving the member with respect to the substrate. In terms of the film quality and crystal size of the organic semiconductor film to be obtained, the relative positional relationship between the substrate and the member is preferably fixed by making the member stand still with respect to the substrate.

The dropping method of the coating liquid in this embodiment is not particularly limited. From the viewpoint that the thickness of the film of the coating liquid on the substrate tends to be thin and drying tends to progress from the end portion of the film of the coating liquid, when the coating liquid is dropped, it is preferable that a single droplet of the coating liquid is dropped, or a single droplet is dropped at a time when two or more droplets are dropped. When the coating liquid is dropped, the volume of a single droplet of the coating liquid is preferably 0.01 to 0.2 mL and more preferably 0.02 to 0.1 mL.

By dropping the coating liquid onto a part of the surface of the substrate so as to be in contact with both the substrate and the member, the thickness of the end portion of the film of the coating liquid can be decreased.

The contact angle (25° C.) of the coating liquid with respect to the substrate is not particularly limited, but is preferably 0° to 90° and more preferably 10° to 20°. The contact angle of the coating liquid with respect to the substrate is determined by measuring the angle between the liquid droplet and the substrate one second after the coating liquid (solid content: 0.1 mass %, solvent: anisole) is dropped. Specifically, the liquid volume is set to 1.0 µL or more, and a static contact angle is measured by a droplet method using a Teflon (registered trademark) needle. This is performed a plurality of times (normally five times) on different substrates obtained in the same manner, and the average value is calculated and used as a contact angle.

The coating liquid preferably forms a meniscus on the member, and more preferably forms a concave meniscus on the member in terms of film quality.

Hereafter, a method for applying the coating liquid while the distance between the substrate and the member is kept constant in this embodiment will be described with reference to FIGS. 3A to 3C. FIGS. 3A to 3C are schematic views illustrating an example of the method for forming an organic semiconductor film of an organic TFT.

In this method, first, a substrate 42 and a member 43 are disposed at predetermined positions. Specifically, before a coating liquid 41 is dropped onto the substrate, the substrate 42 and the member 43 are disposed at positions illustrated in FIG. 3A. At this time, the distance between the substrate 42 and the member 43 that is not in contact with the substrate 42 is kept constant. The distance between the substrate 42 and the member 43 cannot be unconditionally determined because the distance varies depending on, for example, the coating amount and viscosity of the coating liquid, but can be appropriately set.

Next, as illustrated in FIG. 3B, the coating liquid 41 is dropped onto a part of the surface of the substrate 42 (the vicinity of a portion where the substrate 42 and the member 43 face each other) so as to be in contact with both the substrate 42 and the member 43.

Then, the coating liquid 41 is dried while the relative positional relationship between the substrate 42 and the member 43 is fixed (FIG. 3C). The drying method is not particularly limited, but the above-described drying method of the organic semiconductor composition is preferred. Thus, the coating liquid 41 is dried from both end portions (end edges) having a small film thickness toward the inside on the substrate 42, and the particular cyclic imide compound is crystallized. As a result, the particular cyclic imide compound can be disposed at a predetermined position as a crystal having a large size.

After the coating liquid 41 is dried, the member 43 is separated from the substrate 42 by, for example, pulling up the member 43 in a direction perpendicular to the main surface of the substrate 42. This can achieve formation of an organic semiconductor film having high film quality without leaving a trace of the member 43 in the formed crystal.

In this manner, an organic semiconductor film made of a crystal of the particular cyclic imide compound can be formed.

Hereafter, a method for applying the coating liquid while the substrate and the member are in contact with each other in this embodiment will be described with reference to FIGS. 4A to 4D. FIGS. 4A to 4D are schematic views for describing another example of the method for forming an organic semiconductor film of an organic TFT.

In this method, first, the substrate 42 and the member 43 are disposed in contact with each other. Specifically, before a coating liquid 41 is dropped onto the substrate 42, the substrate 42 and the member 43 are disposed at positions illustrated in FIG. 4A.

Next, as illustrated in FIGS. 4B1 and 4B2, the coating liquid 41 is dropped onto a part of the surface of the substrate 42 (the vicinity of a contact portion between the substrate 42 and the member 43) so as to be in contact with both the substrate 42 and the member 43. At this time, as illustrated in FIG. 4B2, the coating liquid 41 preferably surrounds the contact portion between the substrate 42 and the member 43. FIG. 4B1 is a front view of the substrate onto which the coating liquid has been applied, and FIG. 4B2 is a plan view of the substrate onto which the coating liquid has been applied. Three-dimensional coordinates (X, Y, Z) are shown in FIGS. 4B1 and 4B2.

Then, the coating liquid 41 is dried preferably as described above while the relative positional relationship between the substrate 42 and the member 43 is fixed (FIG. 4C). The drying method is not particularly limited, but the above-described drying method of the organic semiconductor composition is preferred. Thus, the coating liquid 41 is dried from end edges having a small film thickness toward the inside on the substrate 42, and the particular cyclic imide compound is crystallized. As a result, the particular cyclic imide compound can be disposed at a predetermined position as a crystal having a large size.

After the coating liquid 41 is dried, the member 43 is separated from the substrate 42 by, for example, pulling up the member 43 in a direction perpendicular to the main surface of the substrate 42. Consequently, as illustrated in FIG. 4D, an organic semiconductor film 5 having high film quality and made of a crystal of the particular cyclic imide compound can be formed without leaving a trace of the member 43 in the crystal of the particular cyclic imide compound.

The method for applying a coating liquid while the substrate 42 and the member 43 are in contact with each other is preferred to the method for applying a coating liquid while the distance between the substrate 42 and the member 43 is kept constant in terms of film quality, in terms of not requiring a mechanism for holding the member 43, and in terms of being able to keep the distance (contact state) between the substrate 42 and the member 43.

Figure 5A:
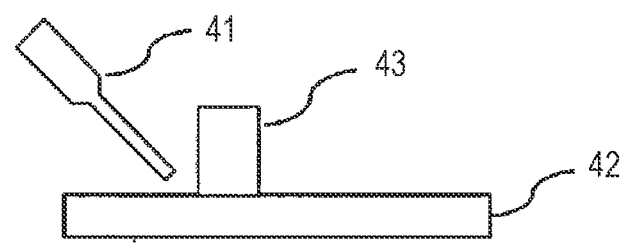
FIGS. 5A to 5C are schematic views for illustrating another example of a method for forming an organic semiconductor film of an organic thin film transistor.
Figure 5B:
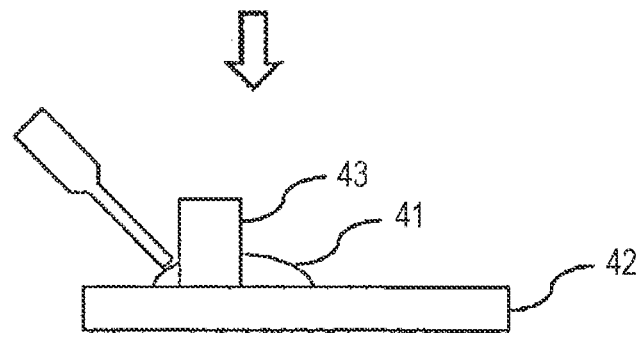
Figure 5C:
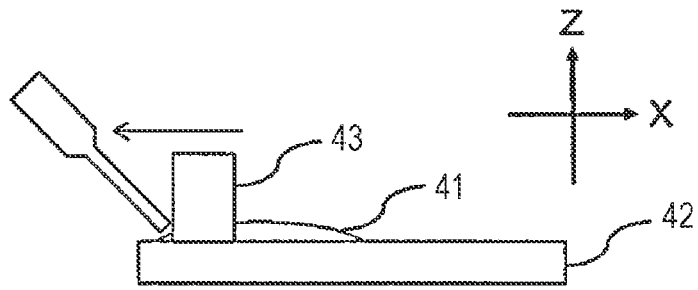

Hereafter, another method for applying the coating liquid while the substrate and the member are in contact with each other in this embodiment will be described with reference to FIGS. 5A to 5C. FIGS. 5A to 5C are schematic views for describing another example of the method for forming an organic semiconductor film of an organic TFT.

This method is different from the method illustrated in FIGS. 4A to 4D in that crystallization of the particular cyclic imide compound is facilitated by moving the member 43 with respect to the substrate 42 while the distance between the substrate 42 and the member 43 is kept constant.

In this method, first, the substrate 42 and the member 43 are disposed in contact with each other. Specifically, before a coating liquid 41 is dropped onto the substrate 42, the substrate 42 and the member 43 are disposed at positions illustrated in FIG. 5A.

Next, as illustrated in FIG. 5B, the coating liquid 41 is dropped onto a part of the surface of the substrate 42 (the vicinity of a contact portion between the substrate 42 and the member 43) so as to be in contact with both the substrate 42 and the member 43. At this time, as illustrated in FIG. 4B2, the coating liquid 41 preferably surrounds the contact portion between the substrate 42 and the member 43.

Then, the coating liquid 41 is dried by moving the member 43 with respect to the substrate 42 while the distance between the substrate 42 and the member 43 is kept constant. For example, the member 43 is moved with respect to the substrate 42 in a direction indicated by an arrow (negative X-axis direction) in FIG. 5C. The drying of the coating liquid 41 progresses from the end portion (the side in a positive X-axis direction) on the side opposite to the moving destination of the member 43 toward the moving destination (the side in a negative X-axis direction), and the particular cyclic imide compound is crystallized. As a result, the particular cyclic imide compound can be disposed at a predetermined position as a crystal having a large size.

After the coating liquid 41 is dried, the member 43 is separated from the substrate 42 by, for example, pulling up the member 43 in a direction perpendicular to the main surface of the substrate 42. Consequently, an organic semiconductor film having high film quality and made of the particular cyclic imide compound can be formed without leaving a trace of the member 43 in the crystal of the particular cyclic imide compound.

The substrate 42 used in this embodiment corresponds to a substrate of an organic TFT, and is preferably a substrate on which a gate insulating film is formed.

The member 43 used in this embodiment is not particularly limited, but the material for the member 43 is preferably an inorganic material (more preferably glass, quartz, or silicon) or a plastic (more preferably Teflon (registered trademark), polyethylene, or polypropylene), and more preferably glass.

The shape of the member 43 used in this embodiment is not particularly limited as long as it has a smooth surface facing the substrate 42, but is preferably a rectangular parallelepiped.

Figure 6:
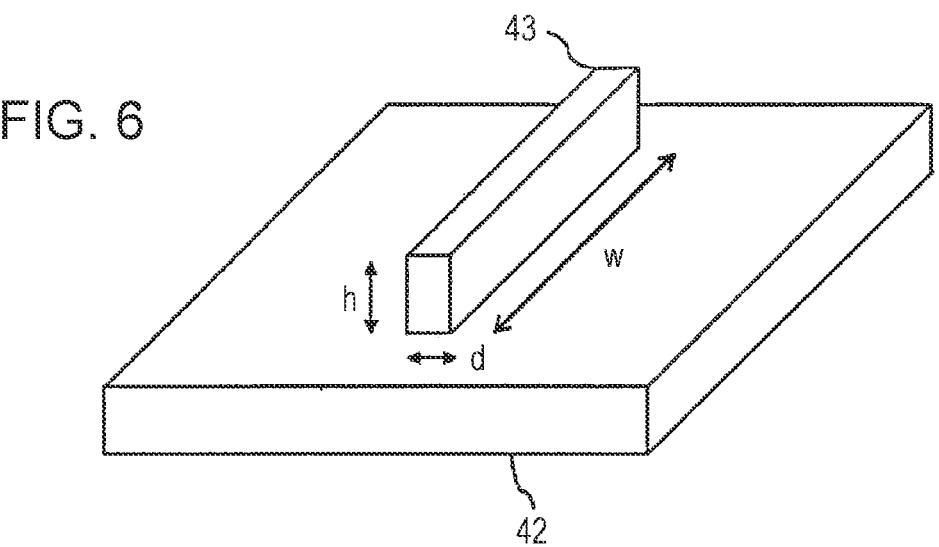
FIG. 6 is a schematic view illustrating an example of a substrate and a member used in a method for forming an organic semiconductor film of an organic thin film transistor.

FIG. 6 is a schematic view illustrating an example of the substrate 42 and the member 43 used in this embodiment. In FIG. 6, the shape of the member 43 is a rectangular parallelepiped, d and w represent the lengths of one side and the other side of a surface of the member 43 facing the substrate 42, respectively, and h represents the height of the member 43.

The size of the member 43 used in this embodiment is not particularly limited. When the member 43 has a rectangular parallelepiped shape as illustrated in FIG. 6, the lower limit of the lengths of one side and the other side (d and w in FIG. 6) of a surface of the member 43 facing the substrate 42 is preferably 0.1% or more, more preferably 1% or more, further preferably 10% or more, and particularly preferably 20% or more relative to the length of one side of a main surface (a surface onto which the coating liquid is applied) of the substrate 42. The upper limit of the lengths of the one side and the other side is preferably 80% or less, more preferably 70% or less, and further preferably 50% or less relative to the length of one side of the main surface of the substrate 42. The height (h in FIG. 6) of the member 43 is preferably 1 to 50 mm and more preferably 5 to 20 mm. Furthermore, the ratio h/d of the height h to the length d of the member 43 is preferably 0.01 to 10 and more preferably 0.1 to 5 in terms of the arrangement stability of the member 43. The ratio w/d of the length w to the length d of the member 43 is preferably 1 to 1000 and more preferably 5 to 100 because the particular cyclic imide compound can be crystallized in a wide area.

In this manner, an organic semiconductor film can be formed by precipitating a crystal of the particular cyclic imide compound. Whether a crystal of the particular cyclic imide compound is precipitated can be checked by observing the organic semiconductor film using a polarizing microscope (trade name: Eclipse LV100N POL (diascopic/episcopic illumination type), manufactured by Nikon Corporation, ocular lens: 10 times, objective lens: 5 to 20 times).

Application of Organic TFT

The applications of the above-described organic TFT are not particularly limited. The organic TFT can be used for, for example, electronic paper, display devices, sensors, and electronic tags.

EXAMPLES

Hereafter, the present invention will be described in further detail based on Examples. Materials, used amounts, ratios, processing contents, processing procedures, and the like shown in Examples below can be appropriately changed without departing from the spirit of the present invention. Therefore, the scope of the present invention should not be construed as being limited by Examples below.

Example 1: Synthesis of Compound (1-1)

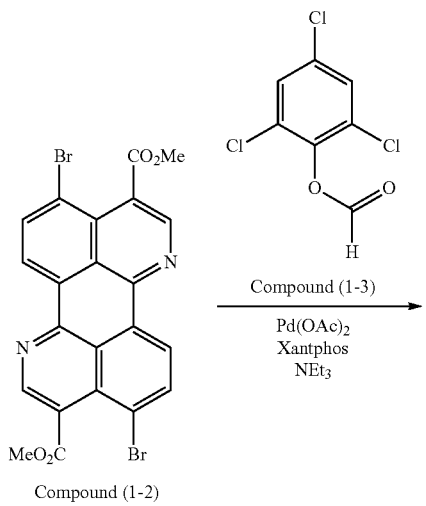

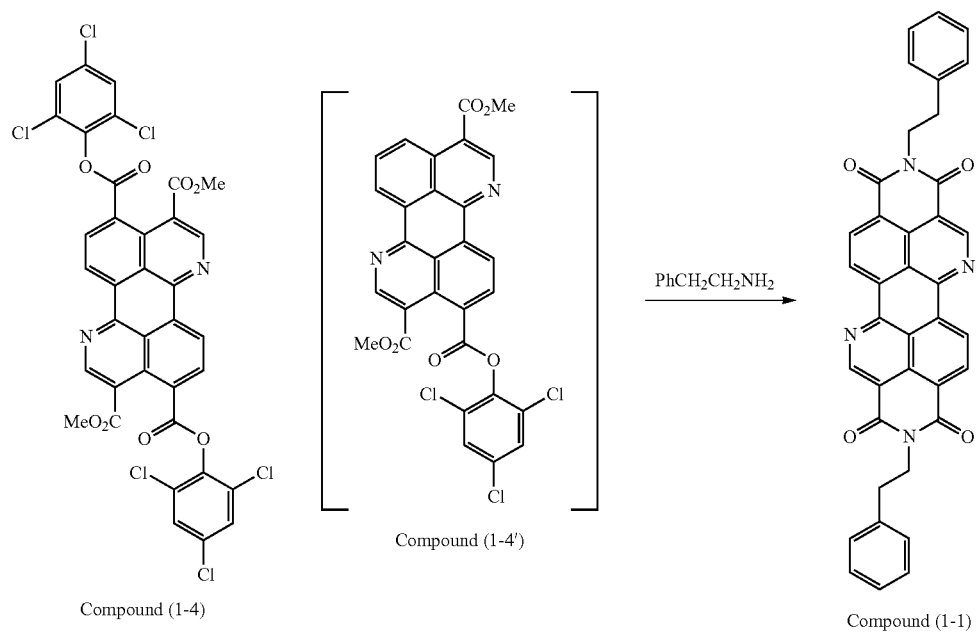

Purification of Compound (1-3)

A compound (1-3) was purified by recrystallization from hexane-ethyl acetate. Synthesis of composition (raw material composition) including compound (1-4)

Into a glass reaction vessel equipped with a pressure-resistant balloon, 20 g (37.9 mmol) of a compound (1-2), 200 mL of toluene, 0.851 g (3.79 mmol) of palladium acetate, 4.39 g (7.58 mmol) of xantphos, and 51.0 g (227 mmol) of the compound (1-3) were charged, and the reaction vessel was nitrogen-purged. After 37.0 mL (265 mmol) of triethylamine was added dropwise with a syringe, stirring was performed at 75° C. to 85° C. for seven hours. After cooling to room temperature, the precipitated solid was filtered. The obtained solid was dispersed in methanol, stirred at room temperature for 30 minutes, and then collected by filtration. The filter residue was dissolved in chloroform, and silica gel was added thereto, and filtration was performed. The filtrate was concentrated under reduced pressure and recrystallized from o-dichlorobenzene to obtain 23.2 g (28.4 mmol, yield 69.6%) of a composition including a compound (1-4). The content of the compound (1-4) in the obtained composition was 98.6 mass % relative to the total solid content of the composition, and the content of the compound (1-4') was 0.1 mass % or less relative to the total solid content of the composition.

The "raw material composition" in the column of Example 1 in Table 5 below refers to a composition including the compound (1-4) obtained herein.

Synthesis of Compound (1-1)

Into a glass reaction vessel, 1.00 g (1.22 mmol) of a composition including the compound (1-4), 40 mL of o-dichlorobenzene, and 593 mg (4.89 mmol) of phenethylamine were charged, and stirring was performed at 150° C. for 2 hours. After cooling to room temperature, methanol was added and the solid was collected by filtration. The obtained solid was dried in vacuum and then purified by sublimation to obtain 466 mg (0.776 mmol, yield 63.6%) of a compound (1-1).

Example 2: Synthesis of Compound (1-1)

Production of Composition (Raw Material Composition) Including Compound (1-4)

A composition including the compound (1-4) was obtained in the same manner as in Example 1, except that the compound (1-3) was not purified by recrystallization. The content of the compound (1-4) in the obtained composition was 94.9 mass % relative to the total solid content of the composition, and the content of the compound (1-4') was 3.0 mass % relative to the total solid content of the composition.

The "raw material composition" in the column of Example 2 in Table 5 below refers to a composition including the compound (1-4) obtained herein.

Synthesis of Compound (1-1)

By the same method as in Example 1, 451 mg (0.751 mmol, yield 61.5%) of a compound (1-1) was obtained.

Example 3: Synthesis of Compound (3-1)

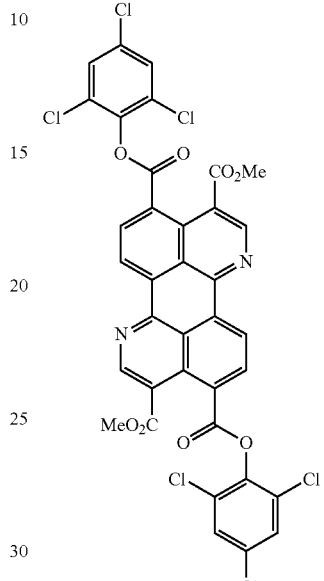

Compound (1-4)

$n\text{-}C_8H_{17}NH_2$ →

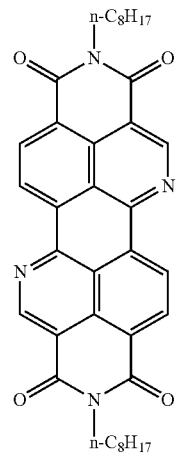

Compound (3-1)

Synthesis of Compound (3-1)

A compound (3-1) was obtained in an amount of 452 mg (0.733 mmol, yield 60.1%) in the same manner as in Example 1, except that 631 mg (4.89 mmol) of n-octylamine was used instead of phenethylamine.

Example 4: Production of Compound (4-1)

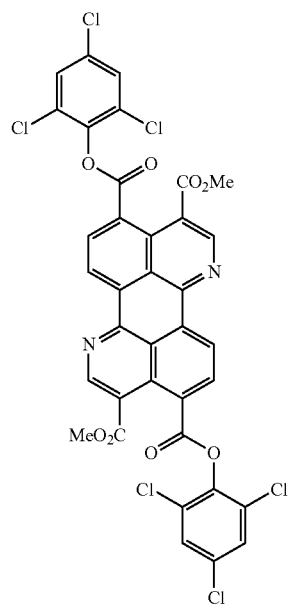

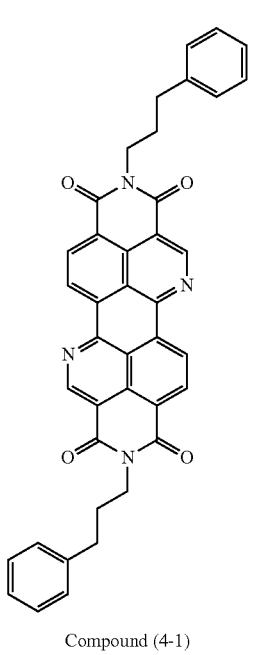

A compound (4-1) was obtained in an amount of 480 mg (0.764 mmol, yield 62.6%) in the same manner as in Example 1, except that 661 mg (4.89 mmol) of 3-phenylpropylamine was used instead of phenethylamine.

Example 5: Synthesis of Compound (1-1)

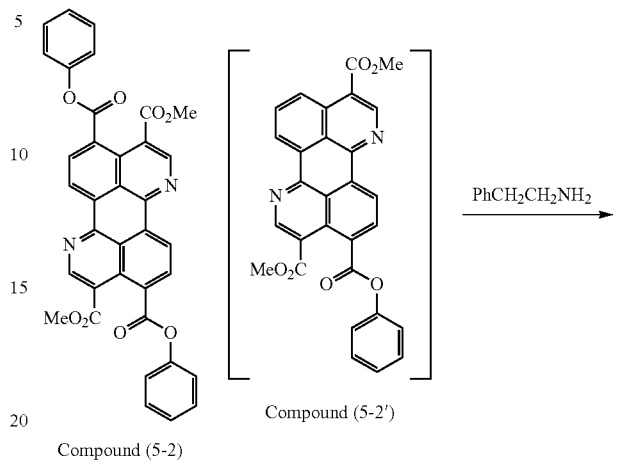

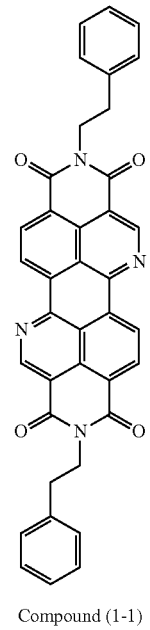

Production of Compound (1-1)

A compound (1-1) was obtained in an amount of 447 mg (0.745 mmol, yield 61.1%) in the same manner as in Example 1, except that 745 mg (1.22 mmol) of a composition including a compound (5-2) below was used instead of the composition including the compound (1-4).

In the composition including the compound (5-2), the content of the compound (5-2) was 98.1 mass % relative to the total solid content of the composition including the compound (5-2), and the content of the compound (5-2') was 0.1 mass % or less relative to the total solid content of the composition including the compound (5-2).

The "raw material composition" in the column of Example 5 in Table 5 below refers to a composition including the compound (5-2).

Example 6: Synthesis of Compound (1-1)

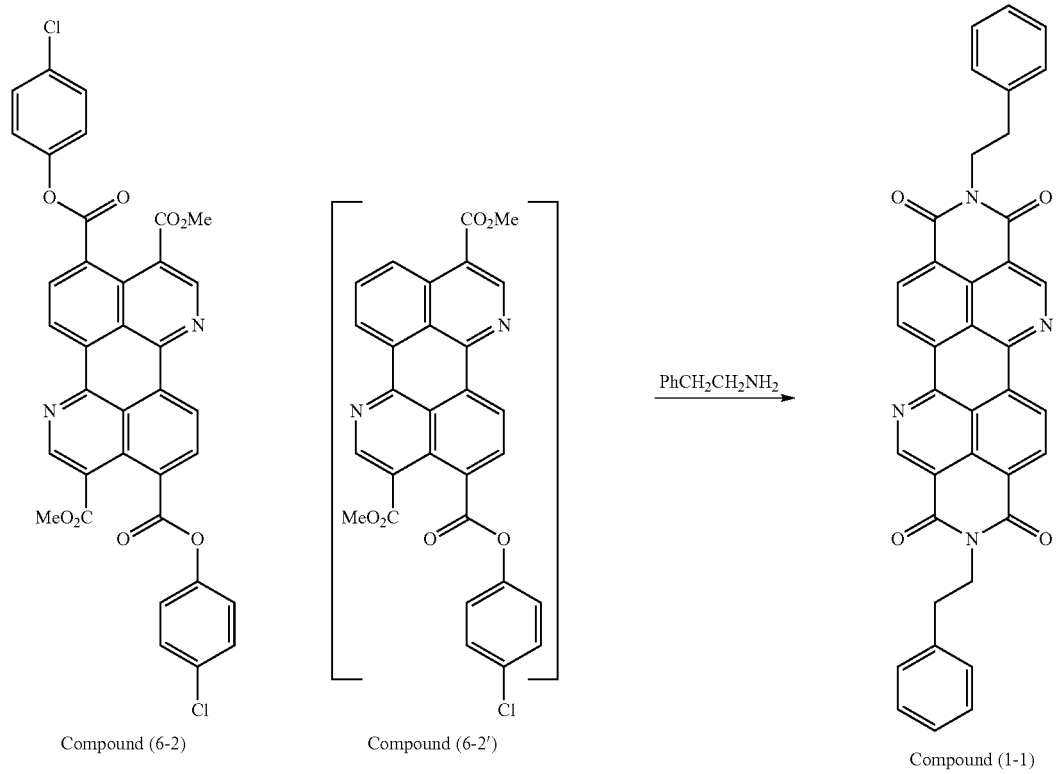

Synthesis of Compound (1-1)

A compound (1-1) was obtained in an amount of 462 mg (0.770 mmol, yield 63.1%) in the same manner as in Example 1, except that 829 mg (1.22 mmol) of a composition including a compound (6-2) was used instead of the composition including the compound (1-4).

In the composition including the compound (6-2), the content of the compound (6-2) was 98.2 mass % relative to the total solid content of the composition including the compound (6-2), and the content of the compound (6-2') was 0.1 mass % or less relative to the total solid content of the composition including the compound (6-2).

The "raw material composition" in the column of Example 6 in Table 5 below refers to a composition including the compound (6-2).

Example 7: Synthesis of Compound (1-1)

Purification of Compound (1-3)

The compound (1-3) was washed with cold hexane.

Synthesis of Composition (Raw Material Composition) Including Compound (1-4)

A composition including the compound (1-4) was obtained in the same manner as in Example 1, except that the compound (1-3) was used. The content of the compound (1-4) in the obtained composition was 97.8 mass % relative to the total solid content of the composition, and the content of the compound (1-4') was 1.0 mass % relative to the total solid content of the composition.

The "raw material composition" in the column of Example 7 in Table 5 below refers to a composition including the compound (1-4) obtained herein.

Synthesis of Compound (1-1)

By the same method as in Example 1, 445 mg (0.741 mmol, yield 60.7%) of a compound (1-1) was obtained.

Comparative Example 1: Synthesis of Compound (1-1)

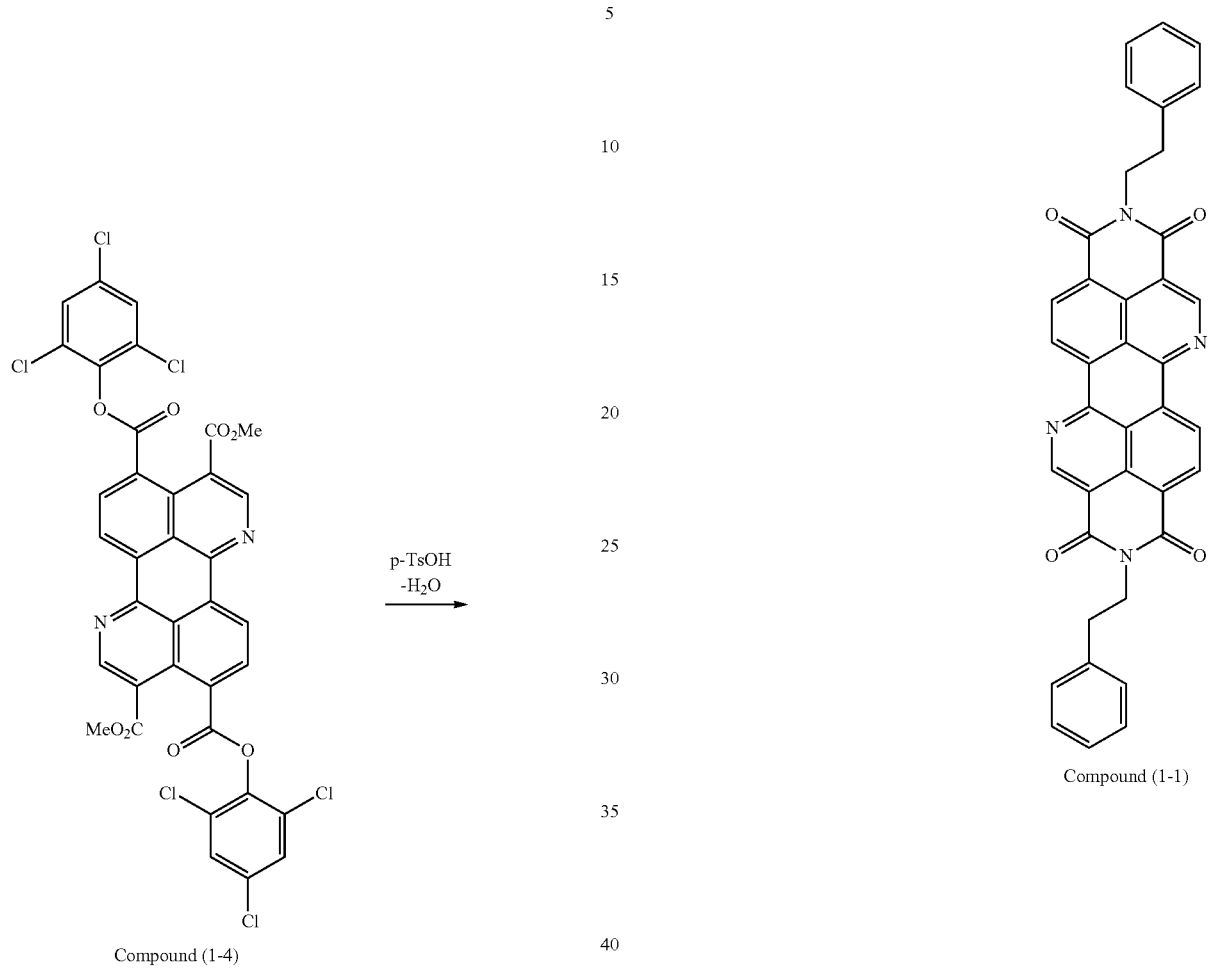

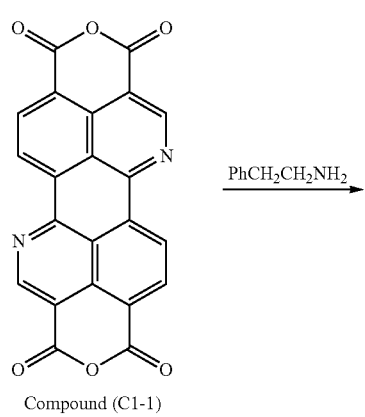

Synthesis of Compound (C1-1)

Into a glass reaction vessel, 410 mg (0.502 mmol) of a compound (1-4), 477 mg (2.51 mmol) of p-toluenesulfonic acid monohydrate, and 40 mL of o-dichlorobenzene were charged, and stirring was performed at 120° C. for 12 hours. After the reaction solution was concentrated under reduced pressure, the solid was dispersed in hexane and collected by filtration. The resulting solid was dispersed in ethyl acetate, then collected by filtration, and washed with ethyl acetate to obtain 95 mg (0.240 mmol, yield 47.8%) of a compound (C1-1).

Synthesis of Compound (1-1)

Into a glass reaction vessel, 500 mg (1.27 mmol) of the compound (C1-1), 615 mg (5.07 mmol) of 2-phenylethylamine, and 20 mL of o-dichlorobenzene were charged, and stirring was performed at 150° C. for 3 hours. After cooling with water, 40 mL of methanol was added, and filtration was performed for collection. The obtained solid was dried under reduced pressure and then purified by sublimation to obtain 375 mg (0.624 mmol, yield 49.1%) of a compound (1-1).

The yield of the compound (1-1), which was a final target compound, relative to the compound (1-4) was 23.5%.

Comparative Example 2: Production of Compound (1-1)

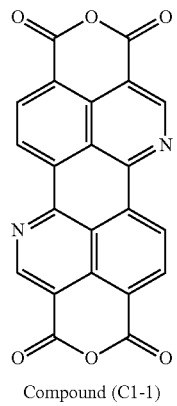

Compound (C1-1)

PhCH₂CH₂NH₂ →

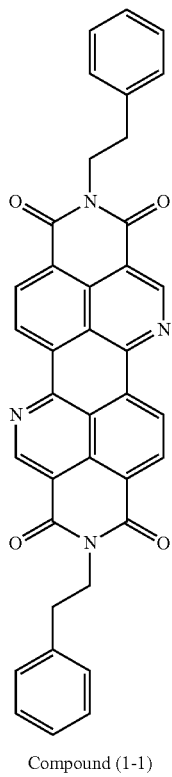 [SMILES: O=C1c2ccc3c4ncc5c6c(ccc(c7ncc(c2c37)C(=O)N1CCc1ccccc1)c64)C(=O)N(CCc1ccccc1)C5=O]

Compound (1-1)

A compound (1-1) was obtained in an amount of 611 mg (1.02 mmol, yield 80.1%) in the same manner as in Comparative Example 1, except that purification by sublimation was not performed.

The yield of the compound (1-1), which was a final target compound, relative to the compound (1-4) was 38.3%.

Evaluation

Analysis of Purity by Liquid Chromatography

The cyclic imide compounds finally obtained by the production methods in Examples and Comparative Examples were analyzed by liquid chromatography under the following conditions and evaluated based on the following criteria.

Column: Tosoh TSKgel Silica-150 (particle size: 5 μm, inner diameter: 4.6 mm, length: 25 cm)

Eluant: chloroform/hexafluoroisopropanol=9/1

Flow rate: 0.8 mL/min

Injection volume: 10 μL

Column temperature: 25° C.

Detection wavelength: 254 nm

Sample: 50 w/v ppm (solvent: chloroform/hexafluoroisopropanol=4/1)

Evaluation Criteria

A: The area percentage of the target is 99% or more.

B: The area percentage of the target is 97.5% or more and less than 99%.

C: The area percentage of the target is 95% or more and less than 97.5%.

D: The area percentage of the target is less than 95%.

Production and Evaluation of Organic Thin Film Transistor

Production of Organic Thin Film Transistor

A substrate (size: 25 mm×25 mm) in which a $SiO_2$ thermally oxidized film (thickness: 200 nm) was formed on a surface of an n-type silicon substrate (thickness: 0.4 mm, corresponding to the substrate 1 provided with the gate electrode 2) 1 was provided as a substrate for measuring FET characteristics. The surface of the thermally oxidized film (gate insulating film 3) of the substrate was cleaned with ultraviolet (UV)-ozone and then treated with β-phenethyltrimethoxysilane.

A glass member having a size of 10 mm in length×2 mm in width×5 mm in height was provided. The member serving as a member 43 illustrated in FIGS. 4A to 4D was disposed at a central portion of the surface of the substrate 1 treated with β-phenethyltrimethoxysilane as illustrated in FIG. 4A while the member was in contact with the treated surface.

Then, as illustrated in FIG. 4A, a single droplet (about 0.05 mL) of a 1-methylnaphthalene solution (0.03 mass %) of the compound obtained by the production method in each of Examples and Comparative Examples was dropped onto the substrate 1 (indicated by reference numeral 42 in FIGS. 4A to 4D) heated to 100° C. near the contact portion between the substrate 42 and the member 43 from the side of the member 43 using a pipet so as to be in contact with the substrate 42 and the member 43. As illustrated in FIGS. 4B1 and 4B2, the coating liquid surrounded the contact portion and formed a concave meniscus at the interface with the member 43. The contact angle (25° C.) of the coating liquid 41 relative to the substrate 42 was 10°.

As illustrated in FIG. 4C, the coating liquid 41 was dried at 150° C. while the substrate 42 and the member 43 were in contact with each other and the positional relationship between the substrate 42 and the member 43 was not changed. Then, the resulting film was dried under a reduced pressure of 10-3 Pa at 60° C. for 8 hours to produce a crystal film of an organic semiconductor film. Subsequently, the member 43 was pulled up in a direction perpendicular to the substrate 42 to separate the member 43 from the substrate 42. Thus, a ring-shaped organic semiconductor film 5 having the above-described uniform thickness (thickness: 10 to 50 nm) was formed as illustrated in FIG. 4D.

The obtained organic semiconductor film 5 was observed with a polarizing microscope Eclipse LV100N POL (diascopic/episcopic illumination type, manufactured by Nikon Corporation, ocular lens: 10 times, objective lens: 5 to 20 times). As a result, the crystal of the above compound was precipitated.

A mask having a predetermined opening was disposed on the obtained organic semiconductor film 5, and vapor deposition was performed using gold to form a source electrode 4A and a drain electrode 4B (each having a thickness of 40 nm, a gate width W of 2 mm, a gate length L of 50 μm, and a ratio W/L of 40). In this manner, an organic thin film transistor for measuring FET characteristics was produced.

For the evaluation described later, ten organic thin film transistors were produced using the compound obtained by the production method in each of Examples and Comparative Examples.

Evaluation of Organic Thin Film Transistor

1. Method for Measuring Carrier Mobility μ

The carrier mobility of each of the produced organic thin film transistors was measured at a normal atmospheric pressure of 1 atm (temperature: room temperature) using a semiconductor parameter analyzer (manufactured by Agilent, 4156C) to which a semi-automatic prober (manufactured by Vector Semiconductor Co., Ltd., AX-2000) was connected. The specific method is as follows.

A voltage of −80 V was applied across the source electrode and the drain electrode of each organic thin film transistor, the gate voltage was changed within the range of +20 V to −100 V, and the carrier mobility μ (cm$^2$/Vs) was calculated using the following formula representing a drain current $I_d$.

$$I_d = (w/2L)\mu C_i (V_g - V_{th})^2$$

In the formula, L represents a gate length, w represents a gate width, μ represents a carrier mobility, $C_i$ represents a capacitance of the gate insulating film per unit area, $V_g$ represents a gate voltage, and $V_{th}$ represents a threshold voltage.

2. Evaluation of Relative Mobility

The carrier mobility was calculated for each of the ten organic thin film transistors produced in each of Examples and Comparative Examples, and the average mobility was determined. Then, the relative mobility was calculated from the following formula using the average mobility in Example 1 as a reference, and evaluated based on the following criteria.

The relative mobility is preferably as high as possible. In this test, the relative mobility is preferably Rank C or higher, more preferably Rank B or higher, and further preferably Rank A.

Relative mobility=(Average mobility in each of Examples or Comparative Examples)/(Average mobility in Example 1)

Evaluation Criteria
A: The relative mobility is 1.0 or more.
B: The relative mobility is 0.6 or more and less than 1.0.
C: The relative mobility is 0.2 or more and less than 0.6.
D: The relative mobility is less than 0.2.

3. Evaluation of Variation

The mobility ratio was calculated from the following formula for each of the ten organic thin film transistors produced in each of Examples and Comparative Examples, and evaluated based on the following criteria.

Mobility ratio=(Highest mobility among ten organic thin film transistors)/(Lowest mobility among ten organic thin film transistors)

Evaluation Criteria
A: The mobility ratio is less than 1.5.
B: The mobility ratio is 1.5 or more and less than 1.8.
C: The mobility ratio is 1.8 or more and less than 2.1.
D: The mobility ratio is 2.1 or more.

Table 5 shows the results.

In Table 5, the "Raw material composition" is intended to be a composition that is used for obtaining the compound represented by the formula (9) in the above-described production method and that includes the compound represented by the formula (8) and the compound represented by the formula (17) (note that the above composition did not include the compound represented by the formula (18)). Specifically, for example, in Example 1, "the composition including a compound (1-4)" obtained in Synthesis of composition (raw material composition) of compound (1-4) corresponds to the "raw material composition" herein. In the raw material composition in Example 1, the compound (1-4) corresponds to the compound represented by the formula (8), and the compound (1-4') corresponds to the compound represented by the formula (17).

The "Content of compound represented by formula (8)" in the column of "Raw material composition" is intended to be a content (mass %) of the compound represented by the formula (8) in the raw material composition relative to the total solid content of the raw material composition.

The "Content of compound represented by formula (17)" in the column of "Raw material composition" is intended to be a content (mass %) of the compound represented by the formula (17) in the raw material composition relative to the total solid content of the raw material composition.

The synthesis methods in Examples 1 to 7 correspond to the synthesis method in the first embodiment-1 described above.

TABLE 5

| | Raw material composition | | | | | Evaluation of organic transistor | | |
|---|---|---|---|---|---|---|---|---|
| | Type and content of compound represented by formula (8) | | Type and content of compound represented by formula (17) | | Product target (final product) | Yield (%) | Purity | Relative mobility | Variation |
| Example 1 | Compound (1-4) | 98.6% | Compound (1-4') | 0.1% or less | Compound (1-1) | 63.6 | A | A | A |
| Example 2 | Compound (1-4) | 94.9% | Compound (1-4') | 3.0% | Compound (1-1) | 61.5 | B | B | B |
| Example 3 | Compound (1-4) | 98.6% | Compound (1-4') | 0.1% or less | Compound (3-1) | 60.1 | A | A | A |
| Example 4 | Compound (1-4) | 98.6% | Compound (1-4') | 0.1% or less | Compound (4-1) | 62.6 | A | A | A |
| Example 5 | Compound (5-2) | 98.1% | Compound (5-2') | 0.1% or less | Compound (1-1) | 61.1 | A | A | A |
| Example 6 | Compound (6-2) | 98.2% | Compound (6-2') | 0.1% or less | Compound (1-1) | 63.1 | A | A | A |

TABLE 5-continued

| | Raw material composition | | | | Evaluation of organic transistor | | |
|---|---|---|---|---|---|---|---|
| | Type and content of compound represented by formula (8) | Type and content of compound represented by formula (17) | Product target (final product) | Yield (%) | Purity | Relative mobility | Variation |
| Example 7 | Compound (1-4) 97.8% | Compound (1-4') 1.0% | Compound (1-1) | 60.7 | A | A | A |
| Comparative Example 1 | Compound (C1-1) — | — — | Compound (1-1) | 23.5 | C | C | C |
| Comparative Example 2 | Compound (C1-1) — | — — | Compound (1-1) | 38.3 | D | D | D |

As is clear from the results in Table 5, the cyclic imide compounds obtained by the production methods in Examples are excellent in terms of yield and purity.

As is also clear from the results in Examples 1 to 7, when the content of the compound represented by the formula (17), which is an impurity, in the raw material composition is equal to or less than a predetermined value (Examples other than Example 2), the target cyclic imide compound has a higher purity.

Furthermore, as is clear from the comparison of Example 1, Example 5, and Example 6, when the compound represented by the formula (8), which is a raw material component, is the compound represented by the formula (10) (preferably the compound represented by the formula (10')), the target cyclic imide compound is obtained at a higher yield.

Example 8: Production of Compound (8-1)

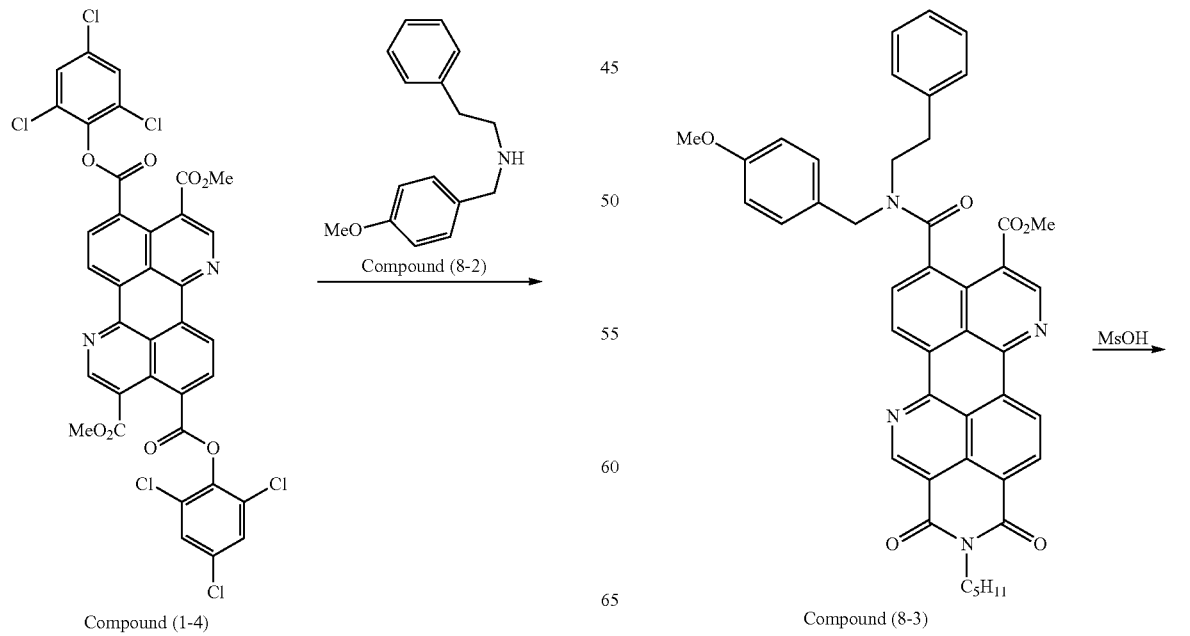

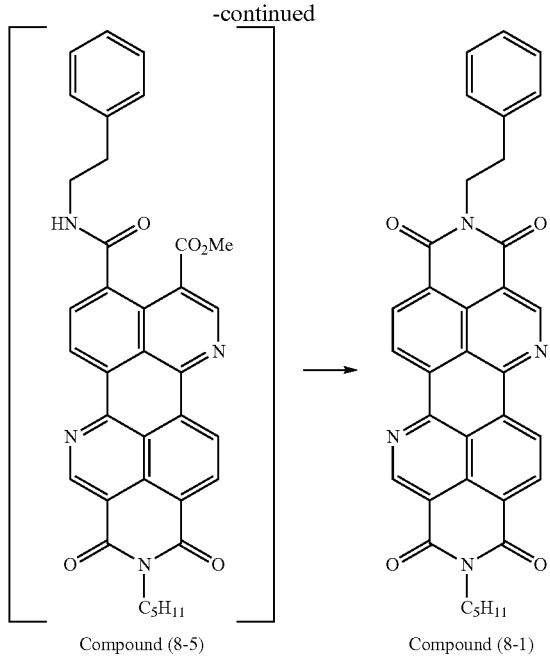

Compound (8-5)　　　　Compound (8-1)

Synthesis of compound (8-3)

A composition including the compound (1-4) purified by the same method as in Example 1 was used. The content of the compound (1-4) in the composition including the compound (1-4) was 98.6 mass % relative to the total solid content of the composition, and the content of the compound (1-4') was 0.1 mass % or less relative to the total solid content of the composition.

Subsequently, 1.60 g (1.96 mmol) of the composition including the compound (1-4), 1.65 g (6.85 mmol) of the compound (8-2), and 32 mL of o-dichlorobenzene were charged into a glass reaction vessel and stirred at 180° C. for 1 hour. After removal of the solvent by distillation under reduced pressure, the resulting product was purified by silica gel column chromatography to obtain 580 mg (0.674 mmol, yield 34.4%) of a compound (8-3).

Compound (8-3): $^1$H NMR (400 MHz, TCE-d$^2$, 100° C.): δ 2.87-3.08 (brm, 2H, Ph-CH$_2$—CH$_2$), 3.62-3.75 (brm, 2H, Ph-CH$_2$-21CH$_2$—), 3.82 (s, 3H, CH$_3$—O-Ph), 3.89 (s, 3H, CH$_3$—O—C=O (ester of the Cl$_3$Ph side)), 3.93-4.08 (brm, 3H, CH$_3$—O—C=O (ester of the PMB group side)), 4.08-5.55 (brm, 2H, Ph-CH$_2$—N), 6.82-7.43 (brm, 9H, ArH), 7.46 (s, 2H, ArH of Cl$_3$Ph), 7.65-8.73 (brm, 1H, ArH), 8.84-9.23 (m, 5H, ArH).

TCE refers to 1,1,2,2-tetrachloroethane.

Synthesis of Compound (8-4)

Into a glass reaction vessel, 300 mg (0.348 mmol) of the compound (8-3), 60.8 mg (0.697 mmol) of n-pentylamine, and 3 mL of o-dichlorobenzene were charged, and reaction was caused at 110° C. for 1 hour. After removal of the solvent by distillation under reduced pressure, the resulting product was dispersed in acetonitrile, collected by filtration, and dried under reduced pressure to obtain 221 mg (0.307 mmol, yield 88.3%) of a compound (8-4).

Compound (8-4): $^1$H NMR (400 MHz, TCE-d$^2$, 100° C.): δ 0.94 (t, J=6.8 MHz, 3H, CH$_2$—CH$_3$), 1.37-1.45 (m, 4H, N—CH$_2$—CH$_2$—(CH$_2$)$_2$—CH$_3$), 1.78 (q, J=6.8 Hz, 2H, N—CH$_2$—CH$_2$—C$_3$H$_7$), 2.89-3.10 (brm, 2H, Ph-CH$_2$—CH$_2$), 3.63-3.75 (brm, 2H, Ph-CH$_2$—CH$_2$—), 3.82 (s, 3H, CH$_3$—O-Ph), 3.97-4.01 (brm, 3H, CH$_3$—O—C=O), 4.19 (t, J=7.2 Hz, 2H, N—CH$_2$—C$_4$H$_9$), 4.30-5.55 (brm, 2H, Ph-CH$_2$—N), 6.84-7.41 (brm, 10H, ArH), 8.68-9.57 (m, 5H, ArH).

Synthesis of Compound (8-1)

Into a glass reaction vessel, 164 mg (0.228 mmol) of the compound (8-4), 8.6 mL of o-dichlorobenzene, and 54.8 mg (0.570 mmol) of methanesulfonic acid were charged, and stirring was performed at 150° C. for 3 hours. After cooling with water, the resulting mixture was filtered and dried under reduced pressure. The obtained solid was purified by sublimation to obtain 35 mg (0.0618 mmol, yield 27.1%) of a compound (8-1).

Compound (8-1): $^1$H NMR (400 MHz, TCE-d$^2$, 100° C.): δ 0.94 (t, J=7.0 Hz, 3H, —CH$_2$—CH$_3$), 1.44-1.40 (m, 4H, N—CH$_2$—CH$_2$—(CH$_2$)$_2$—CH$_3$), 1.79 (q, 2H, J=7.2 Hz, N—CH$_2$—CH$_2$—C$_3$H$_7$), 3.07 (t, J=7.8 Hz, 2H, Ph-CH$_2$—), 4.20 (t, J=7.4 Hz, 2H, N—CH$_2$—C$_4$H$_9$), 4.45 (t, J=7.8 Hz, 2H, Ph-CH$_2$—CH$_2$—), 7.34-7.18 (m, 5H, ArH of phenyl), 8.84 (d, J=7.6 Hz, 2H, ArH), 9.27 (d, J=8.0 Hz, 2H, ArH), 9.64 (s, 2H, ArH).

Example 9

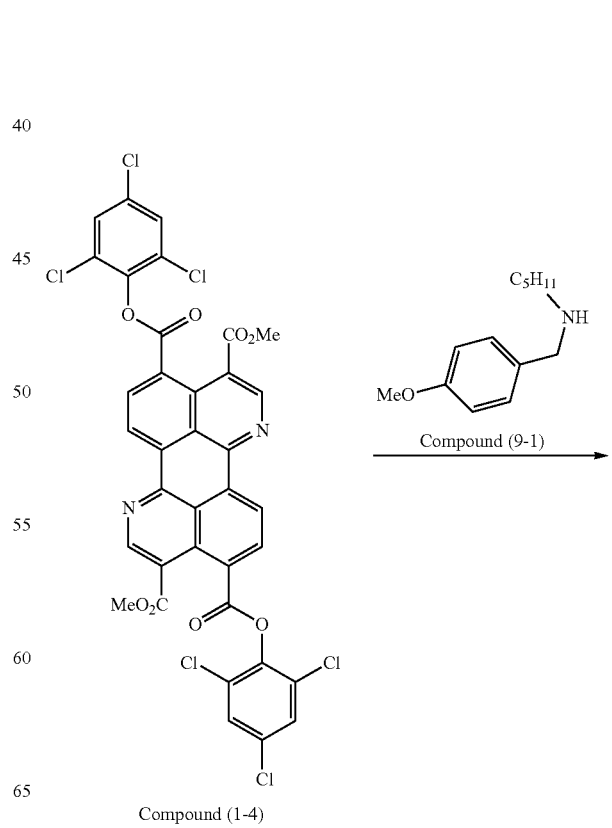

Compound (1-4)

189
-continued
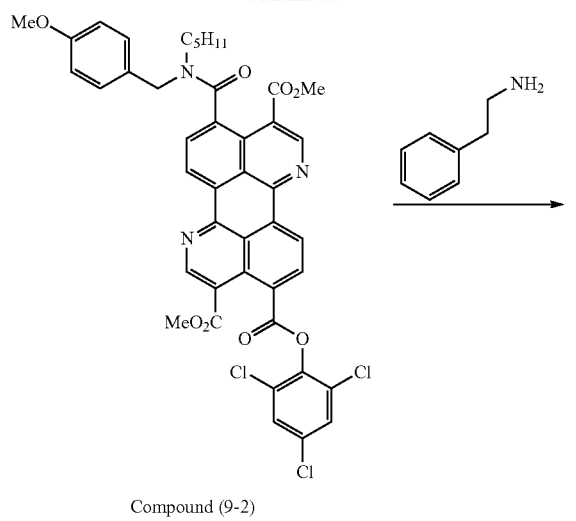
Compound (9-2)
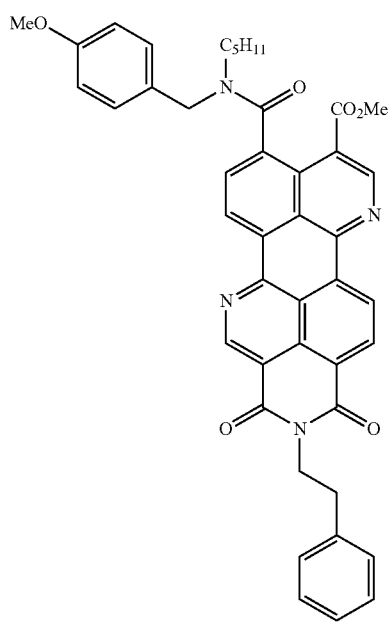
Compound (9-4)
190
-continued
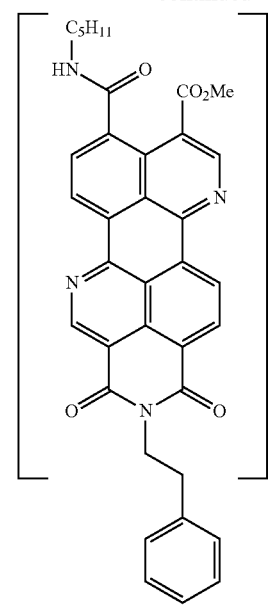
Compound (9-4)
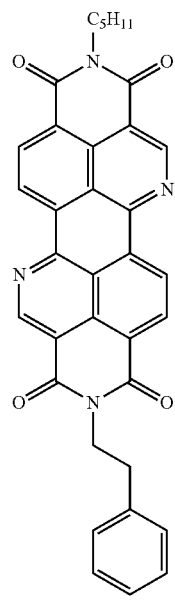
Compound (8-1)
Synthesis of Compound (9-2)
A compound (8-1) was obtained in the same manner as in Example 8, except that the compound (9-1) was used instead of the compound (8-2), and phenethylamine was used instead of the pentylamine.

Example 10
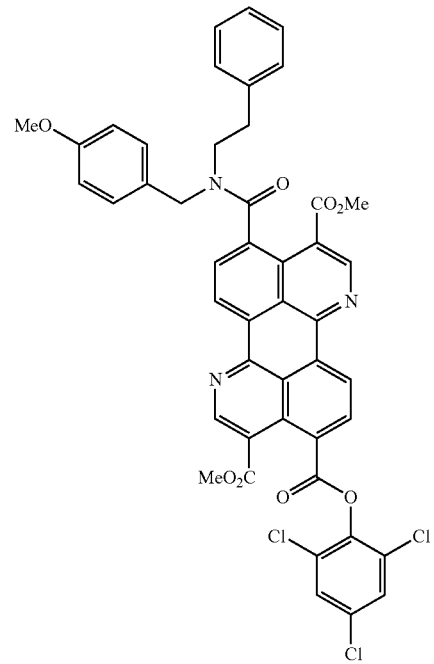
Compound (8-3)
n-C₈H₁₇NH₂ →
[Compound (10-3)] →
Compound (10-2)  MsOH→  Compound (10-1)

Production of Compound (10-1)

A compound (10-1) was obtained in the same manner as in Example 8, except that octylamine was used instead of the pentylamine.

Compound (10-2): $^1$H NMR (400 MHz, TCE-d$^2$, 100° C.): δ 0.83 (t, J=6.6 MHz, 3H, CH$_2$—C$\underline{H}_3$), 1.19-1.38 (m, 10H, CH$_2$—(C$\underline{H}_2$)$_5$—CH$_3$), 1.69 (q, J=6.4 Hz, 2H, N—CH$_2$—C$\underline{H}_2$—C$_6$H$_{13}$), 2.85-3.14 (m, 2H, Ph-C$\underline{H}_2$—CH$_2$), 3.53-3.74 (m, 2H, Ph-CH$_2$—C$\underline{H}_2$—), 3.79-3.83 (m, 3H, C$\underline{H}_3$—O-Ph), 3.92-4.02 (m, 3H, C$\underline{H}_3$—O—C=O), 4.13 (t, J=7.2 Hz, 2H, N—C$\underline{H}_2$—C$_7$H$_{15}$), 4.31-5.24 (m, 2H, Ph-C$\underline{H}_2$—N), 6.87-7.41 (m, 9H, Ar$\underline{H}$), 7.53-8.20 (m, 1H, Ar$\underline{H}$), 8.64-9.47 (m, 5H, Ar$\underline{H}$).

Compound (10-1): $^1$H NMR (400 MHz, TCE-d$^2$, 100° C.): δ 0.88 (t, J=7.0 Hz, 3H, CH$_2$—C$\underline{H}_3$), 1.50-1.30 (m, 10H, N—CH$_2$—CH$_2$—(C$\underline{H}_2$)$_5$—CH$_3$), 1.78 (q, J=7.2 Hz, 2H, N—CH$_2$—C$\underline{H}_2$—C$_6$H$_{13}$), 3.07 (t, J=7.8 Hz, 2H, Ph-C$\underline{H}_2$—), 4.19 (t, J=7.4 Hz, 2H, N—C$\underline{H}_2$—C$_7$H$_{15}$), 4.44 (t, J=7.8 Hz, 2H, Ph-CH$_2$—C$\underline{H}_2$—), 7.18-7.34 (m, 5H, Ar$\underline{H}$ of phenyl), 8.85 (d, J=7.6 Hz, 2H, Ar$\underline{H}$), 9.28 (d, J=8.0 Hz, 2H, Ar$\underline{H}$), 9.64 (s, 2H, Ar$\underline{H}$).

Evaluation

"Analysis of purity by liquid chromatography" and "Production and evaluation of organic thin film transistor" were performed in the same manner as in Example 1 using the compounds obtained by the production methods in Examples 8 to 10. Table 6 shows the results.

In Table 6, the "Raw material composition" is intended to be a composition that is used for obtaining the compound represented by the formula (9) in the above-described production method and that includes the compound represented by the formula (8) and the compound represented by the formula (17) (note that the above composition did not include the compound represented by the formula (18)). Specifically, "the composition including a compound (1-4)" in Examples 8 to 10 corresponds to the "raw material composition" herein. In the raw material compositions in Examples 8 to 10, the compound (1-4) corresponds to the compound represented by the formula (8), and the compound (1-4') corresponds to the compound represented by the formula (17).

The "Content of compound represented by formula (8)" in the column of "Raw material composition" is intended to be a content (mass %) of the compound represented by the formula (8) in the raw material composition relative to the total solid content of the raw material composition.

The "Content of compound represented by formula (17)" in the column of "Raw material composition" is intended to be a content (mass %) of the compound represented by the formula (17) in the raw material composition relative to the total solid content of the raw material composition.

The numerical value in the column of "yield" refers to a yield of a final target compound (e.g., the compound (8-1) in Example 8) relative to the compound (1-4).

The production methods in Examples 8 to 10 correspond to the production method in the above-described second embodiment.

TABLE 6

| | Raw material composition | | Product (final target product) | Yield (%) | Evaluation of organic transistor | | |
|---|---|---|---|---|---|---|---|
| | Type and content of compound represented by formula (8) | Type and content of c ompound represented by formula (17) | | | purity | Relative mobility | Variation |
| Example 8 | Compound (1-4) 98.6% | Compound (1-4') 0.1% or less | Compound (8-1) | 8.23 | A | A | A |
| Example 9 | Compound (1-4) 98.6% | Compound (1-4') 0.1% or less | Compound (8-1) | 7.21 | A | A | A |
| Example 10 | Compound (1-4) 98.6% | Compound (1-4') 0.1% or less | Compound (10-1) | 8.19 | A | B | A |

Furthermore, the following derivatives can be synthesized by using the production method according to an embodiment of the present invention.

Example 11

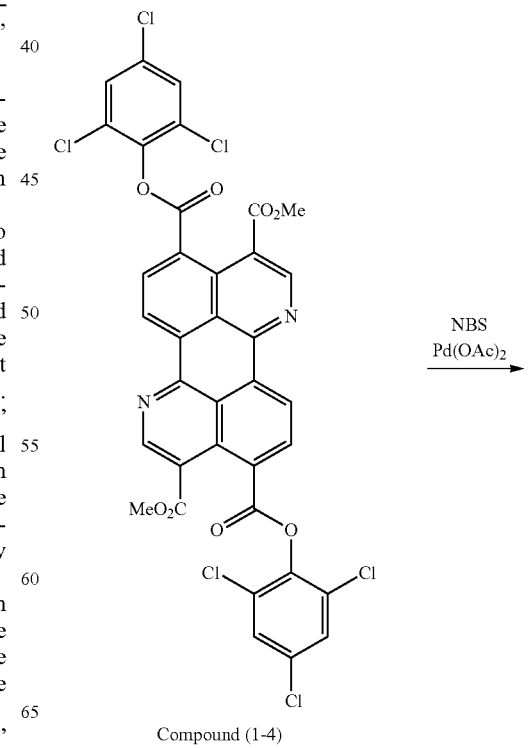

Compound (1-4)

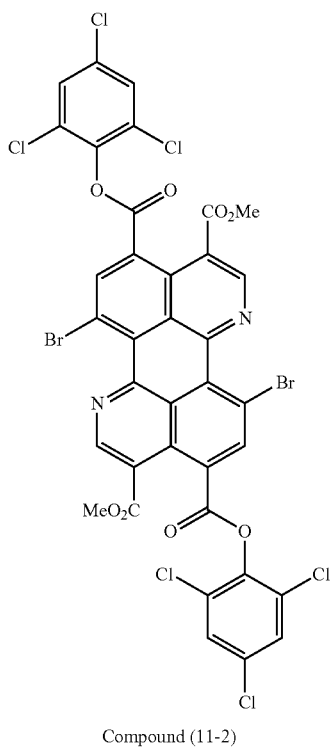

Compound (11-2)

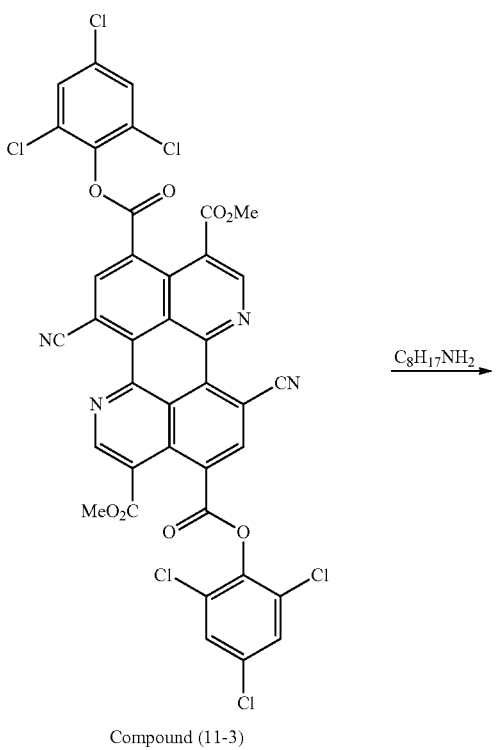

Compound (11-3)

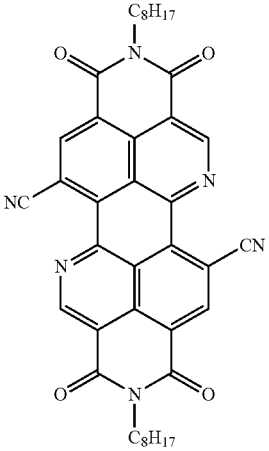

Compound (11-1)

Synthesis of compound (11-2)

Into a glass reaction vessel, 1 g (1.14 mmol) of the composition including the compound (1-4) and prepared in Example 1, 25.5 mg (0.114 mmol) of palladium acetate, 205 mg (0.567 mmol) of copper(II) trifluoromethanesulfonate, 609 mg (3.42 mmol) of N-bromosuccinimide, 33 mL of 1,1,2-trichloroethane, and 5 mL of N,N-dimethylformamide were charged, and reaction was caused in a nitrogen atmosphere at 60° C. for 2 hours. The resulting product was allowed to cool to room temperature and poured into 80 mL of methanol. The precipitated solid was collected by filtration. The obtained solid was purified by silica gel column chromatography to obtain 0.887 g (0.910 mmol, yield 79.8%) of a compound (11-2).

Compound (11-2): $^1$H NMR (CDCl$_3$) δ 3.95 (6H, s), 7.48 (4H, s), 9.18 (2H, s), 9.27 (2H, s)

Synthesis of Compound (11-3)

Into a glass reaction vessel, 224 mg (0.229 mmol) of the compound (11-2), 370 g (4.13 mmol) of copper cyanide, and 9.2 mL of N,N-dimethylformamide were charged, and reaction was caused in a nitrogen atmosphere at 100° C. for 1 hour. The resulting product was allowed to cool to room temperature and then added to 200 mL of methanol. The precipitated solid was collected by filtration. The obtained solid was purified by silica gel column chromatography to obtain 168 mg (0.194 mmol, yield 84.7%) of a compound (11-3).

Compound (11-3): $^1$H NMR (CDCl$_3$) δ 3.99 (6H, s), 7.51 (4H, s), 9.16 (2H, s), 9.45 (2H, s) Production of compound (11-1)

Into a glass reaction vessel, 140 mg (0.161 mmol) of the compound (11-3), 45.8 mg (0.354 mmol) of octylamine, and 5.6 mL of o-dichlorobenzene were charged, and reaction was caused in a nitrogen atmosphere at 150° C. for 6 hours. After cooling, the resulting product was collected by filtration. The obtained solid was purified by silica gel column chromatography to obtain 60.3 mg (0.0905 mmol, yield 56.2%) of a compound (11-1).

Compound (11-1): $^1$H NMR (TCE-d$^2$, 100° C.) δ 0.90 (t, J=7.0 Hz, 6H), 1.25-1.48 (m, 20H), 1.78 (m, 4H), 4.23 (t, J=7.8 Hz, 4H), 9.12 (s, 2H), 9.37 (s, 2H)

Example 12

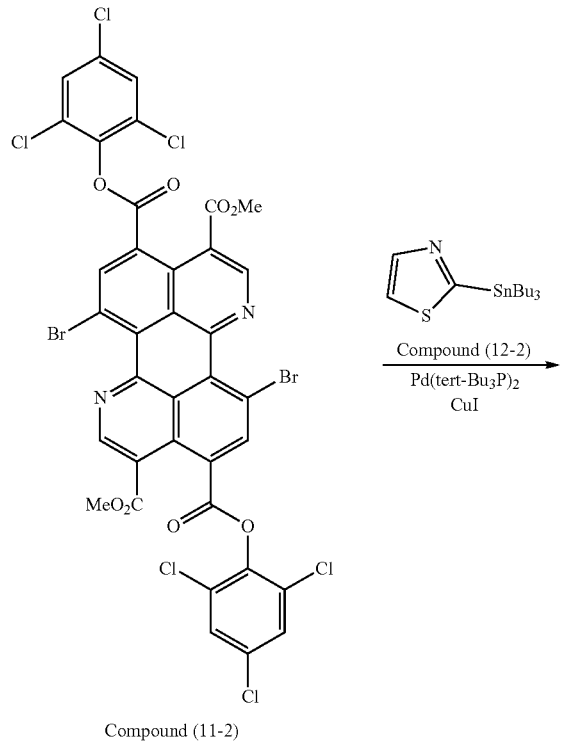

Compound (11-2)

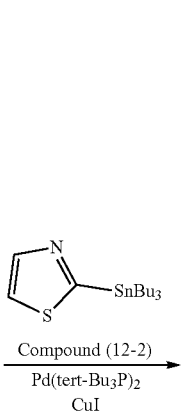

Compound (12-2)
Pd(tert-Bu₃P)₂
CuI

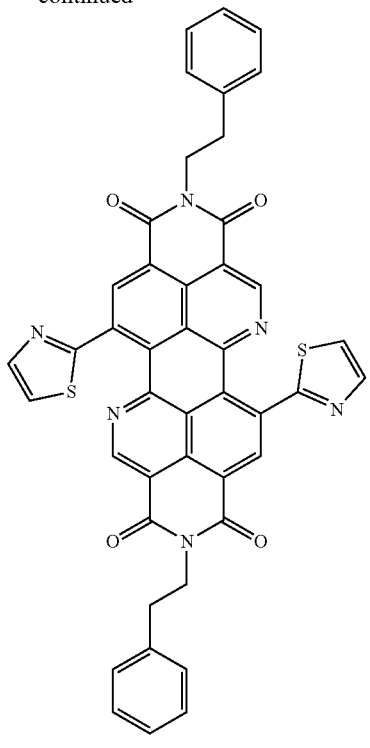

Compound (12-1)

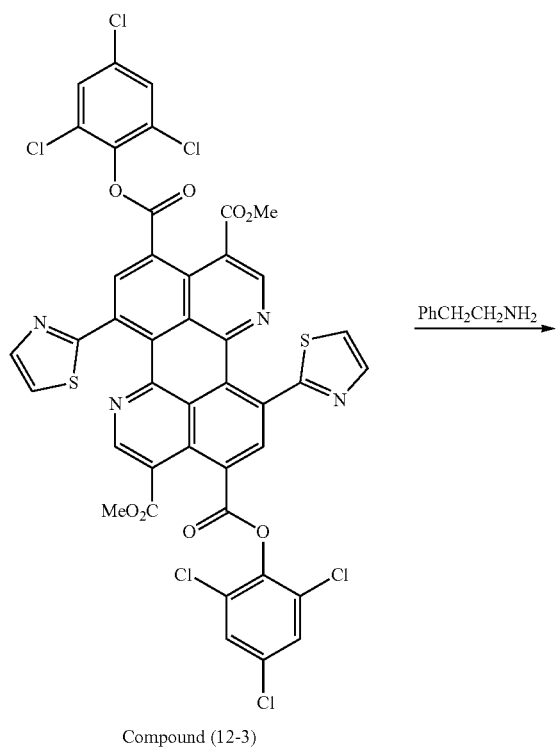

Compound (12-3)

PhCH₂CH₂NH₂ →

Synthesis of Compound (12-3)

Into a glass reaction vessel, 0.900 g (0.923 mmol) of the compound (11-2), 0.863 g (2.31 mmol) of the compound (12-2), 0.0472 g (0.0923 mmol) of bis(tri-tert-butylphosphine)palladium(0), 0.0352 g (0.185 mmol) of copper(I) iodide, and 46 mL of tetrahydrofuran were charged, and reaction was caused in a nitrogen atmosphere at 60° C. for 1 hour. After cooling to room temperature, 100 mL of methanol was added thereto. The precipitated solid was collected by filtration. The obtained solid was purified by silica gel column chromatography to obtain 0.853 g (0.868 mmol, yield 94.0%) of a compound (12-3). Compound (12-3): $^1$H NMR (CDCl₃) δ 3.89 (6H, s), 7.44 (4H, s), 7.57 (2H, d, J=4 Hz), 7.99 (2H, d, J=4 Hz), 8.77 (2H, s), 9.07 (2H, s)

Synthesis of Compound (12-1)

Into a glass reaction vessel, 0.620 g (0.630 mmol) of the compound (12-3), 0.384 g (3.15 mmol) of phenethylamine, and 31 mL of o-dichlorobenzene were charged, and reaction was caused at 80° C. for 2 hours. The resulting product is allowed to cool to room temperature, then added to 100 mL of methanol cooled with ice, and stirred under cooling with ice for 20 minutes. The precipitated solid was collected by filtration and dried under reduced pressure to obtain 0.452 g (0.590 mmol, yield 93.7%) of a compound (12-1).

Compound (12-1): $^1$H NMR (CDCl₃) δ 3.02-3.06 (4H, m), 4.40-4.44 (4H, m), 7.23-7.34 (10H, m), 7.67 (2H, d, J=4 Hz), 8.04 (2H, d, J=4 Hz), 8.92 (2H, s), 9.27 (2H, s)

Example 13
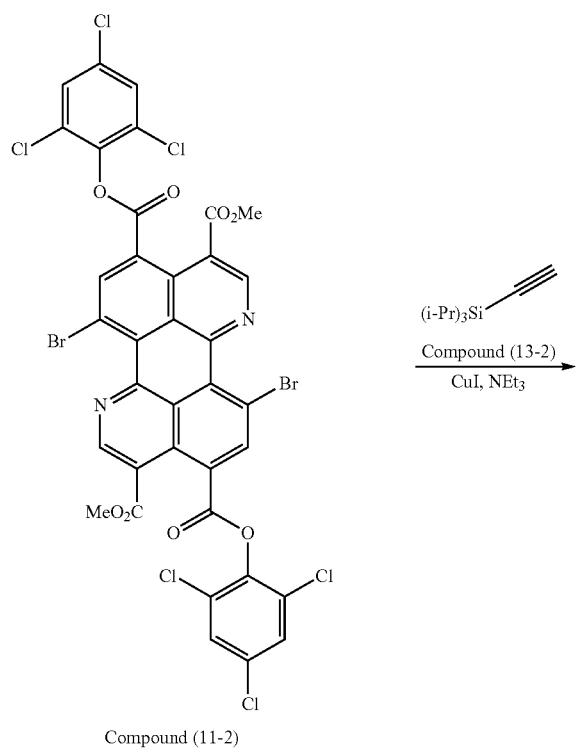
Compound (11-2)
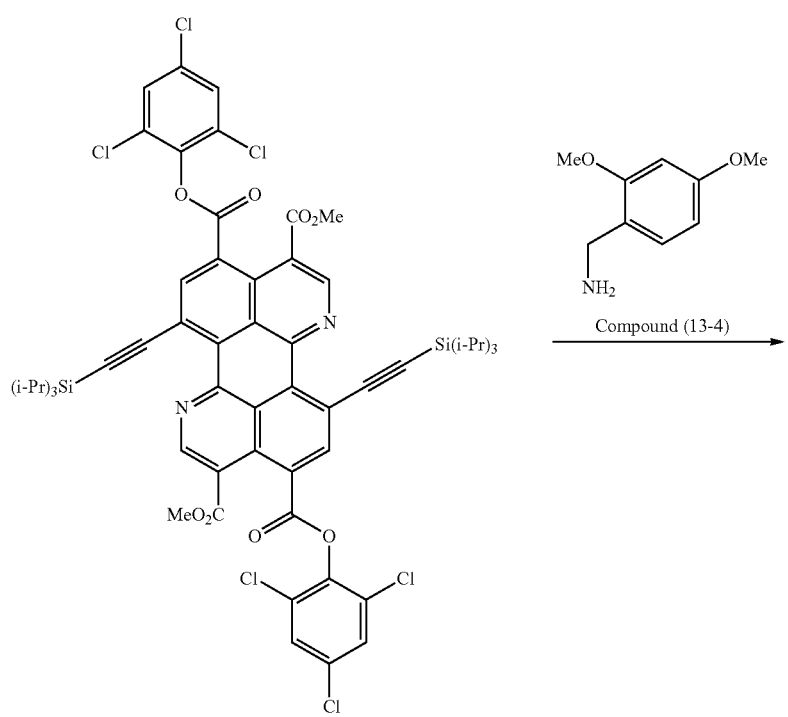
Compound (13-3)

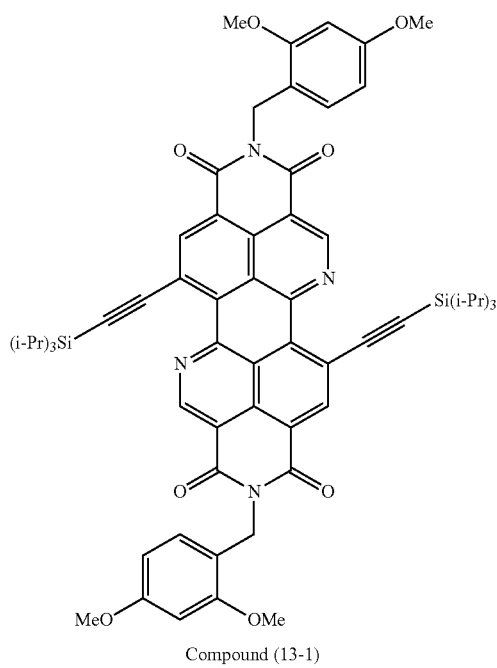

Compound (13-1)

Synthesis of Compound (13-1)

Into a glass reaction vessel, 35 mg (0.0306 mmol) of the compound (13-3), 15.3 mg (0.0918 mmol) of the compound (13-4), and 1.7 mL of o-dichlorobenzene were charged, and reaction was caused in a nitrogen atmosphere at 100° C. for 1 hour. The resulting product was allowed to cool to room temperature and then poured into 17 mL of methanol. The precipitated solid was collected by filtration. The obtained solid was purified by silica gel column chromatography to obtain 15.0 mg (0.0143 mmol, yield 46.6%) of a compound (13-1).

Compound (13-1): $^1$H NMR (CDCl$_3$) δ 1.22-1.35 (42H, m), 3.77 (6H, s), 3.87 (6H, s), 5.40 (4H, s), 6.42 (2H, d, J=10 Hz), 6.48 (2H, s), 7.15 (2H, d, J=10 Hz), 8.98 (2H, s), 9.69 (2H, s)

Among the compounds (11-1), (12-1), and (13-1), the compound (11-1) was evaluated for transistor characteristics in the same manner as in Example 1. As a result, the compound (11-1) was confirmed to have the same transistor characteristics as those of the compound (1-1).

Examples 14 to 19

The compound represented by the formula (2) could also be synthesized from the following compounds in the same manner as in Example 1. In Examples 14 to 19, it was found that the solubility of the raw materials was improved, which provides synthetic advantages such as reducing the amount of reaction solvents. The following synthetic methods are the same as the synthetic method in Example 1, except that the compound serving as a starting material is different, and only the results are shown.

As is clear from the comparison of the results in Examples 14 to 19 and Examples 1, 5, and 6, the yield is better when the number of carbon atoms of the aliphatic hydrocarbon group in the compound represented by the formula (8) (or the compound represented by the formula (11A)) is 2 or more.

Example 14
Synthesis of Compound (1-1)
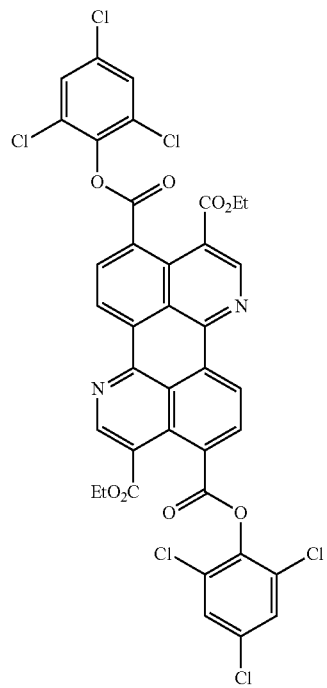
Compound (14-1)
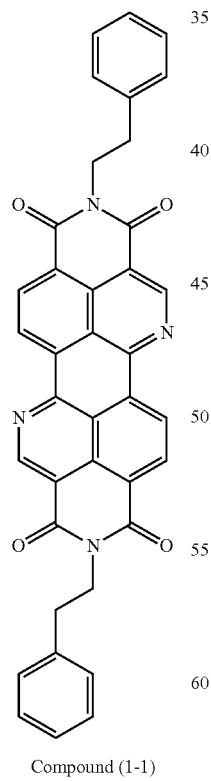
Compound (1-1)
Compound (1-1): yield 470 mg (0.782 mmol, yield 64.1%)
Example 15
Synthesis of Compound (1-1)
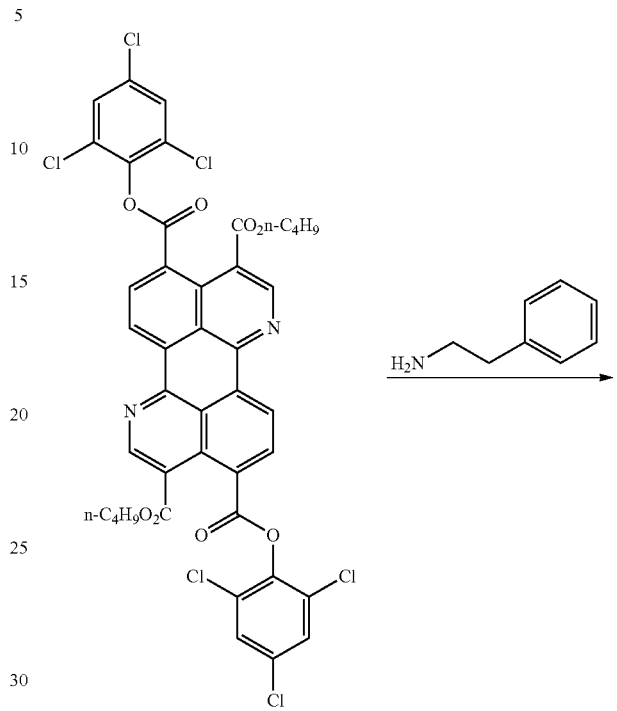
Compound (15-1)
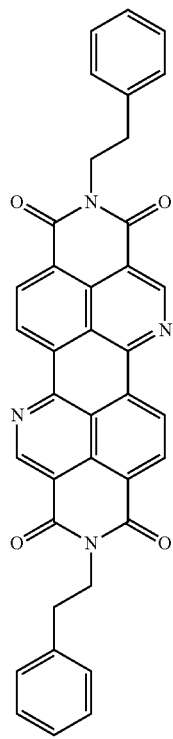
Compound (1-1)
Compound (1-1): 471 mg (0.784 mmol, yield 64.3%)

Example 16
Synthesis of Compound (1-1)
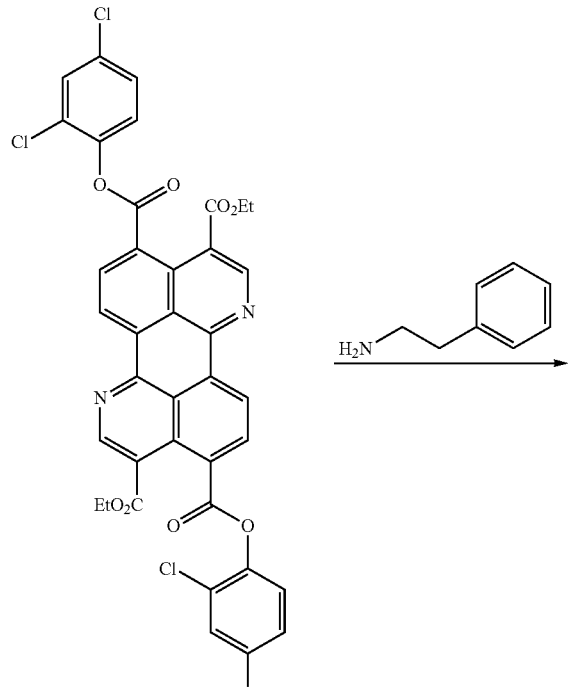
Compound (16-1)
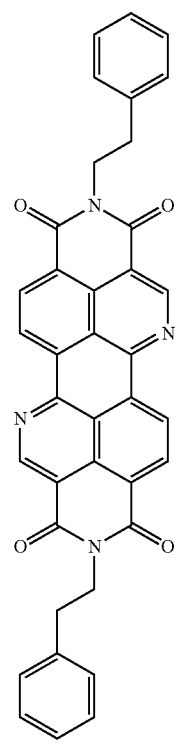
Compound (1-1)
Compound (1-1): yield 469 mg (0.779 mmol, yield 63.9%)
Example 17
Synthesis of Compound (1-1)
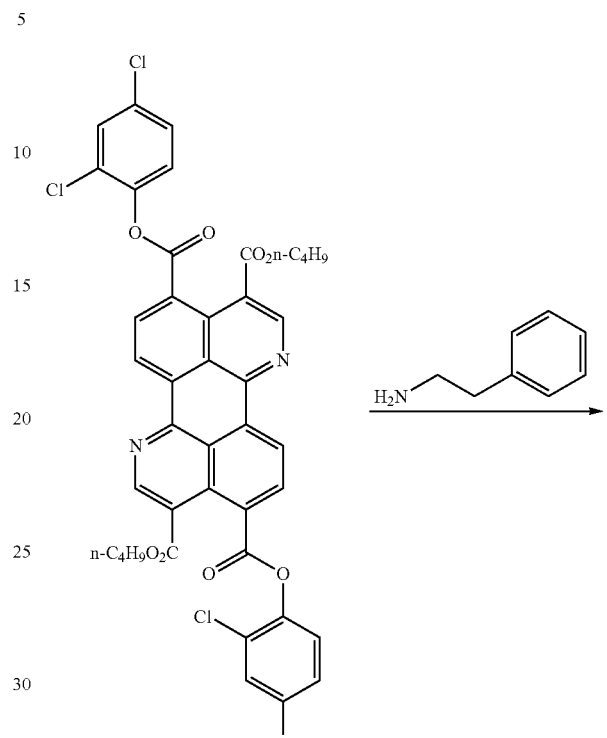
Compound (17-1)
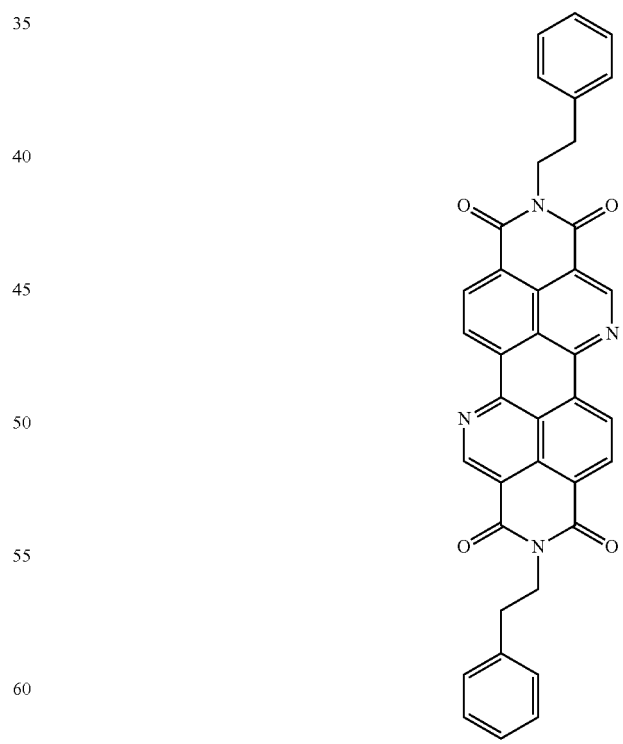
Compound (1-1)
Compound (1-1): yield 470 mg (0.781 mmol, yield 64.0%)

Example 18
Synthesis of Compound (1-1)
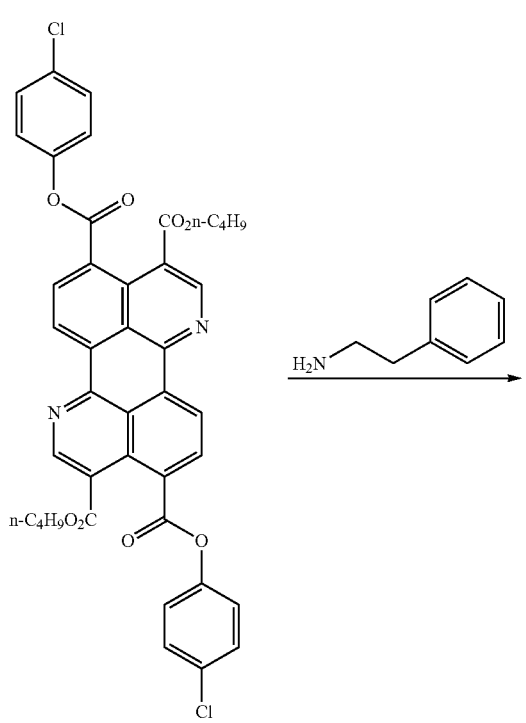
Compound (18-1)
Compound (1-1): yield 468 mg (0.778 mmol, yield 63.8%)
Example 19
Synthesis of Compound (1-1)
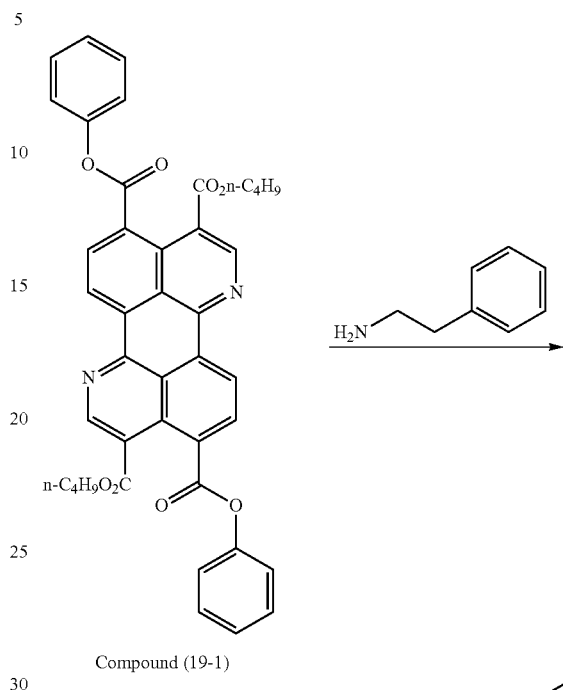
Compound (19-1)
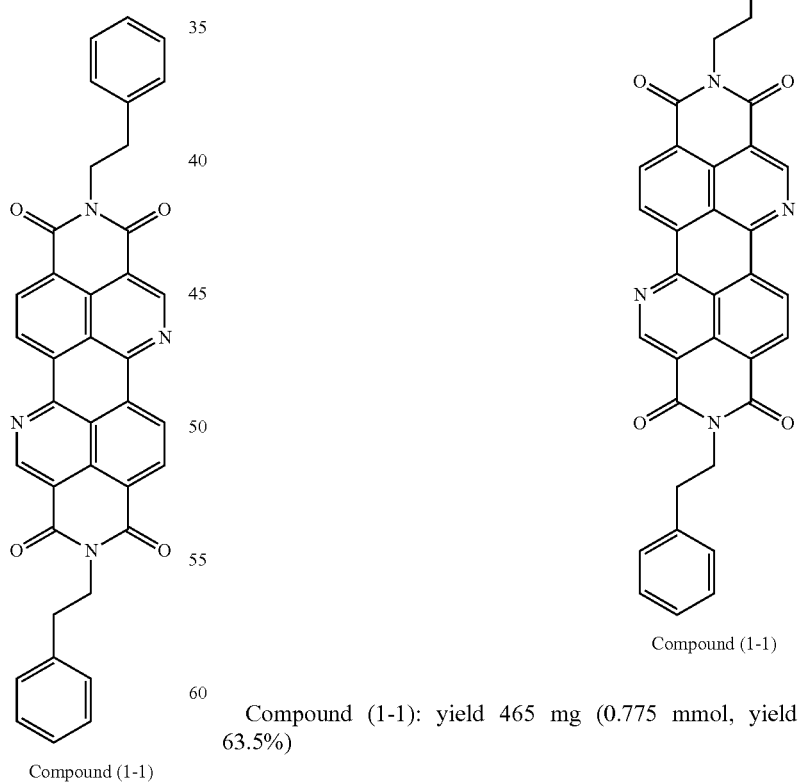
Compound (1-1)
Compound (1-1): yield 465 mg (0.775 mmol, yield 63.5%)
Example 20
The compound represented by the formula (2) could also be synthesized from the following compounds in the same manner as in Example 8. The following synthetic methods are the same as the synthetic method in Example 8, except that the compound serving as a starting material is different, and only the results are shown.

As is clear from the comparison of the results in Example 20 and Example 8, the yield is better when the number of carbon atoms of the aliphatic hydrocarbon group in the compound represented by the formula (8) (or the compound represented by the formula (11A)) is 2 or more.

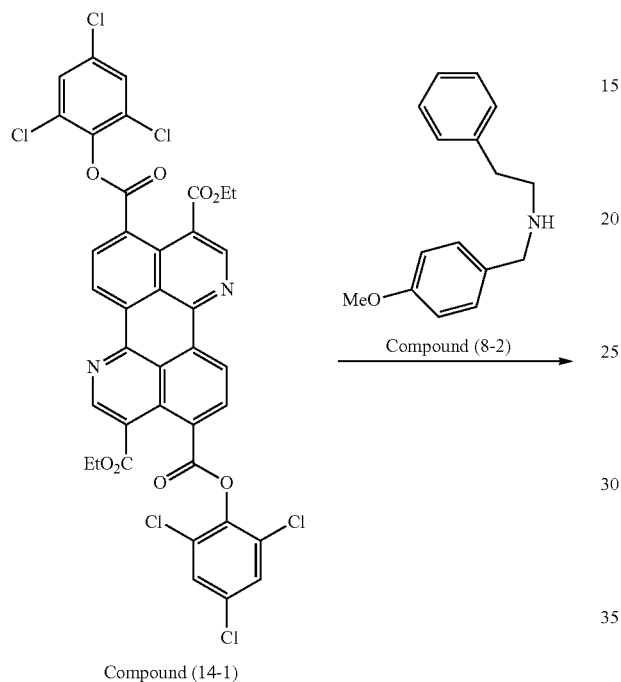

Compound (14-1)

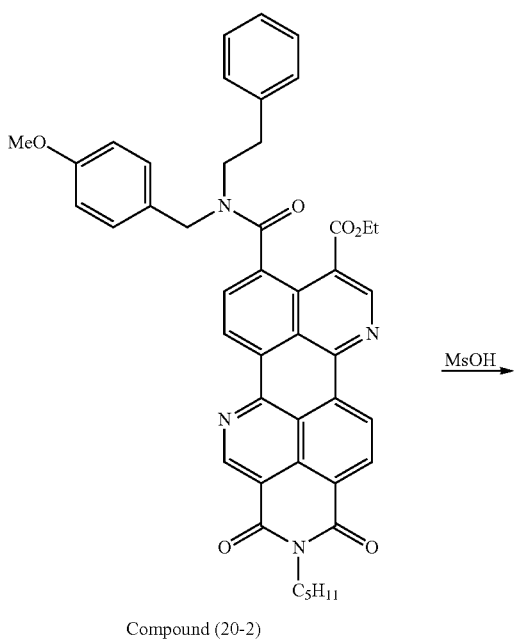

Compound (20-2)

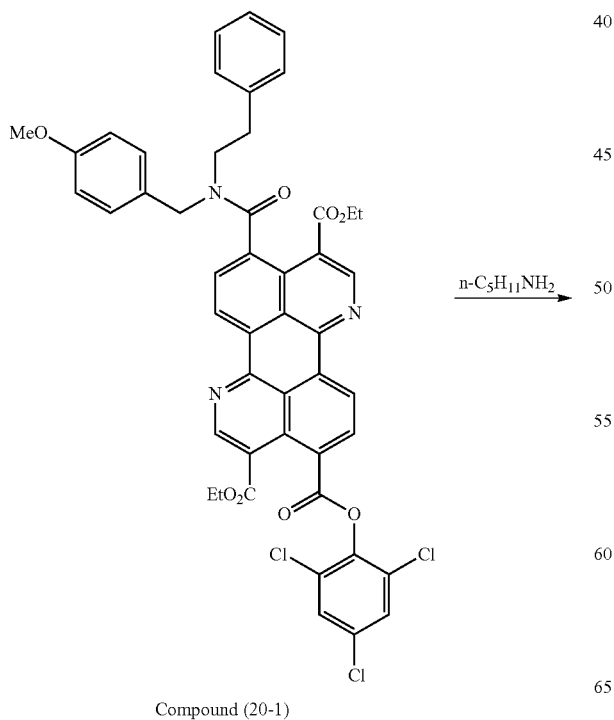

Compound (20-1)

Compound (20-3)

-continued

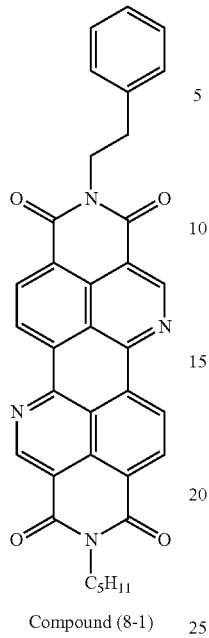

Compound (8-1)

Compound (8-1): yield 36.1 mg (0.0637 mmol, yield 8.50% relative to the compound (14-1))

REFERENCE SIGNS LIST

1 substrate
2 gate electrode
3 gate insulating film
4A source electrode
4B drain electrode
5 organic semiconductor film (organic semiconductor layer)
6 sealing layer
10, 20 organic thin film transistor (organic TFT)
41 coating liquid
42 substrate
43 member

What is claimed is:

1. A method for producing a cyclic imide comprising:
   a step Y1 of reacting a compound represented by formula (1) with a first amine compound represented by formula (3) below to obtain a compound represented by formula (4) below;
   a step Y2 of reacting the compound represented by the formula (4) with a second amine compound represented by formula (5) below to obtain a compound represented by formula (6) below;
   a step Y3 of removing $P^{31}$ serving as a protecting group from the compound represented by the formula (6) to obtain a compound represented by formula (7) below; and
   a step Y4 of obtaining the compound represented by formula (2) from the compound represented by the formula (7),

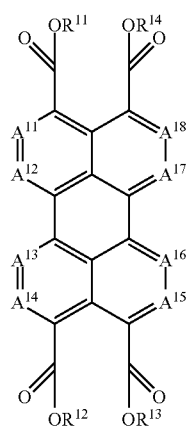 (1)

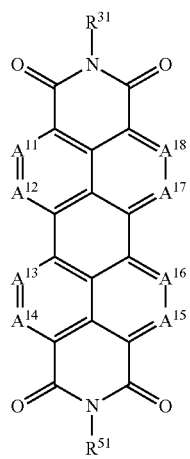 (2)

(3)

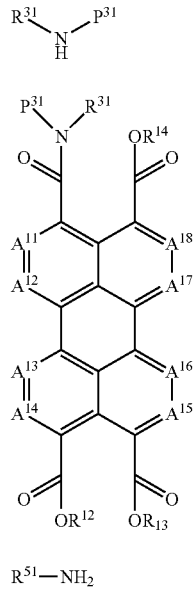 (4)

$R^{51}$—$NH_2$ (5)

-continued

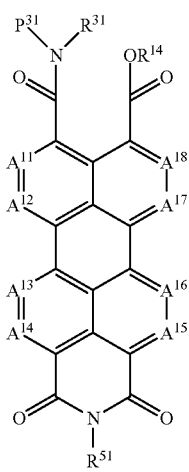

(6)

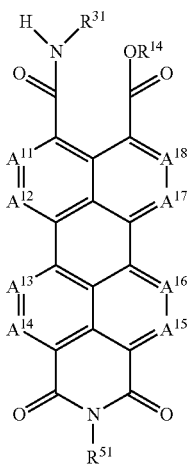

(7)

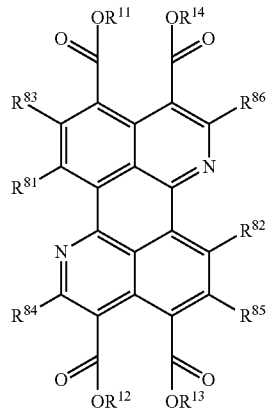

(8)

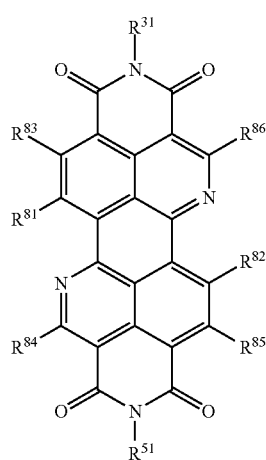

(9)

wherein in the formulae (2), (3), (4), (6), and (7), $R^{31}$ represents an alkyl group, an alkenyl group, an alkynyl group, an aryl group, or a heteroaryl group, in the formulae (2), (5), (6), and (7), $R^{51}$ represents an alkyl group, an alkenyl group, an alkynyl group, an aryl group, or a heteroaryl group, in the formulae (1), (2), (4), (6) and (7), $A^{11}$, $A^{12}$, $A^{14}$, $A^{15}$, $A^{16}$, and $A^{18}$ each independently represent —C($R^{15}$)═, $A^{13}$ and $A^{17}$ each independently represent —N═, $R^{15}$ represents a hydrogen atom, in the formulae (1), (4), (6) and (7), $R^{11}$ represents an aryl group or a heteroaryl group, $R^{14}$ represents an aliphatic hydrocarbon group, $R^{12}$ and $R^{13}$ each independently represent an aliphatic hydrocarbon group, an aryl group, or a heteroaryl group, and one of $R^{12}$ and $R^{13}$ represents an aliphatic hydrocarbon group and the other represents an aryl group or a heteroaryl group, and in the formulae (3), (4) and (6), $P^{31}$ represents a protecting group.

2. A method for producing a cyclic imide compound, comprising reacting a compound represented by formula (8) below with amine compounds to obtain a compound represented by formula (9) below, wherein in the formula (8), $R^{11}$ to $R^{14}$ each independently represent an aliphatic hydrocarbon group, an aryl group, or a heteroaryl group, and one of $R^{11}$ and $R^{14}$ represents an aliphatic hydrocarbon group and the other represents an aryl group or a heteroaryl group, and one of $R^{12}$ and $R^{13}$ represents an aliphatic hydrocarbon group and the other represents an aryl group or a heteroaryl group, in the formulae (8) and (9), $R^{81}$ to $R^{86}$ each independently represent a hydrogen atom, in the formula (9), $R^{31}$ represents an alkyl group, an alkenyl group, an alkynyl group, an aryl group, or a heteroaryl group, and, in the formula (9), $R^{51}$ represents an alkyl group, an alkenyl group, an alkynyl group, an aryl group, or a heteroaryl group.

3. The method for producing a cyclic imide compound according to claim 1, wherein the compound represented by the formula (1) is a compound represented by formula (10) below,

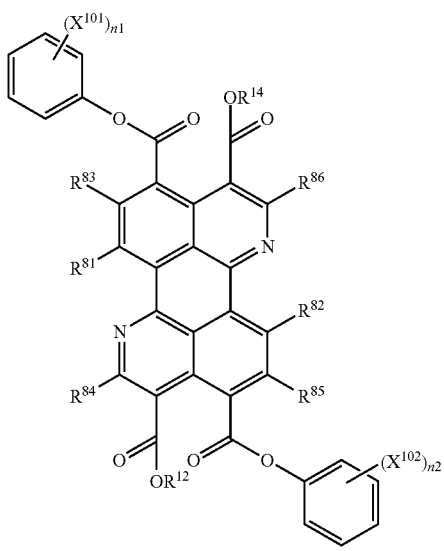

(10)

wherein in the formula (10), $X^{101}$ and $X^{102}$ each independently represent an electron-withdrawing group, n1 and n2 each independently represent an integer of 1 to 5, $R^{12}$ and $R^{14}$ each independently represent an aliphatic hydrocarbon group, and $R^{81}$ to $R^{86}$ each independently represent a hydrogen atom.

4. The method for producing a cyclic imide compound according to claim 3, wherein the compound represented by the formula (10) is a compound represented by formula (10') below,

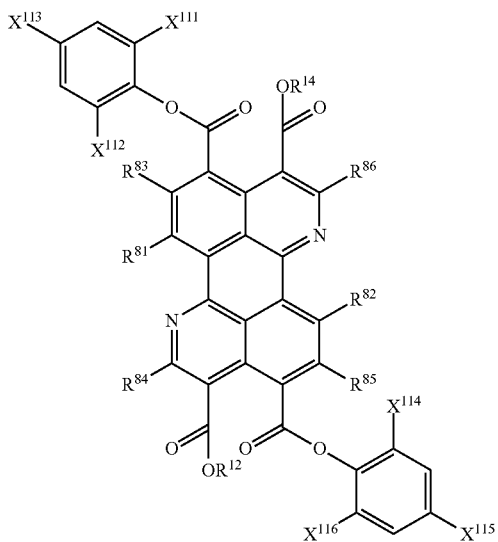

(10')

wherein in the formula (10'), $X^{111}$ to $X^{116}$ each independently represent a halogen atom, $R^{12}$ and $R^{14}$ each independently represent an aliphatic hydrocarbon group, and $R^{81}$ to $R^{86}$ each independently represent a hydrogen atom.

5. The method for producing a cyclic imide compound according to claim 4, wherein $X^{111}$ to $X^{116}$ represent a chlorine atom.

6. A method for producing a cyclic imide compound, comprising:

a step Y1' of reacting a compound represented by formula (X1) below with a compound represented by formula (X2) below to obtain a composition including a compound represented by formula (11A) below and a compound represented by formula (11B) below, and then reacting the composition with a first amine compound represented by formula (12) below without subjecting the composition to column purification to obtain a compound represented by formula (13) below;

a step Y2' of reacting the compound represented by the formula (13) with a second amine compound represented by formula (14) below to obtain a compound represented by formula (15) below;

a step Y3' of removing $P^{31}$ serving as a protecting group from the compound represented by the formula (15) to obtain a compound represented by formula (16) below; and a step Y4' of obtaining the compound represented by the formula (9) from the compound represented by the formula (16),

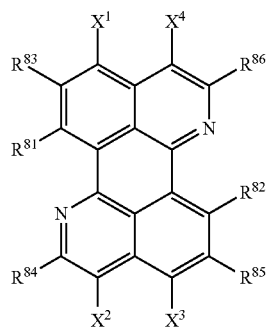

(X1)

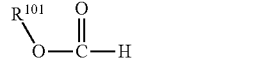

(X2)

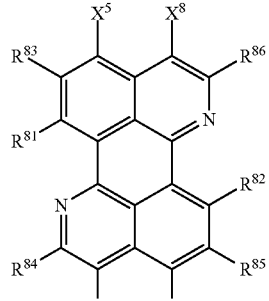

(11A)

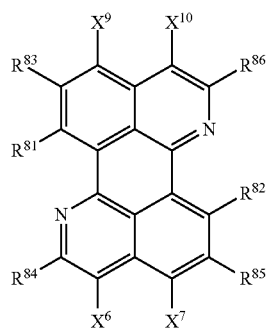

(11B)

-continued

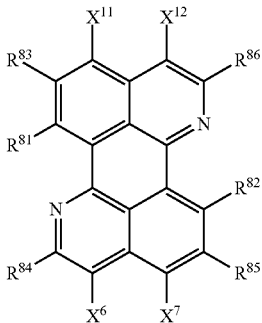

R⁵¹—NH₂

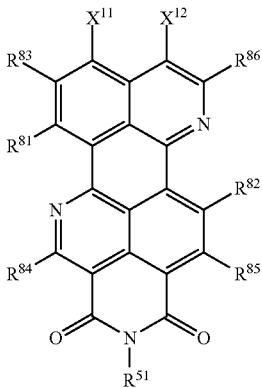

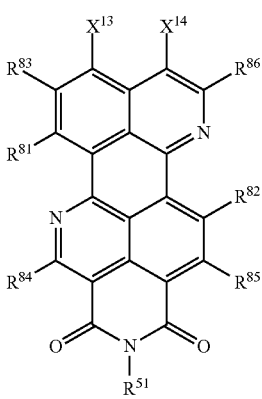

-continued

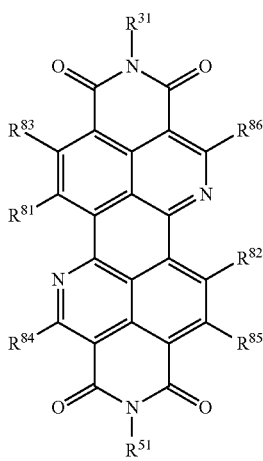

wherein in the formula (X1), $X^1$ to $X^4$ each represent a halogen atom or —CO—O—$R^{101}$, $R^{101}$ represents an aliphatic hydrocarbon group, an aryl group, or a heteroaryl group, one of $X^1$ and $X^4$ represents a halogen atom and the other represents —CO—O—$R^{101}$, one of $X^2$ and $X^3$ represents a halogen atom and the other represents —CO—O—$R^{101}$, and $R^{81}$ to $R^{86}$ each independently represent a hydrogen atom, in the formula (X2), $R^{101}$ represents an aliphatic hydrocarbon group, an aryl group, or a heteroaryl group, in the formula (11A), $X^5$ to $X^8$ each independently represent —CO—O—$R^{101}$, each $R^{101}$ independently represents an aliphatic hydrocarbon group, an aryl group, or a heteroaryl group, and $R^{101}$ in $X^5$ and $R^{101}$ in $X^8$ are different from each other, and one of $R^{101}$ in $X^5$ and $R^{101}$ in $X^8$ represents an aliphatic hydrocarbon group and the other represents an aryl group or a heteroaryl group, $R^{101}$ in $X^6$ and $R^{101}$ in $X^7$ are different from each other, and one of $R^{101}$ in $X^6$ and $R^{101}$ in $X^7$ represents an aliphatic hydrocarbon group and the other represents an aryl group or a heteroaryl group, and $R^{81}$ to $R^{86}$ each independently represent a hydrogen atom, in the formula (11B), one of $X^9$ and $X^{10}$ represents a hydrogen atom and the other represents —CO—O—$R^{101}$, $R^{101}$ represents an aliphatic hydrocarbon group, an aryl group, or a heteroaryl group, $X^6$ and $X^7$ each independently represent —CO—O—$R^{101}$, each $R^{101}$ independently represents an aliphatic hydrocarbon group, an aryl group, or a heteroaryl group, and $R^{101}$ in $X^6$ and $R^{101}$ in $X^7$ are different from each other, and one of $R^{101}$ in $X^6$ and $R^{101}$ in $X^7$ represents an aliphatic hydrocarbon group and the other represents an aryl group or a heteroaryl group, and $R^{81}$ to $R^{86}$ each independently represent a hydrogen atom, in the formula (12), $R^{31}$ represents an alkyl group, an alkenyl group, an alkynyl group, an aryl group, or a heteroaryl group, and $P^{31}$ represents a protecting group, in the formula (13), one of $X^{11}$ and $X^{12}$ represents —CO—O—$R^{101}$ and the other represents —CO—N($R^{31}$)($P^{31}$), $R^{101}$ represents an aliphatic hydrocarbon group, an aryl group, or a heteroaryl group, $R^{31}$ represents an alkyl group, an alkenyl group, an alkynyl group, an aryl group, or a heteroaryl group, $P^{31}$ represents a protecting group, $X^6$ and $X^7$ each independently represent —CO—O—$R^{101}$, each $R^{101}$ independently represents an aliphatic hydrocarbon group, an aryl group, or a heteroaryl group, and $R^{101}$ in $X^6$ and $R^{101}$ in $X^7$ are different from each other, and one of $R^{101}$ in $X^6$ and $R^{101}$ in $X^7$ represents an aliphatic hydrocarbon group and the other represents an aryl group or a heteroaryl group, and $R^{81}$ to $R^{86}$ each independently represent a hydrogen atom, in the formula (14), $R^{51}$ represents an alkyl group, an alkenyl group, an alkynyl group, an aryl group, or a heteroaryl group, in the formula (15), one of $X^{11}$ and $X^{12}$ represents —CO—O—$R^{101}$ and the other represents -CO—N($R^{31}$) ($P^{31}$), $R^{101}$ represents an aliphatic hydrocarbon group, an aryl group, or a heteroaryl group, $R^{31}$ represents an alkyl group, an alkenyl group, an alkynyl group, an aryl group, or a heteroaryl group, $P^{31}$ represents a protecting group, $R^{51}$ represents an alkyl group, an alkenyl group, an alkynyl group, an aryl group, or a heteroaryl group, and $R^{81}$ to $R^{86}$ each independently represent a hydrogen atom, in the formula (16), one of $X^{13}$ and $X^{14}$ represents —CO—O—$R^{101}$ and the other represents -CO—N($R^{31}$) (H), $R^{31}$ represent an alkyl group, an alkenyl group, an alkynyl group, an aryl group, or a heteroaryl group, $R^{101}$ represents an aliphatic hydrocarbon group, an aryl group, or a heteroaryl group, $R^{51}$ represents an alkyl group, an alkenyl group, an alkynyl group, an aryl group, or a heteroaryl group, and $R^{81}$ to $R^{86}$ each independently represent a hydrogen atom, and in the formula (9), $R^{81}$ to $R^{86}$ each independently represent a hydrogen atom, $R^{31}$ represents an alkyl group, an alkenyl group, an alkynyl group, an aryl group, or a heteroaryl group, and $R^{51}$ represents an alkyl group, an alkenyl group, an alkynyl group, an aryl group, or a heteroaryl group.

7. A method for producing a cyclic imide compound, comprising:

a step of reacting a compound represented by formula (X1) below with a compound represented by formula (X2) below to obtain a composition including a compound represented by formula (11A) below and a compound represented by formula (11B) below, and then reacting the composition with an amine compound represented by formula (14) below without subjecting the composition to column purification to obtain a compound represented by formula (9') below,

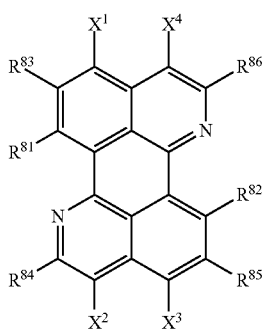
(X1)

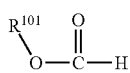
(X2)

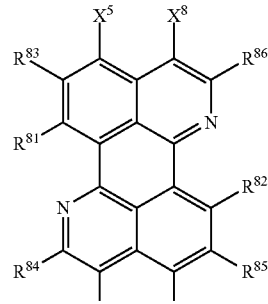
(11A)

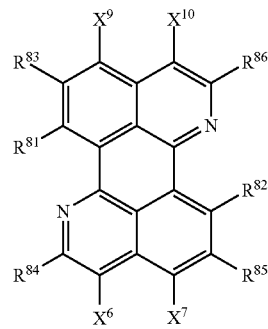
(11B)

$R^{51}$—$NH_2$ (14)

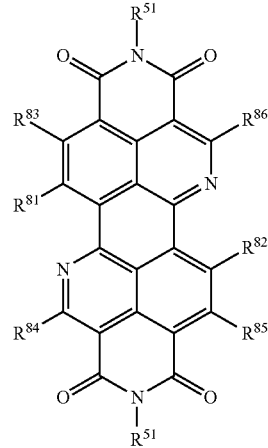
(9')

wherein in the formula (X1), $X^1$ to $X^4$ each independently represent a halogen atom or —CO—O—$R^{101}$, $R^{101}$ represents an aliphatic hydrocarbon group, an aryl group, or a heteroaryl group, one of $X^1$ and $X^4$ represents a halogen atom and the other represents —CO—O—$R^{101}$, one of $X^2$ and $X^3$ represents a halogen atom and the other represents —CO—O—$R^{101}$, and $R^{81}$ to $R^{86}$ each independently represent a hydrogen atom, in the formula (X2), $R^{101}$ represents an aliphatic hydrocarbon group, an aryl group, or a heteroaryl group, in the formula (11A), $X^5$ to $X^8$ each independently represent —CO—O—$R^{101}$, each $R^{101}$ independently represents an aliphatic hydrocarbon group, an aryl group, or a heteroaryl group, and $R^{101}$ in $X^5$ and $R^{101}$ in $X^8$ are different from each other, and one of $R^{101}$ in $X^5$ and $R^{101}$ in $X^8$ represents an aliphatic hydrocarbon group and the other represents an aryl group or a heteroaryl group, $R^{101}$ in $X^6$ and $R^{101}$ in $X^7$ are different from each other, and one of $R^{101}$ in $X^6$ and $R^{101}$ in $X^7$ represents an aliphatic hydrocarbon group and the other represents an aryl group or a heteroaryl group, and $R^{81}$ to $R^{86}$ each independently represent a hydrogen atom in the formula (11B), one of $X^9$ and $X^{10}$ represents a hydrogen atom and the other represents —CO—O—$R^{101}$, $R^{101}$ represents an aliphatic hydrocarbon group, an aryl group, or a heteroaryl group, $X^6$ and $X^7$ each independently represent —CO—O—$R^{101}$, each $R^{101}$ independently represents an aliphatic hydrocarbon group, an aryl group, or a heteroaryl group, and $R^{101}$ in $X^6$ and $R^{101}$ in $X^7$ are different from each other, and one of $R^{101}$ in $X^6$ and $R^{101}$ in $X^7$ represents an aliphatic hydrocarbon group and the other represents an aryl group or a heteroaryl group, and $R^{81}$ to $R^{86}$ each independently represent a hydrogen atom, in the formula (14), $R^{51}$ represents an alkyl group, an alkenyl group, an alkynyl group, an aryl group, or a heteroaryl group, and in the formula (9'), $R^{51}$ represents an alkyl group, an alkenyl group, an alkynyl group, an aryl group, or a heteroaryl group.

8. The method for producing a cyclic imide compound according to claim 6, further comprising:

a step Y0' of purifying the compound represented by the formula (X2) before reacting the compound represented by the formula (X1) with the compound represented by the formula (X2).

9. The method for producing a cyclic imide compound according to claim 7, further comprising:

a step Y0' of purifying the compound represented by the formula (X2) before reacting the compound represented by the formula (X1) with the compound represented by the formula (X2).

* * * * *